(12) United States Patent
Whitehead

(10) Patent No.: US 7,915,255 B2
(45) Date of Patent: Mar. 29, 2011

(54) METABOLISM-MODULATING AGENTS AND USES THEREFOR

(75) Inventor: Jonathan Paul Whitehead, Brisbane (AU)

(73) Assignee: Verva Pharmaceuticals Pty Ltd, Melbourne (AU)

( * ) Notice: Subject to any disclaimer, the term of this patent is extended or adjusted under 35 U.S.C. 154(b) by 691 days.

(21) Appl. No.: 11/205,279

(22) Filed: Aug. 16, 2005

(65) Prior Publication Data

US 2006/0106097 A1    May 18, 2006

Related U.S. Application Data

(60) Provisional application No. 60/601,797, filed on Aug. 16, 2004.

(51) Int. Cl.
*A61K 31/535* (2006.01)
(52) U.S. Cl. .................................. 514/233.5; 514/909
(58) Field of Classification Search ................ 514/233.5, 514/909
See application file for complete search history.

(56) References Cited

U.S. PATENT DOCUMENTS 4,753,935 A * 6/1988 Nelson et al. ............... 514/233.5

FOREIGN PATENT DOCUMENTS

| DE | 19948126 A1 | 4/2001 |
| JP | 2002-241276 | 8/2002 |
| JP | 2002241276 A * | 8/2002 |
| WO | WO 02/055018 A2 | 7/2002 |

OTHER PUBLICATIONS

Whitehead, J.P. et al. (2004) "Insulin and Oleate Promote Translocation of Inosine-5' Monophosphate Dehydrogenase to Lipid Bodies," Traffic 5:739-749.
Witters, L.A. et al. (1987) "Modulation of Acetyl-CoA Carboxylase by Inhibitors of IMP Dehydrogenase: Implications for Insulin Regulation," Archives Biochem Biophys 252:130-135.
International Search Report dated Sep. 12, 2005 from International Application PCT/AU2005/001235.
Brasaemle DL et al. 1997 "Adipose differentiation-related protein is an ubiquitously expressed lipid storage droplet-associated protein." *J Lipid Res* 38:2249-2263.
Brown DA. 2001 "Lipid droplets: Proteins floating on a pool of fat." *Curr Biol* 11:R446-R449.
Browne SJ et al. 2002 "Mutations in the inosine monophosphate dehydrogenase 1 gene (IMPDH1) cause the RP10 form of autosomal dominant retinitis pigmentosa." *Hum Mol Genet* 11:559-568.
Carr SF et al. 1993 "Characterization of human type I and type II IMP dehydrogenases." *J Biol Chem* 268:27286-27290.
Clark SF et al. 1998 "Intracellular localization of phosphatidylinositide 3-kinase and insulin receptor substrate-1 in adipocytes: Potential involvement of a membrane skeleton." *J Cell Biol* 140:1211-1225.

Collart FR and Huberman E. 1988 "Cloning and sequence analysis of the human and Chinese hamster inosine-5'-monophosphate dehydrogenase cDNAs." *J Biol Chem* 263:15769-15772.
Demoulin, J.-B. et al. 2004 "Platelet-derived growth factor stimulates membrane lipid synthesis through activation of phosphatidylinositol 3-kinase and sterol regulatory elementbinding proteins." *J. Biol. Chem.* 34:35392-35402.
Egan J et al. 1990 "Control of endogenous phosphorylation of the major cAMP-dependent protein kinase substrate in adipocytes by insulin and β-adrenergic stimulation." *J Biol Chem* 265:18769-18775.
Eisinger DP and Serrero G. 1993 "Structure of the gene encoding mouse adipose differentiationrelated protein (ADRP)." *Genomics* 16:638-644.
Fujimoto T et al. 2001 "Caveolin-2 Is Targeted to Lipid Droplets, a New "Membrane Domain" in the Cell." *J Cell Biol* 152:1079-1085.
Glesne DA et al. 1991 "Regulation of IMP dehydrogenase gene expression by its end products, guanine nucleotides." *Mol Cell Biol* 11:5417-5425.
Greenberg A et al. 1991 "Perilipin, a major hormonally regulated adipocyte-specific phosphoprotein associated with the periphery of lipid storage droplets." *J Biol Chem* 266:11341-11346.
Hakumaki JM and Kauppinen RA. 2000 "$^1$H NMR visible lipids in the life and death of cells.". *Trends in Biochemical Sciences* 25:357-362.
Hardy S et al. 2000 "Oleate activates phosphatidylinositol 3-kinase and promotes proliferation and reduces apoptosis of MDA-MB-231 breast cancer cells, whereas palmitate has opposite effects." *Cancer Res* 60:6353-6358.
Hill MM et al. 2000 "Differential Protein Phosphorylation in 3T3-L1 Adipocytes in Response to Insulin Versus Platelet-derived Growth Factor. No evidence for a phosphatidylinositide 3-kinase-independent pathway in insulin signaling." *J Biol Chem* 275:24313-24320.
Holwell TA et al. 1997 "Tetracycline regulated expression of vimentin in fibroblasts derived from vimentin null mice." *J Cell Sci* 110:1947-1956.
Hwang JH et al. 2001 "Regional differences in intramyocellular lipids in humans observed by in vivo $^1$H-MR spectroscopic imaging." *J Appl Physiol* 90:1267-1274.
Hyle JW et al. 2003 "Functional Distinctions between IMP Dehydrogenase Genes in Providing Mycophenolate Resistance and Guanine Prototrophy to Yeast." *J Biol Chem* 278:28470-28478.
Imamura M et al. 2002 "ADRP stimulates lipid accumulation and lipid droplet formation in murine fibroblasts." *Am J Physiol Endocrinol Metab* 283:E775-E783.

(Continued)

*Primary Examiner* — Kevin Weddington
(74) *Attorney, Agent, or Firm* — Knobbe Martens Olson & Bear LLP

(57) ABSTRACT

The present invention is directed to methods and agents for modulating adipogenesis. More particularly, the present invention relates to molecules that modulate the level or functional activity of inosine-5' monophosphate dehydrogenase (IMPDH) and to their use in modulating the accumulation of lipids in adipocytes and/or the differentiation of preadipocytes to adipocytes for treating or preventing adiposity-related conditions including, but not limited to, obesity, lipoma, lipomatosis, cachexia or lipodystrophy or the loss of adipose tissue in trauma or atrophic conditions.

10 Claims, 11 Drawing Sheets

OTHER PUBLICATIONS

Imanishi Y et al. 2004 "Noninvasive two photon imaging reveals retinyl ester storage structures in the eye." *J. Cell Biol.* 164:373-383.

Ingley E and Hemmings BA. 2000 "PKB/Akt interacts with inosine-5' monophosphate dehydrogenase through its pleckstrin homology domain." *FEBS Letters* 478:253-259.

Jackson RC et al. 1975 "IMP dehydrogenase, an enzyme linked with proliferation and malignancy." *Nature* 256:331-333.

Jiang HP and Serrero G. 1992 "Isolation and characterization of a full-length cDNA coding for an adipose differentiation-related protein." *Proc Natl Acad Sci USA* 89:7856-7860.

Kennan A et al. 2002 "Identification of an IMPDHI mutation in autosomal dominant retinitis pigmentosa (RP10) revealed following comparative microarray analysis of transcripts derived from retinas of wildtype and Rho(−/−) mice." *Hum Mol Genet* 11:547-558.

Litvak V et al. 2002 "Targeting of Nir2 to Lipid Droplets Is Regulated by a Specific Threonine Residue within Its P1-Transfer Domain." *Curr Biol* 12:1513-1518.

Liu P et al. 2004 "Chinese Hampster Ovary K2 cell lipid droplets appear to be metabolic organelles involved in membrane traffic." *J Biol Chem* 279:3787-3792.

Londos C et al. 1999 "Perilipins, ADRP, and other proteins that associate with intracellular neutral lipid droplets in animal cells." *Semin Cell Dev Biol* 10:51-58.

Miele C et al. 2003 "Human Glycated Albumin Affects Glucose Metabolism in L6 Skeletal Muscle Cells by Impairing Insulin-induced Insulin Receptor Substrate (IRS) Signaling through a Protein Kinase Cα-mediated Mechanism." *J Biol Chem* 278:47376-47387.

Molero JC et al. 2001 "Nocodazole inhibits insulinstimulated glucose transport in 3T3-L1 adipocytes via a microtubule-independent mechanism." *J Biol Chem* 276:43829-43835.

Murphy DJ and Vance J. 1999 "Mechanisms of lipid-body formation." *Trends Biochem Sci* 24:109-115.

Murphy DJ. 2001 "The biogenesis and functions of lipid bodies in animals, plants and microorganisms." *Prog Lipid Res* 40:325-438.

Natsumeda Y et al. 1990 "Two distinct cDNAs for human IMP dehydrogenase." *J Biol Chem* 265:5292-5295.

Ostermeyer AG et al. 2001 "Accumulation of caveolin in the endoplasmic reticulum redirects the protein to lipid storage droplets." *J Cell Biol* 152:1071-1078.

Ostermeyer AG et al. 2004 "Role of the hydrophobic domain in targeting caveolin-1 to lipid droplets." *J Cell Biol* 164:69-78.

Phelan JK and Bok D. 2000 "A brief review of retinitis pigmentosa and the identified retinitis pigmentosa genes." *Mol Vis* 6:116-124.

Pol A et al. 2001 "A caveolin dominant negative mutant associates with lipid bodies and induces intracellular cholesterol imbalance." *J Cell Biol* 152:1057-1070.

Pol A et al. 2004 "Dynamic and Regulated Association of Caveolin with Lipid Bodies: Modulation of Lipid Body Motility and Function by a Dominant Negative Mutant." *Mol Biol Cell* 15:99-110.

Proffitt RT et al. 1983 "Sensitive radiochemical assay for inosine 5'-monophosphate dehydrogenase and determination of activity in murine tumor and tissue extracts." *Cancer Res* 43:1620-1623.

Saltiel AR and Kahn CR 2001 "Insulin signalling and the regulation of glucose and lipid metabolism." *Nature* 414:799-806.

Sintchak MD and Nimmesgern E. 2000 "The structure of inosine 5'monophosphate dehydrogenase and the design of novel inhibitors." *Immunopharmacology* 47:163-184.

Stone J et al. 1999 "Mechanisms of photoreceptor death and survival in mammalian retina." *Prog Retin Eye Res* 18:689-735.

Summers SA et al. 1998 "Regulation of insulin-stimulated glucose transporter GLUT4 translocation and Akt kinase activity by ceramide." *Mol Cell Biol* 18:5457-5464.

Tauchi-Sato K et al. 2002 "The Surface of Lipid Droplets Is a Phospholipid Monolayer with a Unique Fatty Acid Composition." *J Biol Chem* 277:44507-44512.

Tian D and Lev S. 2002 "Cellular and developmental distribution of human homologues of the *Drosophilia* rdgB protein in the rat retina." *Invest Ophthalmol Vis Sci* 43:1946-1953.

Umlauf E et al. 2004 "Association of stomatin with lipid bodies." *J Biol Chem* 279:23699-23709.

White MF. "The insulin receptor tyrosine kinase" in *Peptide Hormone Action: A Practical Approach*, Siddle K, Hutton JC, editors. New York: Oxford University Press; 1990. pp. 223-250.

Whitehead JP et al. 2001 "The role of $Ca^{2+}$ in insulin-stimulated glucose transport in 3T3-L1 cells." *J Biol Chem* 276:27816-27824.

Wolins NE et al. 2003 "Adipocyte protein S3-12 coats nascent lipid droplets." *J Biol Chem* 278:37713-37721.

Yaffe MB et al. 2001 "A motif-based profile scanning approach for genome-wide prediction of signaling pathways." *Nat Biotechnol* 19:348-353.

Yu C et al. 2002 "Mechanism by which fatty acids inhibit insulin activation of insulin receptor substrate-1 (IRS-1) associated phosphatidylinositol 3-kinase activity in muscle." *J Biol Chem* 277:50230-50236.

Ailhaud, G. et al. 1989 "Coupling growth arrest and adipocyte differentiation" *Environmental Health Perspectives* 80:17-23.

Bachmeier, M and Löffler, G. 1995 "Influence of growth factors on growth and differentiation of 3T3-L1 preadipocytes in serum-free conditions" *Eur J Cell Biol* 68:323-329. (Abstract Only).

Green, H. and Meuth, M. 1974 "An established pre-adipose cell line and its differentiation in culture" *Cell* 3:127-133.

Hauner, H. et al. 1995 "Effects of epidermal growth factor (EGF), platelet-derived growth factor (PDGF) and fibroblast growth factor (FGF) on human adipocyte development and function" *Eur J Clin Invest* 25:90-96. (Abstract Only).

Li, Z.-H. et al. 1998 "Adipocyte differentiation factor (ADF): A protein secreted by mature fat cells that induces preadipocyte differentiation in culture" *Cell Biol Int* 22:253-270.

Serreno, G. 1987 "EGF inhibits the differentiation of adipocyte precursors in primary cultures" *Biochem Biophys Res Comm* 146:194-202.

Serreno, G. and Lepak, N.M. 1995 "Prostaglandin $F_{2α}$ inhibits epidermal growth factor binding to cellular receptors on adipocyte precursors in primary culture" *Biochem Biophys Res Comm* 212:1125-1132.

Russell, T.R. and Ho, R.-J. 1976 "Conversion of 3T3 fibroblasts into adipose cells: Triggering of differentiation by prostaglandin $F_{2α}$ and 1-methyl-3-isobutyl xanthine" *Proc Natl Acad Sci USA* 73:4516-4520.

Schmidt, W. et al. 1990 "Adipose conversion of 3T3-L1 cells in a serum-free culture system depends on epidermal growth factor, insulin-like growth factor I, corticosterone, and cyclic AMP" *J Biol Chem* 265:15489-15495.

Shillabeer, G. et al. 1989 "Induction of preadipocyte differentiation by mature fat cells in the rat" *J Clin Invest* 84:3881-387.

Supplemental European Search Report for European Application No. EP 05773612, dated Dec. 21, 2009.

* cited by examiner

METABOLISM-MODULATING AGENTS AND USES THEREFOR

FIELD OF THE INVENTION

This invention relates generally to methods and agents for modulating adipogenesis. More particularly, the present invention relates to molecules that modulate the level or functional activity of inosine-5' monophosphate dehydrogenase (IMPDH) and to their use in modulating the accumulation of lipids in adipocytes and/or the differentiation of preadipocytes to adipocytes. Even more particularly, the present invention relates to molecules that reduce, impair or abrogate the level or functional activity of IMPDH, including antagonist molecules that are specific for Impdh polynucleotides or their expression products, and to the use of these molecules for the negative regulation of adipogenesis, including downregulating the differentiation potential and/or proliferation of preadipocytes and/or the accumulation of lipids in adipocytes. The present invention also extends to the use of IMPDH agonist molecules, including Impdh polynucleotides and IMPDH polypeptides, as well as their biologically active fragments, variants and derivatives, for increasing the differentiation potential and/or proliferation of preadipocytes and/or for increasing the accumulation of lipids in adipocytes. Furthermore, the invention relates to the use of IMPDH modulatory agents in methods for treating or preventing adiposity-related conditions including, but not limited to, obesity, lipoma, lipomatosis, cachexia or lipodystrophy or the loss of adipose tissue in trauma or atrophic conditions.

Bibliographic details of certain publications numerically referred to in this specification are collected at the end of the description.

BACKGROUND OF THE INVENTION

Insulin is the major anabolic hormone promoting uptake and storage of molecules, including glucose, amino acids and fatty acids (1). Insulin acts through a cell surface tyrosine kinase receptor that phosphorylates downstream substrates. Tyrosine phosphorylation of substrates, such as the Insulin Receptor Substrate (IRS) family of scaffold proteins, serves to recruit SH2 domain containing proteins, including PI 3-kinase, leading to propagation of insulin signalling cascades (1). Whilst many of the molecules that act downstream of PI 3-kinase are known, such as the Ser/Thr kinases Akt and atypical PKCs, knowledge of the signalling pathways is incomplete (1). In an effort to address this, a proteomic screen was performed to identify novel insulin-regulated phosphoproteins that may act downstream of PI 3-kinase in 3T3-L1 adipocytes (2).

Inosine-5' monophosphate dehydrogenase (IMPDH) is a highly conserved, ubiquitously expressed enzyme, which catalyses a key step in the de novo biosynthesis of guanine nucleotide, the NAD-dependent conversion of inosine monophosphate (IMP) to xanthosine monophosphate (XMP) (3). In mammals there are two IMPDH isoforms, termed type I and type II, that show 84% amino acid identity and exist as homotetramers (4, 5). Increased IMPDH activity is associated with proliferation and malignancy, an observation that was recognised almost thirty years ago (6). As such, IMPDH represents a principal target for therapeutic intervention in anti-neoplastic and immunosuppressive treatments and has been the subject of intensive biochemical research (7). Recently mutations in IMPDH type I have been shown to cause the RP10 form of the degenerative retinal disorder autosomal dominant retinitis pigmentosa (adRP) in humans (8, 9).

Lipid bodies facilitate storage of intracellular lipid in mammalian cells (10). They are ubiquitous, ranging in size from 50 nm to 100 µm, and are made up of a neutral lipid core of diacylglycerol, triacylglycerol (TAG) and sterol ester surrounded by a phospholipid monolayer. Several proteins have been shown to associate with lipid bodies, the best characterised being adipocyte differentiation-related protein (ADRP) or adipophilin (the latter will be referred to as adipophilin to prevent confusion with adRP) (11, 12) and perilipin (13, 14) which form a proteinaceous coat around the lipid bodies (15). Treatment of cells with oleic acid, which is used as a substrate for TAG synthesis, promotes accumulation of lipid bodies and has recently been shown to be sufficient to promote translocation of several proteins to these structures (16-19). Whilst current understanding of the biogenesis of lipid bodies is incomplete they are believed to form between the two leaflets of the Endoplasmic Reticulum (ER), prior to budding off into the cytoplasm (20).

In work leading up to the present invention, it was discovered that IMPDH is a target of the insulin signal transduction pathway and a novel lipid body associated protein. The present inventor also found that insulin stimulates phosphorylation and translocation of IMPDH to lipid bodies, the sites of intracellular lipid storage, and both events are blocked by inhibition of PI 3-kinase. By contrast, oleate was shown to stimulate robust translocation of IMPDH to lipid bodies in the absence of detectable phosphorylation although this translocation was found to be sensitive to PI 3-kinase inhibition.

In addition, it was shown that inhibition of oleate induced IMPDH translocation correlates with decreased lipid accumulation. It was also shown that inhibition of IMPDH translocation correlates with a reduction in lipid accumulation (by ≧60%), that IMPDH protein expression is markedly (≧10 fold) and transiently increased during the differentiation of preadipocytes (both 3T3-L1 and primary human preadipocytes), but not other cell types such as myoblasts, and that the period of maximal IMPDH expression correlates with the period of lipid body accumulation.

Further, it was established that platelet derived growth factor (PDGF) stimulates IMPDH phosphorylation in 3T3-L1 fibroblasts, and this was shown to be dependent upon PI 3-kinase activation. This indicated, therefore, that the PI 3-kinase dependent phosphorylation of IMPDH is not specific to insulin, but may represent a common effect of agonists that are able to promote activation of PI 3-kinase. PDGF has recently been shown to promote increased synthesis of membrane lipids, and this also occurs through a PI 3-kinase dependent pathway (51).

From the foregoing, the present inventor proposed that adipogenesis or lipid accumulation can be modulated in vivo by modulating the level or functional activity (e.g., enzymic activity or level of phosphorylation) of IMPDH. This proposal has been reduced to practice in molecules and methods for modulating the level or functional activity of IMPDH as means of inhibiting or promoting adipogenesis in adiposity-related conditions, or for diagnosing predisposition to obesity, as described hereinafter.

SUMMARY OF THE INVENTION

Accordingly, in one aspect, the present invention provides methods for modulating adipogenesis, which are useful inter alia in the treatment or prevention of adiposity-related conditions. These methods generally comprise contacting a cell with an agent for a time and under conditions sufficient to modulate an IMPDH. In some embodiments, the IMPDH is selected from IMPDH type I and IMPDH type II. Non limiting examples of suitable agents include small molecules, such as nucleic acids, peptides, polypeptides, peptidomimetics, carbohydrates, lipids or other organic (carbon containing) or inorganic molecules, as further described herein. Typically, the cell is contacted with an agent that modulates the expression of an Impdh gene or the level or functional activity of an expression product of that gene. The cell is suitably an adipocyte, typically a white adipocyte, or precursor thereof (e.g., a preadipocyte).

In some embodiments, the agent reduces the expression of an Impdh gene or the level or functional activity of an expression product of that gene. For example, the agent may antagonise the function of an IMPDH, including reducing or abrogating the activity of its catalytic site or the interaction between an IMPDH and a protein kinase (e.g., PI 3-kinase and PDK1). Alternatively, the agent may antagonise the function of a protein kinase that phosphorylates IMPDH (e.g., PI 3-kinase and PDK1) or an upstream activator of the protein kinase (e.g., a PDGF or a PDGF receptor). Suitably, the agent inhibits the function of a molecule (e.g., a protein kinase) that interacts directly with IMPDH. In these embodiments, the agents antagonise the IMPDH and are therefore useful for directly or indirectly reducing or abrogating the accumulation of lipids in an adipocyte or the differentiation potential and/or proliferation of a preadipocyte.

In some embodiments, the agent increases the expression of an Impdh gene or the level or functional activity of an expression product of that gene. For example, the agent may agonise the function of an IMPDH, including enhancing, promoting or otherwise capacitating the activity of its catalytic site or the interaction between an IMPDH and a protein kinase. In these embodiments, the agents agonise IMPDH and are useful therefore for directly or indirectly increasing the accumulation of lipids in an adipocyte or the differentiation potential and/or proliferation of a preadipocyte.

Suitably, the agent increases or reduces the expression of the Impdh gene or the level or functional activity of an expression product of that gene by at least 10%, 20%, 30%, 40%, 50%, 60%, 70%, 80%, 90% relative to the expression, level or functional activity in the absence of the agent.

In yet another aspect, the invention provides methods for identifying agents that modulate adipogenesis: These methods typically comprise contacting a preparation with a test agent, wherein the preparation comprises (i) a polypeptide comprising an amino acid sequence corresponding to at least a biologically active fragment of an IMPDH polypeptide, or to a variant or derivative thereof; or (ii) a polynucleotide comprising at least a portion of a genetic sequence that regulates the expression of an Impdh gene, which is operably linked to a reporter gene. A detected change in the level and/or functional activity of the polypeptide, or an expression product of the reporter gene, relative to a normal or reference level and/or functional activity in the absence of the test agent, indicates that the agent modulates adipogenesis.

In accordance with the present invention, agents that test positive in the above methods are useful for modulating adipogenesis in adiposity-related conditions. The adiposity-related conditions include, but are not restricted to, obesity, lipoma, lipomatosis, cachexia or lipodystrophy or the loss of adipose tissue in trauma or atrophic conditions. Thus, another aspect of the present invention contemplates the use of an agent, which is optionally formulated with a pharmaceutically acceptable carrier or diluent, for inhibiting or decreasing adipogenesis, or for controlling adipogenesis in obesity or in conditions of localised, abnormal increases in adipogenesis, wherein the agent antagonises IMPDH, as broadly described above.

In yet another aspect, the present invention resides in the use of an agent, which is optionally formulated with a pharmaceutically acceptable carrier or diluent, for stimulating adipogenesis in the treatment or prophylaxis of cachexia or in conditions of localised deficiencies in adiposity, wherein the agent agonises IMPDH, as broadly described above.

The agent used in the above methods is characterised in that it binds to an expression product of an Impdh gene or to a genetic sequence (e.g., a transcriptional element) that modulates the expression of the gene, as determined by: contacting a preparation comprising at least a portion of an expression product of a gene as broadly described above, or a variant or derivative of the expression product, or a genetic sequence that modulates the expression of the gene, with the agent; and detecting a change in the level or functional activity of the at least a portion of the expression product, or the variant or derivative, or of a product expressed from the genetic sequence.

In some embodiments, an agent which inhibits or otherwise decreases adipogenesis binds to an IMPDH or to a genetic sequence (e.g., a transcriptional element) that modulates the expression of an Impdh gene, as determined by: contacting a preparation comprising an IMPDH polypeptide or biologically active fragment thereof, or variant or derivative of these, or a genetic sequence that modulates the expression of an Impdh gene; and detecting a decrease in the level or functional activity of the IMPDH polypeptide or biologically active fragment thereof, or variant or derivative, or of a product expressed from the genetic sequence.

In other embodiments, an agent which inhibits or otherwise decreases adipogenesis antagonises the binding between an IMPDH and a protein kinase, as determined by: contacting an IMPDH and a protein kinase with the agent and measuring the binding of the IMPDH with the protein kinase. In these embodiments, agents can bind to the IMPDH or to the protein kinase and test positive when they reduce or abrogate the binding of the IMPDH with the protein kinase. The agents can be small molecules or antigen-binding molecules specific for the IMPDH or for the protein kinase.

In still other embodiments, an agent which inhibits or otherwise decreases adipogenesis antagonises an IMPDH, as determined by: contacting a first sample of cells selected from adipocytes or their precursors with insulin and measuring lipid accumulation in those cells; contacting a second sample of cells selected from adipocytes or their precursors with insulin and with an agent, and measuring lipid accumulation in those cells; and comparing the lipid accumulation in the first sample of cells with the lipid accumulation in the second sample of cells, wherein lower lipid accumulation in the second sample of cells than in the first sample of cells is indicative of an agent that inhibits or otherwise decreases adipogenesis. In these embodiments, the agents may antagonise the IMPDH, for example, by interfering with the phosphorylation of the IMPDH, or by interfering with the catalytic site or inhibiting the catalytic activity of the IMPDH.

In further embodiments, an agent which inhibits or otherwise decreases adipogenesis antagonises an IMPDH, as determined by: administering to an animal model, or a human, an agent that antagonises IMPDH, and measuring the animal's responsiveness to the agent. In these embodiments, the method can be practiced with agents as described above and animals can be examined for inhibition or reduction of adipogenesis in obesity or in conditions of localised, abnormal increases in adipogenesis.

In still other embodiments, an agent which stimulates adipogenesis binds to an IMPDH or to a genetic sequence (e.g., a transcriptional element) that modulates the expression of an Impdh gene as determined by: contacting a preparation comprising an IMPDH polypeptide or biologically active fragment thereof, or variant or derivative of these, or a genetic sequence that modulates the expression of an Impdh gene; and detecting an increase in the level or functional activity of the IMPDH polypeptide or biologically active fragment thereof, or variant or derivative, or of a product expressed from the genetic sequence.

In other embodiments, an agent which stimulates adipogenesis agonises an IMPDH, as determined by: contacting an IMPDH and a protein kinase with the agent and measuring the binding of the IMPDH with the protein kinase. In these embodiments, agents can bind to the IMPDH or to the protein kinase and test positive when they stimulate the IMPDH interaction with the protein kinase. The agents can be small molecules or antigen-binding molecules specific for the IMPDH or the protein kinase.

In still other embodiments, an agent which stimulates adipogenesis agonises an IMPDH, as determined by: contacting a first sample of cells selected from adipocytes or their precursors with insulin and measuring lipid accumulation in those cells; contacting a second sample of cells selected from adipocytes or their precursors with insulin and with an agent, and measuring lipid accumulation in those cells; and comparing the lipid accumulation in the first sample of cells with the lipid accumulation in the second sample of cells, wherein higher lipid accumulation in the second sample of cells than in the first sample of cells is indicative of an agent that stimulates adipogenesis. In these embodiments, compounds may agonise IMPDH, for example, by stimulating the association of the IMPDH with a protein kinase, by stimulating the phosphorylation of the IMPDH, or by stimulating the catalytic activity of IMPDH.

In still other embodiments, an agent which stimulates adipogenesis agonises an IMPDH, as determined by: administering to an animal model, or a human, an agent that agonises IMPDH, and measuring the animal's responsiveness to the agent. In these embodiments, the method can be practiced with agents as described above and animals can be examined for stimulating adipogenesis in the treatment or prophylaxis of cachexia or in conditions of localised deficiencies in adiposity.

Still another aspect of the present invention provides methods of producing an agent for modulating adipogenesis in adiposity-related conditions. These methods generally comprise: testing an agent suspected of modulating IMPDH as broadly described above; and synthesising the agent on the basis that it tests positive for the modulation. Suitably, the method further comprises derivatising the agent, and optionally formulating the derivatised agent with a pharmaceutically acceptable carrier and/or diluent, to improve the efficacy of the agent for treating or preventing the adiposity-related condition(s).

According to another aspect, the present invention provides methods for detecting the presence or diagnosing the risk of an adiposity-related condition in a patient. These methods generally comprise determining the presence of an aberrant Impdh gene or of an aberrant expression product of that gene in a biological sample obtained from the patient, wherein the aberrant gene or the aberrant expression product correlates with the presence or risk of the condition.

In yet another aspect, the present invention encompasses methods for detecting the presence or diagnosing the risk of a condition associated with aberrantly increased adiposity in a patient. These methods generally comprise determining the presence of an aberrant Impdh gene or of an aberrant expression product of that gene in a biological sample obtained from the patient, wherein the aberrant gene or the aberrant expression product correlates with the presence or risk of the condition. Conditions associated with aberrantly increased adiposity include, but are not limited to, obesity or conditions of localised, abnormal increases in adipogenesis such as lipoma and lipomatosis.

Another aspect of the present invention provides methods for detecting the presence or diagnosing the risk of a condition associated with aberrantly increased adiposity in a patient. These methods generally comprise determining in a cell a level or functional activity of an expression product of an Impdh gene, which is different than a normal (e.g., non-obese) reference level or functional activity of the expression product. Suitably, the method comprises determining an increase or elevation in the level or functional activity of the expression product of the Impdh gene.

Another aspect of the present invention contemplates methods for inhibiting or reducing adipogenesis in obesity or in conditions of localised, abnormal increases in adipogenesis. These methods generally comprise administering to a patient in need of such treatment an adipogenesis-inhibiting effective amount of an agent which reduces the level or functional activity of IMPDH as broadly described above, and optionally a pharmaceutically acceptable carrier or diluent.

Yet another aspect of the present invention contemplates methods for treatment or prophylaxis of cachexia or conditions of localised deficiencies in adiposity. These methods generally comprising administering to a patient in need of such treatment an adipogenesis-enhancing effective amount of an agent which increases the level or functional activity of an IMPDH as broadly described above, and optionally a pharmaceutically acceptable carrier or diluent.

Still another aspect of the present invention provides the use of an agent as broadly described above in the preparation of a medicament for treating or preventing an adiposity-related condition.

L1 cells and primary human preadipocytes. (A) 3T3-L1 preadipocytes and (B) primary human preadipocytes were induced to differentiate (day 0) into mature adipocytes and cell number and protein accumulation was determined on the days indicated by Syto60 staining and protein assay. Data are representative of at least 3 independent experiments with measurements performed in triplicate. (sem were less than 10%—not shown).

Figure 9:
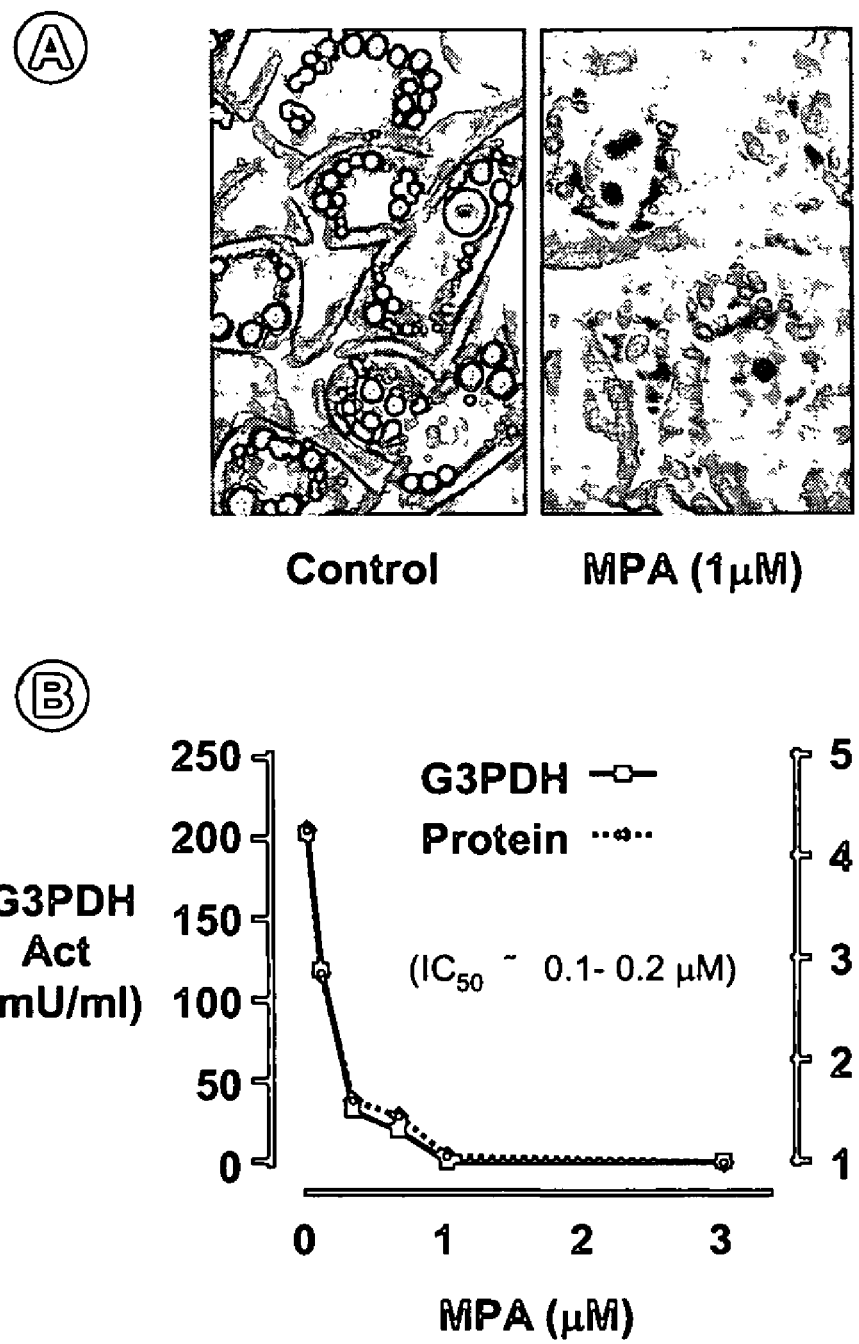

FIG. 9 consists of photographic and graphical representations showing that inhibition of IMPDH with MPA blocks adipogenesis. (A) 3T3-L1 preadipocytes were induced to differentiate in the absence (control) or presence of the specific inhibitor mycophenolic acid (MPA—1 µM) for 6 days. Images were captured on day 8 of differentiation. MPA treatment blocks lipid accumulation as observed in control cells by the appearance of large lipid droplets. (B) 3T3-L1 adipocytes were induced to differentiate in the absence or presence of increasing MPA for the first 6 days of differentiation. Cells were harvested on day 8 and G3PDH activity and total protein determined. The graph shows G3PDH activity (mU/mL) and fold increase in protein (compared to non-differentiated cells). The $IC_{50}$ of MPA is 0.1-0.2 µM. Data are representative of at least 3 independent experiments with measurements performed in duplicate. (sem were less than 10%—not shown)

Figure 10:
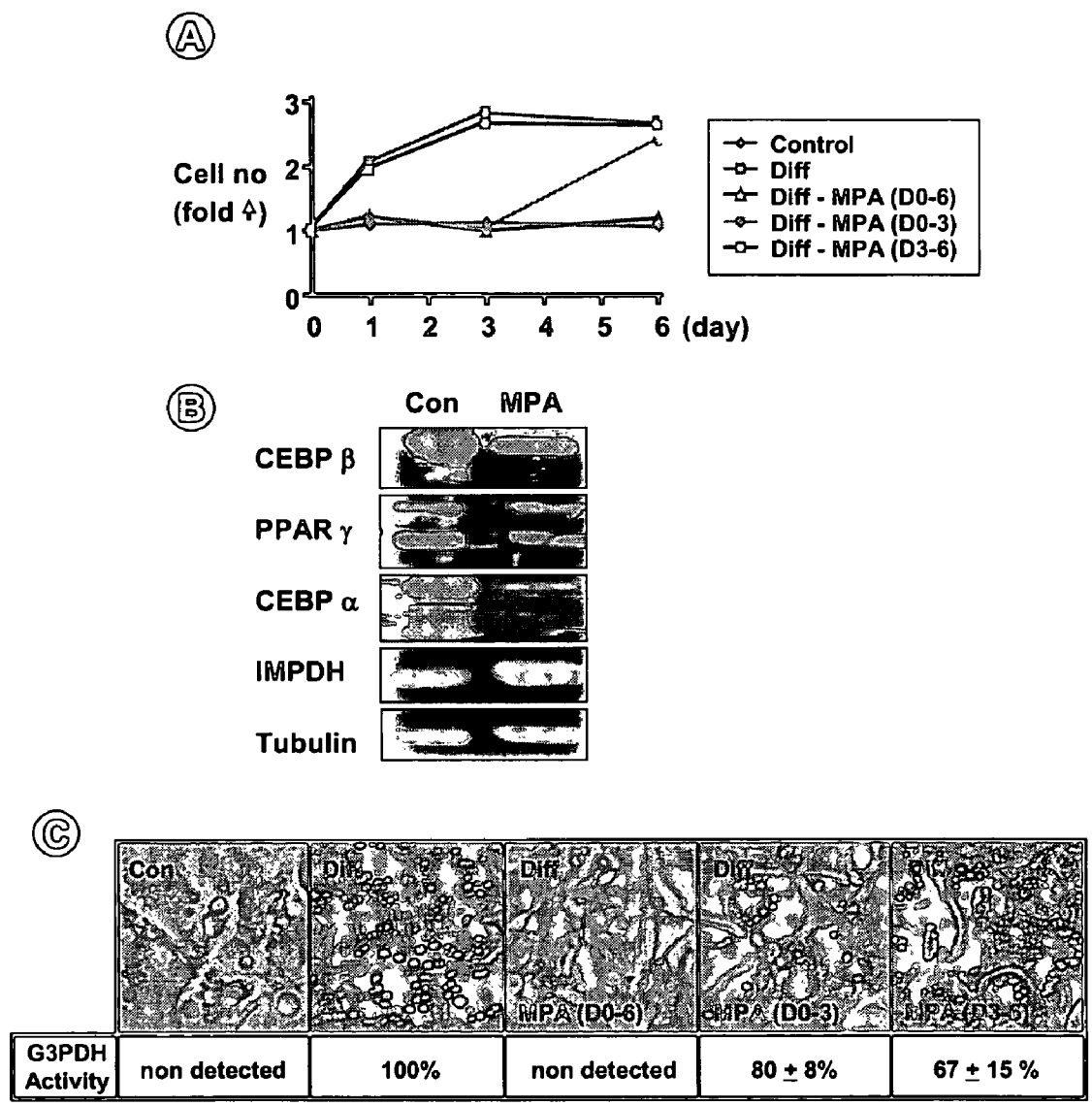

FIG. 10 consists of graphical and photographic representations characterizing the inhibition of adipogenesis of 3T3-L1 cells by MPA. A) MPA blocks proliferation/clonal expansion of 3T3-L1 preadipocytes. Cells were induced to differentiate at day 0 in the presence or absence of 1 µM MPA for the periods indicated. Cell no was determined using Syto 60. (B) Cells were differentiated in the absence (Con) or presence of 1 µM MPA and harvested at day 3. Induction of expression of key adipogenic transcription factors was performed by western blotting using specific antisera. MPA blocks expression of CEBPα, but not CEBPβ or PPARγ. MPA treatment also promotes increased IMPDH expression. Tubulin was used as a loading control. (C) Images showing reduced lipid accumulation (day 6) and decreased G3PDH activity (day 8) following treatment of cells with 1 µM MPA as indicated. Data are representative of at least 2 independent experiments.

Figure 11:
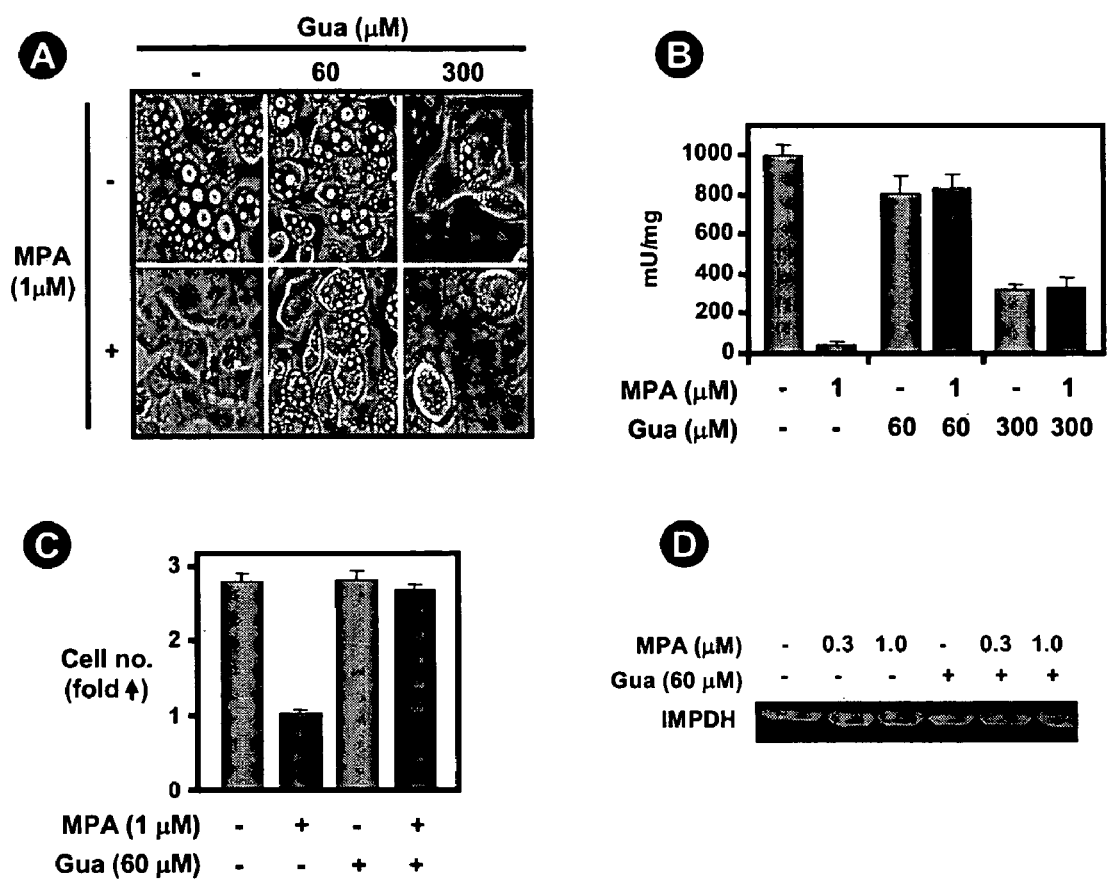

FIG. 11 consists of photographic and graphical representations showing that supplementation with guanosine reverses the effects of inhibition of IMPDH. (A) Lipid accumulation and (B) G3PDH activity in 3T3-L1 cells treated −/+1 µM MPA −/+60 or 300 µM guanosine. 60 µM guanosine reversed the effects of MPA treatment, whereas treatment with 300 µM guanosine alone reduced adipogenesis as determined morphologically and biochemically. (C) Reversal of MPA induced increase in IMPDH expression by co-treatment with guanosine. (D) Reversal of effects of MPA on clonal expansion by co-treatment with 60 µM guanosine.

Figure 12:
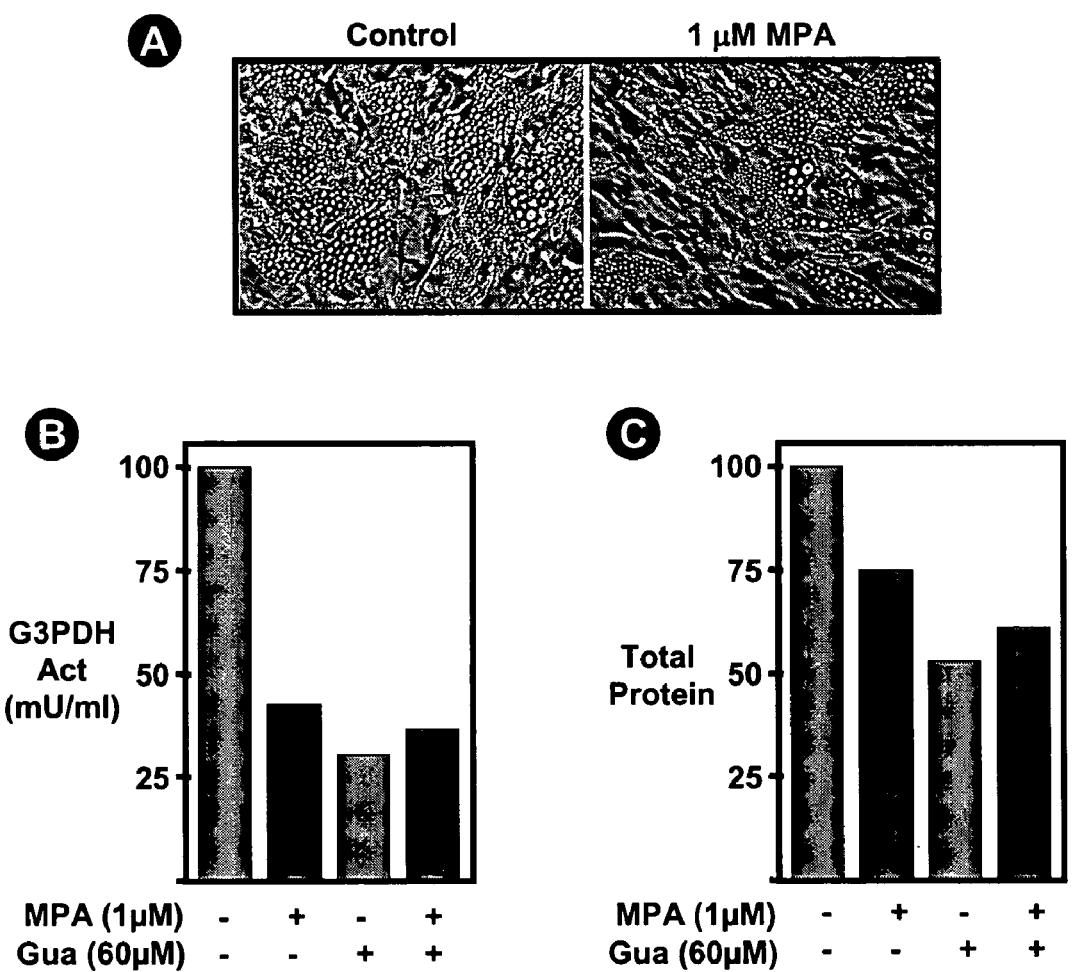

FIG. 12 consists of photographic and graphical representations showing that MPA and guanosine inhibit adipogenesis of primary human preadipocytes. (A) Primary human preadipocytes were differentiated in the absence (control) or presence of 1 µM MPA. MPA treatment reduced lipid accumulation as determined by the reduction in appearance of lipid droplets. (B) Induction of G3PDH activity was reduced by inhibition of IMPDH by treatment with 1 µM MPA. Surprisingly, treatment with 60 µM guanosine also reduced induction of G3PDH activity. (C) Similar results were also observed when protein accumulation was determined. Data are representative of 3 independent experiments with measurements performed in duplicate.

DETAILED DESCRIPTION OF THE INVENTION

1. Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e. to at least one) of the grammatical object of the article. By way of example, "an element" means one element or more than one element.

The term "aberrant polynucleotide" as used herein refers to a polynucleotide which is distinguished from a "normal" reference polynucleotide by the substitution, deletion or addition of at least one nucleotide and which correlates with the presence or risk of adipogenic defects including an elevated rate of adipogenesis compared to a non-obese, reference value.

The term "aberrant polypeptide" refers to a polypeptide which is distinguished from a "normal" reference polypeptide by the substitution, deletion or addition of at least one amino acid residue and which correlates with the presence or risk of adipogenic defects including an elevated rate of adipogenesis compared to a non-obese, reference value.

The term "aliphatic ring" or "cycloalkyl" means a monocyclic saturated aliphatic hydrocarbon group and may have a specified number of carbon atoms. For example, "cycloalkyl" includes, but is not limited to, cyclopropyl, methyl-cyclopropyl, 2,2-dimethyl-cyclobutyl, 2-ethyl-cyclopentyl, cyclohexyl.

If no number of carbon atoms is specified, the term "alkenyl" refers to a non-aromatic hydrocarbon radical, straight, branched or cyclic, containing from 2 to 10 carbon atoms and at least one carbon to carbon double bond. Suitably one carbon to carbon double bond is present, and up to four non-aromatic carbon-carbon double bonds may be present. Thus, "$C_2$-$C_6$alkenyl" means an alkenyl radical having from 2 to 6 carbon atoms. Alkenyl groups include, but are not limited to, ethenyl, propenyl, butenyl, 2-methylbutenyl and cyclohexenyl. The straight, branched or cyclic portion of the alkenyl group may contain double bonds and may be substituted if a substituted alkenyl group is indicated.

As used herein, "alkenylene" refers to a straight, branched or cyclic, preferably straight or branched, bivalent aliphatic hydrocarbon group, preferably having from 2 to about 20 carbon atoms and at least one double bond, more preferably 2 to 12 carbons, even more preferably lower alkenylene. The alkenylene group is optionally substituted with one or more "alkyl group substituents." There may be optionally inserted along the alkenylene group one or more oxygen, sulphur or substituted or unsubstituted nitrogen atoms, where the nitrogen substituent is alkyl as previously described. Exemplary alkenylene groups include —CH═CH—CH═CH— and —CH═CH—CH$_2$—. The term "lower alkenylene" refers to alkenylene groups having 2 to 6 carbons. Preferred alkenylene groups are lower alkenylene, with alkenylene of 3 to 4 carbon atoms being particularly preferred.

"Alkoxy" represents either a cyclic or non-cyclic alkyl group attached through an oxygen bridge. "Alkoxy" therefore encompasses the definitions of alkyl and cycloalkyl above.

For example, alkoxy groups include but are not limited to methoxy, oxy ethoxy, n-propyloxy, i-propyloxy, cyclopentyloxy and cyclohexyloxy.

As used herein, "alkyl" is intended to include both branched and straight-chain saturated aliphatic hydrocarbon group and may have a specified number of carbon atoms. For example, $C_1$-$C_{10}$, as in "$C_1$-$C_{10}$alkyl" is defined to include groups having 1, 2, 3, 4, 5, 6, 7, 8, 9 or 10 carbons in linear or branched arrangement. For example, "$C_1$-$C_{10}$alkyl" specifically includes, but is not limited to, methyl, ethyl, n-propyl, i-propyl, n-butyl, t-butyl, i-butyl, pentyl, hexyl, heptyl, octyl, nonyl, decyl.

As used herein, "alkylidene" refers to a bivalent group, such as =CR9R0, which is attached to one atom of another group, forming a double bond. Exemplary alkylidene groups are methylidene (=$CH_2$) and ethylidene (=$CHCH_3$). As used herein, "arylalkylidene" refers to an alkylidene group in which either R9 or R0 is and aryl group. As used herein, "diarylalkylidene" refers to an alkylidene group in which R9 and R0 are both aryl groups. "diheteroarylalkylidene" refers to an alkylidene group in which R9 and R0 are both heteroaryl groups.

The term "alkynyl" refers to a hydrocarbon radical straight, branched or cyclic, containing from 2 to 10 carbon atoms and at least one carbon to carbon triple bond. Up to three carbon-carbon triple bonds may be present. Thus, "$C_2$-$C_6$alkynyl" means an alkynyl radical having from 2 to 6 carbon atoms. Alkynyl groups include, but are not limited to, ethynyl, propynyl, butynyl, 3-methylbutynyl and so on. The straight, branched or cyclic portion of the alkynyl group may contain triple bonds and may be substituted if a substituted alkynyl group is indicated.

As used herein, "alkylene" refers to a straight, branched or cyclic, preferably straight or branched, bivalent aliphatic hydrocarbon group, preferably having from 1 to about 20 carbon atoms, more preferably 1 to 12 carbons, even more preferably lower alkylene. The alkylene group is optionally substituted with one or more "alkyl group substituents." There may be optionally inserted along the alkylene group one or more oxygen, sulphur or substituted or unsubstituted nitrogen atoms, where the nitrogen substituent is alkyl as previously described. Exemplary alkylene groups include methylene (—$CH_2$—), ethylene (—$CH_2CH_2$—), propylene (—$(CH_2)_3$—), cyclohexylene (—$C_6H_{10}$—), methylenedioxy (—O—$CH_2$—O—) and ethylenedioxy (—O—$(CH_2)_2$—O—). The term "lower alkylene" refers to alkylene groups having 1 to 6 carbons. Preferred alkylene groups are lower alkylene, with alkylene of 1 to 3 carbon atoms being particularly preferred.

As used herein, "alkynylene" refers to a straight, branched or cyclic, preferably straight or branched, bivalent aliphatic hydrocarbon group, preferably having from 2 to about 20 carbon atoms and at least one triple bond, more preferably 2 to 12 carbons, even more preferably lower alkynylene. The alkynylene group is optionally substituted with one or more "alkyl group substituents." There may be optionally inserted along the alkynylene group one or more oxygen, sulphur or substituted or unsubstituted nitrogen atoms, where the nitrogen substituent is alkyl as previously described. Exemplary alkynylene groups include —C≡C—C≡C—, —C≡C— and —C≡C—$CH_2$—. The term "lower alkynylene" refers to alkynylene groups having 2 to 6 carbons. Preferred alkynylene groups are lower alkynylene, with alkynylene of 3 to 4 carbon atoms being particularly preferred.

By "antigen-binding molecule" is meant a molecule that has binding affinity for a target antigen. It will be understood that this term extends to immunoglobulins, immunoglobulin fragments and non-immunoglobulin derived protein frameworks that exhibit antigen-binding activity.

"Antigenic or immunogenic activity" refers to the ability of a polypeptide, fragment, variant or derivative according to the invention to produce an antigenic or immunogenic response in an animal, suitably a mammal, to which it is administered, wherein the response includes the production of elements which specifically bind the polypeptide or fragment thereof.

"Aralkyl" means alkyl as defined above which is substituted with an aryl group as defined above, e.g., —$CH_2$phenyl, —$(CH_2)_2$phenyl, —$(CH_2)_3$phenyl, —$H_2CH(CH_3)$ $CH_2$phenyl, and the like and derivatives thereof.

As used herein, "aromatic" or "aryl" is intended to mean any stable monocyclic or bicyclic carbon ring of up to 7 atoms in each ring, wherein at least one ring is aromatic. Examples of such aryl elements include, but are not limited to, phenyl, naphthyl, tetrahydronaphthyl, indanyl, biphenyl, phenanthryl, anthryl or acenaphthyl.

In certain instances, substituents may be defined with a range of carbons that includes zero, such as ($C_0$-$C_6$)alkylene-aryl. If aryl is taken to be phenyl, this definition would include phenyl itself as well as, for example, —$CH_2$Ph, —$CH_2CH_2$Ph, $CH(CH_3)CH_2CH(CH_3)$Ph.

As used herein, "arylene" refers to a monocyclic or polycyclic, preferably monocyclic, bivalent aromatic group, preferably having from 3 to about 20 carbon atoms and at least one aromatic ring, more preferably 3 to 12 carbons, even more preferably lower arylene. The arylene group is optionally substituted with one or more "alkyl group substituents." There may be optionally inserted around the arylene group one or more oxygen, sulphur or substituted or unsubstituted nitrogen atoms, where the nitrogen substituent is alkyl as previously described. Exemplary arylene groups include 1,2-, 1,3- and 1,4-phenylene. The term "lower arylene" refers to arylene groups having 5 or 6 carbons. Preferred arylene groups are lower arylene.

As used herein, "arylidene" refers to an unsaturated cyclic bivalent group where both points of attachment are on the same atom of the ring. Exemplary arylidene groups include, but are not limited to, quinone methide moieties that have the formula:

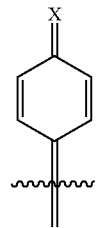

where X is O, S or NR9. "Heteroarylidene" groups are arylidene groups where one or two, preferably two, of the atoms in the ring are heteroatoms, such as, but not limited to, O, S and N.

It will also be recognised that the compounds described herein may possess asymmetric centres and are therefore capable of existing in more than one stereoisomeric form. The invention thus also relates to compounds in substantially pure isomeric form at one or more asymmetric centres e.g., greater than about 90% ee, such as about 95% or 97% ee or greater than 99% ee, as well as mixtures, including racemic mixtures, thereof. Such isomers may be naturally occurring or may be prepared by asymmetric synthesis, for example using chiral intermediates, or by chiral resolution.

By "biologically active fragment" is meant a fragment of a full-length parent polypeptide which fragment retains an activity of the parent polypeptide. As used herein, the term "biologically active fragment" includes deletion variants and small peptides, for example of at least 6, 7, 8, 9, 10, 11, 12, 13, 14, 15, 16, 17, 18, 19, 20, 21, 22, 23, 24, 25, 26, 27, 28, 29, 30, 35, 40, 45, 50 contiguous amino acid residues, which comprise an activity of the parent polypeptide. Peptides of this type may be obtained through the application of standard recombinant nucleic acid techniques or synthesised using conventional liquid or solid phase synthesis techniques. For example, reference may be made to solution synthesis or solid phase synthesis as described, for example, in Chapter 9 entitled "Peptide Synthesis" by Atherton and Shephard which is included in a publication entitled "Synthetic Vaccines" edited by Nicholson and published by Blackwell Scientific Publications. Alternatively, peptides can be produced by digestion of a polypeptide of the invention with proteinases such as endoLys-C, endoArg-C, endoGlu-C and staphylococcus V8-protease. The digested fragments can be purified by, for example, high performance liquid chromatographic (HPLC) techniques.

The term "biological sample" as used herein refers to a sample that may be extracted, untreated, treated, diluted or concentrated from a patient. Suitably, the biological sample is a tissue biopsy, more preferably from subcutaneous or omental tissue biopsy.

Throughout this specification, unless the context requires otherwise, the words "comprise", "comprises" and "comprising" will be understood to imply the inclusion of a stated step or element or group of steps or elements but not the exclusion of any other step or element or group of steps or elements.

The phrase "conditions of localised, abnormal increases in adipogenesis" as used herein includes pathologies characterised by and/or associated with anatomically localised disregulated adipogenesis that lead to circumscribed depositions of fat tissue. Such conditions include but are not limited to lipoma and lipomatosis.

By "corresponds to" or "corresponding to" is meant (a) a polynucleotide having a nucleotide sequence that is substantially identical or complementary to all or a portion of a reference polynucleotide sequence or encoding an amino acid sequence identical to an amino acid sequence in a peptide or protein; or (b) a peptide or polypeptide having an amino acid sequence that is substantially identical to a sequence of amino acids in a reference peptide or protein.

By "derivative" is meant a polypeptide that has been derived from the basic sequence by modification, for example by conjugation or complexing with other chemical moieties or by post-translational modification techniques as would be understood in the art. The term "derivative" also includes within its scope alterations that have been made to a parent sequence including additions or deletions that provide for functional equivalent molecules.

The term "differentiation potential" as used herein means the capacity of a preadipocyte to respond, or the magnitude of the response, to a signal which promotes its functional maturation into an adipocyte. An "increase in differentiation potential" may be seen to be conferred by a test molecule wherein, for example, a co-culture of preadipocytes with the test molecule for a sufficient time and under appropriate conditions results in an increase in the response of the preadipocytes to a differentiation-inducing agent, which may be observed inter alia as a rise in the number of preadipocytes undergoing differentiation or an increase in the rate at which the preadipocytes undergo differentiation.

By "effective amount", in the context of modulating an activity or of treating or preventing a condition is meant the administration of that amount of active ingredient to an individual in need of such modulation, treatment or prophylaxis, either in a single dose or as part of a series, that is effective for modulation of that effect or for treatment or prophylaxis or improvement of that condition. Non-limiting examples of such improvements in an individual suffering conditions of localised, abnormal increases in adipogenesis include reduced fat deposits, increased leanness, weight loss and an improvement in the symptoms relating to cardiovascular disease and diabetes. The effective amount will vary depending upon the health and physical condition of the individual to be treated, the taxonomic group of individual to be treated, the formulation of the composition, the assessment of the medical situation, and other relevant factors. It is expected that the amount will fall in a relatively broad range that can be determined through routine trials.

As used herein, the term "function" refers to a biological, enzymatic, or therapeutic function.

By "functional Impdh polynucleotide" or "functional IMPDH polypeptide" is meant an Impdh polynucleotide or an IMPDH polypeptide having no structural or functional defects and which do not correlate with the presence or risk of adipogenic defects including elevated or impaired adipogenesis.

The term "gene" as used herein refers to any and all discrete coding regions of the cell's genome, as well as associated non-coding and regulatory regions. The gene is also intended to mean the open reading frame encoding specific polypeptides, introns, and adjacent 5' and 3' non-coding nucleotide sequences involved in the regulation of expression. In this regard, the gene may further comprise control signals such as promoters, enhancers, termination and/or polyadenylation signals that are naturally associated with a given gene, or heterologous control signals. The DNA sequences may be cDNA or genomic DNA or a fragment thereof. The gene may be introduced into an appropriate vector for extrachromosomal maintenance or for integration into the host.

As appreciated by those of skill in the art, "halo" or "halogen" as used herein is intended to include chloro, fluoro, bromo and iodo.

"Heteroaralkyl" group means alkyl as defined above which is substituted with a heteroaryl group, e.g., —$CH_2$pyridinyl, —$(CH_2)_2$pyrimidinyl, —$(CH_2)_3$imidazolyl, and the like, and derivatives thereof.

The term "heteroaryl" or "heteroaromatic", as used herein, represents a stable monocyclic or bicyclic ring of up to 7 atoms in each ring, wherein at least one ring is aromatic and contains from 1 to 4 heteroatoms selected from the group consisting of O, N and S. Heteroaryl groups within the scope of this definition include but are not limited to: acridinyl, carbazolyl, cinnolinyl, quinoxalinyl, pyrrazolyl, indolyl, benzotriazolyl, furanyl, thienyl, benzothienyl, bezofuranyl, quinolinyl, isoquinolinyl, oxazolyl, isoxazolyl, indolyl, pyrazinyl, pyridazinyl, pyridinyl, pyrimidinyl, pyrrolyl, tetrahydroquinoline. As with the definition of heterocycle below, "heteroaryl" is also understood to include the N-oxide derivative of any nitrogen-containing heteroaryl.

Further examples of "heterocyclyl" and "heteroaryl" include, but are not limited to, the following: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazoyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrazolyl, tetrahydropyranyl, tetrazolopyridyl, thiadiazolyl, thiazolyl, thienyl, triazolyl, azetidinyl, aziridinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof. Attachment of a heterocyclyl substituent can occur via a carbon atom or via a heteroatom.

As used herein, "heteroarylene" refers to a bivalent monocyclic or multicyclic ring system, preferably of about 3 to about 15 members where one or more, more preferably 1 to 3 of the atoms in the ring system is a heteroatom, that is, an element other than carbon, for example, nitrogen, oxygen and sulfur atoms. The heteroarylene group may be optionally substituted with one or more, preferably 1 to 3, aryl group substituents. Exemplary heteroarylene groups include, for example, 1,4-imidazolylene.

The term "heterocycle", "heteroaliphatic" or "heterocyclyl" as used herein is intended to mean a 5- to 10-membered nonaromatic heterocycle containing from 1 to 4 heteroatoms selected from the group consisting of O, N and S, and includes bicyclic groups.

"Heterocyclylalkyl" group means alkyl as defined above which is substituted with a heterocycle group, e.g., —CH$_2$pyrrolidin-1-yl, —(CH$_2$)$_2$piperidin-1-yl, and the like, and derivatives thereof.

"Hybridisation" is used herein to denote the pairing of complementary nucleotide sequences to produce a DNA-DNA hybrid or a DNA-RNA hybrid. Complementary base sequences are those sequences that are related by the base-pairing rules. In DNA, A pairs with T and C pairs with G. In RNA U pairs with A and C pairs with G. In this regard, the terms "match" and "mismatch" as used herein refer to the hybridisation potential of paired nucleotides in complementary nucleic acid strands. Matched nucleotides hybridise efficiently, such as the classical A-T and G-C base pair mentioned above. Mismatches are other combinations of nucleotides that do not hybridise efficiently.

The term "hydrocarbyl" as used herein includes any radical containing carbon and hydrogen including saturated, unsaturated, aromatic, straight or branched chain or cyclic including polycyclic groups. Hydrocarbyl includes but is not limited to C$_1$-C$_8$alkyl, C$_2$-C$_8$alkenyl, C$_2$-C$_8$alkynyl, C$_3$-C$_{10}$cycloalkyl, aryl such as phenyl and naphthyl, Ar(C$_1$-C$_8$)alkyl such as benzyl, any of which may be optionally substituted.

Reference herein to "immuno-interactive" includes reference to any interaction, reaction, or other form of association between molecules and in particular where one of the molecules is, or mimics, a component of the immune system.

By "isolated" is meant material that is substantially or essentially free from components that normally accompany it in its native state.

By "modulating" is meant increasing or decreasing, either directly or indirectly, the level or functional activity of a target molecule. For example, an agent may indirectly modulate the level/activity by interacting with a molecule other than the target molecule. In this regard, indirect modulation of a gene encoding a target polypeptide includes within its scope modulation of the expression of a first nucleic acid molecule, wherein an expression product of the first nucleic acid molecule modulates the expression of a nucleic acid molecule encoding the target polypeptide.

The term "obesity" as used herein includes conditions where there is an increase in body fat beyond the physical requirement as a result of excess accumulation of adipose tissue in the body. The term obesity includes but is not limited to the following conditions: adult-onset obesity; alimentary obesity; endogenous or metabolic obesity; endocrine obesity; familial obesity; hyperinsulinar obesity; hyperplastic-hypertrophic obesity; hypogonadal obesity; hypothyroid obesity; lifelong obesity; morbid obesity and exogenous obesity.

By "obtained from" is meant that a sample such as, for example, a polynucleotide extract or polypeptide extract is isolated from, or derived from, a particular source of the host. For example, the extract can be obtained from a tissue or a biological fluid isolated directly from the host.

The term "oligonucleotide" as used herein refers to a polymer composed of a multiplicity of nucleotide residues (deoxyribonucleotides or ribonucleotides, or related structural variants or synthetic analogues thereof) linked via phosphodiester bonds (or related structural variants or synthetic analogues thereof). Thus, while the term "oligonucleotide" typically refers to a nucleotide polymer in which the nucleotide residues and linkages between them are naturally occurring, it will be understood that the term also includes within its scope various analogues including, but not restricted to, peptide nucleic acids (PNAs), phosphoramidates, phosphorothioates, methyl phosphonates, 2-O-methyl ribonucleic acids, and the like. The exact size of the molecule can vary depending on the particular application. An oligonucleotide is typically rather short in length, generally from about 10 to 30 nucleotide residues, but the term can refer to molecules of any length, although the term "polynucleotide" or "nucleic acid" is typically used for large oligonucleotides.

By "operably linked" is meant that transcriptional and translational regulatory polynucleotides are positioned relative to a polypeptide-encoding polynucleotide in such a manner that the polynucleotide is transcribed and the polypeptide is translated.

The term "patient" refers to patients of human or other animal origin and includes any individual it is desired to examine or treat using the methods of the invention. However, it will be understood that "patient" does not imply that symptoms are present. Suitable animals that fall within the scope of the invention include, but are not restricted to, primates, livestock animals (e.g., sheep, cows, horses, donkeys, pigs), laboratory test animals (e.g., rabbits, mice, rats, guinea pigs, hamsters), companion animals (e.g., cats, dogs) and captive wild animals (e.g., foxes, deer, dingoes, avians, reptiles).

By "pharmaceutically acceptable carrier" is meant a solid or liquid filler, diluent or encapsulating substance that can be safely used in topical or systemic administration to a mammal.

"Phenylalkyl" means alkyl as defined above which is substituted with phenyl, e.g., —CH$_2$phenyl, —(CH$_2$)$_2$phenyl, —(CH$_2$)$_3$phenyl, CH$_3$CH(CH$_3$)CH$_2$phenyl, and the like and derivatives thereof. Phenylalkyl is a subset of the aralkyl group.

The term "polynucleotide" or "nucleic acid" as used herein designates mRNA, RNA, cRNA, cDNA or DNA. The term typically refers to oligonucleotides greater than 30 nucleotide residues in length.

The terms "polynucleotide variant" and "variant" refer to polynucleotides displaying substantial sequence identity with a reference polynucleotide sequence or polynucleotides that hybridise with a reference sequence under stringent conditions as known in the art (see for example Sambrook et al., Molecular Cloning. A Laboratory Manual", Cold Spring Harbor Press, 1989). These terms also encompass polynucleotides in which one or more nucleotides have been added or deleted, or replaced with different nucleotides. In this regard, it is well understood in the art that certain alterations inclusive of mutations, additions, deletions and substitutions can be made to a reference polynucleotide whereby the altered polynucleotide retains a biological function or activity of the reference polynucleotide. The terms "polynucleotide variant" and "variant" also include naturally-occurring allelic variants.

"Polypeptide", "peptide" and "protein" are used interchangeably herein to refer to a polymer of amino acid residues and to variants and synthetic analogues of the same. Thus, these terms apply to amino acid polymers in which one or more amino acid residues is a synthetic non-naturally occurring amino acid, such as a chemical analogue of a corresponding naturally occurring amino acid, as well as to naturally occurring amino acid polymers.

The term "polypeptide variant" refers to polypeptides in which one or more amino acids have been replaced by different amino acids. It is well understood in the art that some amino acids may be changed to others with broadly similar properties without changing the nature of the activity of the polypeptide (conservative substitutions) as described hereinafter. These terms also encompass polypeptides in which one or more amino acids have been added or deleted, or replaced with different amino acids.

By "primer" is meant an oligonucleotide which, when paired with a strand of DNA, is capable of initiating the synthesis of a primer extension product in the presence of a suitable polymerising agent. The primer is preferably single-stranded for maximum efficiency in amplification but can alternatively be double-stranded. A primer must be sufficiently long to prime the synthesis of extension products in the presence of the polymerisation agent. The length of the primer depends on many factors, including application, temperature to be employed, template reaction conditions, other reagents, and source of primers. For example, depending on the complexity of the target sequence, the oligonucleotide primer typically contains 15 to 35 or more nucleotide residues, although it can contain fewer nucleotide residues. Primers can be large polynucleotides, such as from about 200 nucleotide residues to several kilobases or more. Primers can be selected to be "substantially complementary" to the sequence on the template to which it is designed to hybridise and serve as a site for the initiation of synthesis. By "substantially complementary", it is meant that the primer is sufficiently complementary to hybridise with a target polynucleotide. Preferably, the primer contains no mismatches with the template to which it is designed to hybridise but this is not essential. For example, non-complementary nucleotide residues can be attached to the 5' end of the primer, with the remainder of the primer sequence being complementary to the template. Alternatively, non-complementary nucleotide residues or a stretch of non-complementary nucleotide residues can be interspersed into a primer, provided that the primer sequence has sufficient complementarity with the sequence of the template to hybridise therewith and thereby form a template for synthesis of the extension product of the primer.

"Probe" refers to a molecule that binds to a specific sequence or sub-sequence or other moiety of another molecule. Unless otherwise indicated, the term "probe" typically refers to a polynucleotide probe that binds to another polynucleotide, often called the "target polynucleotide", through complementary base pairing. Probes can bind target polynucleotides lacking complete sequence complementarity with the probe, depending on the stringency of the hybridisation conditions. Probes can be labelled directly or indirectly.

The term "recombinant polynucleotide" as used herein refers to a polynucleotide formed in vitro by the manipulation of a polynucleotide into a form not normally found in nature. For example, the recombinant polynucleotide can be in the form of an expression vector. Generally, such expression vectors include transcriptional and translational regulatory polynucleotide operably linked to the polynucleotide.

As used herein, "pseudohalides" are groups that behave substantially similar to halides. Such groups can be used in the same manner and treated in the same manner as halides (X, in which X is a halogen, such as Cl or Br). Pseudohalides include, but are not limited to cyanide, cyanate, thiocyanate, selenocyanate, trifluoromethyl and azide.

By "recombinant polypeptide" is meant a polypeptide made using recombinant techniques, i.e., through the expression of a recombinant or synthetic polynucleotide.

By "reporter molecule" as used in the present specification is meant a molecule that, by its chemical nature, provides an analytically identifiable signal that allows the detection of a complex comprising an antigen-binding molecule and its target antigen. The term "reporter molecule" also extends to use of cell agglutination or inhibition of agglutination such as red blood cells on latex beads, and the like.

By "vector" is meant a polynucleotide molecule, preferably a DNA molecule derived, for example, from a plasmid, bacteriophage, yeast or virus, into which a polynucleotide can be inserted or cloned. A vector preferably contains one or more unique restriction sites and can be capable of autonomous replication in a defined host cell including a target cell or tissue or a progenitor cell or tissue thereof, or be integratable with the genome of the defined host such that the cloned sequence is reproducible. Accordingly, the vector can be an autonomously replicating vector, i.e., a vector that exists as an extrachromosomal entity, the replication of which is independent of chromosomal replication, e.g., a linear or closed circular plasmid, an extrachromosomal element, a minichromosome, or an artificial chromosome. The vector can contain any means for assuring self-replication. Alternatively, the vector can be one which, when introduced into the host cell, is integrated into the genome and replicated together with the chromosome(s) into which it has been integrated. A vector system can comprise a single vector or plasmid, two or more vectors or plasmids, which together contain the total DNA to be introduced into the genome of the host cell, or a transposon. The choice of the vector will typically depend on the compatibility of the vector with the host cell into which the vector is to be introduced. In the present case, the vector is preferably a viral or viral-derived vector, which is operably functional in animal and preferably mammalian cells. Such vector may be derived from a poxvirus, an adenovirus or yeast. The vector can also include a selection marker such as an antibiotic resistance gene that can be used for selection of suitable transformants. Examples of such resistance genes are known to those of skill in the art and include the nptII gene that confers resistance to the antibiotics kanamycin and G418 (Geneticin®) and the hph gene which confers resistance to the antibiotic hygromycin B.

The terms "wild-type" and "normal" are used interchangeably to refer to the phenotype that is characteristic of most of the members of the species occurring naturally and contrast for example with the phenotype of a mutant.

As used herein, underscoring or italicising the name of a gene shall indicate the gene, in contrast to its protein product, which is indicated by the name of the gene in the absence of any underscoring or italicising. For example, "Impdh-1" shall mean the Impdh-1 gene, whereas "IMPDH-1" shall indicate the protein product or products generated from transcription and translation and alternative splicing of the "Impdh-1" gene.

2. Abbreviations

The following abbreviations are used throughout the application:
nt=nucleotide
nts=nucleotides
aa=amino acid(s)
kb=kilobase(s) or kilobase pair(s)
kDa=kilodalton(s)
d=day
h=hour
s=seconds

3. Method of Modulating Adipogenesis

The present invention is predicated in part on the identification of inosine-5' monophosphate dehydrogenase (IMPDH), a key enzyme in de novo guanine nucleotide biosynthesis, as a novel lipid body-associated protein. IMPDH was identified as a protein which was phosphorylated in a PI 3-kinase-dependent manner upon insulin treatment. Although insulin was without significant effect on IMPDH activity, the inventor observed translocation of IMPDH to lipid bodies following insulin treatment. Induction of lipid body formation with oleic acid promoted dramatic redistribution of IMPDH to lipid bodies which appeared to be in contact with the endoplasmic reticulum (ER), the site of lipid body synthesis and recycling. Inhibition of PI 3-kinase blocked insulin- or oleate-induced translocation of IMPDH and reduced oleate-induced lipid accumulation. However, the inventor found no evidence for oleate-induced IMPDH phosphorylation, suggesting phosphorylation and translocation may not be coupled events. Additionally, it was found that IMPDH protein expression is markedly ($\geq$10 fold) and transiently increased during the differentiation of preadipocytes (both 3T3-L1 and primary human preadipocytes), but not other cell types such as myoblasts. Further, it was shown that the period of maximal IMPDH expression correlates with the period of lipid body accumulation. From the foregoing, the inventor considers that IMPDH plays a role in the dynamic regulation of lipid bodies and fatty acid metabolism and that its activity is regulated by subcellular redistribution in response to extracellular factors that modify lipid metabolism. It is proposed, therefore, that modulators of the level or functional activity of IMPDH will be useful inter alia for the treatment or prevention of adiposity-related conditions including, but not restricted to, obesity, conditions of localised, abnormal increases in adipogenesis, cachexia and conditions of localised deficiencies in adiposity as well as in the study of excess adipogenesis and insufficient adipogenesis.

Accordingly, the present invention provides methods for modulating adipogenesis, comprising contacting a cell with an agent for a time and under conditions sufficient to modulate the level or functional activity of IMPDH, including agents that interact directly with IMPDH or with elements that modulate Impdh gene expression or with an intracellular binding partner of IMPDH (e.g., a protein kinase such as PI 3-kinase and PDK1). Typically, the cell is an adipocyte or a precursor thereof such as but not limited to a preadipocyte.

In some embodiments, the agent modulates the expression of an Impdh gene (e.g., Impdh-1, Impdh-2) or an upstream regulator of its expression or the level or functional activity of an expression product of such genes. In these embodiments, adipogenesis is stimulated by enhancing the expression of the Impdh gene or the level or functional activity of its expression product or by enhancing or reducing the expression of the regulator gene or the level or functional activity of its expression product, depending upon whether it is a repressor or activator of the Impdh gene or its expression product. By contrast, adipogenesis is decreased or abrogated by reducing or abrogating the expression of the Impdh gene or the level or functional activity of its expression product or by enhancing or reducing the expression of the regulator gene or the level or functional activity of its expression product, depending upon whether it is a repressor or activator of the Impdh gene or its expression product, respectively.

3.1 IMPDH Antagonists

Accordingly, when reduced adipogenesis is required, the agent is used to reduce or impair the adipogenic potential of adipocytes or their precursors including, for example, reducing or impairing the formation of adipocytes or lipid accumulation within adipocytes in the treatment of obesity or conditions of localised abnormal increases in adipogenesis. Conditions contemplated in such treatment regimes include pathologies which are associated with or secondary to, obesity, such as atherosclerosis, hypertension, diabetes including insulin resistance/type II diabetes and endocrine or other metabolic diseases or conditions. Conditions of localised, abnormal increases in adipogenesis may include adipose tumours (lipomas and liposarcomas) and lipomatosis. Alternatively, when increased adipogenesis is required, the agent is used to enhance adipogenesis including, for example, improving fat deposition in conditions associated with cachexia or in conditions of localised deficiencies in adiposity.

Suitable agents for reducing or abrogating gene expression include, but are not restricted to, oligoribonucleotide sequences, including anti-sense RNA and DNA molecules and ribozymes, that function to inhibit the translation, for example, of IMPDH-encoding mRNA. Anti-sense RNA and DNA molecules act to directly block the translation of mRNA by binding to targeted mRNA and preventing protein translation. In regard to antisense DNA, oligodeoxyribonucleotides derived from the translation initiation site, e.g., between −10 and +10 regions are preferred.

Ribozymes are enzymatic RNA molecules capable of catalysing the specific cleavage of RNA. The mechanism of ribozyme action involves sequence specific hybridisation of the ribozyme molecule to complementary target RNA, followed by a endonucleolytic cleavage. Within the scope of the invention are engineered hammerhead motif ribozyme molecules that specifically and efficiently catalyse endonucleolytic cleavage of target sequences. Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for predicted structural features such as secondary structure that may render the oligonucleotide sequence unsuitable. The suitability of candidate targets may also be evaluated by testing their accessibility to hybridisation with complementary oligonucleotides, using ribonuclease protection assays.

Both anti-sense RNA and DNA molecules and ribozymes may be prepared by any method known in the art for the synthesis of RNA molecules. These include techniques for chemically synthesising oligodeoxyribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesise antisense RNA constitutively or inducibly, depending on the promoter used, can be introduced stably into cell lines.

Various modifications to the DNA molecules may be introduced as a means of increasing intracellular stability and half-life. Possible modifications include but are not limited to the addition of flanking sequences of ribo- or deoxy-nucleotides to the 5' or 3' ends of the molecule or the use of phosphorothioate or 2' O-methyl rather than phosphodiesterase linkages within the oligodeoxyribonucleotide backbone.

Alternatively, RNA molecules that mediate RNA interference (RNAi) of a target gene or gene transcript can be used to reduce or abrogate gene expression. RNAi refers to interference with or destruction of the product of a target gene by introducing a single stranded, and typically a double stranded RNA (dsRNA) that is homologous to the transcript of a target gene. Thus, in some embodiments, dsRNA per se and especially dsRNA-producing constructs corresponding to at least a portion of a target gene may be used to reduce or abrogate its expression. RNAi-mediated inhibition of gene expression may be accomplished using any of the techniques reported in the art, for instance by transfecting a nucleic acid construct encoding a stem-loop or hairpin RNA structure into the genome of the target cell, or by expressing a transfected nucleic acid construct having homology for a target gene from between convergent promoters, or as a head to head or tail to tail duplication from behind a single promoter. Any similar construct may be used so long as it produces a single RNA having the ability to fold back on itself and produce a dsRNA, or so long as it produces two separate RNA transcripts which then anneal to form a dsRNA having homology to a target gene.

Absolute homology is not required for RNAi, with a lower threshold being described at about 85% homology for a dsRNA of about 200 base pairs (Plasterk and Ketting, 2000, Current Opinion in Genetics and Dev. 10: 562-67). Therefore, depending on the length of the dsRNA, the RNAi-encoding nucleic acids can vary in the level of homology they contain toward the target gene transcript, i.e., with dsRNAs of 100 to 200 base pairs having at least about 85% homology with the target gene, and longer dsRNAs, i.e., 300 to 100 base pairs, having at least about 75% homology to the target gene. RNA-encoding constructs that express a single RNA transcript designed to anneal to a separately expressed RNA, or single constructs expressing separate transcripts from convergent promoters, are suitably at least about 100 nucleotides in length. RNA-encoding constructs that express a single RNA designed to form a dsRNA via internal folding are usually at least about 200 nucleotides in length.

The promoter used to express the dsRNA-forming construct may be any type of promoter if the resulting dsRNA is specific for a gene product in the cell lineage targeted for destruction. Alternatively, the promoter may be lineage specific in that it is only expressed in cells of a particular development lineage. This might be advantageous where some overlap in homology is observed with a gene that is expressed in a non-targeted cell lineage. The promoter may also be inducible by externally controlled factors, or by intracellular environmental factors.

In other embodiments, RNA molecules of about 21 to about 23 nucleotides, which direct cleavage of specific mRNA to which they correspond, as for example described by Tuschl et al. in U.S. Patent Application Publication No. 20020086356, can be utilised for mediating RNAi. Such 21-23 nt RNA molecules can comprise a 3' hydroxyl group, can be single-stranded or double stranded (as two 21-23 nt RNAs) wherein the dsRNA molecules can be blunt ended or comprise overhanging ends (e.g., 5', 3').

In still other embodiments, the functional activity of an IMPDH polypeptide in the cell is inhibited through use of an anti-IMPDH antigen-binding molecule (e.g., a neutralising antibody) as described for example by Gu et al. (2003, Molecular and Cellular Biology 23(18): 6702-6712), which is suitably expressed in the cell in which the IMPDH polypeptide is produced.

In other embodiments, inhibition or abrogation of IMPDH activity is achieved through reduction in IMPDH expression, IMPDH mutation (in particular, but not exclusively, of phosphorylation sites), prevention of IMPDH multimerisation or aggregation, through approaches that interfere with phosphorylation e.g., by blockading the interaction between IMPDH and a protein kinase (e.g., PI 3 kinase or PDK1) or through approaches that interfere with ligand (e.g., inosine monophosphate (IMP))-enzyme interaction e.g., via blockade of the active binding sites or relevant associated motifs. Such strategies include blocking antibodies to, or small molecule inhibitors of, IMPDH multimerisation, phosphorylation or enzyme site (e.g., catalytic or cofactor site). Additionally, IMPDH antagonist molecules may include IMPDH inhibitor fragments, e.g., fragments which comprise IMPDH tetramerisation/oligomerisation sites but which lack the IMPDH active site, or fragments that comprise a mutated IMPDH active site which can bind IMP but which is unable to convert IMP to XMP.

Advantageously, the IMPDH antagonists are small molecule inhibitors. In some embodiments of this type, the IMPDH antagonist is selected from mycophenolic acid and derivatives thereof as disclosed, for example, in

| Patent Number | Issued/Published | Entitled: |
|---|---|---|
| U.S. Pat. No. 5,688,529 | Nov. 18, 1997 | Mycophenolate mofetil high dose oral suspensions |
| U.S. Pat. No. 5,633,279 | May 27, 1997 | 5-Substituted derivatives of mycophenolic acid |
| U.S. Pat. No. 5,554,612 | Sep. 10, 1996 | 4-Amino-6-substituted mycophenolic acid and derivatives |
| U.S. Pat. No. 5,554,384 | Sep. 10, 1996 | High dose formulations of mycophenolate mofetil and mycophenolic acid |
| U.S. Pat. No. 5,545,637 | Aug. 13, 1996 | Process for preparing pharmaceutical compositions containing crystalline anhydrous mycophenolate mofetil |
| U.S. Pat. No. 5,543,408 | Aug. 6, 1996 | Crystalline anhydrous mycophenolate mofetil and intravenous formulation thereof |
| U.S. Pat. No. 5,538,969 | Jul. 23, 1996 | 4-Amino derivatives of 5-substituted mycophenolic acid |

-continued

| Patent Number | Issued/Published | Entitled: |
|---|---|---|
| U.S. Pat. No. 5,536,747 | Jul. 16, 1996 | 6-Substituted mycophenolic acid and derivatives |
| U.S. Pat. No. 5,493,030 | Feb. 20, 1996 | 5-Substituted derivatives of mycophenolic acid |
| U.S. Pat. No. 5,455,045 | Oct. 3, 1995 | High dose formulations |
| U.S. Pat. No. 5,444,072 | Aug. 22, 1995 | 6-Substituted mycophenolic acid and derivatives |
| U.S. Pat. No. 5,441,953 | Aug. 15, 1995 | 4-Amino derivatives of mycophenolic acid |
| U.S. Pat. No. 5,380,879 | Jan. 10, 1995 | Derivatives of mycophenolic acid |
| WO 94/12184 | Jun. 9, 1994 | Use of mycophenolic acid, mycophenolate mofetil or derivative thereof to inhibit stenosis |
| WO 94/01105 | Jan. 20, 1994 | Method of treating hyperproliferative vascular disease |
| U.S. Pat. No. 5,247,083 | Sep. 21, 1993 | Direct esterification of mycophenolic acid |
| U.S. Pat. No. 4,959,387 | Sep. 25, 1990 | Mycophenolic acid derivatives in the treatment of rheumatoid arthritis |
| U.S. Pat. No. 4,952,579 | Aug. 28, 1990 | Method of treating diseases by administering morpholino-ethylester of mycophenolic acid or derivatives thereof |
| U.S. Pat. No. 4,861,776 | Aug. 29, 1989 | Heterocyclic aminoalkyl esters of mycophenolic acid and derivatives thereof, compositions and use |
| U.S. Pat. No. 4,808,592 | Feb. 28, 1989 | Method of treating diseases by administering morpholinoethylester of mycophenolic acid and derivatives thereof |
| U.S. Pat. No. 4,786,637 | Nov. 22, 1988 | Treatment of allograft rejection with mycophenolic acid morpholinoethylester and derivatives thereof |
| U.S. Pat. No. 4,753,935 | Jun. 28, 1988 | Morpholinoethylesters of mycophenolic acid and pharmaceutical compositions |
| U.S. Pat. No. 4,748,173 | May 31, 1988 | Heterocyclic aminoalkyl esters of mycophenolic acid and derivatives thereof and pharmaceutical compositions |
| U.S. Pat. No. 4,727,069 | Feb. 23, 1988 | Heterocyclic aminoalkyl esters of mycophenolic acid, derivatives thereof and pharmaceutical compositions |
| U.S. Pat. No. 4,725,622 | Feb. 16, 1988 | Mycophenolic acid derivatives in the treatment of rheumatoid arthritis |
| U.S. Pat. No. 4,686,234 | Aug. 11, 1987 | Mycophenolic acid derivatives in the treatment of inflammatory diseases, in particular rheumatoid arthritis |

Illustrative examples of such compounds include those having a structure represented by any one of formulae (I)-(V):

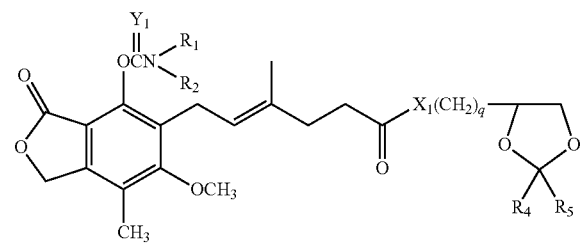

(I)

and pharmaceutically acceptable salts thereof,
wherein:
$R_1$ is H or lower alkyl having 1 to 6 carbon atoms;
$R_2$ is H, lower alkyl having 1 to 6 carbon atoms or -phenyl-4-$CO_2R_3$, in which
$R_3$ is H, lower alkyl having 1 to 6 carbon atoms or a pharmaceutically acceptable cation;
$R_4$ and $R_5$ are each independently H or lower alkyl having 1 to 6 carbon atoms;
$X_1$ and $Y_1$ are each independently O or S; and
q is an integer of 1-6.

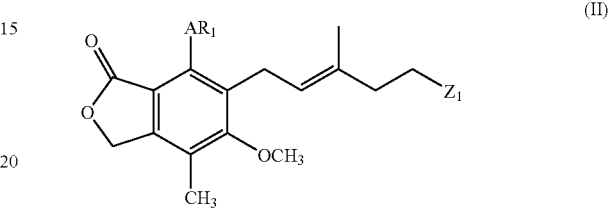

(II)

and pharmaceutically acceptable salts thereof,
wherein:
$R_1$ is selected from the group consisting of:

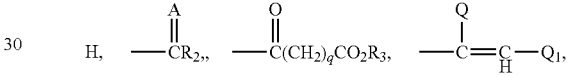

in which:
A is oxygen or sulfur;
q is an integer from 0-6;
$R_2$ is alkyl, haloalkyl or —$NR_4R_5$, where:
$R_4$ and $R_5$ are independently H, alkyl, haloalkyl, cycloalkyl, phenyl optionally monosubstituted with halogen, hydroxy, carboxy, chlorocarbonyl, sulfonylamino, nitro, cyano, phenyl, alkyl, acyl, alkoxycarbonyl, acylamino, dialkylamino or dialkylaminoethoxycarbonyl, phenyl optionally disubstituted with hydroxy, carboxy, nitro or alkyl, or benzyl optionally substituted with dialkylamino;
$R_3$ is H, alkyl or a pharmaceutically acceptable cation;
Q and $Q_1$ are independently H or —$CO_2R_3$; and
$Z_1$ is selected from the group consisting of: 1H-tetrazolyl, —$CH_2OH$, —CHO, —CN, —$C(O)A_2R_6$ and —$C(O)NR_7R_8$, in which:
$A_2$ is oxygen or sulfur;
$R_6$ is H, alkyl, alkenyl, cycloalkyl, optionally substituted phenyl, optionally substituted benzyl or a pharmaceutically acceptable cation; and
$R_7$ and $R_8$ are independently H, alkyl or cycloalkyl, or $R_7$ and $R_8$ taken together are —$(CH_2)_2O(CH_2)_2$—, —$(CH_2)_4$— or —$(CH_2)_5$—.

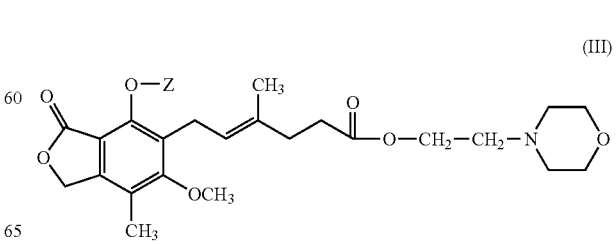

(III)

wherein:

Z is hydrogen or —C(O)R, where R is lower alkyl or aryl, and the pharmaceutically acceptable salts thereof.

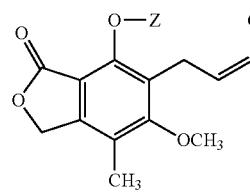
(IV)

wherein:

m is an integer from two to four;

Z is selected from Formulae (a), (b), (c), or (d), as follows:

(a)

in which:

$R^2$ is hydrogen, alkyl having seven or more carbon atoms including cycloalkyl such as adamantyl, or —$NR^2R^3$, where $R^2$ is hydrogen or lower alkyl, and $R^3$ is hydrogen, lower alkyl, -phenyl-4-$CO_2R^2$ or a pharmaceutically acceptable cation;

(b)

in which:

$R^4$ is hydrogen, alkyl, aryl or —$NR^2R^3$;

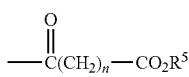
(c)

in which:

n is an integer from zero to six, and;

$R^5$ is hydrogen, lower alkyl, or a pharmaceutically acceptable cation;

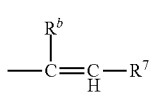
(d)

in which:

$R^6$ and $R^7$ are independently hydrogen or $O_2R^5$; and

Y is lower alkylene of four to six carbon atoms, or lower alkylene of three to five carbon atoms and one member that is —O—, —S— or

where $R^8$ is hydrogen or alkyl of one to five carbon atoms.

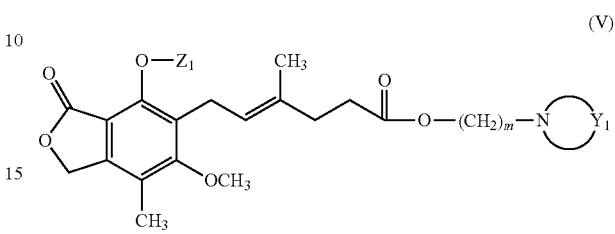
(V)

wherein:

m is an integer from two to four;

$Z^1$ is hydrogen or —$C(O)R^9$, where $R^9$ is lower alkyl or aryl; and $Y^1$ is lower alkylene of four to six carbon atoms, or lower alkylene of three to five carbon atoms and one member that is —O—, —S—, or

where $R^8$ is hydrogen or alkyl of one to five carbon atoms; and the pharmaceutically acceptable salts thereof;

except that when m is two, $Y^1$ does not include —$(CH_2)_2$—O—$(CH_2)_2$.

Exemplary compounds include mycophenolate mofetil, the morpholinoethyl ester of mycophenolic acid, which has the chemical name morpholinoethyl E-6-(1,3-dihydro-4hydroxy-6-methoxy-7-methyl-3-oxo-5-isobenzofuranyl)-4-methyl-4-hexenoate, and derivatives thereof, which are described, for example, in U.S. Pat. No. 4,753,935.

The above compounds and methods for their preparation are disclosed in WO 94/12184 and in references cited therein.

Other illustrative examples of mycophenolic acid derivatives have a structure represented by formula (VI):

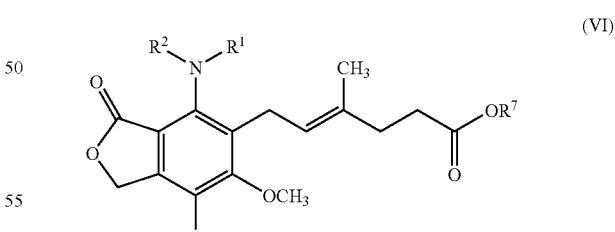
(VI)

wherein:

$R^1$ is hydrogen or lower alkyl;

$R^2$ is hydrogen, lower alkyl, —$C(O)R_3$, —$C(O)NR^4R^5$, —$CO_2R6$, or —$SO_2R^3$ where:

$R^3$ is hydrogen, lower alkyl, halo lower alkyl or optionally substituted phenyl;

$R^4$ is hydrogen, lower alkyl or optionally substituted phenyl;

$R^5$ is hydrogen, lower alkyl or optionally substituted phenyl;

$R^6$ is lower alkyl or optionally substituted phenyl; and $R^7$ is hydrogen, lower alkyl, optionally substituted phenyl, or —(CH$_2$)$_m$—N=Y, wherein:

m is an integer from two to four; and

Y is lower alkylene of four to six carbon atoms or lower alkylene of three to five carbon atoms and one member that is —O—, —S—, or —N(R$^8$)— where R$^8$ is hydrogen or lower alkyl, and the pharmaceutically acceptable salts thereof.

Suitably, the moiety "—N=Y" represents a heterocycle radical such as pyrrolidino, piperidino, hexamethyleneimino, imidazolidino, thiazolidino, morpholino, thiomorpholino, piperazino, thiopentamethyleneimino, and the like.

Representative compounds falling within the scope of Formula (VI) include, but are not limited to: ethyl (E)-6-(1,3-dihydro-4-amino-6-methoxy-7-methyl-3-oxoisobenzofuran-5-yl)-4-methyl-4-hexenoate; n-propyl (E)-6-(1,3-dihydro-4-amino-6-methoxy-7-methyl-3-oxoisobenzofuran-5-yl)-4-methyl-4-hexenoate; isopropyl (E)-6-(1,3-dihydro-4-amino-6-methoxy-7-methyl-3-oxoisobenzofuran-5-yl)-4-methyl-4-hexenoate; t-butyl (E)-6-(1,3-dihydro-4-amino-6-methoxy-7-methyl-3-oxoisobenzofuran-5-yl)-4-methyl-4-hexenoate; isoamyl (E)-6-(1,3-dihydro-4-amino-6-methoxy-7-methyl-3-oxoisobenzofuran-5-yl)-4-methyl-4-hexenoate; phenyl (E)-6-(1,3-dihydro-4-amino-6-methoxy-7-methyl-3-oxoisobenzofuran-5-yl)-4-methyl-4-hexenoate; 2-chlorophenyl (E)-6-(1,3-dihydro-4-amino-6-methoxy-7-methyl-3-oxoisobenzofuran-5-yl)-4-methyl-4-hexenoate; 2-trifluoromethylphenyl (E)-6-(1,3-dihydro-4-amino-6-methoxy-7-methyl-3-oxoisobenzofuran-5-yl)-4-methyl-4-hexenoate; 2-chloro-3,4-dimethoxyphenyl (E)-6-(1,3-dihydro-4-amino-6-methoxy-7-methyl-3-oxoisobenzofuran-5-yl)-4-methyl-4-hexenoate; 2-(pyrrolidin-1-yl)ethyl (E)-6-(1,3-dihydro-4-amino-6-methoxy-7-methyl-3-oxoisobenzofuran-5-yl)-4-methyl-4-hexenoate; 2-(piperidin-1-yl)ethyl (E)-6-(1,3-dihydro-4-amino-6-methoxy-7-methyl-3-oxoisobenzofuran-5-yl)-4-methyl-4-hexenoate; 2-(thiazolidin-3-yl)ethyl (E)-6-(1,3-dihydro-4-amino-6-methoxy-7-methyl-3-oxoisobenzofuran-5-yl)-4-methyl-4-hexenoate; 3-(morpholin-4-yl)propyl (E)-6-(1,3-dihydro-4-amino-6-methoxy-7-methyl-3-oxoisobenzofuran-5-yl)-4-methyl-4-hexenoate; 4-(morpholin-4-yl)butyl (E)-6-(1,3-dihydro-4-amino-6-methoxy-7-methyl-3-oxoisobenzofuran-5-yl)-4-methyl-4-hexenoate; 2-(imidazolidin-1-yl)ethyl (E)-6-(1,3-dihydro-4-amino-6-methoxy-7-methyl-3-oxoisobenzofuran-5-yl)-4-methyl-4-hexenoate; 2-(2-methyl-1,2-pyrazolidin-1-yl)ethyl (E)-6-(1,3-dihydro-4-amino-6-methoxy-7-methyl-3-oxoisobenzofuran-5-yl)-4-methyl-4-hexenoate; methyl (E)-6-(1,3-dihydro-4-(3-methyl)ureido-6-methoxy-7-methyl-3-oxoisobenzofuran-5-yl)-4-methyl-4-hexenoate; methyl (E)-6-(1,3-dihydro-4-ureido-6-methoxy-7-methyl-3-oxoisobenzofuran-5-yl)-4-methyl-4-hexenoate; methyl (E)-6-(1,3-dihydro-4-(3,3-diethyl)ureido-6-methoxy-7-methyl-3-oxoisobenzofuran-5-yl)-4-methyl-4-hexenoate; methyl (E)-6-(1,3-dihydro-4-(3-ethyl)ureido-6-methoxy-7-methyl-3-oxoisobenzofuran-5-yl)-4-methyl-4-hexenoate; methyl (E)-6-(1,3-dihydro-4-(3-methyl-3-ethyl)ureido-6-methoxy-7-methyl-3-oxoisobenzofuran-5-yl)-4-methyl-4-hexenoate; methyl (E)-6-(1,3-dihydro-4-(3,3-diphenyl)ureido-6-methoxy-7-methyl-3-oxoisobenzofuran-5-yl)-4-methyl-4-hexenoate; methyl (E)-6-(1,3-dihydro-4-(3-phenyl)ureido-6-methoxy-7-methyl-3-oxoisobenzofuran-5-yl)-4-methyl-4-hexenoate, methyl (E)-6-(1,3-dihydro-4-(3-methyl-3-phenyl)ureido-6-methoxy-7-methyl-3-oxoisobenzofuran-5-yl)-4-methyl-4-hexenoate; methyl (E)-6-(1,3-dihydro-4-(3-butyl-3-propyl)ureido-6-methoxy-7-methyl-3-oxoisobenzofuran-5-yl)-4-methyl-4-hexenoate; methyl (E)-6-(1,3-dihydro-4-(3-(2-chlorophenyl)ureido)-6-methoxy-7-methyl-3-oxoisobenzofuran-5-yl)-4-methyl-4-hexenoate; E)-6-[1,3-dihydro-4-(3-methyl)ureido-6-methoxy-7-methyl-3-oxoisobenzofuran-5-yl]-4-methyl-4-hexenoic acid; (E)-6-(1,3-dihydro-4-ureido-6-methoxy-7-methyl-3-oxoisobenzofuran-5-yl)-4-methyl-4-hexenoic acid; (E)-6-[1,3-dihydro-4-(3,3-diethyl)ureido-6-methoxy-7-methyl-3-oxoisobenzofuran-5-yl]-4-methyl-4-hexenoic acid; (E)-6-[1,3-dihydro-4-(3-ethyl)ureido-6-methoxy-7-methyl-3-oxoisobenzofuran-5-yl]-4-methyl-4-hexenoic acid; (E)-6-[1,3-dihydro-4-(3-methyl-3-ethyl)ureido-6-methoxy-7-methyl-3-oxoisobenzofuran-5-yl]-4-methyl-4-hexenoic acid; (E)-6-[1,3-dihydro-4-(3,3-diphenyl)ureido-6-methoxy-7-methyl-3-oxoisobenzofuran-5-yl]-4-methyl-4-hexenoic acid; (E)-6-[1,3-dihydro-4-(3-phenyl)ureido-6-methoxy-7-methyl-3-oxoisobenzofuran-5-yl]-4-methyl-4-hexenoic acid; (E)-6-[1,3-dihydro-4-(3-methyl-3-phenyl)ureido-6-methoxy-7-methyl-3-oxoisobenzofuran-5-yl]-4-methyl-4-hexenoic acid; methyl E-6-[1,3-dihydro-4-(3,3-dimethylureido)-6-methoxy-7-methyl-3-oxoisobenzofuran-5-yl]-4-methyl-4-hexenoate; methyl (E)-6-[1,3-dihydro-4-(3-methyl)ureido-6-methoxy-7-methyl-3-oxoisobenzofuran-5-yl]-4-methyl-4-hexenoate; methyl (E)-6-(1,3-dihydro-4-ureido-6-methoxy-7-methyl-3-oxoisobenzofuran-5-yl)-4-methyl-4-hexenoate; methyl (E)-6-[1,3-dihydro-4-(3,3-diethyl)ureido-6-methoxy-7-methyl-3-oxoisobenzofuran-5-yl]-4-methyl-4-hexenoate; methyl (E)-6-[1,3-dihydro-4-(3-ethyl)ureido-6-methoxy-7-methyl-3-oxoisobenzofuran-5-yl]-4-methyl-4-hexenoate; methyl (E)-6-[1,3-dihydro-4-(3-methyl-3-ethyl)ureido-6-methoxy-7-methyl-3-oxoisobenzofuran-5-yl]-4-methyl-4-hexenoate; methyl (E)-6-[1,3-dihydro-4-(3,3-diphenyl)ureido-6-methoxy-7-methyl-3-oxoisobenzofuran-5-yl]-4-methyl-4-hexenoate; methyl (E)-6-[1,3-dihydro-4-(3-phenyl)ureido-6-methoxy-7-methyl-3-oxoisobenzofuran-5-yl]-4-methyl-4-hexenoate; methyl (E)-6-[1,3-dihydro-4-(3-methyl-3-phenyl)ureido-6-methoxy-7-methyl-3-oxoisobenzofuran-5-yl]-4-methyl-4-hexenoate; ethyl (E)-6-[1,3-dihydro-4-(3,3-dimethylureido)-6-methoxy-7-methyl-3-oxoisobenzofuran-5-yl]-4-methyl-4-hexenoate; n-propyl (E)-6-[1,3-dihydro-4-(3,3-dimethylureido)-6-methoxy-7-methyl-3-oxoisobenzofuran-5-yl]-4-methyl-4-hexenoate; isopropyl (E)-6-[1,3-dihydro-4-(3,3-dimethylureido)-6-methoxy-7-methyl-3-oxoisobenzofuran-5-yl]-4-methyl-4-hexenoate; t-butyl (E)-6-[1,3-dihydro-4-(3,3-dimethylureido)-6-methoxy-6-methyl-3-oxoisobenzofuran-5-yl]-4-methyl-4-hexenoate; isoamyl (E)-6-[1,3-dihydro-4-(3,3-dimethylureido)-6-methoxy-7-methyl-3-oxoisobenzofuran-5-yl]-4-methyl-4-hexenoate; phenyl (E)-6-[1,3-dihydro-4-(3,3-dimethylureido)-6-methoxy-7-methyl-3-oxoisobenzofuran-5-yl]-4-methyl-4-hexenoate; 2-chlorophenyl (E)-6-[1,3-dihydro-4-(3,3-dimethylureido)-6-methoxy-7-methyl-3-oxoisobenzofuran-5-yl]-4-methyl-4-hexenoate; 2-trifluoromethylphenyl (E)-6-[1,3-dihydro-4-(3,3-dimethylureido)-6-methoxy-7-methyl-3-oxoisobenzofuran-5-yl]-4-methyl-4-hexenoate; 2-chloro-3,4-dimethoxyphenyl (E)-6-[1,3-dihydro-4-(3,3-dimethylureido)-6-methoxy-7-methyl-3-oxoisobenzofuran-5-yl]-4-methyl-4-hexenoate; ethyl (E)-6-[1,3-dihydro-4-(3-methyl)ureido-6-methoxy-7-methyl-3-oxoisobenzofuran-5-yl]-4-methyl-4-hexenoate; n-propyl (E)-6-[1,3-dihydro-4-(3-methyl)ureido-6-methoxy-7-methyl-3-oxoisobenzofuran-5-yl]-4-methyl-4-hexenoate; isopropyl (E)-6-[1,3-dihydro-4-(3-methyl)ureido-6-methoxy- 7-methyl-3-oxoisobenzofuran-5-yl]-4-methyl-4-hexenoate; t-butyl (E)-6-[1,3-dihydro-4-(3-methyl)ureido-6-methoxy-7-methyl-3-oxoisobenzofuran-5-yl]-4-methyl-4-hexenoate; isoamyl (E)-6-[1,3-dihydro-4-(3-methyl)ureido-6-methoxy-7-methyl-3-oxoisobenzofuran-5-yl]-4-methyl-4-hexenoate; phenyl (E)-6-[1,3-dihydro-4-(3-methyl)ureido-6-methoxy-7-methyl-3-oxoisobenzofuran-5-yl]-4-methyl-4-hexenoate; 2-chlorophenyl (E)-6-[1,3-dihydro-4-(3-methyl)ureido-6-methoxy-7-methyl-3-oxoisobenzofuran-5-yl]-4-methyl-4-hexenoate; 2-trifluoromethylphenyl (E)-6-[1,3-dihydro-4-(3-methyl)ureido-6-methoxy-7-methyl-3-oxoisobenzofuran-5-yl]-4-methyl-4-hexenoate; 2-chloro-3,4-dimethoxyphenyl (E)-6-[1,3-dihydro-4-(3-methyl)ureido-6-methoxy-7-methyl-3-oxoisobenzofuran-5-yl]-4-methyl-4-hexenoate; ethyl (E)-6-(1,3-dihydro-4-ureido-6-methoxy-7-methyl-3-oxoisobenzofuran-5-yl)-4-methyl-4-hexenoate; n-propyl (E)-6-(1,3-dihydro-4-ureido-6-methoxy-7-methyl-3-oxoisobenzofuran-5-yl)-4-methyl-4-hexenoate; isopropyl (E)-6-(1,3-dihydro-4-ureido-6-methoxy-7-methyl-3-oxoisobenzofuran-5-yl)-4-methyl-4-hexenoate; t-butyl (E)-6-(1,3-dihydro-4-ureido-6-methoxy-7-methyl-3-oxoisobenzofuran-5-yl)-4-methyl-4-hexenoate; isoamyl (E)-6-(1,3-dihydro-4-ureido-6-methoxy-7-methyl-3-oxoisobenzofuran-5-yl)-4-methyl-4-hexenoate; phenyl (E)-6-(1,3-dihydro-4-ureido-6-methoxy-7-methyl-3-oxoisobenzofuran-5-yl)-4-methyl-4-hexenoate; 2-chlorophenyl (E)-6-(1,3-dihydro-4-ureido-6-methoxy-7-methyl-3-oxoisobenzofuran-5-yl)-4-methyl-4-hexenoate; 2-trifluoromethylphenyl (E)-6-(1,3-dihydro-4-ureido-6-methoxy-7-methyl-3-oxoisobenzofuran-5-yl)-4-methyl-4-hexenoate; 2-chloro-3,4-dimethoxyphenyl (E)-6-(1,3-dihydro-4-ureido-6-methoxy-7-methyl-3-oxoisobenzofuran-5-yl)-4-methyl-4-hexenoate; ethyl (E)-6-[1,3-dihydro-4-(3,3-diethyl)ureido-6-methoxy-7-methyl-3-oxoisobenzofuran-5-yl]-4-methyl-4-hexenoate; n-propyl (E)-6-[1,3-dihydro-4-(3,3-diethyl)ureido-6-methoxy-7-methyl-3-oxoisobenzofuran-5-yl]-4-methyl-4-hexenoate; isopropyl (E)-6-[1,3-dihydro-4-(3,3-diethyl)ureido-6-methoxy-7-methyl-3-oxoisobenzofuran-5-yl]-4-methyl-4-hexenoate; t-butyl (E)-6-[1,3-dihydro-4-(3,3-diethyl)ureido-6-methoxy-7-methyl-3-oxoisobenzofuran-5-yl]-4-methyl-4-hexenoate; isoamyl (E)-6-[1,3-dihydro-4-(3,3-diethyl)ureido-6-methoxy-7-methyl-3-3-oxoisobenzofuran-5-yl]-4-methyl-4-hexenoate; phenyl (E)-6-[1,3-dihydro-4-(3,3-diethyl)ureido-6-methoxy-7-methyl-3-oxoisobenzofuran-5-yl]-4-methyl-4-hexenoate; 2-chlorophenyl (E)-6-[1,3-dihydro-4-(3,3-diethyl)ureido-6-methoxy-7-methyl-3-oxoisobenzofuran-5-yl]-4-methyl-4-hexenoate; 2-trifluoromethylphenyl (E)-6-[1,3-dihydro-4-(3,3-diethyl)ureido-6-methoxy-7-methyl-3-oxoisobenzofuran-5-yl]-4-methyl-4-hexenoate; 2-chloro-3,4-dimethoxyphenyl (E)-6-[1,3-dihydro-4-(3,3-diethyl)ureido-6-methoxy-7-methyl-3-oxoisobenzofuran-5-yl]-4-methyl-4-hexenoate; ethyl (E)-6-[1,3-dihydro-4-(3-ethyl)ureido-6-methoxy-7-methyl-3-oxoisobenzofuran-5-yl]-4-methyl-4-hexenoate; n-propyl (E)-6-[1,3-dihydro-4-(3-ethyl)ureido-6-methoxy-7-methyl-3-oxoisobenzofuran-5-yl]-4-methyl-4-hexenoate; isopropyl (E)-6-[1,3-dihydro-4-(3-ethyl)ureido-6-methoxy-7-methyl-3-oxoisobenzofuran-5-yl]-4-methyl-4-hexenoate; t-butyl (E)-6-[1,3-dihydro-4-(3-ethyl)ureido-6-methoxy-7-methyl-3-oxoisobenzofuran-5-yl]-4-methyl-4-hexenoate; isoamyl (E)-6-[1,3-dihydro-4-(3-ethyl)ureido-6-methoxy-7-methyl-3-oxoisobenzofuran-5-yl]-4-methyl-4-hexenoate; phenyl (E)-6-[1,3-dihydro-4-(3-ethyl)ureido-6-methoxy-7-methyl-3-oxoisobenzofuran-5-yl]-4-methyl-4-hexenoate; 2-chlorophenyl (E)-6-[1,3-dihydro-4-(3-ethyl)ureido-6-methoxy-7-methyl-3-oxoisobenzofuran-5-yl]-4-methyl-4-hexenoate; 2-trifluoromethylphenyl (E)-6-[1,3-dihydro-4-(3-ethyl)ureido-6-methoxy-7-methyl-3-oxoisobenzofuran-5-yl]-4-methyl-4-hexenoate; 2-chloro-3,4-dimethoxyphenyl (E)-6-[1,3-dihydro-4-(3-ethyl)ureido-6-methoxy-7-methyl-3-oxoisobenzofuran-5-yl]-4-methyl-4-hexenoate; ethyl (E)-6-[1,3-dihydro-4-(3-methyl-3-ethyl)ureido-6-methoxy-7-methyl-3-oxoisobenzofuran-5-yl]-4-methyl-4-hexenoate; n-propyl (E)-6-[1,3-dihydro-4-(3-methyl-3-ethyl)ureido-6-methoxy-7-methyl-3-oxoisobenzofuran-5-yl]-4-methyl-4-hexenoate; isopropyl (E)-6-[1,3-dihydro-4-(3-methyl-3-ethyl)ureido-6-methoxy-7-methyl-3-oxoisobenzofuran-5-yl]-4-methyl-4-hexenoate; t-butyl (E)-6-[1,3-dihydro-4-(3-methyl-3-ethyl)ureido-6-methoxy-7-methyl-3-oxoisobenzofuran-5-yl]-4-methyl-4-hexenoate; isoamyl (E)-6-[1,3-dihydro-4-(3-methyl-3-ethyl)ureido-6-methoxy-7-methyl-3-oxoisobenzofuran-5-yl]-4-methyl-4-hexenoate; phenyl (E)-6-[1,3-dihydro-4-(3-methyl-3-ethyl)ureido-6-methoxy-7-methyl-3-oxoisobenzofuran-5-yl]-4-methyl-4-hexenoate; 2-chlorophenyl (E)-6-[1,3-dihydro-4-(3-methyl-3-ethyl)ureido-6-methoxy-7-methyl-3-oxoisobenzofuran-5-yl]-4-methyl-4-hexenoate; 2-trifluoromethylphenyl (E)-6-[1,3-dihydro-4-(3-methyl-4-3-ethyl)ureido-6-methoxy-7-methyl-3-oxoisobenzofuran-5-yl]-4-methyl-4-hexenoate; 2-chloro-3,4-dimethoxyphenyl (E)-6-[1,3-dihydro-4-(3-methyl-3-ethyl)ureido-6-methoxy-7-methyl-3-oxoisobenzofuran-5-yl]-4-methyl-4-hexenoate; ethyl (E)-6-[1,3-dihydro-4-(3,3-diphenyl)ureido-6-methoxy-7-methyl-3-oxoisobenzofuran-5-yl]-4-methyl-4-hexenoate; n-propyl (E)-6-[1,3-dihydro-4-(3,3-diphenyl)ureido-6-methoxy-7-methyl-3-oxoisobenzofuran-5-yl]-4-methyl-4-hexenoate; isopropyl (E)-6-[1,3-dihydro-4-(3,3-diphenyl)ureido-6-methoxy-7-methyl-3-oxoisobenzofuran-5-yl]-4-methyl-4-hexenoate; t-butyl (E)-6-[1,3-dihydro-4-(3,3-diphenyl)ureido-6-methoxy-7-methyl-3-oxoisobenzofuran-5-yl]-4-methyl-4-hexenoate; isoamyl (E)-6-[1,3-dihydro-4-(3,3-diphenyl)ureido-6-methoxy-7-methyl-3-oxoisobenzofuran-5-yl]-4-methyl-4-hexenoate; phenyl (E)-6-[1,3-dihydro-4-(3,3-diphenyl)ureido-6-methoxy-7-methyl-3-oxoisobenzofuran-5-yl]-4-methyl-4-hexenoate; 2-chlorophenyl (E)-6-[1,3-dihydro-4-(3,3-diphenyl)ureido-6-methoxy-7-methyl-3-oxoisobenzofuran-5-yl]-4-methyl-4-hexenoate; 2-trifluoromethylphenyl (E)-6-[1,3-dihydro-4-(3,3-diphenyl)ureido-6-methoxy-7-methyl-3-oxoisobenzofuran-5-yl]-4-methyl-4-hexenoate; 2-chloro-3,4-dimethoxyphenyl (E)-6-[1,3-dihydro-4-(3,3-diphenyl)ureido-6-methoxy-7-methyl-3-oxoisobenzofuran-5-yl]-4-methyl-4-hexenoate; ethyl (E)-6-[1,3-dihydro-4-(3-phenyl)ureido-6-methoxy-7-methyl-3-oxoisobenzofuran-5-yl]-4-methyl-4-hexenoate; n-propyl (E)-6-[1,3-dihydro-4-(3-phenyl)ureido-6-methoxy-7-methyl-3-oxoisobenzofuran-5-yl]-4-methyl-4-hexenoate; isopropyl (E)-6-[1,3-dihydro-4-(3-phenyl)ureido-6-methoxy-7-methyl-3-oxoisobenzofuran-5-yl]-4-methyl-4-hexenoate; t-butyl (E)-6-[1,3-dihydro-4-(3-phenyl)ureido-6-methoxy-7-methyl-3-oxoisobenzofuran-5-yl]-4-methyl-4-hexenoate; isoamyl (E)-6-[1,3-dihydro-4-(3-phenyl)ureido-6-methoxy-7-methyl-3-oxoisobenzofuran-5-yl]-4-methyl-4-hexenoate; phenyl (E)-6-[1,3-dihydro-4-(3-phenyl)ureido-6-methoxy-7-methyl-3-oxoisobenzofuran-5-yl]-4-methyl-4-hexenoate; 2-chlorophenyl (E)-6-[1,3-dihydro-4-(3-phenyl)ureido-6-methoxy-7-methyl-3-oxoisobenzofuran-5-yl]-4-methyl-4-hexenoate; 2-trifluoromethylphenyl (E)-6-[1,3-dihydro-4-(3-phenyl)ureido-6-methoxy-7-methyl-3-oxoisobenzofuran-5-yl]-4-methyl-4-hexenoate; 2-chloro-3,4-dimethoxyphenyl (E)-6-[1,3-dihydro-4-(3-phenyl)ureido-6-methoxy-7-methyl-3-oxoisobenzofuran-5-yl]-4-methyl-4-hexenoate; ethyl (E)-6-[1,3-dihydro-4-(3-methyl-3-phenyl)ureido-6-methoxy-7-methyl-3-oxoisobenzofuran-5-yl]-4-methyl-4-hexenoate; n-propyl (E)-6-[1,3-dihydro-4-(3-methyl-3-phenyl) ureido-6-methoxy-7-methyl-3-oxoisobenzofuran-5-yl]-4-methyl-4-hexenoate; isopropyl (E)-6-[1,3-dihydro-4-(3-methyl-3-phenyl) ureido-6-methoxy-7-methyl-3-oxoisobenzofuran-5-yl]-4-methyl-4-hexenoate; t-butyl (E)-6-[1,3-dihydro-4-(3-methyl-3-phenyl) ureido-6-methoxy-7-methyl-3-oxoisobenzofuran-5-yl]-4-methyl-4-hexenoate; isoamyl (E)-6-[1,3-dihydro-4-(3-methyl-3-phenyl) ureido-6-methoxy-7-methyl-3-oxoisobenzofuran-5-yl]-4-methyl-4-hexenoate; phenyl (E)-6-[1,3-dihydro-4-(3-methyl-3-phenyl)ureido-6-methoxy-7-methyl-3-oxoisobenzofuran-5-yl]-4-methyl-4-hexenoate; 2-chlorophenyl (E)-6-[1,3-dihydro-4-(3-methyl-3-phenyl)ureido-6-methoxy-7-methyl-3-oxoisobenzofuran-5-yl]-4-methyl-4-hexenoate; 2-trifluoromethylphenyl (E)-6-[1,3-dihydro-4-(3-methyl-3-phenyl)ureido-6-methoxy-7-methyl-3-oxoisobenzofuran-5-yl]-4-methyl-4-hexenoate; 2-chloro-3,4-dimethoxyphenyl (E)-6-[1,3-dihydro-4-(3-methyl-3-phenyl)ureido-6-methoxy-7-methyl-3-oxoisobenzofuran-5-yl]-4-methyl-4-hexenoate; ethyl (E)-6-[1,3-dihydro-4-(3-butyl-3-propyl) ureido-6-methoxy-7-methyl-3-oxoisobenzofuran-5-yl]-4-methyl-4-hexenoate; n-propyl (E)-6-[1,3-dihydro-4-(3-butyl-3-propyl)ureido-6-methoxy-7-methyl-3-oxoisobenzofuran-5-yl]-4-methyl-4-hexenoate; isopropyl (E)-6-[1,3-dihydro-4-(3-butyl-3-propyl)ureido-6-methoxy-7-methyl-3-oxoisobenzofuran-5-yl]-4-methyl-4-hexenoate; t-butyl (E)-6-[1,3-dihydro-4-(3-butyl-3-propyl) ureido-6-methoxy-7-methyl-3-oxoisobenzofuran-5-yl]-4-methyl-4-hexenoate; isoamyl (E)-6-[1,3-dihydro-4-(3-butyl-3-propyl) ureido-6-methoxy-7-methyl-3-oxoisobenzofuran-5-yl]-4-methyl-4-hexenoate; phenyl (E)-6-[1,3-dihydro-4-(3-butyl-3-propyl)ureido-6-methoxy-7-methyl-3-oxoisobenzofuran-5-yl]-4-methyl-4-hexenoate; 2-chlorophenyl (E)-6-[1,3-dihydro-4-(3-butyl-3-propyl)ureido-6-methoxy-7-methyl-3-oxoisobenzofuran-5-yl]-4-methyl-4-hexenoate; 2-trifluoromethylphenyl (E)-6-[1,3-dihydro-4-(3-butyl-3-propyl)ureido-6-methoxy-7-methyl-3-oxoisobenzofuran-5-yl]-4-methyl-4-hexenoate; 2-chloro-3,4-dimethoxyphenyl (E)-6-[1,3-dihydro-4-(3-butyl-3-propyl)ureido-6-methoxy-7-methyl-3-oxoisobenzofuran-5-yl]-4-methyl-4-hexenoate; ethyl (E)-6-[1,3-dihydro-4-(3-(2-chlorophenyl)ureido)-6-methoxy-7-methyl-3-oxoisobenzofuran-5-yl]-4-methyl-4-hexenoate; n-propyl (E)-6-[1,3-dihydro-4-(3-(2-chlorophenyl)ureido)-6-methoxy-7-methyl-3-oxoisobenzofuran-5-yl]-4-methyl-4-hexenoate; isopropyl (E)-6-[1,3-dihydro-4-(3-(2-chlorophenyl)ureido)-6-methoxy-7-methyl-3-oxoisobenzofuran-5-yl]-4-methyl-4-hexenoate; t-butyl (E)-6-[1,3-dihydro-4-(3-(2-chlorophenyl)ureido)-6-methoxy-7-methyl-3-oxoisobenzofuran-5-yl]-4-methyl-4-hexenoate; isoamyl (E)-6-[1,3-dihydro-4-(3-(2-chlorophenyl)ureido)-6-methoxy-7-methyl-3-oxoisobenzofuran-5-yl]-4-methyl-4-hexenoate; phenyl (E)-6-[1,3-dihydro-4-(3-(2-chlorophenyl)ureido)-6-methoxy-7-methyl-3-oxoisobenzofuran-5-yl]-4-methyl-4-hexenoate; 2-chlorophenyl (E)-6-[1,3-dihydro-4-(3-(2-chlorophenyl)ureido)-6-methoxy-7-methyl-3-oxoisobenzofuran-5-yl]-4-methyl-4-hexenoate; 2-trifluoromethylphenyl (E)-6-[1,3-dihydro-4-(3-(2-chlorophenyl)ureido)-6-methoxy-7-methyl-3-oxoisobenzofuran-5-yl]-4-methyl-4-hexenoate; 2-chloro-3,4-dimethoxyphenyl (E)-6-[1,3-dihydro-4-(3-(2-chlorophenyl)ureido)-6-methoxy-7-methyl-3-oxoisobenzofuran-5-yl]-4-methyl-4-hexenoate; 2-(morpholin-4-yl)ethyl E-6-[1,3-dihydro-4-(3,3-dimethylureido)-6-methoxy-7-methyl-3-oxoisobenzofuran-5-yl]-4-methyl-4-hexenoate; 2-(morpholin-4-yl)ethyl (E)-6-[1,3-dihydro-4-(3-methyl)ureido-6-methoxy-7-methyl-3-oxoisobenzofuran-5-yl]-4-methyl-4-hexenoate; 2-(morpholin-4-yl)ethyl (E)-6-(1,3-dihydro-4-ureido-6-methoxy-7-methyl-3-oxoisobenzofuran-5-yl)-4-methyl-4-hexenoate; 2-(morpholin-4-yl)ethyl (E)-6-[1,3-dihydro-4-(3,3-diethyl)ureido-6-methoxy-7-methyl-3-oxoisobenzofuran-5-yl]-4-methyl-4-hexenoate; 2-(morpholin-4-yl)ethyl (E)-6-[1,3-dihydro-4-(3-ethyl)ureido-6-methoxy-7-methyl-3-oxoisobenzofuran-5-yl]-4-methyl-4-hexenoate; 2-(morpholin-4-yl)ethyl (E)-6-[1,3-dihydro-4-(3-methyl-4-3-ethyl)ureido-6-methoxy-7-methyl-3-oxoisobenzofuran-5-yl]-4-methyl-4-hexenoate; 2-(morpholin-4-yl)ethyl (E)-6-[1,3-dihydro-4-(3,3-diphenyl)ureido-6-methoxy-7-methyl-3-oxoisobenzofuran-5-yl]-4-methyl-4-hexenoate; 2-(morpholin-4-yl)ethyl (E)-6-[1,3-dihydro-4-(3-phenyl)ureido-6-methoxy-7-methyl-3-oxoisobenzofuran-5-yl]-4-methyl-4-hexenoate; 2-(morpholin-4-yl)ethyl (E)-6-[1,3-dihydro-4-(3-methyl-4-3-phenyl)ureido-6-methoxy-7-methyl-3-oxoisobenzofuran-5-yl]-4-methyl-4-hexenoate; 2-(pyrrolidin-1-yl)ethyl (E)-6-[1,3-dihydro-4-(3,3-dimethylureido)-6-methoxy-7-methyl-3-oxoisobenzofuran-5-yl]-4-methyl-4-hexenoate; 2-(piperidin-1-yl)ethyl (E)-6-[1,3-dihydro-4-(3,3-dimethylureido)-6-methoxy-7-methyl-3-oxoisobenzofuran-5-yl]-4-methyl-4-hexenoate; 2-(thiazolidin-3-yl)ethyl (E)-6-[1,3-dihydro-4-(3,3-dimethylureido)-6-methoxy-7-methyl-3-oxoisobenzofuran-5-yl]-4-methyl-4-hexenoate; 3-(morpholin-4-yl)propyl (E)-6-[1,3-dihydro-4-(3,3-dimethylureido)-6-methoxy-7-methyl-3-oxoisobenzofuran-5-yl]-4-methyl-4-hexenoate; 4-(morpholin-4-yl)butyl (E)-6-[1,3-dihydro-4-(3,3-dimethylureido)-6-methoxy-7-methyl-3-oxoisobenzofuran-5-yl]-4-methyl-4-hexenoate; 2-(imidazolidin-1-yl)ethyl (E)-6-[1,3-dihydro-4-(3,3-dimethylureido)-6-methoxy-7-methyl-3-oxoisobenzofuran-5-yl]-4-methyl-4-hexenoate; 2-(2-methyl-1,2-pyrazolidin-1-yl)ethyl (E)-6-[1,3-dihydro-4-(3,3-dimethylureido)-6-methoxy-7-methyl-3-oxoisobenzofuran-5-yl]-4-methyl-4-hexenoate; 2-(pyrrolidin-1-yl)ethyl (E)-6-[1,3-dihydro-4-(3-methyl)ureido-6-methoxy-7-methyl-3-oxoisobenzofuran-5-yl]-4-methyl-4-hexenoate; 2-(piperidin-1-yl) ethyl (E)-6-[1,3-dihydro-4-(3-methyl)ureido-6-methoxy-7-methyl-3-oxoisobenzofuran-5-yl]-4-methyl-4-hexenoate; 2-(thiazolidin-3-yl)ethyl (E)-6-[1,3-dihydro-4-(3-methyl)ureido-6-methoxy-7-methyl-3-oxoisobenzofuran-5-yl]-4-methyl-4-hexenoate; 3-(morpholin-4-yl)propyl (E)-6-[1,3-dihydro-4-(3-methyl)ureido-6-methoxy-7-methyl-3-oxoisobenzofuran-5-yl]-4-methyl-4-hexenoate; 4-(morpholin-4-yl)butyl (E)-6-[1,3-dihydro-4-(3-methyl)ureido-6-methoxy-7-methyl-3-oxoisobenzofuran-5-yl]-4-methyl-4-hexenoate; 2-(imidazolidin-1-yl) ethyl (E)-6-[1,3-dihydro-4-(3-methyl)ureido-6-methoxy-7-methyl-3-oxoisobenzofuran-5-yl]-4-methyl-4-hexenoate; 2-(2-methyl-1,2-pyrazolidin-1-yl)ethyl (E)-6-[1,3-dihydro-4-(3-methyl)ureido-6-methoxy-7-methyl-3-oxoisobenzofuran-5-yl]-4-methyl-4-hexenoate; 2-(pyrrolidin-1-yl)ethyl (E)-6-(1,3-dihydro-4-ureido-6-methoxy-7-methyl-3-oxoisobenzofuran-5-yl)-4-methyl-4-hexenoate; 2-(piperidin-1-yl) ethyl (E)-6-(1,3-dihydro-4-ureido-6-methoxy-7-methyl-3-oxoisobenzofuran-5-yl)-4-methyl-4-hexenoate, 2-(thiazolidin-3-yl)ethyl (E)-6-(1,3-dihydro-4-ureido-6-methoxy-7-methyl-3-oxoisobenzofuran-5-yl)-4-methyl-4-hexenoate; 3-(morpholin-4-yl)propyl (E)-6-(1,3-dihydro-4-ureido-6-methoxy-7-methyl-3-oxoisobenzofuran-5-yl)-4-methyl-4-hexenoate; 4-(morpholin-4-yl)butyl (E)-6-(1,3-dihydro-4-ureido-6-methoxy-7-methyl-3-oxoisobenzofuran-5-yl)-4-methyl-4-hexenoate; 2-(imidazolidin-1-yl)ethyl (E)-6-(1,3-dihydro-4-ureido-6-methoxy-7-methyl-3-oxoisobenzofuran-5-yl)-4-methyl-4-hexenoate; 2-(2-methyl-1,2-pyrazolidin-1-yl)ethyl (E)-6-(1,3-dihydro-4-ureido-6-methoxy-7-methyl-3-oxoisobenzofuran-5-yl)-4-methyl-4-hexenoate; 2-(pyrrolidin-1-yl)ethyl (E)-6-[1,3-dihydro-4-(3,3-diethyl)ureido-6-methoxy-7-methyl-3-oxoisobenzofuran-5-yl]-4-methyl-4-hexenoate; 2-(piperidin-1-yl)ethyl (E)-6-[1,3-dihydro-4-(3,3-diethyl)ureido-6-methoxy-7-methyl-3-oxoisobenzofuran-5-yl]-4-methyl-4-hexenoate; 2-(thiazolidin-3-yl)ethyl (E)-6-[1,3-dihydro-4-(3,3-diethyl)ureido-6-methoxy-7-methyl-3-oxoisobenzofuran-5-yl]-4-methyl-4-hexenoate; 3-(morpholin-4-yl)propyl (E)-6-[1,3-dihydro-4-(3,3-diethyl)ureido-6-methoxy-7-methyl-3-oxoisobenzofuran-5-yl]-4-methyl-4-hexenoate; 4-(morpholin-4-yl)butyl (E)-6-[1,3-dihydro-4-(3,3-diethyl)ureido-6-methoxy-7-methyl-3-oxoisobenzofuran-5-yl]-4-methyl-4-hexenoate; 2-(imidazolidin-1-yl)ethyl (E)-6-[1,3-dihydro-4-(3,3-diethyl)ureido-6-methoxy-7-methyl-3-oxoisobenzofuran-5-yl]-4-methyl-4-hexenoate; 2-(2-methyl-1,2-pyrazolidin-1-yl)ethyl (E)-6-[1,3-dihydro-4-(3,3-diethyl)ureido-6-methoxy-7-methyl-3-oxoisobenzofuran-5-yl]-4-methyl-4-hexenoate; 2-(pyrrolidin-1-yl)ethyl (E)-6-[1,3-dihydro-4-(3-ethyl)ureido-6-methoxy-7-methyl-3-oxoisobenzofuran-5-yl]-4-methyl-4-hexenoate; 2-(piperidin-1-yl)ethyl (E)-6-[1,3-dihydro-4-(3-ethyl)ureido-6-methoxy-7-methyl-3-oxoisobenzofuran-5-yl]-4-methyl-4-hexenoate; 2-(thiazolidin-3-yl)ethyl (E)-6-[1,3-dihydro-4-(3-ethyl)ureido-6-methoxy-7-methyl-3-oxoisobenzofuran-5-yl]-4-methyl-4-hexenoate; 3-(morpholin-4-yl)propyl (E)-6-[1,3-dihydro-4-(3-ethyl)ureido-6-methoxy-7-methyl-3-oxoisobenzofuran-5-yl]-4-methyl-4-hexenoate; 4-(morpholin-4-yl)butyl (E)-6-[1,3-dihydro-4-(3-ethyl)ureido-6-methoxy-7-methyl-3-oxoisobenzofuran-5-yl]-4-methyl-4-hexenoate; 2-(imidazolidin-1-yl)ethyl (E)-6-[1,3-dihydro-4-(3-ethyl)ureido-6-methoxy-7-methyl-3-oxoisobenzofuran-5-yl]-4-methyl-4-hexenoate; 2-(2-methyl-1,2-pyrazolidin-1-yl)ethyl (E)-6-[1,3-dihydro-4-(3-ethyl)ureido-6-methoxy-7-methyl-3-oxoisobenzofuran-5-yl]-4-methyl-4-hexenoate; 2-(pyrrolidin-1-yl)ethyl (E)-6-[13-dihydro-4-(3-methyl-3-ethyl)ureido-6-methoxy-7-methyl-3-oxoisobenzofuran-5-yl]-4-methyl-4-hexenoate; 2-(piperidin-1-yl)ethyl (E)-6-[1,3-dihydro-4-(3-methyl-3-ethyl)ureido-6-methoxy-7-methyl-3-oxoisobenzofuran-5-yl]-4-methyl-4-hexenoate; 2-(thiazolidin-3-yl)ethyl (E)-6-[1,3-dihydro-4-(3-methyl-3-ethyl)ureido-6-methoxy-7-methyl-3-oxoisobenzofuran-5-yl]-4-methyl-4-hexenoate; 3-(morpholin-4-yl)propyl (E)-6-[1,3-dihydro-4-(3-methyl-3-ethyl)ureido-6-methoxy-7-methyl-3-oxoisobenzofuran-5-yl]-4-methyl-4-hexenoate; 4-(morpholin-4-yl)butyl (E)-6-[1,3-dihydro-4-(3-methyl-3-ethyl)ureido-6-methoxy-7-methyl-3-oxoisobenzofuran-5-yl]-4-methyl-4-hexenoate; 2-(imidazolidin-1-yl)ethyl (E)-6-[1,3-dihydro-4-(3-methyl-3-ethyl)ureido-6-methoxy-7-methyl-3-oxoisobenzofuran-5-yl]-4-methyl-4-hexenoate; 2-(2-methyl-1,2-pyrazolidin-1-yl)ethyl (E)-6-[1,3-dihydro-4-(3-methyl-3-ethyl)ureido-6-methoxy-7-methyl-3-oxoisobenzofuran-5-yl]-4-methyl-4-hexenoate; 2-(pyrrolidin-1-yl)ethyl (E)-6-[1,3-dihydro-4-(3,3-diphenyl)ureido-6-methoxy-7-methyl-3-oxoisobenzofuran-5-yl]-4-methyl-4-hexenoate; 2-(piperidin-1-yl)ethyl (E)-6-[1,3-dihydro-4-(3,3-diphenyl)ureido-6-methoxy-7-methyl-3-oxoisobenzofuran-5-yl]-4-methyl-4-hexenoate; 2-(thiazolidin-3-yl)ethyl (E)-6-[1,3-dihydro-4-(3,3-diphenyl)ureido-6-methoxy-7-methyl-3-oxoisobenzofuran-5-yl]-4-methyl-4-hexenoate; 3-(morpholin-4-yl)propyl (E)-6-[1,3-dihydro-4-(3,3-diphenyl)ureido-6-methoxy-7-methyl-3-oxoisobenzofuran-5-yl]-4-methyl-4-hexenoate; 4-(morpholin-4-yl)butyl (E)-6-[1,3-dihydro-4-(3,3-diphenyl)ureido-6-methoxy-7-methyl-3-oxoisobenzofuran-5-yl]-4-methyl-4-hexenoate; 2-(imidazolidin-1-yl)ethyl (E)-6-[1,3-dihydro-4-(3,3-diphenyl)ureido-6-methoxy-7-methyl-3-oxoisobenzofuran-5-yl]-4-methyl-4-hexenoate; 2-(2-methyl-1,2-pyrazolidin-1-yl)ethyl (E)-6-[1,3-dihydro-4-(3,3-diphenyl)ureido-6-methoxy-7-methyl-3-oxoisobenzofuran-5-yl]-4-methyl-4-hexenoate; 2-(pyrrolidin-1-yl)ethyl (E)-6-[1,3-dihydro-4-(3-phenyl)ureido-6-methoxy-7-methyl-3-oxoisobenzofuran-5-yl]-4-methyl-4-hexenoate; 2-(piperidin-1-yl)ethyl (E)-6-[1,3-dihydro-4-(3-phenyl)ureido-6-methoxy-7-methyl-3-oxoisobenzofuran-5-yl]-4-methyl-4-hexenoate; 2-(thiazolidin-3-yl)ethyl (E)-6-[1,3-dihydro-4-(3-phenyl)ureido-6-methoxy-7-methyl-3-oxoisobenzofuran-5-yl]-4-methyl-4-hexenoate; 3-(morpholin-4-yl)propyl (E)-6-[1,3-dihydro-4-(3-phenyl)ureido-6-methoxy-7-methyl-3-oxoisobenzofuran-5-yl]-4-methyl-4-hexenoate; 4-(morpholin-4-yl)butyl (E)-6-[1,3-dihydro-4-(3-phenyl)ureido-6-methoxy-7-methyl-3-oxoisobenzofuran-5-yl]-4-methyl-4-hexenoate; 2-(imidazolidin-1-yl)ethyl (E)-6-[1,3-dihydro-4-(3-phenyl)ureido-6-methoxy-7-methyl-3-oxoisobenzofuran-5-yl]-4-methyl-4-hexenoate; 2-(2-methyl-1,2-pyrazolidin-1-yl)ethyl (E)-6-[1,3-dihydro-4-(3-phenyl)ureido-6-methoxy-7-methyl-3-oxoisobenzofuran-5-yl]-4-methyl-4-hexenoate; 2-(pyrrolidin-1-yl)ethyl (E)-6-[1,3-dihydro-4-(3-methyl-3-phenyl)ureido-6-methoxy-7-methyl-3-oxoisobenzofuran-5-yl]-4-methyl-4-hexenoate; 2-(piperidin-1-yl)ethyl (E)-6-[1,3-dihydro-4-(3-methyl-3-phenyl)ureido-6-methoxy-7-methyl-3-oxoisobenzofuran-5-yl]-4-methyl-4-hexenoate; 2-(thiazolidin-3-yl)ethyl (E)-6-[1,3-dihydro-4-(3-methyl-3-phenyl)ureido-6-methoxy-7-methyl-3-oxoisobenzofuran-5-yl]-4-methyl-4-hexenoate; 3-(morpholin-4-yl) propyl (E)-6-[1,3-dihydro-4-(3-methyl-3-phenyl)ureido-6-methoxy-7-methyl-3-oxoisobenzofuran-5-yl]-4-methyl-4-hexenoate; 4-(morpholin-4-yl)butyl (E)-6-[1,3-dihydro-4-(3-methyl-3-phenyl)ureido-6-methoxy-7-methyl-3-oxoisobenzofuran-5-yl]-4-methyl-4-hexenoate; 2-(imidazolidin-1-yl)ethyl (E)-6-[1,3-dihydro-4-(3-methyl-3-phenyl)ureido-6-methoxy-7-methyl-3-oxoisobenzofuran-5-yl]-4-methyl-4-hexenoate; 2-(2-methyl-1,2-pyrazolidin-1-yl)ethyl (E)-6-[1,3-dihydro-4-(3-methyl-3-phenyl)ureido-6-methoxy-7-methyl-3-oxoisobenzofuran-5-yl]-4-methyl-4-hexenoate; 2-(pyrrolidin-1-yl)ethyl (E)-6-[1,3-dihydro-4-(3-butyl-3-propyl)ureido-6-methoxy-7-methyl-3-oxoisobenzofuran-5-yl]-4-methyl-4-hexenoate; 2-(piperidin-1-yl)ethyl (E)-6-[1,3-dihydro-4-(3-butyl-3-propyl)ureido-6-methoxy-7-methyl-3-oxoisobenzofuran-5-yl]-4-methyl-4-hexenoate; 2-(thiazolidin-3-yl)ethyl (E)-6-[1,3-dihydro-4-(3-butyl-3-propyl)ureido-6-methoxy-7-methyl-3-oxoisobenzofuran-5-yl]-4-methyl-4-hexenoate; 3-(morpholin-4-yl) propyl (E)-6-[1,3-dihydro-4-(3-butyl-3-propyl)ureido-6-methoxy-7-methyl-3-oxoisobenzofuran-5-yl]-4-methyl-4-hexenoate; 4-(morpholin-4-yl)butyl (E)-6-[1,3-dihydro-4-(3-butyl-3-propyl)ureido-6-methoxy-7-methyl-3-oxoisobenzofuran-5-yl]-4-methyl-4-hexenoate; 2-(imidazolidin-1-yl)ethyl (E)-6-[1,3-dihydro-4-(3-butyl-3-propyl)ureido-6-methoxy-7-methyl-3-oxoisobenzofuran-5-yl]-4-methyl-4-hexenoate; 2-(2-methyl-1,2-pyrazolidin-1-yl)ethyl (E)-6-[1,3-dihydro-4-(3-butyl-3-propyl)ureido-6-methoxy-7-methyl-3-oxoisobenzofuran-5-yl]-4-methyl-4-hexenoate; 2-(pyrrolidin-1-yl)ethyl (E)-6-[1,3-dihydro-4-(3-(2-chlorophenyl)ureido)-6-methoxy-7-methyl-3-oxoisobenzofuran-5-yl]-4-methyl-4-hexenoate; 2-(piperidin-1-yl)ethyl (E)-6-[1,3-dihydro-4-3-(2-chlorophenyl)ureido)-6-methoxy-7-methyl-3-oxoisobenzofuran-5-yl]-4-methyl-4-hexenoate; 2-(thiazolidin-3-yl)ethyl (E)-6-[1,3-dihydro-4-(3-(2-chlorophenyl)ureido)-6-methoxy-7-methyl-3-oxoisobenzofuran-5-yl]-4-methyl-4-hexenoate; 3-(morpholin-4-yl)propyl (E)-6-[1,3-dihydro-4-(3-

(2-chlorophenyl)ureido)-6-methoxy-7-methyl-3-oxoisobenzofuran-5-yl]-4-methyl-4-hexenoate; 4-(morpholin-4-yl)butyl (E)-6-[1,3-dihydro-4-(3-(2-chlorophenyl)ureido)-6-methoxy-7-methyl-3-oxoisobenzofuran-5-yl]-4-methyl-4-hexenoate; 2-(imidazolidin-1-yl)ethyl (E)-6-[1,3-dihydro-4-(3-(2-chlorophenyl)ureido)-6-methoxy-7-methyl-3-oxoisobenzofuran-5-yl]-4-methyl-4-hexenoate; 2-(2-methyl-1,2-pyrazolidin-1-yl)ethyl (E)-6-[1,3-dihydro-4-(3-(2-chlorophenyl)ureido)-6-methoxy-7-methyl-3-oxoisobenzofuran-5-yl]-4-methyl-4-hexenoate; methyl (E)-6-[1,3-dihydro-4-(difluoroacetyl)amino-6-methoxy-7-methyl-3-oxoisobenzofuran-5-yl]-4-methyl-4-hexenoate; methyl (E)-6-[1,3-dihydro-4-(fluoroacetyl)amino-6-methoxy-7-methyl-3-oxoisobenzofuran-5-yl]-4-methyl-4-hexenoate; methyl (E)-6-[1,3-dihydro-4-(trichloroacetyl)amino-6-methoxy-7-methyl-3-oxoisobenzofuran-5-yl]-4-methyl-4-hexenoate; methyl (E)-6-[1,3-dihydro-4-(fluorodichloroacetyl)amino-6-methoxy-7-methyl-3-oxoisobenzofuran-5-yl]-4-methyl-4-hexenoate; (E)-6-[1,3-dihydro-4-(difluoroacetyl)amino-6-methoxy-7-methyl-3-oxoisobenzofuran-5-yl]-4-methyl-4-hexenoic acid; (E)-6-[1,3-dihydro-4-(fluoroacetyl)amino-6-methoxy-7-methyl-3-oxoisobenzofuran-5-yl]-4-methyl-4-hexenoic acid; (E)-6-[1,3-dihydro-4-(trichloroacetyl)amino-6-methoxy-7-methyl-3-oxoisobenzofuran-5-yl]-4-methyl-4-hexenoic acid; (E)-6-[1,3-dihydro-4-(fluorodichloroacetyl)amino-6-methoxy-7-methyl-3-oxoisobenzofuran-5-yl]-4-methyl-4-hexenoic acid; methyl E-6-[1,3-dihydro-4-(trifluoroacetyl)amino-6-methoxy-7-methyl-3-oxoisobenzofuran-5-yl]-4-methyl-4-hexenoate; methyl (E)-6-[1,3-dihydro-4-(difluoroacetyl)amino-6-methoxy-7-methyl-3-oxoisobenzofuran-5-yl]-4-methyl-4-hexenoate; methyl (E)-6-[1,3-dihydro-4-(fluoroacetyl)amino-6-methoxy-7-methyl-3-oxoisobenzofuran-5-yl]-4-methyl-4-hexenoate; methyl (E)-6-[1,3-dihydro-4-(trichloroacetyl)amino-6-methoxy-7-methyl-3-oxoisobenzofuran-5-yl]-4-methyl-4-hexenoate; methyl (E)-6-[1,3-dihydro-4-(fluorodichloroacetyl)-amino-6-methoxy-7-methyl-3-oxoisobenzofuran-5-yl]-4-methyl-4-hexenoate; ethyl (E)-6-[1,3-dihydro-4-(trifluoroacetyl)amino-6-methoxy-7-methyl-3-oxoisobenzofuran-5-yl]-4-methyl-4-hexenoate; n-propyl (E)-6-[1,3-dihydro-4-(trifluoroacetyl)amino-6-methoxy-7-methyl-3-oxoisobenzofuran-5-yl]-4-methyl-4-hexenoate; isopropyl (E)-6-[1,3-dihydro-4-(trifluoroacetyl)amino-6-methoxy-7-methyl-3-oxoisobenzofuran-5-yl]-4-methyl-4-hexenoate; t-butyl (E)-6-[1,3-dihydro-4-(trifluoroacetyl)amino-6-methoxy-7-methyl-3-oxoisobenzofuran-5-yl]-4-methyl-4-hexenoate; isoamyl (E)-6-[1,3-dihydro-4-(trifluoroacetyl)amino-6-methoxy-7-methyl-3-oxoisobenzofuran-5-yl]-4-methyl-4-hexenoate; phenyl (E)-6-[1,3-dihydro-4-(trifluoroacetyl)amino-6-methoxy-7-methyl-3-oxoisobenzofuran-5-yl]-4-methyl-4-hexenoate; 2-chlorophenyl (E)-6-[1,3-dihydro-4-(trifluoroacetyl)amino-6-methoxy-7-methyl-3-oxoisobenzofuran-5-yl]-4-methyl-4-hexenoate; 2-trifluoromethylphenyl (E)-6-[1,3-dihydro-4-(trifluoroacetyl)amino-6-methoxy-7-methyl-3-oxoisobenzofuran-5-yl]-4-methyl-4-hexenoate; 2-chloro-3,4-dimethoxyphenyl (E)-6-[1,3-dihydro-4-(trifluoroacetyl)amino-6-methoxy-7-methyl-3-oxoisobenzofuran-5-yl]-4-methyl-4-hexenoate; ethyl (E)-6-[1,3-dihydro-4-(difluoroacetyl)amino-6-methoxy-7-methyl-3-oxoisobenzofuran-5-yl]-4-methyl-4-hexenoate; n-propyl (E)-6-[1,3-dihydro-4-(difluoroacetyl)amino-6-methoxy-7-methyl-3-oxoisobenzofuran-5-yl]-4-methyl-4-hexenoate; isopropyl (E)-6-[1,3-dihydro-4-(difluoroacetyl)amino-6-methoxy-7-methyl-3-oxoisobenzofuran-5-yl]-4-methyl-4-hexenoate; t-butyl (E)-6-[1,3-dihydro-4-(difluoroacetyl)amino-6-methoxy-7-methyl-3-oxoisobenzofuran-5-yl]-4-methyl-4-hexenoate; isoamyl (E)-6-[1,3-dihydro-4-(difluoroacetyl)amino-6-methoxy-7-methyl-3-oxoisobenzofuran-5-yl]-4-methyl-4-hexenoate; phenyl (E)-6-[1,3-dihydro-4-(difluoroacetyl)amino-6-methoxy-7-methyl-3-oxoisobenzofuran-5-yl]-4-methyl-4-hexenoate; 2-chlorophenyl (E)-6-[1,3-dihydro-4-(difluoroacetyl)amino-6-methoxy-7-methyl-3-oxoisobenzofuran-5-yl]-4-methyl-4-hexenoate; 2-trifluoromethylphenyl (E)-6-[1,3-dihydro-4-(difluoroacetyl)amino-6-methoxy-7-methyl-3-oxoisobenzofuran-5-yl]-4-methyl-4-hexenoate; 2-chloro-3,4-dimethoxyphenyl (E)-6-[1,3-dihydro-4-(difluoroacetyl)amino-6-methoxy-7-methyl-3-oxoisobenzofuran-5-yl]-4-methyl-4-hexenoate; ethyl (E)-6-[1,3-dihydro-4-(fluoroacetyl)amino-6-methoxy-7-methyl-3-oxoisobenzofuran-5-yl]-4-methyl-4-hexenoate; n-propyl (E)-6-[1,3-dihydro-4-(fluoroacetyl)amino-6-methoxy-7-methyl-3-oxoisobenzofuran-5-yl]-4-methyl-4-hexenoate; isopropyl (E)-6-[1,3-dihydro-4-(fluoroacetyl)amino-6-methoxy-7-methyl-3-oxoisobenzofuran-5-yl]-4-methyl-4-hexenoate; t-butyl (E)-6-[1,3-dihydro-4-(fluoroacetyl)amino-6-methoxy-7-methyl-3-oxoisobenzofuran-5-yl]-4-methyl-4-hexenoate; isoamyl (E)-6-[1,3-dihydro-4-(fluoroacetyl)amino-6-methoxy-7-methyl-3-oxoisobenzofuran-5-yl]-4-methyl-4-hexenoate; phenyl (E)-6-[1,3-dihydro-4-(fluoroacetyl)amino-6-methoxy-7-methyl-3-oxoisobenzofuran-5-yl]-4-methyl-4-hexenoate; 2-chlorophenyl (E)-6-[1,3-dihydro-4-(fluoroacetyl)amino-6-methoxy-7-methyl-3-oxoisobenzofuran-5-yl]-4-methyl-4-hexenoate; 2-trifluoromethylphenyl (E)-6-[1,3-dihydro-4-(fluoroacetyl)amino-6-methoxy-7-methyl-3-oxoisobenzofuran-5-yl]-4-methyl-4-hexenoate; 2-chloro-3,4-dimethoxyphenyl (E)-6-[1,3-dihydro-4-(fluoroacetyl)amino-6-methoxy-7-methyl-3-oxoisobenzofuran-5-yl]-4-methyl-4-hexenoate; ethyl (E)-6-[1,3-dihydro-4-(trichloroacetyl)amino-6-methoxy-7-methyl-3-oxoisobenzofuran-5-yl]-4-methyl-4-hexenoate; n-propyl (E)-6-[1,3-dihydro-4-(trichloroacetyl)amino-6-methoxy-7-methyl-3-oxoisobenzofuran-5-yl]-4-methyl-4-hexenoate; isopropyl (E)-6-[1,3-dihydro-4-(trichloroacetyl)amino-6-methoxy-7-methyl-3-oxoisobenzofuran-5-yl]-4-methyl-4-hexenoate; t-butyl (E)-6-[1,3-dihydro-4-(trichloroacetyl)amino-6-methoxy-7-methyl-3-oxoisobenzofuran-5-yl]-4-methyl-4-hexenoate; isoamyl (E)-6-[1,3-dihydro-4-(trichloroacetyl)amino-6-methoxy-7-methyl-3-oxoisobenzofuran-5-yl]-4-methyl-4-hexenoate; phenyl (E)-6-[1,3-dihydro-4-(trichloroacetyl)amino-6-methoxy-7-methyl-3-oxoisobenzofuran-5-yl]-4-methyl-4-hexenoate; 2-chlorophenyl (E)-6-[1,3-dihydro-4-(trichloroacetyl)amino-6-methoxy-7-methyl-3-oxoisobenzofuran-5-yl]-4-methyl-4-hexenoate; 2-trifluoromethylphenyl (E)-6-[1,3-dihydro-4-(trichloroacetyl)amino-6-methoxy-7-methyl-3-oxoisobenzofuran-5-yl]-4-methyl-4-hexenoate; 2-chloro-3,4-dimethoxyphenyl (E)-6-[1,3-dihydro-4-(trichloroacetyl)amino-6-methoxy-7-methyl-3-oxoisobenzofuran-5-yl]-4-methyl-4-hexenoate; ethyl (E)-6-[1,3-dihydro-4-(fluorodichloroacetyl)amino-6-methoxy-7-methyl-3-oxoisobenzofuran-5-yl]-4-methyl-4-hexenoate; n-propyl (E)-6-[1,3-dihydro-4-(fluorodichloroacetyl)amino-6-methoxy-7-methyl-3-oxoisobenzofuran-5-yl]-4-methyl-4-hexenoate; isopropyl (E)-6-[1,3-dihydro-4-(fluorodichloroacetyl)amino-6-methoxy-7-methyl-3-oxoisobenzofuran-5-yl]-4-methyl-4-hexenoate; t-butyl (E)-6-[1,3-dihydro-4-(fluorodichloroacetyl)amino-6-methoxy-7-methyl-3-oxoisobenzofuran-5-yl]-4-methyl-4-hexenoate; isoamyl (E)-6-[1,3-dihydro-4-(fluorodichloroacetyl)amino-6-methoxy-7-methyl-3-oxoisobenzofuran-5-yl]-4-methyl-4-hexenoate;

phenyl (E)-6-[1,3-dihydro-4-(fluorodichloroacetyl)amino-6-methoxy-7-methyl-3-oxoisobenzofuran-5-yl]-4-methyl-4-hexenoate; 2-chlorophenyl (E)-6-[1,3-dihydro-4-(fluorodichloroacetyl)amino-6-methoxy-7-methyl-3-oxoisobenzofuran-5-yl]-4-methyl-4-hexenoate; 2-trifluoromethylphenyl (E)-6-[1,3-dihydro-4-(fluorodichloroacetyl)amino-6-methoxy-7-methyl-3-oxoisobenzofuran-5-yl]-4-methyl-4-hexenoate; 2-chloro-3,4-dimethoxyphenyl (E)-6-[1,3-dihydro-4-(fluorodichloroacetyl)amino-6-methoxy-7-methyl-3-oxoisobenzofuran-5-yl]-4-methyl-4-hexenoate; 2-(morpholin-4-yl)ethyl (E)-6-[1,3-dihydro-4-(difluoroacetyl)amino-6-methoxy-7-methyl-3-oxoisobenzofuran-5-yl]-4-methyl-4-hexenoate; 2-(morpholin-4-yl)ethyl (E)-6-[1,3-dihydro-4-(fluoroacetyl)amino-6-methoxy-7-methyl-3-oxoisobenzofuran-5-yl]-4-methyl-4-hexenoate; 2-(morpholin-4-yl)ethyl (E)-6-[1,3-dihydro-4-(trichloroacetyl)amino-6-methoxy-7-methyl-3-oxoisobenzofuran-5-yl]-4-methyl-4-hexenoate; 2-(morpholin-4-yl)ethyl (E)-6-[1,3-dihydro-4-(fluorodichloroacetyl)amino-6-methoxy-7-methyl-3-oxoisobenzofuran-5-yl]-4-methyl-4-hexenoate; 2-(pyrrolidin-1-yl)ethyl (E)-6-[1,3-dihydro-4-(trifluoroacetyl)amino-6-methoxy-7-methyl-3-oxoisobenzofuran-5-yl]-4-methyl-4-hexenoate; 2-(piperidin-1-yl)ethyl (E)-6-[1,3-dihydro-4-(trifluoroacetyl)amino-6-methoxy-7-methyl-3-oxoisobenzofuran-5-yl]-4-methyl-4-hexenoate; 2-(thiazolidin-3-yl)ethyl (E)-6-[1,3-dihydro-4-(trifluoroacetyl)amino-6-methoxy-7-methyl-3-oxoisobenzofuran-5-yl]-4-methyl-4-hexenoate; 3-(morpholin-4-yl)propyl (E)-6-[1,3-dihydro-4-(trifluoroacetyl)amino-6-methoxy-7-methyl-3-oxoisobenzofuran-5-yl]-4-methyl-4-hexenoate; 4-(morpholin-4-yl)butyl (E)-6-[1,3-dihydro-4-(trifluoroacetyl)amino-6-methoxy-7-methyl-3-oxoisobenzofuran-5-yl]-4-methyl-4-hexenoate; 2-(imidazolidin-1-yl)ethyl (E)-6-[1,3-dihydro-4-(trifluoroacetyl)amino-6-methoxy-7-methyl-3-oxoisobenzofuran-5-yl]-4-methyl-4-hexenoate; 2-(2-methyl-1,2-pyrazolidin-1-yl)ethyl (E)-6-[1,3-dihydro-4-(trifluoroacetyl)amino-6-methoxy-7-methyl-3-oxoisobenzofuran-5-yl]-4-methyl-4-hexenoate; 2-(pyrrolidin-1-yl)ethyl (E)-6-[1,3-dihydro-4-(difluoroacetyl)amino-6-methoxy-7-methyl-3-oxoisobenzofuran-5-yl]-4-methyl-4-hexenoate; 2-(piperidin-1-yl)ethyl (E)-6-[1,3-dihydro-4-(difluoroacetyl)amino-6-methoxy-7-methyl-3-oxoisobenzofuran-5-yl]-4-methyl-4-hexenoate; 2-(thiazolidin-3-yl)ethyl (E)-6-[1,3-dihydro-4-(difluoroacetyl)amino-6-methoxy-7-methyl-3-oxoisobenzofuran-5-yl]-4-methyl-4-hexenoate; 3-(morpholin-4-yl)propyl (E)-6-[1,3-dihydro-4-(difluoroacetyl)amino-6-methoxy-7-methyl-3-oxoisobenzofuran-5-yl]-4-methyl-4-hexenoate; 4-(morpholin-4-yl)butyl (E)-6-[1,3-dihydro-4-(difluoroacetyl)amino-6-methoxy-7-methyl-3-oxoisobenzofuran-5-yl]-4-methyl-4-hexenoate; 2-(imidazolidin-1-yl)ethyl (E)-6-[1,3-dihydro-4-(difluoroacetyl)amino-6-methoxy-7-methyl-3-oxoisobenzofuran-5-yl]-4-methyl-4-hexenoate; 2-(2-methyl-1,2-pyrazolidin-1-yl)ethyl (E)-6-[1,3-dihydro-4-(difluoroacetyl)amino-6-methoxy-7-methyl-3-oxoisobenzofuran-5-yl]-4-methyl-4-hexenoate; 2-(pyrrolidin-1-yl)ethyl (E)-6-[1,3-dihydro-4-(fluoroacetyl)amino-6-methoxy-7-methyl-3-oxoisobenzofuran-5-yl]-4-methyl-4-hexenoate; 2-(piperidin-1-yl)ethyl (E)-6-[1,3-dihydro-4-(fluoroacetyl)amino-6-methoxy-7-methyl-3-oxoisobenzofuran-5-yl]-4-methyl-4-hexenoate; 2-(thiazolidin-3-yl)ethyl (E)-6-[1,3-dihydro-4-(fluoroacetyl)amino-6-methoxy-7-methyl-3-oxoisobenzofuran-5-yl]-4-methyl-4-hexenoate; 3-(morpholin-4-yl)propyl (E)-6-[1,3-dihydro-4-(fluoroacetyl)amino-6-methoxy-7-methyl-3-oxoisobenzofuran-5-yl]-4-methyl-4-hexenoate; 4-(morpholin-4-yl)butyl (E)-6-[1,3-dihydro-4-(fluoroacetyl)amino-6-methoxy-7-methyl-3-oxoisobenzofuran-5-yl]-4-methyl-4-hexenoate; 2-(imidazolidin-1-yl)ethyl (E)-6-[1,3-dihydro-4-(fluoroacetyl)amino-6-methoxy-7-methyl-3-oxoisobenzofuran-5-yl]-4-methyl-4-hexenoate; 2-(2-methyl-1,2-pyrazolidin-1-yl)ethyl (E)-6-[1,3-dihydro-4-(fluoroacetyl)amino-6-methoxy-7-methyl-3-oxoisobenzofuran-5-yl]-4-methyl-4-hexenoate; 2-(pyrrolidin-1-yl)ethyl (E)-6-[1,3-dihydro-4-(trichloroacetyl)amino-6-methoxy-7-methyl-3-oxoisobenzofuran-5-yl]-4-methyl-4-hexenoate; 2-(piperidin-1-yl)ethyl (E)-6-[1,3-dihydro-4-(trichloroacetyl)amino-6-methoxy-7-methyl-3-oxoisobenzofuran-5-yl]-4-methyl-4-hexenoate; 2-(thiazolidin-3-yl)ethyl (E)-6-[1,3-dihydro-4-(trichloroacetyl)amino-6-methoxy-7-methyl-3-oxoisobenzofuran-5-yl]-4-methyl-4-hexenoate; 3-(morpholin-4-yl)propyl (E)-6-[1,3-dihydro-4-(trichloroacetyl)amino-6-methoxy-7-methyl-3-oxoisobenzofuran-5-yl]-4-methyl-4-hexenoate; 4-(morpholin-4-yl)butyl (E)-6-[1,3-dihydro-4-(trichloroacetyl)amino-6-methoxy-7-methyl-3-oxoisobenzofuran-5-yl]-4-methyl-4-hexenoate; 2-(imidazolidin-1-yl)ethyl (E)-6-[1,3-dihydro-4-(trichloroacetyl)amino-6-methoxy-7-methyl-3-oxoisobenzofuran-5-yl]-4-methyl-4-hexenoate; 2-(2-methyl-1,2-pyrazolidin-1-yl)ethyl (E)-6-[1,3-dihydro-4-(trichloroacetyl)amino-6-methoxy-7-methyl-3-oxoisobenzofuran-5-yl]-4-methyl-4-hexenoate; 2-(pyrrolidin-1-yl)ethyl (E)-6-[1,3-dihydro-4-(fluorodichloroacetyl) amino-6-methoxy-7-methyl-3-oxoisobenzofuran-5-yl]-4-methyl-4-hexenoate; 2-(piperidin-1-yl)ethyl (E)-6-[1,3-dihydro-4-(fluorodichloroacetyl) amino-6-methoxy-7-methyl-3-oxoisobenzofuran-5-yl]-4-methyl-4-hexenoate; 2-(thiazolidin-3-yl)ethyl (E)-6-[1,3-dihydro-4-(fluorodichloroacetyl)amino-6-methoxy-7-methyl-3-oxoisobenzofuran-5-yl]-4-methyl-4-hexenoate; 3-(morpholin-4-yl)propyl (E)-6-[1,3-dihydro-4-(fluorodichloroacetyl)amino-6-methoxy-7-methyl-3-oxoisobenzofuran-5-yl]-4-methyl-4-hexenoate; 4-(morpholin-4-yl)butyl (E)-6-[1,3-dihydro-4-(fluorodichloroacetyl)amino-6-methoxy-7-methyl-3-oxoisobenzofuran-5-yl]-4-methyl-4-hexenoate; 2-(imidazolidin-1-yl)ethyl (E)-6-[1,3-dihydro-4-(fluorodichloroacetyl)amino-6-methoxy-7-methyl-3-oxoisobenzofuran-5-yl]-4-methyl-4-hexenoate; 2-(2-methyl-1,2-pyrazolidin-1-yl)ethyl (E)-6-[1,3-dihydro-4-(fluorodichloroacetyl)amino-6-methoxy-7-methyl-3-oxoisobenzofuran-5-yl]-4-methyl-4-hexenoate; methyl (E)-6-[1,3-dihydro-4-(N-(trifluoroacetyl)-N-ethyl)amino-6-methoxy-7-methyl-3-oxoisobenzofuran-5-yl]-4-methyl-4-hexenoate; methyl (E)-6-[1,3-dihydro-4-(N-(trifluoroacetyl)-N-isopropyl)amino-6-methoxy-7-methyl-3-oxoisobenzofuran-5-yl]-4-methyl-4-hexenoate; (E)-6-[1,3-dihydro-4-(N-(trifluoroacetyl)-N-ethyl)amino-6-methoxy-7-methyl-3-oxoisobenzofuran-5-yl]-4-methyl-4-hexenoic acid; (E)-6-[1,3-dihydro-4-(N-(trifluoroacetyl)-N-isopropyl)amino-6-methoxy-7-methyl-3-oxoisobenzofuran-5-yl]-4-methyl-4-hexenoic acid; methyl (E)-6-[1,3-dihydro-4-(N-(trifluoroacetyl)-N-methyl)amino-6-methoxy-7-methyl-3-oxoisobenzofuran-5-yl]-4-methyl-4-hexenoate; methyl (E)-6-[1,3-dihydro-4-(N-(trifluoroacetyl)-N-ethyl)amino-6-methoxy-7-methyl-3-oxoisobenzofuran-5-yl]-4-methyl-4-hexenoate; methyl (E)-6-[1,3-dihydro-4-(N-(trifluoroacetyl)-N-isopropyl)amino-6-methoxy-7-methyl-3-oxoisobenzofuran-5-yl]-4-methyl-4-hexenoate; ethyl (E)-6-[1,3-dihydro-4-(N-(trifluoroacetyl)-N-methyl)amino-6-methoxy-7-methyl-3-oxoisobenzofuran-5-yl]-4-methyl-4-hexenoate; n-propyl (E)-6-[1,3-dihydro-4-(N-(trifluoroacetyl)-N-methyl)amino-6-methoxy-7-methyl-3-oxoisobenzofuran-5-yl]-4-methyl-4-hexenoate; isopropyl (E)-6-[1,3-dihydro-4-(N-(trifluoroacetyl)-N-methyl)amino- 6-methoxy-7-methyl-3-oxoisobenzofuran-5-yl]-4-methyl-4-hexenoate; t-butyl (E)-6-[1,3-dihydro-4-(N-(trifluoroacetyl)-N-methyl)amino-6-methoxy-7-methyl-3-oxoisobenzofuran-5-yl]-4-methyl-4-hexenoate; isoamyl (E)-6-[1,3-dihydro-4-(N-(trifluoroacetyl)-N-methyl)amino-6-methoxy-7-methyl-3-oxoisobenzofuran-5-yl]-4-methyl-4-hexenoate; phenyl (E)-6-[1,3-dihydro-4-(N-(trifluoroacetyl)-N-methyl)amino-6-methoxy-7-methyl-3-oxoisobenzofuran-5-yl]-4-methyl-4-hexenoate; 2-chlorophenyl (E)-6-[1,3-dihydro-4-(N-(trifluoroacetyl)-N-methyl)amino-6-methoxy-7-methyl-3-oxoisobenzofuran-5-yl]-4-methyl-4-hexenoate; 2-trifluoromethylphenyl (E)-6-[1,3-dihydro-4-(N-(trifluoroacetyl)-N-methyl)amino-6-methoxy-7-methyl-3-oxoisobenzofuran-5-yl]-4-methyl-4-hexenoate; 2-chloro-3,4-dimethoxyphenyl (E)-6-[1,3-dihydro-4-(N-(trifluoroacetyl)-N-methyl)amino-6-methoxy-7-methyl-3-oxoisobenzofuran-5-yl]-4-methyl-4-hexenoate; ethyl (E)-6-[1,3-dihydro-4-(N-(trifluoroacetyl)-N-ethyl)amino-6-methoxy-7-methyl-3-oxoisobenzofuran-5-yl]-4-methyl-4-hexenoate; n-propyl (E)-6-[1,3-dihydro-4-(N-(trifluoroacetyl)-N-ethyl)amino-6-methoxy-7-methyl-3-oxoisobenzofuran-5-yl]-4-methyl-4-hexenoate; isopropyl (E)-6-[1,3-dihydro-4-(N-(trifluoroacetyl)-N-ethyl)amino-6-methoxy-7-methyl-3-oxoisobenzofuran-5-yl]-4-methyl-4-hexenoate; t-butyl (E)-6-[1,3-dihydro-4-(N-(trifluoroacetyl)-N-ethyl)amino-6-methoxy-7-methyl-3-oxoisobenzofuran-5-yl]-4-methyl-4-hexenoate; isoamyl (E)-6-[1,3-dihydro-4-(N-(trifluoroacetyl)-N-ethyl)amino-6-methoxy-7-methyl-3-oxoisobenzofuran-5-yl]-4-methyl-4-hexenoate; phenyl (E)-6-[1,3-dihydro-4-(N-(trifluoroacetyl)-N-ethyl)amino-6-methoxy-7-methyl-3-oxoisobenzofuran-5-yl]-4-methyl-4-hexenoate; 2-chlorophenyl (E)-6-[1,3-dihydro-4-(N-(trifluoroacetyl)-N-ethyl)amino-6-[1,3-dihydro-4-(N-(trifluoroacetyl)-N-ethyl)amino-6-methoxy-7-methyl-3-oxoisobenzofuran-5-yl]-4-methyl-4-hexenoate; 2-chloro-3,4-dimethoxyphenyl (E)-6-[1,3-dihydro-4-(N-(trifluoroacetyl)-N-ethyl)amino-6-methoxy-7-methyl-3-oxoisobenzofuran-5-yl]-4-methyl-4-hexenoate; ethyl (E)-6-[1,3-dihydro-4-(N-(trifluoroacetyl)-N-isopropyl)amino-6-methoxy-7-methyl-3-oxoisobenzofuran-5-yl]-4-methyl-4-hexenoate; n-propyl (E)-6-[1,3-dihydro-4-(N-(trifluoroacetyl)-N-isopropyl)amino-6-methoxy-7-methyl-3-oxoisobenzofuran-5-yl]-4-methyl-4-hexenoate; isopropyl (E)-6-[1,3-dihydro-4-(N-(trifluoroacetyl)-N-isopropyl)amino-6-methoxy-7-methyl-3-oxoisobenzofuran-5-yl]-4-methyl-4-hexenoate; t-butyl (E)-6-[1,3-dihydro-4-(N-(trifluoroacetyl)-N-isopropyl)amino-6-methoxy-7-methyl-3-oxoisobenzofuran-5-yl]-4-methyl-4-hexenoate; isoamyl (E)-6-[1,3-dihydro-4-(N-(trifluoroacetyl)-N-isopropyl)amino-6-methoxy-7-methyl-3-oxoisobenzofuran-5-yl]-4-methyl-4-hexenoate; phenyl (E)-6-[1,3-dihydro-4-(N-(trifluoroacetyl)-N-isopropyl)amino-6-methoxy-7-methyl-3-oxoisobenzofuran-5-yl]-4-methyl-4-hexenoate; 2-chlorophenyl (E)-6-[1,3-dihydro-4-(N-(trifluoroacetyl)-N-isopropyl)amino-6-methoxy-7-methyl-3-oxoisobenzofuran-5-yl]-4-methyl-4-hexenoate; 2-trifluoromethylphenyl (E)-6-[1,3-dihydro-4-(N-(trifluoroacetyl)-N-isopropyl)amino-6-methoxy-7-methyl-3-oxoisobenzofuran-5-yl]-4-methyl-4-hexenoate; 2-chloro-3,4-dimethoxyphenyl (E)-6-[1,3-dihydro-4-(N-(trifluoroacetyl)-N-isopropyl)amino-6-methoxy-7-methyl-3-oxoisobenzofuran-5-yl]-4-methyl-4-hexenoate; 2-(morpholin-4-yl)ethyl (E)-6-[1,3-dihydro-4-(N-(trifluoroacetyl)-N-methyl)amino-6-methoxy-7-methyl-3-oxoisobenzofuran-5-yl]-4-methyl-4-hexenoate; 2-(morpholin-4-yl)ethyl (E)-6-[1,3-dihydro-4-(N-(trifluoroacetyl)-N-ethyl)amino-6-methoxy-7-methyl-3-oxoisobenzofuran-5-yl]-4-methyl-4-hexenoate; 2-(morpholin-4-yl)ethyl (E)-6-[1,3-dihydro-4-(N-(trifluoroacetyl)-N-isopropyl)amino-6-methoxy-7-methyl-3-oxoisobenzofuran-5-yl]-4-methyl-4-hexenoate; 2-(pyrrolidin-1-yl)ethyl (E)-6-[1,3-dihydro-4-(N-(trifluoroacetyl)-N-methyl)amino-6-methoxy-7-methyl-3-oxoisobenzofuran-5-yl]-4-methyl-4-hexenoate; 2-(piperidin-1-yl)ethyl (E)-6-[1,3-dihydro-4-(N-(trifluoroacetyl)-N-methyl)amino-6-methoxy-7-methyl-3-oxoisobenzofuran-5-yl]-4-methyl-4-hexenoate; 2-(thiazolidin-3-yl)ethyl (E)-6-[1,3-dihydro-4-(N-(trifluoroacetyl)-N-methyl)amino-6-methoxy-7-methyl-3-oxoisobenzofuran-5-yl]-4-methyl-4-hexenoate; 3-(morpholin-4-yl)propyl (E)-6-[13-dihydro-4-(N-(trifluoroacetyl)-N-methyl)amino-6-methoxy-7-methyl-3-oxoisobenzofuran-5-yl]-4-methyl-4-hexenoate; 4-(morpholin-4-yl)butyl (E)-6-[1,3-dihydro-4-(N-(trifluoroacetyl)-N-methyl)amino-6-methoxy-7-methyl-3-oxoisobenzofuran-5-yl]-4-methyl-4-hexenoate; 2-(imidazolidin-1-yl)ethyl (E)-6-1,3-dihydro-4-(N-(trifluoroacetyl)-N-methyl)amino-6-methoxy-7-methyl-3-oxoisobenzofuran-5-yl]-4-methyl-4-hexenoate; 2-(2-methyl-1,2-pyrazolidin-1-yl)ethyl (E)-6-[1,3-dihydro-4-(N-(trifluoroacetyl)-N-methyl)amino-6-methoxy-7-methyl-3-oxoisobenzofuran-5-yl]-4-methyl-4-hexenoate; 2-(pyrrolidin-1-yl)ethyl (E)-6-[1,3-dihydro-4-(N-(trifluoroacetyl)-N-ethyl)amino-6-methoxy-7-methyl-3-oxoisobenzofuran-5-yl]-4-methyl-4-hexenoate; 2-(piperidin-1-yl)ethyl (E)-6-[1,3-dihydro-4-(N-(trifluoroacetyl)-N-ethyl)amino-6-methoxy-7-methyl-3-oxoisobenzofuran-5-yl]-4-methyl-4-hexenoate; 2-(thiazolidin-3-yl)ethyl (E)-6-[1,3-dihydro-4-(N-(trifluoroacetyl)-N-ethyl)amino-6-methoxy-7-methyl-3-oxoisobenzofuran-5-yl]-4-methyl-4-hexenoate; 3-(morpholin-4-yl)propyl (E)-6-[1,3-dihydro-4-(N-(trifluoroacetyl) N-ethyl)amino-6-methoxy-7-methyl-3-oxoisobenzofuran-5-yl]-4-methyl-4-hexenoate; 4-(morpholin-4-yl)butyl (E)-6-[1,3-dihydro-4-(N-(trifluoroacetyl)-N-ethyl)amino-6-methoxy-7-methyl-3-oxoisobenzofuran-5-yl]-4-methyl-4-hexenoate; 2-(imidazolidin-1-yl)ethyl (E)-6-[1,3-dihydro-4-(N-(trifluoroacetyl)-N-ethyl)amino-6-methoxy-7-methyl-3-oxoisobenzofuran-5-yl]-4-methyl-4-hexenoate; 2-(2-methyl-1,2-pyrazolidin-1-yl)ethyl (E)-6-[1,3-dihydro-4-(N-(trifluoroacetyl)-N-ethyl)amino-6-methoxy-7-methyl-3-oxoisobenzofuran-5-yl]-4-methyl-4-hexenoate; 2-(pyrrolidin-1-yl)ethyl (E)-6-[1,3-dihydro-4-(N-(trifluoroacetyl)-N-isopropyl)amino-6-methoxy-7-methyl-3-oxoisobenzofuran-5-yl]-4-methyl-4-hexenoate; 2-(piperidin-1-yl)ethyl (E)-6-[1,3-dihydro-4-(N-(trifluoroacetyl)-N-isopropyl)amino-6-methoxy-7-methyl-3-oxoisobenzofuran-5-yl]-4-methyl-4-hexenoate; 2-(thiazolidin-3-yl)ethyl (E)-6-[1,3-dihydro-4-(N-(trifluoroacetyl)-N-isopropyl)amino-6-methoxy-7-methyl-3-oxoisobenzofuran-5-yl]-4-methyl-4-hexenoate; 3-(morpholin-4-yl) propyl (E)-6-[1,3-dihydro-4-(N-(trifluoroacetyl)-N-isopropyl)amino-6-methoxy-7-methyl-3-oxoisobenzofuran-5-yl]-4-methyl-4-hexenoate; 4-(morpholin-4-yl)butyl (E)-6-[1,3-dihydro-4-(N-(trifluoroacetyl)-N-isopropyl)amino-6-methoxy-7-methyl-3-oxoisobenzofuran-5-yl]-4-methyl-4-hexenoate; 2-(imidazolidin-1-yl)ethyl (E)-6-[1,3-dihydro-4-(N-(trifluoroacetyl)-N-isopropyl)amino-6-methoxy-7-methyl-3-oxoisobenzofuran-5-yl]-4-methyl-4-hexenoate; 2-(2-methyl-1,2-pyrazolidin-1-yl)ethyl (E)-6-[1,3-dihydro-4-(N-(trifluoroacetyl)-N-isopropyl)amino-6-methoxy-7-methyl-3-oxoisobenzofuran 5-yl]-4-methyl-4-hexenoate; (E)-6-(1,3-dihydro-4-ethylamino-6-methoxy-7-methyl-3-oxoisobenzofuran-5-yl)-4-methyl-4-hexenoic acid; (E)-6-(1,3-dihydro-4-isopropylamino-6-methoxy-7-methyl-3-oxoisobenzofuran-5-yl)-4-methyl-4-hexenoic acid; methyl (E)-6-(1,3-dihydro-4-methylamino-6-methoxy-7-methyl-3-oxoisobenzofuran-5-yl)-4-methyl-4-hexenoate; methyl (E)-

6-(1,3-dihydro-4-ethylamino-6-methoxy-7-methyl-3-oxoisobenzofuran-5-yl)-4-methyl-4-hexenoic acid; methyl (E)-6-(1,3-dihydro-4-isopropylamino-6-methoxy-7-methyl-3-oxoisobenzofuran-5-yl)-4-methyl-4-hexenoic acid; ethyl (E)-6-(1,3-dihydro-4-methylamino-6-methoxy-7-methyl-3-oxoisobenzofuran-5-yl)-4-methyl-4-hexenoate; n-propyl (E)-6-(1,3-dihydro-4-methylamino-6-methoxy-7-methyl-3-oxoisobenzofuran-5-yl)-4-methyl-4-hexenoate; isopropyl (E)-6-(1,3-dihydro-4-methylamino-6-methoxy-7-methyl-3-oxoisobenzofuran-5-yl)-4-methyl-4-hexenoate; t-butyl (E)-6-(1,3-dihydro-4-methylamino-6-methoxy-7-methyl-3-oxoisobenzofuran-5-yl)-4-methyl-4-hexenoate; isoamyl (E)-6-(1,3-dihydro-4-methylamino-6-methoxy-7-methyl-3-oxoisobenzofuran-5-yl)-4-methyl-4-hexenoate; phenyl (E)-6-(1,3-dihydro-4-methylamino-6-methoxy-7-methyl-3-oxoisobenzofuran-5-yl)-4-methyl-4-hexenoate; 2-chlorophenyl (E)-6-(1,3-dihydro-4-methylamino-6-methoxy-7-methyl-3-oxoisobenzofuran-5-yl)-4-methyl-4-hexenoate; 2-trifluoromethylphenyl (E)-6-(1,3-dihydro-4-methylamino-6-methoxy-7-methyl-3-oxoisobenzofuran-5-yl)-4-methyl-4-hexenoate; 2-chloro-3,4-dimethoxyphenyl (E)-6-(1,3-dihydro-4-methylamino-6-methoxy-7-methyl-3-oxoisobenzofuran-5-yl)-4-methyl-4-hexenoate; ethyl (E)-6-(1,3-dihydro-4-ethylamino-6-methoxy-7-methyl-3-oxoisobenzofuran-5-yl)-4-methyl-4-hexenoate; n-propyl (E)-6-(1,3-dihydro-4-ethylamino-6-methoxy-7-methyl-3-oxoisobenzofuran-5-yl)-4-methyl-4-hexenoate; isopropyl (E)-6-(1,3-dihydro-4-ethylamino-6-methoxy-7-methyl-3-oxoisobenzofuran-5-yl)-4-methyl-4-hexenoate; t-butyl (E)-6-(1,3-dihydro-4-ethylamino-6-methoxy-7-methyl-3-oxoisobenzofuran-5-yl)-4-methyl-4-hexenoate; isoamyl (E)-6-(1,3-dihydro-4-ethylamino-6-methoxy-7-methyl-3-oxoisobenzofuran-5-yl)-4-methyl-4-hexenoate; phenyl (E)-6-(1,3-dihydro-4-ethylamino-6-methoxy-7-methyl-3-oxoisobenzofuran-5-yl)-4-methyl-4-hexenoate; 2-chlorophenyl (E)-6-(1,3-dihydro-4-ethylamino-6-methoxy-7-methyl-3-oxoisobenzofuran-5-yl)-4-methyl-4-hexenoate; 2-trifluoromethylphenyl (E)-6-(1,3-dihydro-4-ethylamino-6-methoxy-7-methyl-3-oxoisobenzofuran-5-yl)-4-methyl-4-hexenoate; 2-chloro-3,4-dimethoxyphenyl (E)-6-(1,3-dihydro-4-ethylamino-6-methoxy-7-methyl-3-oxoisobenzofuran-5-yl)-4-methyl-4-hexenoate; ethyl (E)-6-(1,3-dihydro-4-isopropylamino-6-methoxy-7-methyl-3-oxoisobenzofuran-5-yl)-4-methyl-4-hexenoate; n-propyl (E)-6-(1,3-dihydro-4-isopropylamino-6-methoxy-7-methyl-3-oxoisobenzofuran-5-yl)-4-methyl-4-hexenoate; isopropyl (E)-6-(1,3-dihydro-4-isopropylamino-6-methoxy-7-methyl-3-oxoisobenzofuran-5-yl)-4-methyl-4-hexenoate; t-butyl (E)-6-(1,3-dihydro-4-isopropylamino-6-methoxy-7-methyl-3-oxoisobenzofuran-5-yl)-4-methyl-4-hexenoate; isoamyl (E)-6-(1,3-dihydro-4-isopropylamino-6-methoxy-7-methyl-3-oxoisobenzofuran-5-yl)-4-methyl-4-hexenoate; phenyl (E)-6-(1,3-dihydro-4-isopropylamino-6-methoxy-7-methyl-3-oxoisobenzofuran-5-yl)-4-methyl-4-hexenoate; 2-chlorophenyl (E)-6-(1,3-dihydro-4-isopropylamino-6-methoxy-7-methyl-3-oxoisobenzofuran-5-yl)-4-methyl-4-hexenoate; 2-trifluoromethylphenyl (E)-6-(1,3-dihydro-4-isopropylamino-6-methoxy-7-methyl-3-oxoisobenzofuran-5-yl)-4-methyl-4-hexenoate; 2-chloro-3,4-dimethoxyphenyl (E)-6-(1,3-dihydro-4-isopropylamino-6-methoxy-7-methyl-3-oxoisobenzofuran-5-yl)-4-methyl-4-hexenoate; 2-(morpholin-4-yl)ethyl (E)-6-(1,3-dihydro-4-methylamino-6-methoxy-7-methyl-3-oxoisobenzofuran-5-yl)-4-methyl-4-hexenoate; 2-(morpholin-4-yl)ethyl (E)-6-(1,3-dihydro-4-ethylamino-6-methoxy-7-methyl-3-oxoisobenzofuran-5-yl)-4-methyl-4-hexenoic acid; 2-(morpholin-4-yl)ethyl (E)-6-(1,3-dihydro-4-isopropylamino-6-methoxy-7-methyl-3-oxoisobenzofuran-5-yl)-4-methyl-4-hexenoic acid; 2-(pyrrolidin-1-yl)ethyl (E)-6-(1,3-dihydro-4-methylamino-6-methoxy-7-methyl-3-oxoisobenzofuran-5-yl)-4-methyl-4-hexenoate; 2-(piperidin-1-yl)ethyl (E)-6-(1,3-dihydro-4-methylamino-6-methoxy-7-methyl-3-oxoisobenzofuran-5-yl)-4-methyl-4-hexenoate; 2-(thiazolidin-3-yl)ethyl (E)-6-(1,3-dihydro-4-methylamino-6-methoxy-7-methyl-3-oxoisobenzofuran-5-yl)-4-methyl-4-hexenoate; 3-(morpholin-4-yl)propyl (E)-6-(1,3-dihydro-4-methylamino-6-methoxy-7-methyl-3-oxoisobenzofuran-5-yl)-4-methyl-4-hexenoate; 4-(morpholin-4-yl) butyl (E)-6-(1,3-dihydro-4-methylamino-6-methoxy-7-methyl-3-oxoisobenzofuran-5-yl)-4-methyl-4-hexenoate; 2-(imidazolidin-1-yl)ethyl (E)-6-(1,3-dihydro-4-methylamino-6-methoxy-7-methyl-3-oxoisobenzofuran-5-yl)-4-methyl-4-hexenoate; 2-(2-methyl-1,2-pyrazolidin-1-yl)ethyl (E)-6-(1,3-dihydro-4-methylamino-6-methoxy-7-methyl-3-oxoisobenzofuran-5-yl)-4-methyl-4hexenoate; 2-(pyrrolidin-1-yl)ethyl (E)-6-(1,3-dihydro-4-ethylamino-6-methoxy-7-methyl-3-oxoisobenzofuran-5-yl)-4-methyl-4-hexenoate; 2-(piperidin-1-yl)ethyl (E)-6-(1,3-dihydro-4-ethylamino-6-methoxy-7-methyl-3-oxoisobenzofuran-5-yl)-4-methyl-4-hexenoate; 2-(thiazolidin-3-yl)ethyl (E)-6-(1,3-dihydro-4-ethylamino-6-methoxy-7-methyl-3-oxoisobenzofuran-5-yl)-4-methyl-4-hexenoate; 3-(morpholin-4-yl)propyl (E)-6-(1,3-dihydro-4-ethylamino-6-methoxy-7-methyl-3-oxoisobenzofuran-5-yl)-4-methyl-4-hexenoate; 4-(morpholin-4-yl) butyl (E)-6-(1,3-dihydro-4-ethylamino-6-methoxy-7-methyl-3-oxoisobenzofuran-5-yl)-4-methyl-4-hexenoate; 2-(imidazolidin-1-yl)ethyl (E)-6-(1,3-dihydro-4-ethylamino-6-methoxy-7-methyl-3-oxoisobenzofuran-5-yl)-4-methyl-4-hexenoate; 2-(2-methyl-1,2-pyrazolidin-1-yl)ethyl (E)-6-(1,3-dihydro-4-ethylamino-6-methoxy-7-methyl-3-oxoisobenzofuran-5-yl)-4-methyl-4-hexenoate; 2-(pyrrolidin-1-yl)ethyl (E)-6-(1,3-dihydro-4-isopropylamino-6-methoxy-7-methyl-3-oxoisobenzofuran-5-yl)-4-methyl-4-hexenoate; 2-(piperidin-1-yl)ethyl (E)-6-(1,3-dihydro-4-isopropylamino-6-methoxy-7-methyl-3-oxoisobenzofuran-5-yl)-4-methyl-4-hexenoate; 2-(thiazolidin-3-yl)ethyl (E)-6-(1,3-dihydro-4-isopropylamino-6-methoxy-7-methyl-3-oxoisobenzofuran-5-yl)-4-methyl-4-hexenoate; 3-(morpholin-4-yl)propyl (E)-6-(1,3-dihydro-4-isopropylamino-6-methoxy-7-methyl-3-oxoisobenzofuran-5-yl)-4-methyl-4-hexenoate; 4-(morpholin-4-yl)butyl (E)-6-(1,3-dihydro-4-isopropylamino-6-methoxy-7-methyl-3-oxoisobenzofuran-5-yl)-4-methyl-4-hexenoate; 2-(imidazolidin-1-yl)ethyl (E)-6-(1,3-dihydro-4-isopropylamino-6-methoxy-7-methyl-3-oxoisobenzofuran-5-yl)-4-methyl-4-hexenoate; and 2-(2-methyl-1,2-pyrazolidin-1-yl)ethyl (E)-6-(1,3-dihydro-4-isopropylamino-6-methoxy-7-methyl-3-oxoisobenzofuran-5-yl)-4-methyl-4-hexenoate.

The above compounds and methods for their preparation are disclosed in U.S. Pat. No. 5,380,879.

Still other illustrative examples of mycophenolic acid derivatives are based on 6-substituted mycophenolic acid, which have a structure represented by formula (VII):

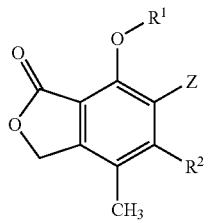
(VII)

wherein:

$R^1$ is H or $C(O)R^{10}$, where $R^{10}$ is lower alkyl, aryl or NH-aryl;

$R^2$ is lower alkyl, cycloalkyl, vinyl, fluorovinyl, difluorovinyl, trifluorovinyl, alkenyl, —C≡C—$R^{11}$, allenyl, CHO or $CH_2OR^{12}$, where
  $R^{11}$ is H or lower alkyl, and
  $R^{12}$ is H or 4-methoxybenzyl; and Z is a side chain selected from Formulae ZA, ZB, ZC, ZD, ZE, ZF, ZG and ZH:

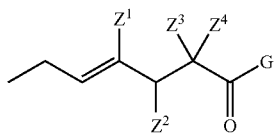
(VII-A)

wherein:

$Z^1$ is H, lower alkyl, halo or $CF_3$;

$Z^2$ is H, lower alkyl, lower alkoxy, aryl, or $CH_2$—$Z^{11}$, where
  $Z^{11}$ is halo, CN, aryl or heteroaryl;

$Z^3$ is H, lower alkyl, lower alkenyl, lower alkoxy, phenyl, or $S(O)_m$-lower alkyl, where m is 0, 1 or 2;

$Z^4$ is H, lower alkyl, or phenyl;

or $Z^3$ and $Z^4$ taken together with the carbon to which they are attached form cycloalkyl of three to five carbon atoms; and G is OH, lower alkoxy, lower thioalkyl, $NG^1G^2$, O—$(CH_2)_n$—$NG^1G^2$, or O—$(CH_2)_n$—N=$G^3$,
  where
  n is an integer from 1 to 6,
  $G^1$ is H or lower alkyl,
  $G^2$ is H or lower alkyl, and
  =$G^3$ is lower alkylene of four to six carbon atoms, or lower alkylene of three to five carbon atoms plus one member that is —O—, —S—, or —N(G4)- where $G^4$ is H or lower alkyl; or

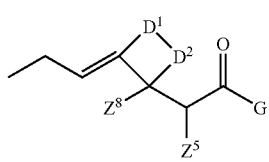
(VII-B)

wherein:

$Z^5$ is H or lower alkyl;

$Z^8$ is H, lower alkyl or forms a double bond with $D^2$;

$D^1$ and $D^2$ together with their adjacent carbon atoms form an optionally substituted, saturated or unsaturated carbocyclic or heterocyclic ring of 3 to 7 atoms; and G is as defined above; or

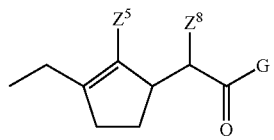
(VII-C)

wherein:

$Z^8$ is H or lower alkyl; and $Z^5$ and G are as defined above; or

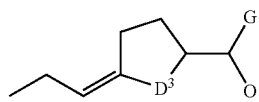
(VII-D)

wherein:

$D^3$ is —$CH_2$— or —$CH_2$—$CH_2$—; and

G is as defined above; or

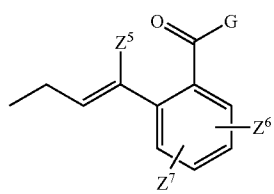
(VII-E)

wherein:

$Z^6$ is H, lower alkyl, COOH, $NH_2$, azido or halo;

$Z^7$ is H, lower alkyl or halo; and $Z^5$ and G are as defined above;

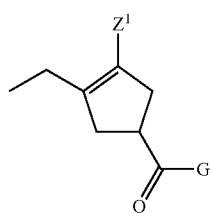
(VII-F)

wherein:

$Z^1$ and G are as defined above; or

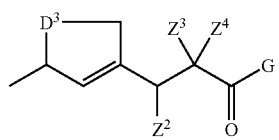
(VII-G)

wherein:
D³, Z², Z³, Z⁴ and G are as defined above; or

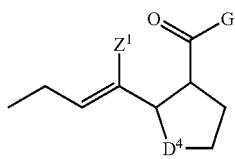

(VII-H)

wherein:
D⁴ is —CH₂—, —CH₂—CH₂—, —CH₂—CH₂—CH₂—, —O—, or —O—CH₂—; and
Z¹ and G are as defined above;
and the pharmaceutically acceptable salts thereof.

Representative compounds falling within the scope of Formula (VII) include, but are not limited to: methyl (E)-2-[2-[2-[1,3-dihydro-6-methoxy-7-methyl-3-oxo-4-p-toluene-sulfonyloxyisobenzofuran-5-yl]ethylidene]cyclopent-1-yl]acetate; methyl 3-(1,3-dihydro-6-methoxy-7-methyl-3-oxo-4-p-toluenesulfonyloxy-5-isobenzofuranylmethyl)-2-methylcyclopent-2-en-1-ylacetate; ethyl (E)-3-[2-(1,3-dihydro-6-methoxy-7-methyl-3-oxo-4-p-toluenesulfonyloxyisobenzofuran-5-yl)ethylidene]cyclopentane-1-carboxylate; methyl (E)-2-[3-(1,3-dihydro-6-methoxy-7-methyl-3-oxo-4-p-toluenesulfonyloxyisobenzofuran-5-yl)-prop-1-en-1-yl]-3-methylbenzoate; methyl 4-(1,3-dihydro-6-methoxy-7-methyl-3-oxo-4-p-toluenesulfonyloxyisobenzofuran-5-ylmethyl)-3-methylcyclopent-3-ene-1-carboxylate; methyl 3-[3-(1,3-dihydro-6-methoxy-7-methyl-3-oxo-4-p-toluene-sulfonyloxyisobenzo-furan-5-yl)cyclopent-1-en-1-yl]-propionate; methyl (E)-2-[-3-(1,3-dihydro-6-methoxy-7-methyl-3-oxo-4-p-toluenesulfonyloxyisobenzofuran-5-yl)-1-methylpropenyl]cyclopentanecarboxylate; (E)-2-[2-[2-[1,3-dihydro-6-hydroxy-7-methyl-3-oxo-4-p-toluenesulfonyloxyisobenzofuran-5-yl]ethylidene]cyclopent-1-yl]acetic acid; 3-(1,3-dihydro-6-hydroxy-7-methyl-3-oxo-4-p-toluenesulfonyl-oxy-5-isobenzofuranylmethyl)-2-methylcyclopent-2-en-1-yl acetic acid; (E)-3-[2-(1,3-dihydro-6-hydroxy-7-methyl-3-oxo-4-p-toluenesulfonyloxyisobenzofuran-5-yl)ethylidene]cyclopentane-1-carboxylic acid; (E)-2-[3-(1,3-dihydro-6-hydroxy-7-methyl-3-oxo-4-p-toluenesulfonyloxyisobenzofuran-5-yl)-prop-1-en-1-yl]-3-methylbenzoic acid; 4-(1,3-dihydro-6-hydroxy-7-methyl-3-oxo-4-p-toluenesulfonyloxyisobenzofuran-5-ylmethyl)-3-methylcyclopent-3-ene-1-carboxylic acid; 3-[3-(1,3-dihydro-6-hydroxy-7-methyl-3-oxo-4-p-toluenesulfonyloxyisobenzo-furan-5-yl)cyclopent-1-en-1-yl]propionic acid; (E)-2-[-3-(1,3-dihydro-6-hydroxy-7-methyl-3-oxo-4-p-toluenesulfonyloxyisobenzofuran-5-yl)-1-methylpropenyl]cyclopentanecarboxylic acid; methyl (E)-2-[2-[2-[1,3-dihydro-6-hydroxy-7-methyl-3-oxo-4-p-toluenesulfonyloxyisobenzofuran-5-yl]ethylidene]cyclopent-1-yl]acetate; methyl 3-(1,3-dihydro-6-hydroxy-7-methyl-3-oxo-4-p-toluenesulfonyloxy-5-isobenzofuranylmethyl)-2-methylcyclopent-2-en-1-ylacetate; methyl (E)-3-[2-(1,3-dihydro-6-hydroxy-7-methyl-3-oxo-4-p-toluenesulfonyloxyisobenzofuran-5-yl)ethylidene]cyclopentane-1-carboxylate; methyl (E)-2-[3-(1,3-dihydro-6-hydroxy-7-methyl-3-oxo-4-p-toluenesulfonyloxyisobenzofuran-5-yl)-prop-1-en-1-yl]-3-methylbenzoate; methyl 4-(1,3-dihydro-6-hydroxy-7-methyl-3-oxo-4-p-toluenesulfonyloxyisobenzofuran-5-ylmethyl)-3-methylcyclopent-3-ene-1-carboxylate; methyl 3-[3-(1,3-dihydro-6-hydroxy-7-methyl-3-oxo-4-p-toluene-sulfonyloxyisobenzo-furan-5-yl)cyclopent-1-en-1-yl]-propionate; methyl (E)-2-[-3-(1,3-dihydro-6-hydroxy-7-methyl-3-oxo-4-p-toluenesulfonyloxyisobenzofuran-5-yl)-1-methylpropenyl]cyclopentanecarboxylate; methyl (E)-2-[2-[2-[1,3-dihydro-7-methyl-3-oxo-4-p-toluenesulfonyloxy-6-trifluoromethanesulfonyloxyisobenzofuran-5-yl]ethylidene]cyclopent-1-yl]acetate; methyl 3-(1,3-dihydro-7-methyl-3-oxo-4-p-toluenesulfonyl-oxy-6-trifluoromethanesulfonyloxy-5-isobenzofuranylmethyl)-2-methylcyclopent-2-en-1-ylacetate; methyl (E)-3-[2-(1,3-dihydro-7-methyl-3-oxo-4-p-toluene-sulfonyloxy-6-trifluoromethanesulfonyloxyisobenzofuran-5-yl)ethylidene]cyclopentane-1-carboxylate; methyl (E)-2-[3-(1,3-dihydro-7-methyl-3-oxo-4-p-toluenesulfonyloxy-6-trifluoromethanesulfonyloxyisobenzofuran-5-yl)-prop-1-en-1-yl]-3-methylbenzoate; methyl 4-(1,3-dihydro-7-methyl-3-oxo-4-p-toluenesulfonyl-oxy-6-trifluoromethanesulfonyloxyisobenzofuran-5-ylmethyl)-3-methylcyclopent-3-ene-1-carboxylate; methyl 3-[3-(1,3-dihydro-7-methyl-3-oxo-4-p-toluenesulfonyloxy-6-trifluoromethanesulfonyloxyisobenzoo-5-yl)cyclopent-1-en-1-yl]-propionate; methyl (E)-2-[-3-(1,3-dihydro-7-methyl-3-oxo-4-p-toluenesulfonyloxy-6-trifluoromethanesulfonyloxyisobenzofuran-5-yl)-1-methylpropenyl]-cyclopentanecarboxylate; methyl (E)-2-[2-[2-[1,3-dihydro-7-methyl-3-oxo-4-p-toluenesulfonyloxy-6-vinylisobenzofuran-5-yl]ethylidene]cyclopent-1-yl]acetate; methyl 3-(1,3-dihydro-7-methyl-3-oxo-4-p-toluenesulfonyl-oxy-6-vinyl-5-isobenzofuranylmethyl)-2-methylcyclopent-2-en-1-ylacetate; methyl (E)-3-[2-(1,3-dihydro-7-methyl-3-oxo-4-p-toluenesulfonyloxy-6-vinylisobenzofuran-5-yl)ethylidene]cyclopentane-1-carboxylate; methyl (E)-2-[3-(1,3-dihydro-7-methyl-3-oxo-4-p-toluenesulfonyloxy-6-vinylisobenzofuran-5-yl)-prop-1-en-1-yl]-3-methylbenzoate; methyl 4-(1,3-dihydro-7-methyl-3-oxo-4-p-toluenesulfonyl-oxy-6-vinylisobenzofuran-5-ylmethyl)-3-methylcyclopent-3-ene-1-carboxylate; methyl 3-[3-(1,3-dihydro-7-methyl-3-oxo-4-p-toluenesulfonyloxy-6-vinylisobenzo-furan-5-yl)cyclopent-1-en-1-yl]-propionate; methyl (E)-2-[-3-(1,3-dihydro-7-methyl-3-oxo-4-p-toluenesulfonyloxy-6-vinylisobenzofuran-5-yl)-1-methylpropenyl]cyclopentanecarboxylate; methyl (E) 6-(1,3-dihydro-6,7-dimethyl-3-oxo-4-p-toluenesulfonyloxyisobenzofuran-5-yl)-4-methyl-4-hexenoate; methyl (E) 6-(6-cyclopropyl-1,3-dihydro-7-methyl-3-oxo-4-p-toluenesulfonyloxyisobenzofuran-5-yl)-4-methyl-4-hexenoate; methyl (E) 6-(1,3-dihydro-6-fluorovinyl-7-methyl-3-oxo-4-p-toluenesulfonyloxyisobenzofuran-5-yl)-4-methyl-4-hexenoate; methyl (E) 6-(1,3-dihydro-7-methyl-3-oxo-4-p-toluenesulfonyloxy-6-trifluorovinylisobenzofuran-5-yl)-4-methyl-4-hexenoate; methyl (E) 6-(1,3-dihydro-7-methyl-3-oxo-4-p-toluene-sulfonyloxy-6-(prop-2-enyl)isobenzofuran-5-yl)-4-methyl-4-hexenoate; methyl (E) 6-(1,3-dihydro-6-ethynyl-7-methyl-3-oxo-4-p-toluenesulfonyloxyisobenzofuran-5-yl)-4-methyl-4-hexenoate; methyl (E) 6-(1,3-dihydro-7-methyl-3-oxo-4-p-toluenesulfonyloxy-6-(pent-2-ynyl)isobenzofuran-5-yl)-4-methyl-4-hexenoate; methyl (E) 6-(6-allyl-1,3-dihydro-7-methyl-3-oxo-4-p-toluenesulfonyloxyisobenzofuran-5-yl)-4-methyl-4-hexenoate; and methyl (E) 6-(1,3-dihydro-6-(4-methoxybenzyloxymethyl)-7-methyl-3-oxo-4-p-toluenesulfonyloxyisobenzofuran-5-yl)-4-methyl-4-hexenoate; (E)-2-[2-[2-[1,3-dihydro-4-hydroxy-7-methyl-3-oxo-6-vinylisobenzofuran-5-yl]ethylidene]cyclopent-1-yl]

acetic acid; 3-(1,3-dihydro-4-hydroxy-7-methyl-3-oxo-6-vinylisobenzofuran-5-ylmethyl)-2-methylcyclopent-2-en-1-ylacetic acid; (E)-3-[2-(1,3-dihydro-4-hydroxy-7-methyl-3-oxo-6-vinylisobenzofuran-5-yl)ethylidene]cyclopentane-1-carboxylic acid; (E)-2-[3-(1,3-dihydro-4-hydroxy-7-methyl-3-oxo-6-vinylisobenzofuran-5-yl)-prop-1-en-1-yl]-3-methylbenzoic acid; 4-(1,3-dihydro-4-hydroxy-7-methyl-3-oxo-6-vinylisobenzofuran-5-ylmethyl)-3-methylcyclopent-3-ene-1-carboxylic acid; 3-[3-(1,3-dihydro-4-hydroxy-7-methyl-3-oxo-6-vinylisobenzofuran-5-yl)cyclopent-1-en-1-yl]-propionic acid; (E)-2-[-3-(1,3-dihydro-4-hydroxy-7-methyl-3-oxo-6-vinylisobenzofuran-5-yl)-1-methylpropenyl]-cyclopentanecarboxylic acid; (E) 6-(1,3-dihydro-4-hydroxy-6,7-dimethyl-3-oxoisobenzofuran-5-yl)-4-methyl-4-hexenoic acid; (E) 6-(1,3-dihydro-6-ethyl-4-hydroxy-7-methyl-3-oxoisobenzofuran-5-yl)-4-methyl-4-hexenoic acid; (E) 6-(6-cyclopropyl-1,3-dihydro-4-hydroxy-7-methyl-3-oxoisobenzofuran-5-yl)-4-methyl-4-hexenoic acid; (E) 6-(1,3-dihydro-6-fluorovinyl-4-hydroxy-7-methyl-3-oxoisobenzofuran-5-yl)-4-methyl-4-hexenoic acid; (E) 6-(1,3-dihydro-4-hydroxy-7-methyl-3-oxo-6-trifluorovinyl-isobenzofuran-5-yl)-4-methyl-4-hexenoic acid; (E) 6-(1,3-dihydro-4-hydroxy-7-methyl-3-oxo-6-(prop-2-enyl)isobenzofuran-5-yl)-4-methyl-4-hexenoic acid; (E) 6-(1,3-dihydro-6-ethynyl-4-hydroxy-7-methyl-3-oxoisobenzofuran-5-yl)-4-methyl-4-hexenoic acid; (E) 6-(1,3-dihydro-4-hydroxy-7-methyl-3-oxo-6-(pent-2-ynyl)isobenzofuran-5-yl)-4-methyl-4-hexenoic acid; (E) 6-(6-allyl-1,3-dihydro-4-hydroxy-7-methyl-3-oxoisobenzofuran-5-yl)-4-methyl-4-hexenoic acid; and (E) 6-(1,3-dihydro-4-hydroxy-6-(4-methoxybenzyloxymethyl)-7-methyl-3-oxoisobenzofuran-5-yl)-4-methyl-4-hexenoic acid; methyl (E)-2-[2-[2-[1,3-dihydro-6-ethyl-7-methyl-3-oxo-4-p-toluenesulfonyloxyisobenzofuran-5-yl]ethylidene]cyclopent-1-yl]acetate; methyl 3-(1,3-dihydro-6-ethyl-7-methyl-3-oxo-4-p-toluenesulfonyloxyisobenzofuran-5-ylmethyl)-2-methylcyclopent-2-en-1-ylacetate; methyl (E)-3-[2-(1,3-dihydro-6-ethyl-7-methyl-3-oxo-4-p-toluenesulfonyloxyisobenzofuran-5-yl)ethylidene]cyclopentane-1-carboxylate; methyl (E)-2-[3-(1,3-dihydro-6-ethyl-7-methyl-3-oxo-4-p-toluenesulfonyloxyisobenzofuran-5-yl)-prop-1-en-1-yl]-3-methylbenzoate; methyl 4-(1,3-dihydro-6-ethyl-7-methyl-3-oxo-4-p-toluenesulfonyloxyisobenzofuran-5-ylmethyl)-3-methylcyclopent-3-ene-1-carboxylate; methyl 3-[3-(1,3-dihydro-6-ethyl-7-methyl-3-oxo-4-p-toluenesulfonyloxyisobenzofuran-5-yl)cyclopent-1-en-1-yl]propionate; methyl (E)-2-[-3-(1,3-dihydro-6-ethyl-7-methyl-3-oxo-4-p-toluenesulfonyloxyisobenzofuran-5-yl)-1-methylpropenyl]cyclopentanecarboxylate; (E)-2-[2-[2-[1,3-dihydro-6-ethyl 4-hydroxy-7-methyl-3-oxoisobenzofuran-5-yl]ethylidene]cyclopent-1-yl]acetic acid; 3-(1,3-dihydro-6-ethyl-4-hydroxy-7-methyl-3-oxoisobenzofuran-5-ylmethyl)-2-methylcyclopent-2-en-1-ylacetic acid; (E)-3-[2-(1,3-dihydro-6-ethyl-4-hydroxy-7-methyl-3-oxoisobenzofuran-5-yl)ethylidene]cyclopentane-1-carboxylic acid; (E)-2-[3-(1,3-dihydro-6-ethyl-4-hydroxy-7-methyl-3-oxoisobenzofuran-5-yl)-prop-1-en-1-yl]-3-methylbenzoic acid; 4-(1,3-dihydro-6-ethyl-4-hydroxy-7-methyl-3-oxoisobenzofuran-5-ylmethyl)-3-methylcyclopent-3-ene-1-carboxylic acid; 3-[3-(1,3-dihydro-6-ethyl-4-hydroxy-7-methyl-3-oxoisobenzofuran-5-yl)cyclopent-1-en-1-yl]-propionic acid; (E)-2-[-3-(1,3-dihydro-6-ethyl-4-hydroxy-7-methyl-3-oxoisobenzofuran-5-yl)-1-methylpropenyl]-cyclopentanecarboxylic acid; (E) 6-(1,3-dihydro-6-(p-methoxybenzyloxymethyl)-7-methyl-3-oxo-4-p-toluenesulfonyloxyisobenzofuran-5-yl)-4-methyl-4-hexenoic acid; (E) 6-(1,3-dihydro-6-hydroxymethyl-7-methyl-3-oxo-4-p-toluenesulfonyloxyisobenzofuran-5-yl)-4-methyl-4-hexenoic acid; and (E) 6-(1,3-dihydro-6-formyl-7-methyl-3-oxo-4-p-toluenesulfonyloxyisobenzofuran-5-yl)-4-methyl-4-hexenoic acid.

The above compounds and methods for their preparation are disclosed in U.S. Pat. No. 5,444,072.

In other embodiments, the IMPDH antagonist is selected from compounds with structures represented by formula (VIII):

wherein:

A is selected from:

$(C_1-C_6)$-straight or branched alkyl, or $(C_2-C_6)$-straight or branched alkenyl or alkynyl; and A optionally comprises up to 2 substituents, wherein:

the first of said substituents, if present, is selected from $R^1$ or $R^3$, and the second of said substituents, if present, is $R^1$;

B is a saturated, unsaturated or partially saturated monocyclic or bicyclic ring system optionally comprising up to 4 heteroatoms selected from N, O, or S and selected from the formulae:

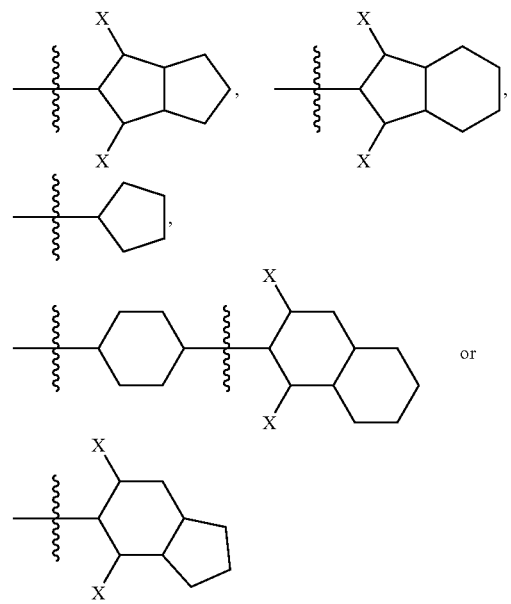

wherein each X is the number of hydrogen atoms necessary to complete proper valence;

and B optionally comprises up to 3 substituents, wherein:

the first of said substituents, if present, is selected from $R^1$, $R^2$, $R^4$ or $R^5$, the second of said substituents, if present, is selected from $R^1$ or $R^4$, and the third of said substituents, if present, is $R^1$; and D is selected from C(O), C(S), or S(O)$_2$; wherein:

each $R^1$ is independently selected from 1,2-methylenedioxy, 1,2-ethylenedioxy, $R^6$ or $(CH_2)_n$—Y;

wherein n is 0, 1 or 2; and

Y is selected from halogen, CN, $NO_2$, $CF_3$, $OCF_3$, OH, $SR^6$, $S(O)R^6$, $SO_2R^6$, $NH_2$, $NHR^6$, $N(R^6)_2$, $NR^6R^8$, COOH, $COOR^6$ or $OR^6$;

each $R^2$ is independently selected from ($C_1$-$C_4$)-straight or branched alkyl, or ($C_1$-$C_4$)-straight or branched alkenyl or alkynyl; and each $R^2$ optionally comprises up to 2 substituents, wherein:

the first of said substituents, if present, is selected from $R^1$, $R^4$ and $R^5$, and the second of said substituents, if present, is $R^1$;

$R^3$ is selected from a monocyclic or a bicyclic ring system consisting of 5 to 6 members per ring, wherein said ring system optionally comprises up to 4 heteroatoms selected from N, O, or S, and wherein a $CH_2$ adjacent to any of said N, O, or S heteroatoms is optionally substituted with C(O); and each $R^3$ optionally comprises up to 3 substituents, wherein:

the first of said substituents, if present, is selected from $R^1$, $R^2$, $R^4$ or $R^5$, the second of said substituents, if present, is selected from $R^1$ or $R^4$, and the third of said substituents, if present, is $R^1$;

each $R^4$ is independently selected from $OR^5$, $OC(O)R^6$, $OC(O)R^5$, $OC(O)OR^6$, $OC(O)OR^5$, $OC(O)N(R^6)_2$, $OP(O)(OR^6)_2$, $SR^6$, $SR^5$, $S(O)R^6$, $S(O)R^5$, $SO_2R^6$, $SO_2R^5$, $SO_2N(R^6)_2$, $SO_2NR^5R^6$, $SO_3R^6$, $C(O)R^5$, $C(O)OR^5$, $C(O)R^6$, $C(O)OR^6$, $NC(O)C(O)R^6$, $NC(O)C(O)R^5$, $NC(O)C(O)OR^6$, $NC(O)C(O)N(R^6)_2$, $C(O)N(R^6)_2$, $C(O)N(OR^6)R^6$, $C(O)N(OR^6)R^5$, $C(NOR^6)R^6$, $C(NOR^6)R^5$, $N(R^6)_2$, $NR^6C(O)R^1$, $NR^6C(O)R^6$, $NR^6C(O)R^5$, $NR^6C(O)OR^6$, $NR^6C(O)OR^5$, $NR^6C(O)N(R^6)_2$, $NR^6C(O)NR^5R^6$, $NR^6SO_2R^6$, $NR^6SO_2R^5$, $NR^6SO_2N(R^6)_2$, $NR^6SO_2NR^5R^6$, $N(OR^6)R^6$, $N(OR^6)R^5$, $P(O)(OR^6)N(R^6)_2$, and $P(O)(OR^6)_2$;

each $R^5$ is a monocyclic or a bicyclic ring system consisting of 5 to 6 members per ring, wherein said ring system optionally comprises up to 4 heteroatoms selected from N, O, or S, and wherein a $CH_2$ adjacent to said N, O or S maybe substituted with C(O); and each $R^5$ optionally comprises up to 3 substituents, each of which, if present, is $R^1$;

each $R^6$ is independently selected from H, ($C_1$-$C_4$)-straight or branched alkyl, or ($C_2$-$C_4$)-straight or branched alkenyl; and each $R^6$ optionally comprises a substituent that is $R^7$;

$R^7$ is a monocyclic or a bicyclic ring system consisting of 5 to 6 members per ring, wherein said ring system optionally comprises up to 4 heteroatoms selected from N, O, or S, and wherein a $CH_2$ adjacent to said N, O or S maybe substituted with C(O); and each $R^7$ optionally comprises up to 2 substituents independently chosen from H, ($C_1$-$C_4$)-straight or branched alkyl, ($C_2$-$C_4$)-straight or branched alkenyl, 1,2-methylenedioxy, 1,2-ethylenedioxy, or $(CH_2)_n$—Z;

wherein n is 0, 1 or 2; and

Z is selected from halogen, CN, $NO_2$, $CF_3$, $OCF_3$, OH, $S(C_1$-$C_4)$-alkyl, $SO(C_1$-$C_4)$-alkyl, $SO_2(C_1$-$C_4)$-alkyl, $NH_2$, $NH(C_1$-$C_4)$-alkyl, $N((C_1$-$C_4)$-alkyl)$_2$, $N((C_1$-$C_4)$-alkyl)$R^8$, COOH, $C(O)O(C_1$-$C_4)$-alkyl or $O(C_1$-$C_4)$-alkyl; and $R^8$ is an amino protecting group; and wherein any carbon atom in any A, $R^2$ or $R^6$ is optionally replaced by O, S, SO, $SO_2$, NH, or $N(C_1$-$C_4)$-alkyl, and the pharmaceutically acceptable salts thereof.

In some embodiments, the compounds of formula (VIII) have structures represented by formula (IX):

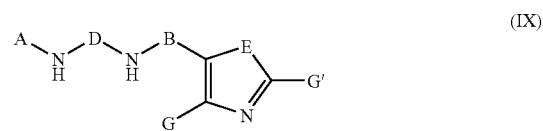

(IX)

wherein:

A, B and D are as defined above;

E is oxygen or sulfur; and

G and G' are independently selected from $R^1$ or hydrogen.

In other embodiments, the compounds of formula (VIII) have structures represented by formula (X):

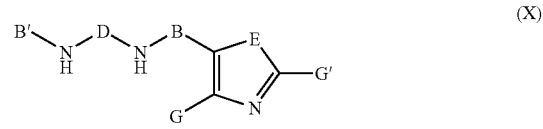

(X)

wherein:

B, D, E, G and G' are defined as above and B' is a saturated, unsaturated or partially saturated monocyclic or bicyclic ring system optionally comprising up to 4 heteroatoms selected from N, O, or S and selected from the formulae:

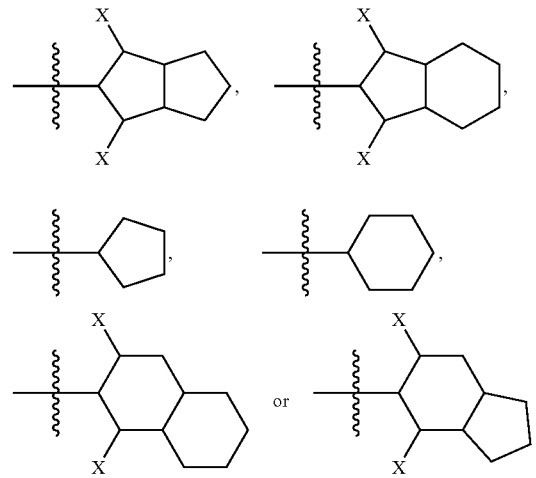

wherein:

each X is the number of hydrogen atoms necessary to complete proper valence; and B' optionally comprises up to 3 substituents, wherein:

the first of said substituents, if present, is selected from $R^1$, $R^2$, $R^4$ or $R^5$, the second of said substituents, if present, is selected from $R^1$ or $R^4$, and the third of said substituents, if present, is $R^1$; wherein X, $R^1$, $R^2$, $R^4$ and $R^5$ are defined as above.

In specific embodiments, B and B' are phenyl groups comprising at least one substituent each. These compounds are suitably represented by formula (XI):

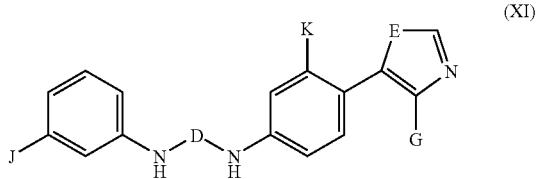

(XI)

wherein:

K is selected from R¹ or R⁴; and J is selected from R¹, R² or R⁴.

Representative compounds of formula (XI) include those wherein D is —C(O)—, those wherein E is oxygen; those wherein J is NR$^6$C(O)R$^5$ or NR$^6$C(O)R$^6$, preferably NR$^6$C(O)R$^6$, more preferably N(CH$_3$)C(O)R$^6$, and more preferably N(CH$_3$)C(O)CH$_3$; those wherein K is (CH$_2$)$_n$—Y, preferably OCH$_3$ (i.e., n is 0, Y is OR$^6$, and R$^6$ is CH$_3$); and those wherein G is hydrogen. More preferred compounds of formula (XI) are those wherein:

E is oxygen
J is NR$^6$C(O)R$^5$ or NR$^6$C(O)R$^6$;
K is (CH$_2$)$_n$—Y; and
G is hydrogen.

Even more preferred compounds of formula (XI) are those wherein:

D is —C(O)—;
E is oxygen;
J is NR$^6$C(O)R$^6$;
K is OCH$_3$; and
G is hydrogen.

Even more preferably in such compounds, J is N(CH$_3$)C(O)R$^6$.

Alternate representative compounds are those of formula (XI) wherein J is R², those wherein D is —C(O)—, those wherein E is oxygen, those wherein J is R² substituted with R⁴, preferably wherein R⁴ is NR$^6$C(O)R$^5$ or NR$^6$C(O)R$^6$, more preferably wherein R⁴ is NR$^6$C(O)R$^5$, more preferably wherein R⁴ is NHC(O)R$^5$, and more preferably wherein R⁴ is NHC(O)O-3-tetrahydrofuranyl, those wherein K is (CH$_2$)$_n$—Y, preferably wherein K is OCH$_3$, those wherein G is hydrogen, and those wherein:

D is —C(O)—;
E is oxygen;
K is OCH$_3$; and
G is hydrogen.

In other embodiments, the compounds of formula (VIII) are those having structures represented by formula (XII):

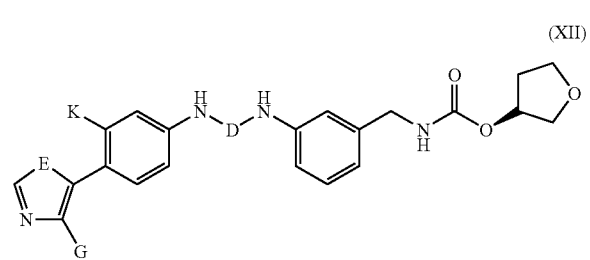

(XII)

those compounds of formula (XII) wherein K is OCH$_3$, and those compounds of formula (XII) wherein G is hydrogen.

In other embodiments, the IMPDH antagonist is selected from compounds of formula XI wherein K is selected from R¹ or R⁴; and J is selected from R¹, R², R⁴, and R⁹ wherein, R¹, R², and R⁴, are as defined above for formula (VIII) and R⁹ is independently selected from (C$_1$-C$_4$)-straight or branched alkyl, or (C$_2$-C$_4$)-straight or branched alkenyl or alkynyl; and each R⁹ optionally comprises up to 2 substituents selected from NR$^6$C(O)OR$^{10}$, wherein R$^6$ is as defined above and R$^{10}$ is selected from (C¹-C⁵)-straight or branched alkyl optionally comprising up to two substituents selected from NR$^6$R$^8$$_1$, SR$^6$, SO$_2$R$^6$, —(CH$_2$)$_n$—SR$^6$, —(CH$_2$)$_n$—OR$^6$, and OR$^6$, wherein n, R$^6$ and R$^8$, are as defined above for formula (VIII).

In still other embodiments, the compounds of formula (VIII) have structures represented by formula (XIII):

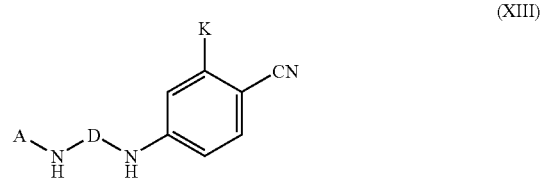

(XIII)

wherein:

K is selected from R¹ and R⁴; and A, D, R¹ and R⁴ are each independently as defined for formula (VIII).

In some embodiments, the IMPDH antagonist is selected from compounds of formula XIII wherein D is —C(O)—, those wherein A is a monocyclic aromatic ring substituted with 1-2 substituents selected from the group consisting of NR$^6$C(O)R$^6$, NR$^6$C(O)R$^5$, CH$_2$NR$^6$C(O)OR$^6$, and CH$_2$NR$^6$C(O)OR$^5$, those wherein A is a monocyclic aromatic ring substituted with 1-2 substituents selected from the group consisting of CH$_2$NR$^6$C(O)OR$^6$ and CH$_2$NR$^6$C(O)OR$^5$, those A is a monocyclic aromatic ring substituted with CH$_2$NR$^6$C(O)OR$^5$, those wherein A is a monocyclic aromatic ring substituted with CH$_2$NHC(O)OR$^5$, those wherein A is a monocyclic aromatic ring substituted with CH$_2$NHC(O)O-3-tetrahydrofuryl, those wherein K is (CH$_2$)$_n$—Y, those wherein K is OCH$_3$, and those wherein:

A is a monocyclic aromatic ring substituted with CH$_2$NHC(O)O-3-tetrahydrofuryl; and
K is OCH$_3$.

In other embodiments, the compounds of formula (VIII) have structures represented by formula (XIV):

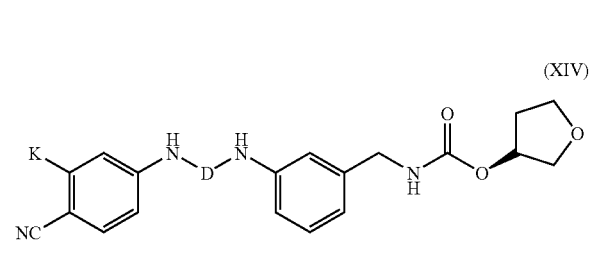

(XIV)

wherein:

D is as defined for formula (VIII) and K is as defined in formula (XI).

In other embodiments, the compounds of formula (VIII) have structures represented by formula (XV):

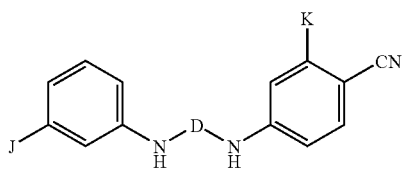

(XV)

wherein:

D is selected from C(O), C(S) and S(O)$_2$;

K is selected from $R^1$ and $R^4$; and

J is selected from $R^1$, $R^2$, and $R^4$.

Preferred compounds of formula (XV) include those wherein D is —C(O)—, those wherein J is $NR^6C(O)R^5$ or $NR^6C(O)R^6$, those wherein J is $NR^6C(O)R^6$, those wherein J is $N(CH_3)C(O)R^6$, those wherein J is $N(CH_3)C(O)CH_3$, those wherein K is $(CH_2)_n$—Y, those wherein K is $OCH_3$, and those wherein:

K is $OCH_3$; and

J is $N(CH_3)C(O)CH_3$.

Representative compounds falling within the scope of formula (VIII) include, but are not limited to:

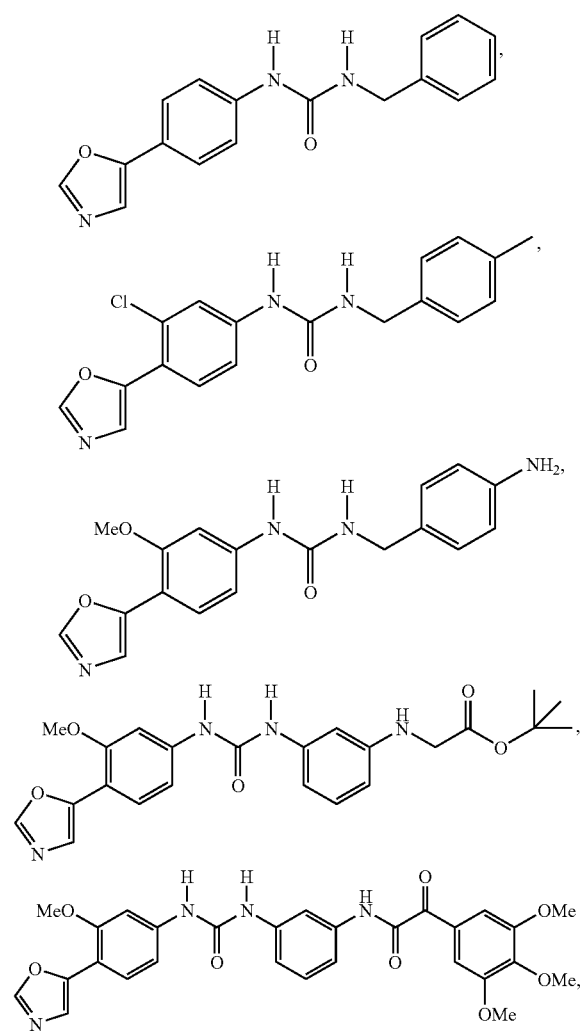

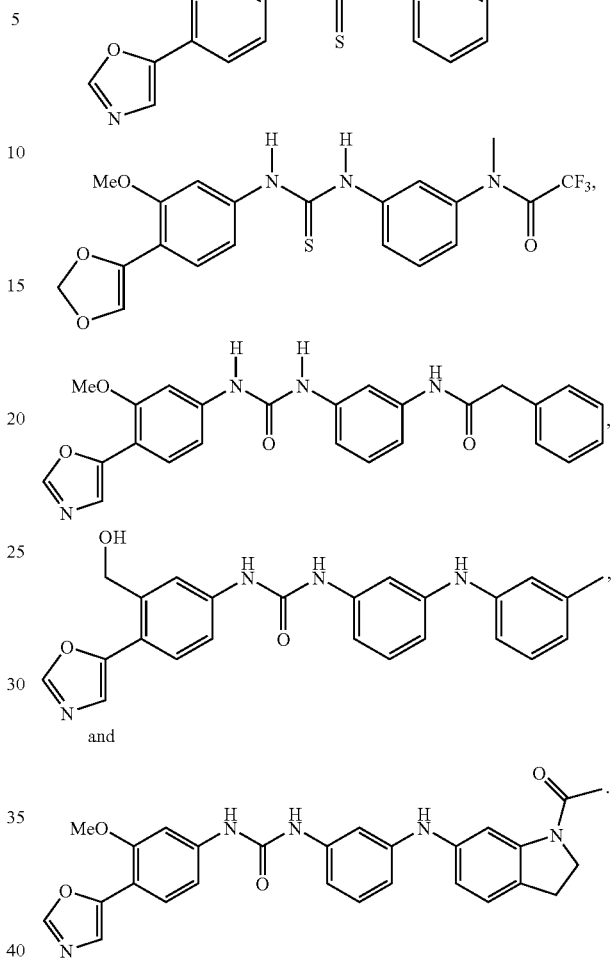

and

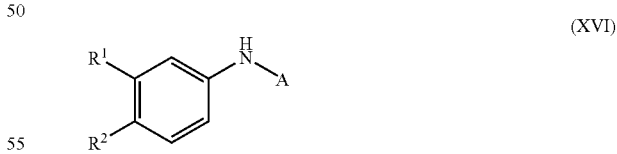

The above compounds and methods for their preparation are disclosed in U.S. Pat. Nos. 5,807,876, 6,054,472, 6,344,465 and 6,541,496.

In other embodiments, the IMPDH antagonist is selected from compounds with structures represented by formula (XVI):

(XVI)

wherein:

A is a saturated, unsaturated or partially saturated monocyclic or bicyclic ring system optionally comprising up to 4 heteroatoms selected from N, O, and S wherein each A optionally comprises up to 4 substituents selected from $R^1$, $R^4$ and $R^5$;

each $R^1$ is halogen, CN, $NO_2$, $CF_3$, $OCF_3$, OH, $R^3$, $OR^3$, 1,2-methylenedioxy, 1,2-ethylenedioxy, $SR^3$, $S(O)R^3$, $SO_2R^3$, $NH_2$, $NHR^3$, $N(R^3)_2$, $NR^3R.sup.9$, COOH, or $COOR^3$;

each $R^2$ is independently $R^1$ or a monocyclic ring system consisting of 5 to 6 members per ring, wherein said ring system optionally comprises up to 4 heteroatoms selected from N, O, and S, and wherein a $CH_2$ adjacent to said N, O or S maybe substituted with C(O); and each $R^2$ optionally comprises up to 2 substituents, each substituent independently selected from $R^1$;

each $R^3$ is independently $(C_1-C_4)$-straight or branched alkyl, or $(C_2-C_4)$-straight or branched alkenyl or alkynyl;

each $R^4$ is independently $(C_1-C_6)$-straight or branched alkyl, or $(C_2-C_6)$-straight or branched alkenyl or alkynyl; and each $R^4$ optionally comprises up to 2 substituents, wherein:

the first of said substituents, if present, is $R^1$, $R^5$ or R.sup.8, and the second of said substituents, if present, is $R^1$;

each $R^5$ is independently selected from $OR^6$, $OC(O)R^7$, $OC(O)R^6$, $OC(O)OR^7$, $OC(O)OR^6$, $OC(O)N(R^7)_2$, $OP(O)(OR^7)_2$, $SR^7$, $SR^6$, $S(O)R^7$, $S(O)R^6$, $SO_2R^7$, $SO_2R^6$, $SO_2N(R^7)_2$, $SO_2NR^6R^7$, $SO_3R^7$, $C(O)R^6$, $C(O)OR^6$, $C(O)R^7$, $C(O)OR^7$, $NC(O)C(O)R^7$, $NC(O)C(O)R^6$, $NC(O)C(O)OR^7$, $NC(O)C(O)N(R^7)_2$, $C(O)N(R^7)_2$, $C(O)N(OR^7)R^7$, $C(O)N(OR^7)R^6$, $C(NOR^7)R^7$, $C(NOR^7)R^6$, $N(R^7)_2$, $NR^7C(O)R^6$, $NR^7C(O)R^7$, $NR^6C(O)R^6$, $NR^7C(O)OR^7$, $NR^7C(O)OR^6$, $NR^7C(O)N(R^7)_2$, $NR^7C(O)NR^6R^7$, $NR^7SO_2R^7$, $NR^7SO_2R^6$, $NR^7SO_2N(R^7)_2$, $NR^7SO_2NR^6R^7$, $N(OR^7)R^7$, $N(OR^7)R^6$, $P(O)(OR^7)N(R^7)_2$, $P(O)(OR^7)_2$, $P(O)(N(R^7)_2)_2$, and $P(O)(OR^7)R^7$.

$R^6$ is a monocyclic or a bicyclic ring system consisting of 5 to 6 members per ring, wherein said ring system optionally comprises up to 4 heteroatoms selected from N, O, and S, and wherein a $CH_2$ adjacent to any of said N, O, or S heteroatoms is optionally substituted with C(O); and each $R^6$ optionally comprises up to 3 substituents, each substituent independently selected from $R^1$;

each $R^7$ is independently H, $(C_1-C_4)$-straight or branched alkyl, or $(C_2-C_4)$ straight or branched alkenyl; and each $R^7$ optionally comprises a substituent that is $R^8$;

$R^8$ is a monocyclic or a bicyclic ring system consisting of 5 to 6 members per ring, wherein said ring system optionally comprises up to 4 heteroatoms selected from N, O, and S, and wherein a $CH_2$ adjacent to said N, O or S maybe substituted with C(O); and each $R^8$ optionally comprises up to 2 substituents independently chosen from H, $(C_1-C_4)$-straight or branched alkyl, $(C_2-C_4)$ straight or branched alkenyl, 1,2-methylenedioxy, 1,2-ethylenedioxy and $(CH_2)_n$—$R^1$;

wherein n is 0, 1 or 2;

$R^9$ is an amino protecting group; and wherein any carbon atom in any $R^3$, $R^4$ or $R^7$ is optionally replaced by O, S, SO, $SO_2NH$, or $N(C_1-C_4)$-alkyl, and the pharmaceutically acceptable salts thereof.

In some embodiments, the compounds of formula (XVI) have a structure represented by formula (XVII):

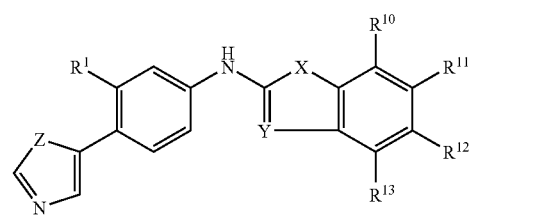

(XVII)

wherein:

$R^{10}$, $R^{11}$, $R^{12}$ and $R^{13}$ are each independently selected from $R^1$ and $R^4$, wherein only one of $R^{10}$, $R^{11}$, $R^{12}$ and $R^{13}$ may simultaneously be $R^4$; and X and Y are independently selected from $CH_2$, $CHR^3$, $CHR^4$, O, S, NH, $NR^3$, $NR^4$, CH, $CR^3$, $CR^4$, and N.

In other embodiments, the compounds of formula (XVI) have a structure represented by formula (XVIII):

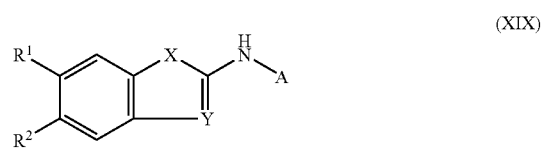

(XVIII)

wherein:

$R^1$, $R^{10}$, $R^{11}$, $R^{12}$, $R^{13}$, X and Y are as defined in formula (X) and Z is O, S, NH or $NR^3$, wherein $R^3$ is as defined in formula (IX).

In other embodiments, the compounds of formula (XVI) have a structure represented by formula (XIX):

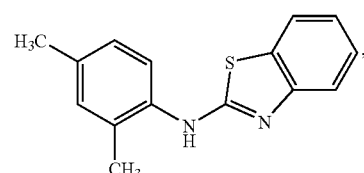

(XIX)

wherein $R^1$, $R^2$, A, X and Y are as defined for formula (XVII).

Representative compounds falling within the scope of formula (XVI) include, but are not limited to:

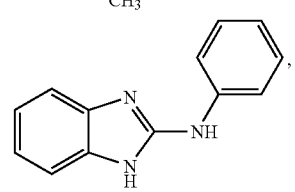

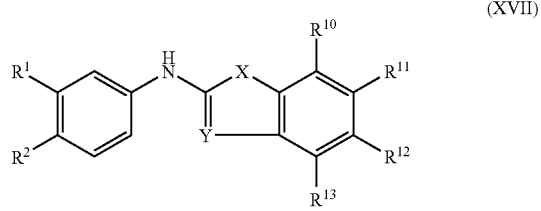

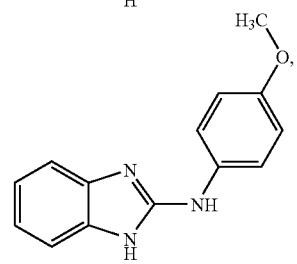

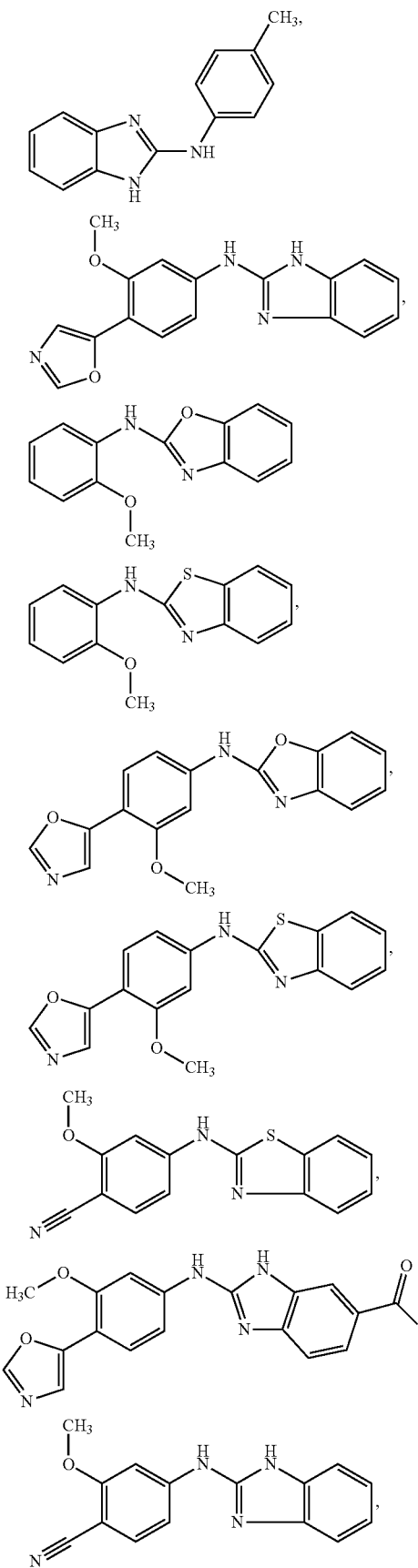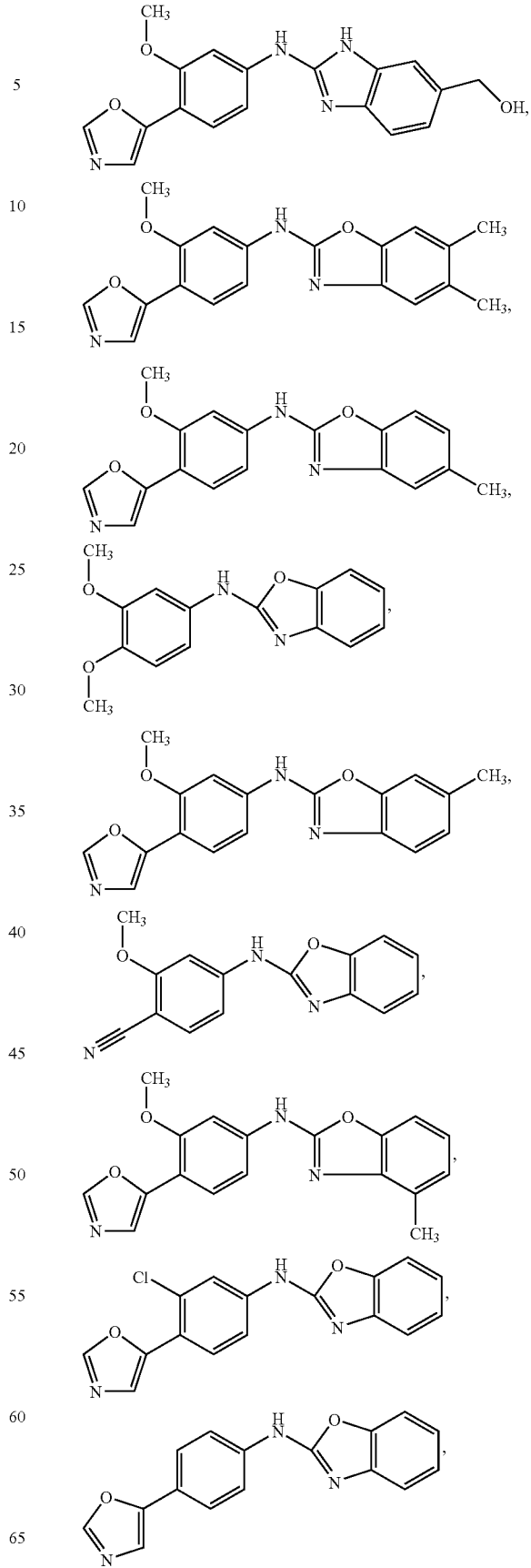

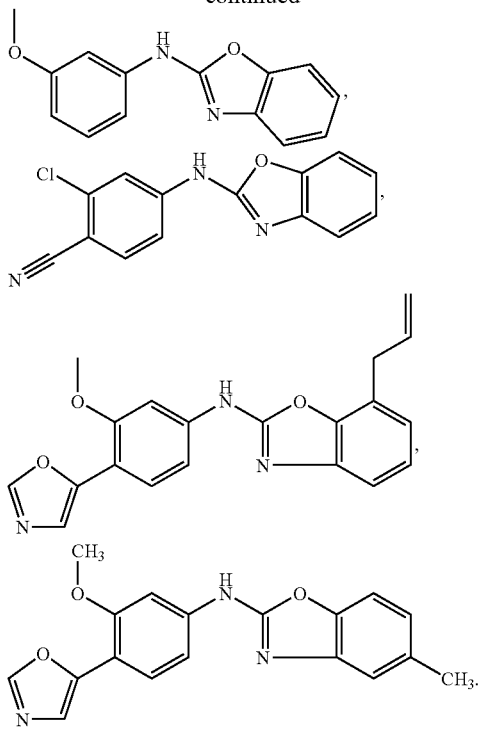

The above compounds and methods for their preparation are disclosed in U.S. Pat. Nos. 5,932,600 and 6,518,291.

In other embodiments, the IMPDH antagonist is selected from compounds with structures represented by formula (XX):

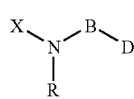
(XX)

wherein:

X is a monocyclic or bicyclic ring system optionally containing up to 4 heteroatoms selected from N, O, and S, and wherein a $CH_2$ adjacent to any of the said N, O or S heteroatoms is optionally substituted with oxo (=O), and wherein X is optionally substituted by 0-5 substituents chosen from A, $R^1$, or $R^2$;

A is $R^3$ or $R^4$;

$R^3$ is a 5- or 6-membered heterocyclic ring system containing up to 4 heteroatoms selected from N, O, and S, said heterocyclic ring system being optionally substituted with 0-3 $R^5$, wherein when $R^5$ is hydroxy, the heterocycle may undergo tautomerisation to an oxo species, or exist as an equilibrium mixture of both tautomers;

$R^4$ is selected from H, F, Cl, Br, I, $NO_2$, $CF_3$, $C_0$-$C_4$ alkylCN, $C_1$-$C_4$ alkoxy-, $C_0$-$C_4$ alkylhydroxy, $C_1$-$C_4$ alkyl-, $C_1$-$C_4$ alkylcarbonyl-, $C_0$-$C_4$ alkylOCOR$^6$, $C_0$-$C_4$ alkylOC(=O) OR$^6$, $C_0$-$C_4$ alkylOC(=O)NR$^6$R$^7$, $NH_2$, NHR$^6$, $C_0$-$C_4$ alkylNR$^6$R$^7$, $C_0$-$C_4$ alkylNR$^7$C(=O)OR$^6$, $C_0$-$C_4$ alkylNR$^6$SO$_2$NR$^6$R$^7$, $C_0$-$C_4$ alkylNR$^7$SO$_2$R$^6$, $C_0$-$C_4$ alkylSR$^6$, $C_0$-$C_4$ alkylS(O)R$^6$, $C_0$-$C_4$ alkylSO$_2$R$^6$, $SO_3R^7$, $C_0$-$C_4$ alkylSO$_2$NR$^6$R$^7$, $C_0$-$C_4$ alkyl SO$_2$NR$^7$CO(CR$^9$R$^{10}$)$_q$ R$^6$, $C_0$-$C_4$ alkylCO$_2$H, $C_0$-$C_4$ alkylCO$_2$R$^6$, $C_0$-$C_4$ alkylCONR$^6$R$^7$, and $C_0$-$C_4$CONR$^7$SO$_2$(CR$^9$R$^{10}$)$_q$R$^6$;

$R^5$ is selected from H, halogen, $NO_2$, $C_1$-$C_4$ alkyl, $C_3$-$C_{10}$ cycloalkyl, $C_2$-$C_6$ alkenyl, $C_2$-$C_6$ alkynyl, haloalkyl, haloalkoxy, OH, oxo, $C_1$-$C_4$ alkoxy, $C_1$-$C_4$ alkylcarbonyl, CN, $NH_2$, NHR$^6$, NR$^6$R$^7$, SR$^7$, S(O)R$^7$, SO$_2$R$^7$, SO$_3$R$^7$, SO$_2$NR$^6$, CO$_2$H, CO$_2$R$^6$, and CONR$^6$R$^7$;

R is H or $C_1$-$C_4$ alkyl;

$R^1$ and $R^2$ are each independently selected from H, halogen, $NO_2$, $C_1$-$C_4$ alkyl, $C_3$-$C_{10}$ cycloalkyl, $C_2$-$C_6$ alkenyl, $C_2$-$C_6$ alkynyl, haloalkyl, haloalkoxy, OH, $C_1$-$C_4$ alkoxy-, OR$^6$, O(CR$^9$R$^{10}$)$_r$CO$_2$R$^6$, O(CR$^9$R$^{10}$)$_m$NR$^6$R$^7$, O(CR$^9$R$^{10}$)$_p$ CN, O(CR$^9$R$^{10}$)$_r$C(=O)NR$^6$R$^7$, $C_1$-$C_4$ alkylcarbonyl-, CN, $NH_2$, NHR$^6$, NR$^6$R$^7$, NR$^7$(CR$^9$R$^{10}$)$_r$CO$_2$R$^6$, NR$^7$OR$^6$, NR$^7$ (CR$^9$R$^{10}$)$_m$OR$^6$, NR$^7$CH[(CR$^9$R$^{10}$)$_p$OR$^6$]$_2$, NR$^7$C [(CR$^9$R$^{10}$)$_p$ OR$^6$]$_3$, NR$^7$C(=O)R$^6$, NR$^7$(CR$^9$R$^{10}$)$_m$OR$^6$, NR$^7$(CR$^9$R$^{10}$)$_m$NR$^6$R$^7$, NR$^7$(CR$^9$R$^{10}$)$_m$SO$_2$(CR$^9$R$^{10}$)$_q$R, SR$^7$, S(O)R$^7$, SO$_2$R$^7$, SO$_2$NR$^6$, SO$_3$R$^7$, SO$_2$NR$^6$, CO$_2$H, CO$_2$R$^6$, and CONR$^6$R$^7$; or, alternatively, $R^1$ and $R^2$, when on adjacent carbon atoms, may be taken together to be methylenedioxy or ethylenedioxy;

$R^6$, $R^7$ and $R^8$ are each independently selected from H, $C_1$-$C_6$ alkyl, $C_3$-$C_{10}$ cycloalkyl, $C_2$-$C_6$ alkenyl, $C_2$-$C_6$ alkynyl, $C_1$-$C_6$ alkylcarbonyl, $C_3$-$C_7$ cycloalkyl($C_1$-$C_5$ alkyl)carbonyl, $C_1$-$C_6$ alkoxycarbonyl, aryl($C_0$-$C_5$ alkyl)carbonyl, aryl($C_1$-$C_5$ alkyloxy)carbonyl, heterocyclic($C_0$-$C_5$ alkyl)carbonyl, heterocyclic($C_1$-$C_5$ alkoxy)carbonyl, $C_1$-$C_6$ alkylsulfonyl, arylsulfonyl, heteroarylsulfonyl, $C_0$-$C_4$ alkylaryl, $C_0$-$C_4$ alkylheterocyclic, wherein said cycloalkyl, aryl or heterocyclic groups are substituted with 0-2 substituents independently selected from the group consisting of $C_1$-$C_4$ alkyl, hydroxy, $C_1$-$C_4$ alkoxy, F, Cl, Br, haloalkyl, $NO_2$ and CN;

or, alternatively, $R^6$ and $R^7$, or $R^6$ and $R^8$, or $R^7$ and $R^8$, when both substituents are on the same nitrogen atom [as in (—NR$^6$R$^7$) or (—NR$^7$R$^8$)], can be taken together with the nitrogen atom to which they are attached to form a heterocycle selected from 1-aziridinyl, 1-azetidinyl, 1-piperidinyl, 1-morpholinyl, 1-pyrrolidinyl, thiamorpholinyl, thiazolidinyl, 1-piperazinyl, 1-imidazolyl, 3-azabicyclo[3,2,2]nonan-3-yl, and 1-tetrazolyl, the said heterocycle being optionally substituted with 0-3 groups selected from oxo, $C_0$-$C_4$ alkylOH, $C_0$-$C_4$ alkylOC$_1$-$C_4$ alkyl, $C_0$-$C_4$ alkylCONH$_2$, $C_0$-$C_4$ alkylCO$_2$ $C_0$-$C_4$ alkyl, $C_1$-$C_6$ alkyl, $C_1$-$C_4$ alkoxy, $C_3$-$C_7$ cycloalkyl, —$C_0$-$C_6$ alkylcarbonyl, $C_3$-$C_7$ cycloalkylcarbonyl, $C_1$-$C_6$ alkoxycarbonyl, $C_3$-$C_7$ cycloalkoxycarbonyl, —NHCOalkyl, aryl, heteroaryl, aryl alkoxycarbonyl, heteroaryl alkoxycarbonyl, $C_1$-$C_6$ alkylsulfonyl, arylsulfonyl and heteroarylsulfonyl;

B is a monocyclic or bicyclic ring system optionally containing up to 4 heteroatoms selected from N, O, and S, and wherein a $CH_2$ adjacent to any of the said N, O or S heteroatoms is optionally substituted with oxo (=O), and wherein B is optionally substituted by one to four $R^{11}$ groups;

D is a monocyclic or bicyclic ring system optionally containing up to 4 heteroatoms selected from N, O, and S, and wherein a $CH_2$ adjacent to any of the said N, O or S heteroatoms is optionally substituted with oxo (=O), and wherein D is optionally substituted by one to four (CR$^9$R$^{10}$)$_n$ E groups;

n is an integer having a value from 0-4;

m is an integer having a value from 2-6;

p is an integer having a value from 1-3;

q is an integer having a value from 0-3;

r is an integer having a value from 0-6;

$R^9$ is H or $C_1$-$C_4$ alkyl;

$R^{10}$ is selected from H or $C_1$-$C_4$ alkyl, $C_1$-$C_4$ alkylhydroxy, $C_1$-$C_4$ alkylaryl or $C_1$-$C_4$ alkylheteroaryl, wherein said aryl or heteroaryl group may be substituted with 0-3 groups independently selected from H, halogen, $NO_2$, $C_1$-$C_4$ alkyl, $C_3$-$C_{10}$ cycloalkyl, $C_2$-$C_6$ alkenyl, $C_2$-$C_6$ alkynyl, haloalkyl, haloalkoxy, OH, $C_1$-$C_4$ alkoxy, $C_1$-$C_4$ alkylcarbonyl, CN, $NH_2$, $NR^6R^7$, $SR^6$, $S(O)R^6$, $SO_2R^6$, $SO_3R^6$, $SO_2NR^6$, $CO_2H$, $CO_2R^6$, and $CONR^6R^7$;

$R^{11}$ is selected from H, halogen, $NO_2$, $C_1$-$C_4$ alkyl, $C_3$-$C_{10}$ cycloalkyl, $C_2$-$C_6$ alkenyl, $C_2$-$C_6$ alkynyl, haloalkyl, haloalkoxy, OH, $C_1$-$C_4$ alkoxy-, $OR^6$, $O(CR^9R^{10})_rCO_2R^6$, $O(CR^9R^{10})_mNR^6R^7$, $O(CR^9R^{10})_pCN$, $O(CR^9R^{10})_rC(=O)NR^6R^7$, $C_1$-$C_4$ alkylcarbonyl-, CN, $NH_2$, $NHR^6$, $NR^6R^7$, $NR^7(CR^9R^{10})_rCO_2R^6$, $NR^7OR^6$, $NR^7(CR^9R^{10})_mOR^6$, $NR^7CH[(CR^9R^{10})_pOR^6]_2$, $NR^7C[(CR^9R^{10})_pOR^6]_3$, $NR^7C(=O)R^6$, $NR^7(CR^9R^{10})_mOR^6$, $NR^7(CR^9R^{10})_mNR^6R^7$, $NR^7(CR^9R^{10})_mSO_2(CR^9R^{10})_qR^6$, $SR^7$, $S(O)R^7$, $SO_2R^7$, $SO_2NR^6$, $SO_3R^7$, $CO_2H$, $CO_2R^6$, and $CONR^6R^7$;

E is selected from H, halogen, $NO_2$, $C_1$-$C_4$ alkyl, $C_3$-$C_{10}$ cycloalkyl, $C_2$-$C_6$ alkenyl, $C_2$-$C_6$ alkynyl, haloalkyl, haloalkoxy, OH, $OR^6$, CN, CHO, $CO_2R^6$, $CONR^6R^7$, $OCOR^6$, $OC(=O)OR^6$, $OC(=O)NR^6R^7$, $OCH_2CO_2R^6$, $C(=O)R^6$, $NH_2$, $NHR^6$, $NR^6R^7$, $NR^7C(=O)R^6$, $NR^7C(=O)OR^6$, $NR^7C(=O)C(=O)OR^6$, $NR^7C(=O)C(=O)NR^6R^7$, $NR^7C(=O)C(=O)(C_1$-$C_6$ alkyl), $NR^7C(=NCN)OR^6$, $NR^7C(=O)NR^6R^7$, $NR^7C(=NCN)NR^6R^7$, $NR^7C(=NR^6)NR^7R^8$, $NR^6SO_2NR^6R^7$, $NR^7SO_2R^6$, $SR^6$, $S(=O)R^6$, $SO_2R^6$, $SO_3R^7$, $SO_2NR^6R^7$, NHOH, $NHOR^6$, $NR^6NR^7NR^8$, $N(COR^6)OH$, $N(CO_2R^6)OH$, $CO_2R^6$, $CONR^6R^7$, $CONR^7(CR^9R^{10})_rR^6$, $CO(CR^9R^{10})_pO(CHR^9)_qCO_2R^6$, $CO(CR^9CR^{10})_rOR^6$, $CO(CR^9R^{10})_pO(CR^9R^{10})_qR^6$, $CO(CR^9CR^{10})_rNR^6R^7$, $OC(O)O(CR^9R^{10})_mNR^6R^7$, $O(CO)N(CR^9R^{10})_rR^6$, $O(CR^9R^{10})_mNR^6R^7$, $NR^7C(O)(CR^9R^{10})_rR^6$, $NR^7C(O)(CR^9R^{10})_rOR^6$, $NR^7C(=NC)(CR^9R^{10})_rOR^6$, $NR^7C(=NC)(CR^9R^{10})_rR^6$, $NR^7CO(CR^9R^{10})_rNR^6R^7$, $NR^7(CR^9R^{10})_mOR^6$, $NR^7(CR^9R^{10})_rCO_2R^6$, $NR^7(CR^9R^{10})_mNR^6R^7$, $NR^7(CR^9R^{10})_nSO_2(CR^9R^{10})_qR^6$, $CONR^7(CR^9R^{10})_n SO_2(CR^9R^{10})_q$, $SO_2NR^7(CR^9R^{10})_nCO(CR^9R^{10})_qR^6$, $SO_2NR^6(CR^9R^{10})_mOR^6$, $C_2$-$C_6$ alkenyl, $C_3$-$C_{10}$ cycloalkyl, $C_3$-$C_{10}$ cycloalkylmethyl, aryl, heterocyclic and alkylaryl, wherein said aryl groups may be substituted with 0-2 substituents independently selected $R^{12}$;

$R^{12}$ at each occurrence are independently selected from H, halogen, $NO_2$, $C_1$-$C_4$ alkyl, $C_3$-$C_{10}$ cycloalkyl, $C_2$-$C_6$ alkenyl, $C_2$-$C_6$ alkynyl, haloalkyl, haloalkoxy, OH, oxo, $C_1$-$C_4$ alkoxy-, $OR^6$, $O(CR^9R^{10})_rCO_2R^6$, $O(CR^9R^{10})_mNR^6R^7$, $O(CR^9R^{10})_pCN$, $O(CR^9R^{10})_rC(=O)NR^6R^7$, $C_1$-$C_4$ alkylcarbonyl-, CN, $NH_2$, $NHR^6$, $NR^6R^7$, $NR^7(CR^9R^{10})_rCO_2R^6$, $NR^7OR^6$, $NR^7(CR^9R^{10})_mOR^6$, $NR^7CH[(CR^9R^{10})_pOR^6]_2$, $NR^7C[(CR^9R^{10})_pOR^6]_3$, $NR^7C(=O)R^6$, $NR^7(CR^9R^{10})_mOR^6$, $NR^7(CR^9R^{10})_mNR^6R^7$, $NR^7(CR^9R^{10})_mSO_2(CR^9R^{10})_qR^6$, $SR^7$, $S(O)R^7$, $SO_2R^7$, $SO_2NR^6$, $SO_3R^7$, $CO_2H$, $CO_2R^6$, and $CONR^6R^7$.

In some embodiments, the compounds of formula (XX) have a structure represented by any one of the following formulae:

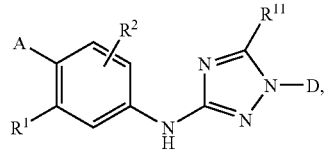
(XXa)

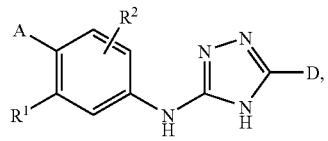
(XXb)

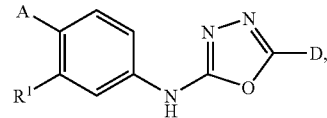
(XXc)

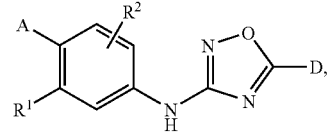
(XXd)

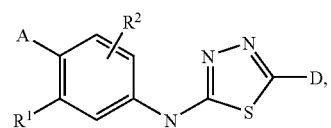
(XXe)

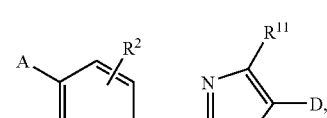
(XXf)

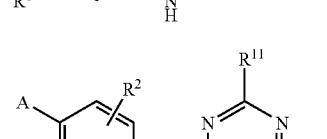
(XXg)

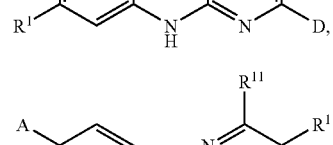
(XXh)

and

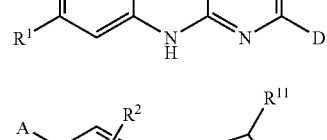
(XXi)

wherein:

$R^3$ is a 5- or 6-membered heterocyclic ring system containing up to 4 heteroatoms selected from N, O, and S, said heterocyclic ring system being optionally substituted with $R^5$, wherein when $R^5$ is hydroxy, the heterocycle may undergo tautomerisation to an oxo species, or exist as an equilibrium mixture of both tautomers.

Representative compounds falling within the scope of formula (XVI) include, but are not limited to: $N^3$-[3-methoxy-4-(5-oxazolyl)phenyl]-1-phenyl-1H-1,2,4-triazole-3,5-diamine; $N^3$-[3-methoxy-4-(5-oxazolyl)phenyl]-1-(2-pyridinyl)-1H-1,2,4-triazole-3,5-diamine; 1-cyclohexyl-$N^5$-[3-methoxy-4-(5-oxazolyl)phenyl]-1H-1,2,4-triazole-3,5-diamine and 1-cyclohexyl-$N^3$-[3-methoxy-4-(5-oxazolyl)phenyl]-1H-1,2,4-triazole-3,5-diamine; $N^3$-[3-methoxy-4-(5-oxazolyl)phenyl]-1-(2-methylphenyl)-1H-1,2,4-triazole-3,5-diamine; $N^3$-[3-methoxy-4-(5-oxazolyl)phenyl]-1-(4-methylphenyl)-1H-1,2,4-triazole-3,5-diamine; $N^3$-[3-methoxy-4-(5-oxazolyl)phenyl]-1-(3-methylphenyl)-1H-1,2,4-triazole-3,5-diamine; $N^3$-[3-methoxy-4-(5-oxazolyl)

phenyl]-1-(3-nitrophenyl)-1H-1,2,4-triazole-3,5-diamine; $N^3$-[3-methoxy-4-(5-oxazolyl)phenyl]-1-(4-nitrophenyl)-1H-1,2,4-triazole-3,5-diamine; 1-(4-aminophenyl)-$N^3$-[3-methoxy-4-(5-oxazolyl)phenyl]-1H-1,2,4-triazole-3,5-diamine; 1-(3-aminophenyl)-$N^3$-[3-methoxy-4-(5-oxazolyl)phenyl]-1H-1,2,4-triazole-3,5-diamine; 1-(3-fluorophenyl)-$N^3$-[3-methoxy-4-(5-oxazolyl)phenyl]-1H-1,2,4-triazole-3,5-diamine; 1-(4-Bromophenyl)-$N^3$-[3-methoxy-4-(5-oxazolyl)phenyl]-1H-1,2,4-triazole-3,5-diamine; $N^3$-[5-Amino-3-[[3-methoxy-4-(5-oxazolyl)phenyl]amino]-1H-1,2,4-triazol-1-yl]benzonitrile; $N^3$-[3-methoxy-4-(5oxazolyl)phenyl]-1-(3-methoxyphenyl)-1H-1,2,4-triazole-3,5-diamine; $N^3$-[3-methoxy-4-(5oxazolyl)phenyl]-1-[4-(methylsulfonyl)phenyl]-1H-1,2,4-triazole-3,5-diamine; 6-[3-[[3-methoxy-4-(5-oxazolyl)phenyl]amino]-1H-1,2,4-triazol-1-yl]-1,3-dimethyl-2,4(1H,3H)-pyrimidinetrione; 1-(2-fluorophenyl)-$N^3$-[3-methoxy-4-(5-oxazolyl)phenyl]-1H-1,2,4-triazole-3,5-diamine; N-[3-methoxy-4-(5-oxazolyl)phenyl]-5-phenyl-1H-1,2,4-triazol-3-amine; N-[3-methoxy-4-(5-oxazolyl)phenyl]-5-(2-methylphenyl)-1H-1,2,4-triazol-3-amine; N-[3-methoxy-4-(5-oxazolyl)phenyl]-5-(3-methylphenyl)-1H-1,2,4-triazol-3-amine; N-[3-methoxy-4-(5-oxazolyl)phenyl]-5-phenyl-1,3,4-oxadiazol-2-amine; N-[3-methoxy-4-(5-oxazolyl)phenyl]-5-phenyl-1,2,4-oxadiazol-3-amine; N-[3-methoxy-4-(5-oxazolyl)phenyl]-5-phenyl-1,3,4-thiadiazol-2-amine; N-[3-[[3-methoxy-4-(5-oxazolyl)phenyl]amino]-1-phenyl-1H-1,2,4-triazol-5-yl]acetamide; $N^3$-[3-methoxy-4-(5-oxazolyl)phenyl]-1-(3-pyridinyl)-1H-1,2,4-triazol-3,5-diamine; $N^3$-[3-methoxy-4-(−5-oxazolyl)phenyl]-1-(4-pyridinyl)-1H-1,2,-triazol-3,5-diamine; $N^3$-[4-(1H-imidazol-1-yl)-3-methoxyphenyl]-1-phenyl-1H-1,2,4-triazol-3,5-diamine; N-[3-methoxy-4-(5-oxazolyl)phenyl]-5-(4-methylphenyl)-1H-1,2,4-triaziol-3-amine; N-[3-methoxy-4-(5-oxazolyl)phenyl][1,1'-biphenyl]-3-amine; N-[3-methoxy-4-(5-oxazolyl)phenyl]-5-phenyl-1,2,4-thiadiazol-3-amine; N-[3-methoxy-4-(5-oxazolyl)phenyl]-5-phenyl-3-isoxazolamine; N-[3-methoxy-4-(5-oxazolyl)phenyl]-2-phenyl-5-thiazolamine; N-[3-methoxy-4-(5-oxazolyl)phenyl]-4-phenyl-2-thiazolamine; N-[3-methoxy-4-(5-oxazolyl)phenyl]-5-phenyl-2-oxazolamine; N-[3-methoxy-4-(5-oxazolyl)phenyl]-4-methyl-5-phenyl-2-oxazolamine; N-[3-methoxy-4-(5-oxazolyl)phenyl]-5-(3-methoxyphenyl)-2-oxazolamine; N-[3-methoxy-4-(5-oxazolyl)phenyl]-5-(2-pyridinyl)-2-oxazolamine; N-[3-methoxy-4-(5-oxazolyl)phenyl]-5-(tetrahydro-2-furanyl)-2-oxazolamine; N-[3-methoxy-4-(5-oxazolyl)phenyl]-5-(2-methoxyphenyl)-2-oxazolamine; N-[3-methoxy-4-(5-oxazolyl)phenyl]-5-(4-methoxyphenyl)-2-oxazolamine; N-[3-methoxy-4-(5-oxazolyl)phenyl]-5-(4-methylphenyl)-2-oxazolamine; N-[3-methoxy-4-(5-oxazolyl)phenyl]-5-(3-methylphenyl)-2-oxazolamine; N-[3-methoxy-4-(5-oxazolyl)phenyl]-5-(2-methylphenyl)-2-oxazolamine; 5-(2,3-dihydro-1,4-benzodioxin-6-yl)-N-[3-methoxy-4-(5-oxazolyl)phenyl]-2-oxazolamine; 5-[4-diethylamino)phenyl]-N-[3-methoxy-4-(5-oxazolyl)phenyl]-2-oxazolamine; 4-ethyl-N-[3-methoxy-4-(5-oxazolyl)phenyl]-5-phenyl-2-oxazolamine; 5-(2,6-dimethoxyphenyl)-N-[3-methoxy-4-(5-oxazolyl)phenyl]-2-oxazolamine; N-[3-methoxy-4-(5-oxazolyl)phenyl]-5-(2-methoxyphenyl)-4-methyl-2-oxazolamine; N-[2-2-[[3-methoxy-4-(5-oxazolyl)phenyl]amino]-5-oxazolyl]phenyl]-N-acetamide; N-[2-2-[[3-methoxy-4-(5-oxazolyl)phenyl]amino]-5-oxazolyl]phenyl]-N-methylacetamide; 5-(2-bromophenyl)-N-[3-methoxy-4-(5-oxazolyl)phenyl]-2-oxazolamine; N-[3-methoxy-4-(5-oxazolyl)phenyl]-5-methyl-4-phenyl-2-oxazolamine; 2-methoxy-N-[2-[2-[[3-methoxy-4-(5-oxazolyl)phenyl]amino]-5-oxazolyl]phenyl] acetamide; N-[2-[2-[[3-methoxy-4-(5-oxazolyl)phenyl]amino]-5-oxazolyl]phenyl]-4-morpholineacetamide; 2-methoxy-N-[2-[2-[[3-methoxy-4-(5-oxazolyl)phenyl]amino]-5-oxazolyl]phenyl]-N-methylacetamide; N-[3-methoxy-4-(5-oxazolyl)phenyl]-5-[2-(phenylmethoxy)phenyl]-2-oxazolamine; 2-[2-[[3-methoxy-4-(5-oxazolyl)phenyl]amino]-5-oxazolyl]benzoic acid ethyl ester; [2-[2-[[3-methoxy-4-(5-oxazolyl)phenyl]amino]-5-oxazolyl]phenyl]carbamic acid tetrahydro-3-furanyl ester; [2-[2-[[3-methoxy-4-(5-oxazolyl)phenyl]amino]-5-oxazolyl]phenyl]methyl-carbamic acid; tetrahydro-3-furanyl ester; 3-[2-[2-[[3-methoxy-4-(5-oxazolyl)phenyl]amino]-5-oxazolyl]phenyl]-2-oxazolidinone; [2-[2-[[3-methoxy-4-(5-oxazolyl)phenyl]amino]-5-oxazolyl]phenyl]methyl-carbamic acidphenylmethyl ester; 2-[2-[[3-methoxy-4-(5-oxazolyl)phenyl]amino]-5-oxazolyl]-N,N-dimethylbenzamide; 5-(2-Furanyl)-N-[3-methoxy-4-(5-oxazolyl)phenyl]-2-oxazolamine; 2-[2-[[3-methoxy-4-(5-oxazolyl)phenyl]amino]-5-oxazolyl]-1-pyrrolidinecarboxylic acidphenylmethyl ester; N-[2-[2-[[3-methoxy-4-(5-oxazolyl)phenyl]amino]-5-oxazolyl]phenyl]-N-ethyl-4-morpholineacetamide; N-[2-[2-[[3-methoxy-4-(5-oxazolyl)phenyl]amino]-5-oxazolyl]phenyl]-N-methyl-4-morpholinepropanamide; N-[2-[2-[[3-methoxy-4-(5-oxazolyl)phenyl]amino]-5-oxazolyl]phenyl]-N,N2,N2-trimethylglycinamide; N-[2-[2-[[3-methoxy-4-(5-oxazolyl)phenyl]amino]-5-oxazolyl]phenyl]-N,N2-dimethylglycinamide; N-[2-[2-[[3-methoxy-4-(5-oxazolyl)phenyl]amino]-5-oxazolyl]phenyl]-N,4-dimethyl-1-piperazineacetamide; N-[2-[2-[[3-methoxy-4-(5-oxazolyl)phenyl]amino]-5-oxazolyl]phenyl]-N-methyl-1H-1,2,4-triazole-1-acetamide; N2-(1,1-dimethylethyl)-N-[2-[2-[[3-methoxy-4-(5-oxazolyl)phenyl]amino]-5-oxazolyl]phenyl]-N-methylglycinamide; N-[2-[2-[[3-methoxy-4-(5-oxazolyl)phenyl]amino]-5-oxazolyl]phenyl]-N-methyl-N-2-(1-methylethyl)glycinamide; N-[2-[2-[[3-methoxy-4-(5-oxazolyl)phenyl]amino]-5-oxazolyl]phenyl]-N-methyl-1H-imidazole-1-acetamide; N-[2-[2-[[3-methoxy-4-(5-oxazolyl)phenyl]amino]-5-oxazolyl]phenyl]-N-methyl-1H-pyrazole-1-acetamide; N-[2-[2-[[3-methoxy-4-(5-oxazolyl)phenyl]amino]-5-oxazolyl]phenyl]-N-methyl-2H-1,2,3-triazole-2-acetamide; N-[2-[2-[[3-methoxy-4-(5-oxazolyl)phenyl]amino]-5-oxazolyl]phenyl]-N-methyl-1H-1,2,3-triazole-1-acetamide; N-[2-[2-[[3-methoxy-4-(5-oxazolyl)phenyl]amino]-5-oxazolyl]phenyl]-N,☐-dimethyl-4-morpholineacetamide; N-[2-[2-[[3-methoxy-4-(5-oxazolyl)phenyl]amino]-5-oxazolyl]phenyl]-N-methyl-2-pyrrolidinecarboxamide; N-[2-[2-[[3-methoxy-4-(5-oxazolyl)phenyl]amino]-5-oxazolyl]phenyl]-N-methyl-4-morpholineacetamide; 2-[2-[[3-methoxy-4-(5-oxazolyl)phenyl]amino]-5-oxazolyl]benzoic acid; N-[3-methoxy-4-(5-oxazolyl)phenyl]-5-(3-nitrophenyl)-2-oxazolamine; 2-[2-[[3-methoxy-4-(5-oxazolyl)phenyl]amino]-5-oxazolyl]-N,N-dimethylbenzamide; 2-[2-[[3-methoxy-4-(5-oxazolyl)phenyl]amino]-5-oxazolyl]-N-methylbenzamide; (S)-2-[2-[[3-methoxy-4-(5-oxazolyl)phenyl]amino]-5-oxazolyl]-N-(tetrahydro-3-furanyl)benzamide; (S)-2-[2-[[3-methoxy-4-(5-oxazolyl)phenyl]amino]-5-oxazolyl]-N-(tetrahydro-3-furanyl)benzamide; 1-[[2-[2-[[3-methoxy-4-(5-oxazolyl)phenyl]amino]-5-oxazolyl]phenyl]carbonyl]-4-methylpyrazine; 2-[2-[[3-methoxy-4-(5-oxazolyl)phenyl]amino]-5-oxazolyl]-N-[2-(4-morpholinyl)ethyl]benzamide; N-[3-methoxy-4-(5-oxazolyl)phenyl]-N-methyl-5-phenyl-2-oxazolamine; 4,5-dihydro-N-[3-methoxy-4-(5-oxazolyl)phenyl]-5-phenyl-2-oxazolamine; N-[3-methoxy-4-(5-oxazolyl)phenyl]-5-(2-pyrrolidinyl)-2-oxazolamine; 2-[2-[[3-methoxy-4-(5oxazolyl)phenyl]amino]-5-oxazolyl]-1-pyrrolidinecarboxylic acid methyl ester; 2-[2-[[3-methoxy- 4-(5-oxazolyl)phenyl]amino]-5-oxazolyl]-N-methoxymethylcarbonyl pyrrolidine; 2-[2-[[3-methoxy-4-(5-5-oxazolyl]-N-[4-morpholinomethylcarbonyl] pyrrolidine; 2-[2-[[3-methoxy-4-(5-oxazolyl)phenyl] amino]-5-oxazolyl]-1-pyrrolidinecarboxylic acid ethyl ester; 2-[2-[[3-methoxy-4-(5-oxazolyl)phenyl]amino]-5-oxazolyl]-1-pyrrolidinecarboxylic acid 2-(methylsulfonyl) ethyl ester; 2-[2-[[3-methoxy-4-(5-oxazolyl)phenyl]amino]-5-oxazolyl]-1-pyrrolidinecarboxylic acid; 3-tetrahydrofuranyl ester; N-[3-hydroxy-4-(5-oxazolyl)phenyl]-5-phenyl-2-oxazolamine; N-[3-[(1,1-dimethylethoxy)carbonylmethoxy](4-(5-oxazolyl)phenyl]-5-phenyl-2-oxazolamine; N-[3-methoxycarbonylmethoxy-4-(5-oxazolyl)phenyl]-5-phenyl-2-oxazolamine; N-[3-ethoxy-4-(5-oxazolyl)phenyl]-5-phenyl-2-oxazolamine; N-[3-(cyanomethoxy)-4-(5-oxazolyl)phenyl]-5-phenyl-2-oxazolamine; 5-(2-Bromophenyl)N-[3-methoxycarbonylmethoxy-4-(5-oxazolyl)phenyl]-2-oxazolamine; 4-Chloro-N-[3-methoxy-4-(5-oxazolyl)phenyl]-6-phenyl-1,3,5-triazin-2-amine (A1); N-[3-methoxy-4-(5-oxazolyl)phenyl]-N'-methyl-6-phenyl-1,3,5-triazine-2,4-diamine; N-[3-methoxy-4-(5-oxazolyl)phenyl]-N'-methyl-6-(2-methylphenyl)-1,3,5-triazine-2,4-diamine; 4-Chloro-N-[3-methoxy-4-(5-oxazolyl)phenyl]-6-(4-methylphenyl)-1,3,5-triazin-2-amine; N-[3-methoxy-4-(5-oxazolyl)phenyl]-N'-methyl-6-(4-methylphenyl)-1,3,5-triazine-2,4-diamine; N-[3-methoxy-4-(5-oxazolyl)phenyl]-6-phenyl-N-(2-phenylethyl)-1,3,5-triazine-2,4-diamine; 4-methoxy-N-[3-methoxy-4-(5-oxazolyl)phenyl]-6-phenyl-1,3,5-triazin-2-amine; N-[3-methoxy-4-(5-oxazolyl)phenyl]-4-(4-phenyl-1-piperazinyl)-6-phenyl-1,3,5-triazin-2-amine; 3-[[4-[[3-methoxy-4-(5-oxazolyl)phenyl]amino]-6-phenyl-1,3,5-triazin-2-yl)amino]propanoic acid; 1,1-dimethylethyl ester N-[4-[[3-methoxy-4-(5-oxazolyl)phenyl]amino]-6-phenyl-1,3,5-triazin-2-yl]glycine ethyl ester; N-[3-methoxy-4-(5-oxazolyl)phenyl]-4-(4-morpholinyl)-6-phenyl-1,3,5-triazin-2-amine; N-[3-methoxy-4-(5-oxazolyl)phenyl]-6-phenyl-N'-(phenylmethyl)-1,3,5-triazine-2,4-diamine; 2-[[4-[[3-methoxy-4-(5-oxazolyl)phenyl]amino]-6-phenyl-1,3,5-triazin-2-yl]amino]ethanol; 4-[[4-[[3-methoxy-4-(5-oxazolyl)phenyl]amino]-6-phenyl-1,3,5-triazin-2-yl]amino]butanoic acid methyl ester; 3-[[4-[[3-methoxy-4-(5-oxazolyl)phenyl]amino]-6-phenyl-1,3,5-triazin-2-yl]amino]-1-propanol; N-[3-methoxy-4-(5-oxazolyl)phenyl]-4-(4-methyl-1-piperazinyl)-6-phenyl-1,3,5-triazin-2-amine; 3-[[4-[[3-methoxy-4-(5-oxazolyl)phenyl]amino]-6-phenyl-1,3,5-triazin-2-yl]amino]propanoic acid; N-[3-methoxy-4-(5-oxazolyl)phenyl]-6-phenyl-N'-(3-pyridinylmethyl)-1,3,5-triazine-2,4-diamine; N-[3-methoxy-4-(5-oxazolyl)phenyl]-N'-[(5-methyl-2-furanyl)methyl]-6-phenyl-1,3,5-triazine-2,4-diamine; (S)-☐-[[4-[[3-methoxy-4-(5-oxazolyl)phenyl]amino]-6-phenyl-1,3,5-triazin-2-yl]amino]benzenepropanol; N-[3-methoxy-4-(5-oxazolyl)phenyl]-6-phenyl-N'-[2-(3-pyridinyl)ethyl]-1,3,5-triazine-2,4-diamine; N-[3-methoxy-4-(5-oxazolyl)phenyl]-6-phenyl-N'-[(tetrahydro-2-furanyl)methyl]-1,3,5-triazine-2,4-diamine; N-[3-(1H-imidazol-1-yl)propyl]-N'-[3-methoxy-4-(5-oxazolyl)phenyl]-6-phenyl-1,3,5-triazine-2,4-diamine; 4-[[4-[[3-methoxy-4-(5-oxazolyl)phenyl]amino]-6-phenyl-1,3,5-triazin-2-yl]amino]-1-piperidinecarboxylic acid ethyl ester; N-[6-(dimethylamino)hexyl]-N'-[3-methoxy-4-(5-oxazolyl)phenyl]-6-phenyl-1,3,5-triazine-2,4-diamine; N-[3-methoxy-4-(5-oxazolyl)phenyl]-6-phenyl-N'-[2-(4-pyridinyl)ethyl]-1,3,5-triazine-2,4-diamine; 4-[[4-[[3-methoxy-4-(5-oxazolyl)phenyl]amino]-6-phenyl-1,3,5-triazin-2-yl]amino)-1-butanol; N-[3-methoxy-4-(5-oxazolyl)phenyl]-6-phenyl-N'-(2-pyridinylmethyl)-1,3,5-triazine-2,4-diamine; N-[(1-ethyl-2-pyrrolidinyl)methyl]-N'-[3-methoxy-4-(5-oxazolyl)phenyl]-6-phenyl-1,3,5-triazine-2,4-diamine; N-[2-[[4-[[3-methoxy-4-(5-oxazolyl)phenyl]amino]-6-phenyl-1,3,5-triazin-2-yl]amino]ethyl]acetamide; N-(3-Butoxypropyl)-N'-[3-methoxy-4-(5-oxazolyl)phenyl]-6-phenyl-1,3,5-triazine-2,4-diamine; N-[3-methoxy-4-(5-oxazolyl)phenyl]-N'-[3-(4-morpholinyl)propyl]-6-phenyl-1,3,5-triazine-2,4-diamine; (S)-4-Hydroxy-.quadrature.-[[4-[[3-methoxy-4-(5-oxazolyl)phenyl]amino]-6-phenyl-1,3,5-triazin-2-yl]amino]benzenepropanol; N-[3-methoxy-4-(5-oxazolyl)phenyl]-N'-(3-methylbutyl)-6-phenyl-1,3,5-triazine-2,4-diamine; N-[3-methoxy-4-(5-oxazolyl)phenyl]-6-phenyl-N'-[2-(1-pyrrolidinyl)ethyl]-1,3,5-triazine-2,4-diamine; N-[3-methoxy-4-(5-oxazolyl)phenyl]-6-phenyl-1,3,5-triazine-2,4-diamine; N-methoxy-N'-[3-methoxy-4-(5-oxazolyl)phenyl]-N-methyl-6-phenyl-1,3,5-triazine-2,4-diamine; N-methoxy-N'-[3-methoxy-4-(5-oxazolyl)phenyl]-6-phenyl-1,3,5-triazine-2,4-diamine; N-(cyclopropylmethyl)-N'-[3-methoxy-4-(5-oxazolyl)phenyl]-6-phenyl-1,3,5-triazine-2,4-diamine; N-Butyl-N'-[3-methoxy-4-(5-oxazolyl)phenyl]-6-phenyl-1,3,5-triazine-2,4-diamine; N-[3-methoxy-4-(5-oxazolyl)phenyl]-6-phenyl-N'-(3-propoxypropyl)-1,3,5-triazine-2,4-diamine; N-[3-methoxy-4-(5-oxazolyl)phenyl]-6-phenyl-N'-(3-propoxypropyl)-1,3,5-triazine-2,4-diamine; 1-[[[4-[[3-methoxy-4-(5-oxazolyl)phenyl]amino]-6-phenyl-1,3,5-triazin-2-yl]amino]methyl]cyclohexanol; N-[3-(diethylamino)propyl]-N'-[3-methoxy-4-(5-oxazolyl)phenyl]-6-phenyl-1,3,5-triazine-2,4-diamine; N-[3-methoxy-4-(5-oxazolyl)phenyl]-N'-(2-methylpropyl)-6-phenyl-1,3,5-triazine-2,4-diamine; N-[2-(1H-Imidazol-4-yl)ethyl]-N'-[3-methoxy-4-(5-oxazolyl)phenyl]-6-phenyl-1,3,5-triazine-2,4-diamine; 3-[[4-[[3-methoxy-4-(5-oxazolyl)phenyl]amino]-6-phenyl-1,3,5-triazin-2-yl]amino]-1,2-propanediol; N-[3-methoxy-4-(5-oxazolyl)phenyl]-N'-[3-(4-methyl-1-piperazinyl)propyl]-6-phenyl-1,3,5-triazine-2,4-diamine; N-[3-methoxy-4-(5-oxazolyl)phenyl]-N'-[3-(4-methyl-1-piperazinyl)propyl]-6-phenyl-1,3,5-triazine-2,4-diamine; 2-[[4-[[3-methoxy-4-(5-oxazolyl)phenyl]amino]-6-phenyl-1,3,5-triazin-2-yl]amino]-1-pentanol; N-(2-furanylmethyl)-N'-[3-methoxy-4-(5-oxazolyl)phenyl]-6-phenyl-1,3,5-triazine-2,4-diamine; N-[3-methoxy-4-(5-oxazolyl)phenyl]-N'-(2-phenoxyethyl)-6-phenyl-1,3,5-triazine-2,4-diamine; N-[3-methoxy-4-(5-oxazolyl)phenyl]-6-phenyl-N'-[2-(1-piperidinyl)ethyl]-1,3,5-triazine-2,4-diamine; S,S-1,1'-[[4-[[3-methoxy-4-(5-oxazolyl)phenyl]amino]-6-phenyl-1,3,5-triazin-2-yl]imino]bis[2-propanol]; N-(cyclopropylmethyl)-N'-[3-methoxy-4-(5-oxazolyl)phenyl]-6-phenyl-N-propyl-1,3,5-triazine-2,4-diamine; 2-[[4-[[3-methoxy-4-(5-oxazolyl)phenyl]amino]-6-phenyl-1,3,5-triazin-2-yl]propylamino]ethanol; 2-[[4-[[3-methoxy-4-(5-oxazolyl)phenyl]amino]-6-phenyl-1,3,5-triazin-2-yl]propylamino]ethanol; N-[3-methoxy-4-(5-oxazolyl)phenyl]-6-phenyl-N'-(4-pyridinylmethyl)-1,3,5-triazine-2,4-diamine; (S)-1-[4-[[3-methoxy-4-(5-oxazolyl)phenyl]amino]-6-phenyl-1,3,5-triazin-2-yl]-2-pyrrolidinemethanol; 4-[4-[[3-methoxy-4-(5-oxazolyl)phenyl]amino]-6-phenyl-1,3,5-triazin-2-yl]-1-piperazinecarboxaldehyde; 1-[4-[[3-methoxy-4-(5-oxazolyl)phenyl]amino]-6-phenyl-1,3,5-triazin-2-yl]-4-piperidineethanol; N'-[3-methoxy-4-(5-oxazolyl)phenyl]-N-methyl-6-phenyl-N-propyl-1,3,5-triazine-2,4-diamine; N-[2-(diethylamino)ethyl]-N'-[3-methoxy-4-(5-oxazolyl)phenyl]-N-methyl-6-phenyl-1,3,5-triazine-2,4-diamine; N-[2-(dimethylamino)ethyl]-N-ethyl-N'-[3-methoxy-4-(5-oxazolyl)phenyl]-6-phenyl-1,3,5-triazine-2-4-diamine; 2-[[4-[[3-methoxy-4-(5-oxazolyl)phenyl]amino]-6-phenyl-1,3,5-triazin-2-yl](1-methylethyl)

amino]ethanol; N-Ethyl-N'-[3-methoxy-4-(5-oxazolyl)phenyl]-6-phenyl-N-(4-pyridinylmethyl)-1,3,5-triazine-2,4-diamine; '1-[4-[[3-methoxy-4-(5-oxazolyl)phenyl]amino]-6-phenyl-1,3,5-triazin-2-yl]-1-piperazineethanol; 1-[4-[[3-methoxy-4-(5-oxazolyl)phenyl]amino]-6-phenyl-1,3,5-triazin-2-yl]-4-piperidinol; N-[1-[4-[[3-methoxy-4-(5-oxazolyl)phenyl]amino]-6-phenyl-1,3,5-triazin-2-yl]3-pyrrolidinyl]acetamide; 2-[[4-[[3-methoxy-4-(5-oxazolyl)phenyl]amino]-6-phenyl-1,3,5-triazin-2-yl](phenylmethyl)amino]-ethanol; 4-[4-(Hexahydro-4-methyl-1H-1,4-diazepin-1-yl)-N-[3-methoxy-4-(5-oxazolyl)phenyl]-6-phenyl-1,3,5-triazin-2-amine; 2-[Cyclohexyl[4-[[3-methoxy-4-(5-oxazolyl)phenyl]amino]-6-phenyl-1,3,5-triazin-2-yl]amino]ethanol; 1-[4-[[3-methoxy-4-(5-oxazolyl)phenyl]amino]-6-phenyl-1,3,5-triazin-2-yl]-4-piperidinecarboxylic acid ethyl ester; 4-[4-[[3-methoxy-4-(5-oxazolyl)phenyl]amino]-6-phenyl-1,3,5-triazin-2-yl]-1-piperazineacetic acid ethyl ester; N-[3-(diethylamino)propyl]-N-[3-methoxy-4-(5-oxazolyl)phenyl]-N-methyl-6-phenyl-1,3,5-triazine-2,4-diamine; N-[3-(diethylamino)propyl]-N'-[3-methoxy-4-(5-oxazolyl)phenyl]-N-methyl-6-phenyl-1,3,5-triazine-2,4-diamine; 1-[4-[[3-methoxy-4-(5-oxazolyl)phenyl]amino]-6-phenyl-1,3,5-triazin-2-yl]-L-prolinamide; 1-[4-[[3-methoxy-4-(5-oxazolyl)phenyl]amino]-6-phenyl-1,3,5-triazin-2-yl]-3-pyrrolidinol; N-[3-methoxy-4-(5-oxazolyl)phenyl]-6-phenyl-4-(4-thiomorpholinyl)-1,3,5-triazin-2-amine; N-[3-methoxy-4-(5-oxazolyl)phenyl]-6-phenyl-4-(4-thiomorpholinyl) 1,3,5-triazin-2-amine; N'-[3-methoxy-4-(5-oxazolyl)phenyl]-N-methyl-6-phenyl-N-(phenylmethyl)-1,3,5-triazine-2,4-diamine; (S)-4-[2-(methoxymethyl)-1-pyrrolidinyl]-N-[3-methoxy-4-(5-oxazolyl)phenyl]-6-phenyl-1,3,5-triazin-2-amine; 4-(3-azabicyclo[3.2.2]nonan-3-yl)-N-[3-methoxy-4-(5-oxazolyl)phenyl]-6-phenyl-1,3,5-triazin-2-amine; N-Ethyl-N-(2-methoxyethyl)-N'-[3-methoxy-4-(5-oxazolyl)phenyl]-6-phenyl-1,3,5-triazine-2,4-diamine; 1-[4-[[3-methoxy-4-(5-oxazolyl)phenyl]amino]-6-phenyl-1,3,5-triazin-2-yl]-4-piperidinemethanol; 2-[Butyl[4-[[3-methoxy-4-(5-oxazolyl)phenyl]amino]-6-phenyl-1,3,5-triazin-2-yl]amino]ethanol; 4-(1H-imidazol-1-yl)-N-[3-methoxy-4-(5-oxazolyl)phenyl]-6-phenyl-1,3,5-triazin-2-amine; N-[4-[[3-methoxy-4-(5-oxazolyl)phenyl]amino]-6-phenyl-1,3,5-triazin-2-yl]glycine 1,1-dimethylethyl ester; N-[4-[[3-methoxy-4-(5-oxazolyl)phenyl]amino]-6-phenyl-1,3,5-triazin-2-yl]glycine; 4-[[4-[[3-methoxy-4-(5-oxazolyl)phenyl]amino]-6-phenyl-1,3,5-triazin-2-yl]amino]butanoic acid; N-[3-methoxy-4-(5-oxazolyl)phenyl]-N'-[3-(1-pyrrolidinyl)propyl]-6-phenyl-1,3,5-triazine-2,4-diamine; N-[3-methoxy-4-(5-oxazolyl)phenyl]-N'-[3-(1-pyrrolidinyl)propyl]-6-phenyl-1,3,5-triazine-2,4-diamine; [S-(R*,R*)-∀-[2-methoxy-1-[[4-[[3-methoxy-4-(5-oxazolyl)phenyl]amino]-6-phenyl-1,3,5-triazin-2-yl]amino]ethyl]benzenemethanol; (R)-1-[4-[[3-methoxy-4-(5-oxazolyl)phenyl]amino]-6-phenyl-1,3,5-triazin-2-yl]-2-pyrrolidinemethanol; N-[4-[[3-methoxy-4-(5-oxazolyl)phenyl]amino]-6-phenyl-1,3,5-triazin-2-yl]-DL-serine methyl ester; N-[3-methoxy-4-(5-oxazolyl)phenyl]-4-phenyl-6-(1-pyrrolidinyl)-1,3,5-triazin-2-amine; N-[3-methoxy-4-(5-oxazolyl)phenyl]-4-(2-methylpropoxy)-6-phenyl-1,3,5-triazin-2-amine; N-[3-methoxy-4-(5-oxazolyl)phenyl]-4-phenyl-6-(phenylmethoxy)-1,3,5-triazin-2-amine; N-[3-methoxy-4-(5-oxazolyl)phenyl]-4-phenyl-6-(3-pyridinylmethoxy)1,3,5-triazin-2-amine; 2-[[4-[[3-methoxy-4-(5-oxazolyl)phenyl]amino]-6-phenyl-1,3,5-triazin-2-yl]oxy]ethanol; N-[3-methoxy-4-(5-oxazolyl)phenyl]-4-phenyl-6-[(tetrahydro-3-furanyl)oxy]-1,3,5-triazin-2-amine; N-[3-methoxy-4-(5-oxazolyl)phenyl]-4-(1-methylethoxy)-6-phenyl 1,3,5-triazin-2-amine; N-[3-methoxy-4-(5-oxazolyl)phenyl]-4-(1-methylethoxy)-6-phenyl-1,3,5-triazin-2-amine; N-[3-methoxy-4-(5-oxazolyl)phenyl]-4-(1-methylethoxy)-6-phenyl-1,3,5-triazin-2-amine; N-[3-methoxy-4-(5-oxazolyl)phenyl]-4-phenyl-6-phenylthio)-1,3,5-triazin-2-amine; 1-[[4-[[3-methoxy-4-(5-oxazolyl)phenyl]amino]-6-phenyl-1,3,5-triazin-2-yl]oxy]-2-propanol; 2-[[4-[[3-methoxy-4-(5oxazolyl)phenyl]amino]-6-phenyl-1,3,5-triazin-2-yl]amino]-1,3-propanediol; 2-[[4-[[3-methoxy-4-(5-oxazolyl)phenyl]amino]-6-phenyl-1,3,5-triazin-2-yl]amino]-1,3-propanediol; 2-[[4-[[3-methoxy-4-(5-oxazolyl)phenyl]amino]-6-phenyl-1,3,5-triazin-2-yl]amino]-1,3-propanediol; [S-(R*,S*)]-2-[[4-[[3-methoxy-4-(5-oxazolyl)phenyl]amino]-6-phenyl-1,3,5-triazin-2-yl]amino]-1-phenyl-1,3-propanediol; 2-[3-methoxy-4-(5-oxazolyl)phenyl]amino]-6-phenyl-4(3H)-triazinone; N-[3-methoxy-4-(5-oxazolyl)phenyl]-N'-methyl-6-(1-pyrrolidinyl)-1,3,5-triazine-2,4-diamine; N-[3-methoxy-4-(5-oxazolyl)phenyl]-N'-methyl-6-(4-methyl-1-piperazinyl)-1,3,5-triazine-2,4-diamine; 4-[4-[[3-methoxy-4-(5-oxazolyl)phenyl]amino]-6-(methylamino)-1,3,5-triazin-2-yl]-1-piperazinecarboxaldehyde; N-[3-methoxy-4-(5-oxazolyl)phenyl]-N'-methyl-6-(4-morpholinyl)-1,3,5-triazine-2,4-diamine; 1-[4-[[3-methoxy-4-(5-oxazolyl)phenyl]amino]-6-(methylamino)-1,3,5-triazin-2-yl]-2-piperidinemethanol; N,N-diethyl-1-[4-[[3-methoxy-4-(5-oxazolyl)phenyl]amino]-6-(methylamino)-1,3,5-triazin-2-yl]-3-piperidinecarboxamide; 1-[4-[[3-methoxy-4-(5-oxazolyl)phenyl]amino]-6-(methylamino)-1,3,5-triazin-2-yl]-4-piperidinol; (R)-1-[4-[[3-methoxy-4-(5-oxazolyl)phenyl]amino]-6-(methylamino)-1,3,5-triazin-2-yl]-3-piperidinol; 6-(2-Ethyl-1-piperidinyl)-N-[3-methoxy-4-(5-oxazolyl)phenyl]-N'-methyl-1,3,5-triazine-2,4-diamine; 1-[4-[[3-methoxy-4-(5-oxazolyl)phenyl]amino]-6-(methylamino)-1,3,5-triazin-2-yl]-L-prolinamide; (S)-6-[2-(methoxymethyl)-1-pyrrolidinyl]-N-[3-methoxy-4-(5-oxazolyl)phenyl]-N'-methyl-1,3,5-triazine-2,4-diamine; 1-[4-[[3-methoxy-4-(5-oxazolyl)phenyl]amino]-6-(methylamino)-1,3,5-triazin-2-yl]-L-proline 1,1-dimethylethyl ester; (R)-1-[4-[[3-methoxy-4-(5-oxazolyl)phenyl]amino]-6-(methylamino)-1,3,5-triazin-2-yl]-2-pyrrolidinemethanol; N-[1-[4-[[3-methoxy-4-(5-oxazolyl)phenyl]amino]-6-(methylamino)-1,3,5-triazin-2-yl]-3-pyrrolidinyl]-N-methylacetamide; (R)-6-[2-(methoxymethyl)-1-pyrrolidinyl]-N-[3-methoxy-4-(5-oxazolyl)phenyl]-N'-methyl-1,3,5-triazine-2,4-diamine; 1-[4-[[3-methoxy-4-(5-oxazolyl)phenyl]amino]-6-(methylamino)-1,3,5-triazin-2-yl]-3-piperidinemethanol; 1-[4-[[3-methoxy-4-(5-oxazolyl)phenyl]amino]-6-(methylamino)-1,3,5-triazin-2-yl]-4-piperidinecarboxamide; 1-[4-[[3-methoxy-4-(5-oxazolyl)phenyl]amino]-6-(methylamino)-1,3,5-triazin-2-yl]-3-oxo-2-piperazineacetic acid ethyl ester; 6-(2,5-dimethyl-1-pyrrolidinyl)-N-[3-methoxy-4-(5-oxazolyl)phenyl]-N'-methyl-1,3,5-triazine-2,4-diamine; 1-[4-[[3-methoxy-4-(5-oxazolyl)phenyl]amino]-6-(methylamino)-1,3,5-triazin-2-yl]-3-pyrrolidinol; (S)-6-[3-(dimethylamino)-1-pyrrolidinyl]-N-[3-methoxy-4-(5-oxazolyl)phenyl]-N'-methyl-1,3,5-triazine-2,4-diamine; (R)-[1-[4-[[3-methoxy-4-(5-oxazolyl)phenyl]amino]-6-(methylamino)-1,3,5-triazin-2-yl]-3-pyrrolidinyl]carbamic acid 1,1-dimethylethyl ester; 1-[4-[[3-methoxy-4-(5-oxazolyl)phenyl]amino]-6-(methylamino)-1,3,5-triazin-2-yl]-4-oxo-3-piperidinecarboxylic acid methyl ester; (S)-1-[4-[[3-methoxy-4-(5-oxazolyl)phenyl]amino]-6-(methylamino)-1,3,5-triazin-2-yl]-2-pyrrolidinemethanol; (S)-1-[4-[[3-methoxy-4-(5-oxazolyl)phenyl]amino]-6-(methylamino)-1,3,5-triazin-2-yl]-2-pyrrolidinemethanol; 1-[4-[[3-methoxy-4-(5-oxazolyl)phenyl]amino]-6-(methylamino)-1,3,5-triazin-2-yl]-2-piperidinecarboxylic acid ethyl ester; 1-[4-[[3-methoxy-4-(5-oxazolyl)phenyl]amino]-6-(methylamino)-1,3,5-triazin-2-yl]-2-piperidinecarboxylic acid ethyl ester; 1-[4-[[3-methoxy-4-(5-oxazolyl)phenyl]amino]-6-(methylamino)-1,3,5-triazin-2-yl]-2-piperidinecarboxylic acid ethyl ester; 2-[[3-methoxy-4(5-oxazolyl)phenyl]amino]-6-phenyl-4(3H)-pyrimidinone; N-[3-methoxy-4-(5-oxazolyl)phenyl]-5-phenyl-1H-imidazol-2-amine; 6-(2-furanyl)-N-[3-methoxy-4-(5-oxazolyl)phenyl]-N'-methyl-1,3,5-triazine-2,4-diamine; $R^1$=H, N-[2-[2-[[3-methoxy-4-(5-oxazolyl)phenyl]amino]-5-oxazolyl]phenyl]-N-methyl-1-piperidineacetamide; $R^1$=H, 4-hydroxy-N-[2-[2-[[3-methoxy-4-(5-oxazolyl)phenyl]amino]-5-oxazolyl]phenyl]-N-methyl-1-piperidineacetamide; $R^1$=H, 2-(cyclohexylmethylamino)-N-[2-[2-[[3-methoxy-4-(5-oxazolyl)phenyl]amino]-5-oxazolyl]phenyl]-N-methylacetamide; $R^1$=H, N-[2-[2-[[3-methoxy-4-(5-oxazolyl)phenyl]amino]-5-oxazolyl]phenyl]-N,2-dimethyl-1-piperidineacetamide; $R^1$=H, (S)-2-(methoxymethyl)-N-[2-[2-[[3-methoxy-4-(5-oxazolyl)phenyl]amino]-5-oxazolyl]phenyl]-N-methyl-1-pyrrolidineacetamide; $R^1$=H, 2-Amino-N-[2-[2-[[3-methoxy-4-(5-oxazolyl)phenylamino]-5-oxazolyl]phenyl]-N-methylacetamide; $R^1$=H, N-[2-[2-[[3-methoxy-4-(5-oxazolyl)phenyl]amino]-5-oxazolyl]phenyl]-N,2-dimethylpropanamide; $R^1$=H, N-[2-[2-[[3-methoxy-4-(5-oxazolyl)phenyl]amino]-5-oxazolyl]phenyl]-2,2-dimethylpropanamide; $R^1$=H, [[2-[2-[[3-methoxy-4-(5-oxazolyl)phenylamino]-5-oxazolyl]phenyl]methylamino]oxoacetic acid ethyl ester; $R^1$=H, [[2-[2-[[3-methoxy-4-(5-oxazolyl)phenyl]amino]-5-oxazolyl]phenyl]methyl-amino]oxoacetic acid; $R^1$=H, 2-[2-[[3-methoxy-4-(5-oxazolyl)phenyl]amino]-5-oxazolyl]benzeneacetic acid phenylmethyl ester; $R^1$=H, N-[(1-ethyl-3-pyrrolidinyl)methyl]-2-[2-[[3-methoxy-4-(5-oxazolyl)phenyl]amino]-5-oxazolyl]benzeneacetamide; 2-(acetyloxy)-N-[2-[2-[[3-bromo-4-(5-oxazolyl)phenyl]amino]-5-oxazolyl]phenyl]-N-methylacetamide; N-[2-[2-[[3-bromo-4-(5-oxazolyl)phenyl]amino]-5-oxazolyl]phenyl]-2-hydroxy-N-methylacetamide; N-[2-[2-[[3-bromo-4-(5-oxazolyl)phenyl]amino]-5-oxazolyl]phenyl]-N-methyl-4-morpholineacetamide; N-[2-[2-[[3-chloro-4-(5-oxazolyl)phenyl]amino]-5-oxazolyl]phenyl]-2-hydroxy-N-methylacetamide; N-[2-[2-[[3-chloro-4-(5-oxazolyl)phenyl]amino]-5-oxazolyl]phenyl]-N-methyl-4-morpholineacetamide; 2-(acetyloxy)-N-methyl-N-[2-[2-[[3-methyl-4-(5-oxazolyl)phenylamino]-5-oxazolyl]phenyl]acetamide; 2-hydroxy-N-[2-[2-[[3-methyl-4-(5-oxazolyl)phenyl]amino]-5-oxazolyl]phenyl]-N-methylacetamide; N-methyl-N-[2-[2-[[3-methyl-4-(5-oxazolyl)phenyl]amino]-5-oxazolyl]phenyl]4-morpholineacetamide; N-[3-methoxy-4-(1H-1,2,4-triazol-1-yl)phenyl]-5-phenyl-2-oxazolamine; and N-[4-(4-methyl-5-oxazolyl)phenyl]-5-phenyl-2-oxazolamine; N-[3-methoxy-4-cyanophenyl]-5-phenyl-2-oxazolamine The above compounds and methods for their preparation are disclosed in U.S. Pat. No. 6,399,773.

In other embodiments, the IMPDH antagonist is selected from compounds with structures represented by formula (XXI):

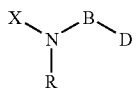

(XXI)

wherein:

X is selected from the group consisting of —C(O)—, —C(S)—, and —S(O)$_2$—;

A is a monocyclic or bicyclic ring system optionally comprising up to 4 heteroatoms selected from N, O, or S, and wherein a CH$_2$ adjacent to any of said N, O, or S, heteroatoms is optionally substituted with oxo (=O); and each ring is optionally substituted with up to 3 substituents, wherein:
the first of said substituents, if present, is selected from the group consisting of $R^1$, $R^2$, and $R^3$;
the second of said substituents, if present, is selected from the group consisting of $R^1$ and $R^2$; and
the third of said substituents, if present, is selected from the group consisting of $R^1$ and $R^2$;

$R^1$ is selected from a monocyclic ring system comprising 4 to 6 members per ring, wherein said ring system optionally comprises up to 4 heteroatoms selected from N, O, or S, and wherein a CH$_2$ adjacent to any of said N, O, or S heteroatoms is optionally substituted with oxo (=O); and each $R^1$ optionally comprises up to 3 substituents selected from $R^2$ or $R^3$;

$R^2$ is selected from halogen, CN, NO$_2$, CF$_3$, (C$_0$-C$_4$ alkyl) OR$^3$, OCF$_3$, OC(O)R$^3$, OC(O)OR$^3$, O(C)NR$^3$R$^4$, (C$_0$-C$_4$ alkyl)C(O)R$^3$, (C$_0$-C$_4$ alkyl)C(O)OR$^3$, (C$_0$-C$_4$ alkyl)C(O)OR$^3$, (C$_0$-C$_4$ alkyl)C(O)NR$^3$R$^4$, (C$_0$-C$_4$ alkyl)CONR$^3$S(O)$_2$R$^5$, (C$_0$-C$_4$ alkyl)C(O)N(OR$^3$)R$^3$, (C$_0$-C$_4$ alkyl)SR$^3$, (C$_0$-C$_4$ alkyl)SR$^3$, (C$_0$-C$_4$ alkyl)S(O)R$^5$, (C$_0$-C$_4$ alkyl)S(O)$_2$R$^5$, (C$_0$-C$_4$ alkyl)S(O)R$^5$, (C$_0$-C$_4$ alkyl)S(O)$_2$R$^5$, (C$_0$-C$_4$ alkyl)S(O)$_2$NR$^3$R$^4$, (C$_0$-C$_4$ alkyl)S(O)$_2$NR$^3$C(O)R$^4$, (C$_0$-C$_4$ alkyl)NR$^3$R$^4$, (C$_0$-C$_4$ alkyl)NR$^3$C(O)NR$^4$, (C$_0$-C$_4$ alkyl)NR$^3$C(O)R$^4$, (C$_0$-C$_4$ alkyl)NR$^3$C(O)OR$^5$, (C$_0$-C$_4$ alkyl)NR$^3$S(O)$_2$R$^5$, (C$_0$-C$_4$ alkyl)S(O)$_2$OR$^3$, (C$_0$-C$_4$ alkyl)P(O)(OH)OR$^3$, -J-(C$_0$-C$_4$ alkyl)OR$^3$, -J-(C$_1$-C$_4$ alkyl)C(O)OR$^3$, -J-(C$_1$-C$_4$ alkyl) CONR$^3$S(O)$_2$R$^5$, -J-(C$_1$-C$_4$ alkyl)S(O)$_2$NR$^3$R$^4$, -J-(C$_1$-C$_4$ alkyl)S(O)$_2$NR$^3$C(O)R$^4$, (C$_0$-C$_4$ alkyl)tetrazol-5-yl, and -J-(C$_1$-C$_4$ alkyl)tetrazol-5-yl, wherein J is chosen from O, S, and NR$^3$;

$R^3$ is selected from hydrogen, (C$_1$-C$_4$) alkyl, (C$_2$-C$_4$)alkenyl or (C$_2$-C$_4$)alkynyl, aryl(C$_0$-C$_4$) alkyl-, heterocyclic(C$_0$-C$_4$) alkyl- and cycloalkyl(C$_0$-C$_4$) alkyl-, wherein said groups are substituted with 0-2 substituents independently selected from R$^6$;

$R^4$ is selected from hydrogen, (C$_1$-C$_4$) alkyl, (C$_2$-C$_4$)-alkenyl, (C$_2$-C$_4$)alkynyl, aryl(C$_0$-C$_4$)alkyl-, heterocyclic(C$_0$-C$_4$) alkyl-, cycloalkyl(C$_0$-C$_4$) alkyl-, (C$_0$-C$_4$)alkylcarbonyl, aryl (C$_0$-C$_4$)alkylcarbonyl, heterocyclic(C$_0$-C$_4$)alkylcarbonyl, (C$_1$-C$_4$)alkyloxycarbonyl, aryl(C$_1$-C$_4$)alkyloxycarbonyl, and heterocyclic(C$_1$-C$_4$)alkyloxycarbonyl, wherein said groups are substituted with 0-2 substituents independently selected from R$^6$;

alternatively, $R^3$ and $R^4$, when both substituents are on the same nitrogen atom, as in (—NR$^3$R$^4$), can be taken together with the nitrogen atom to which they are attached to form a heterocycle selected from the group consisting of 1-aziridinyl, 1-azetidinyl, 1-piperidinyl, 1-morpholinyl, 1-pyrrolidinyl, thiamorpholinyl, thiazolidinyl, and 1-piperazinyl, said heterocycle being optionally substituted with 0-3 groups selected from the group consisting of oxo, R$^6$, C$_1$-C$_6$ alkyl, C$_3$-C$_7$ cycloalkyl(C$_0$-C$_4$ alkyl)-, C$_1$-C$_6$ alkylcarbonyl, C$_3$-C$_7$ cycloalkyl(C$_0$-C$_5$ alkyl)carbonyl, C$_1$-C$_6$ alkoxycarbonyl, C$_3$-C$_7$ cycloalkyl(C$_0$-C$_5$ alkoxy)carbonyl, aryl(C$_0$-C$_5$ alkyl), heterocyclic(C$_0$-C$_5$ alkyl), aryl(C$_1$-C$_5$ alkoxy)carbonyl, heterocyclic(C$_1$-C$_5$ alkoxy)carbonyl, C$_1$-C$_6$ alkylsulfonyl, arylsulfonyl, and heterocyclicsulfonyl,
wherein said aryl or heterocyclic groups are substituted with 0-2 substituents independently selected from the group consisting of C$_1$-C$_4$ alkyl, C$_1$-C$_4$ alkoxy, F, Cl, Br, CF$_3$, CN, and NO$_2$;

$R_5$ is selected from $(C_1-C_4)$ alkyl, $(C_2-C_4)$ alkenyl, $(C_2-C_4)$ alkynyl, aryl$(C_0-C_4)$ alkyl-, heterocyclic$(C_0-C_4)$ alkyl-, and cycloalkyl$(C_0-C_4)$ alkyl-, and each $R^3$ optionally comprises up to 2 different or identical substituents selected from $R^6$;

$R^6$ is selected from H, halogen, $NO_2$, CN, $C_1-C_4$ alkyl, $C_3-C_{10}$ cycloalkyl, $C_2-C_6$ alkenyl, $C_2-C_6$ alkynyl, haloalkyl, haloalkoxy, OH, hydroxy $C_1-C_4$ alkyl, $C_1-C_4$ alkoxy, $C_1-C_4$ alkylcarbonyl, $NH_2$, $(C_0-C_4$ alkyl$)_0$-2 alkylamino, $C_0-C_4$ alkylthio, $C_1-C_4$ alkylsulfonyl, aryl $C_0-C_4$ alkylsulfonyl, $(C_0-C_4$ alkyl$)_0$, alkylaminosulfonyl-, $(C_0-C_4$ alkylcarbonylamino-sulfonyl-, aryl$C_0-C_4$ alkylsulfonylaminocarbonyl, $C_1-C_4$ alkylsulfonylaminocarbonyl carboxylate, $C_1-C_4$ alkyloxycarbonyl, $(C_0-C_4$ alkyl$)_{02}$ aminocarbonyl-, and $(C_0-C_4$ alkyl$)$ tetrazol-5-yl;

B is a monocyclic or bicyclic ring system optionally comprising up to 4 heteroatoms selected from N, O, or S, and wherein a $CH_2$ adjacent to any of said N, O, or S heteroatoms is optionally substituted with oxo (=O); wherein each ring system is substituted with one substituent selected from $R^7$, $R^8$ or $R^9$, and is optionally substituted with a second and/or a third substituent, wherein:

the second of said substituents, if present, is selected from $R^7$, $R^8$, $R^9$, $R_{10}$, $R^{11}$, $R^{12}$; and the third of said substituents, if present is selected from $R^{10}$, $R^{11}$, and $R^{12}$;

$R^7$ is selected from $(C_0-C_6)$ alkyl, $(C_2-C_6)$ alkenyl or $(C_2-C_6)$ alkynyl and $R^7$ is substituted with:

$$\underset{Z^1}{\overset{N^{Z^2}}{\underset{\xi}{\bigvee}}}Z^3$$

$R^8$ is selected from $(C_0-C_6)$ alkyl, $(C_2-C_6)$ alkenyl or $(C_2-C_6)$alkynyl and $R^8$ is substituted with:

$$\underset{Z^1}{\overset{Z^4}{\underset{\xi}{\bigvee}}}\overset{Z^5}{Z^3}$$

$R^9$ is selected from $(C_0-C_6)$-alkyl or $(C_2-C_6)$-alkenyl or $(C_2-C_6)$alkynyl and $R^9$ is substituted with:

$$\underset{Z^7}{\overset{N^{Z^6}}{\underset{\xi}{\bigvee}}}$$

$Z^1$ is selected from the group consisting of O, S, and $NR^3$;

$Z^2$ is selected from the group consisting of H, $C_1-C_4$ alkyl, $C_3-C_6$ cycloalkyl, CN, $CF_3$, $OR^3$, heterocycle, $NO_2$, $C(O)R^3$, $C(O)_2R^3$, $C(O)NR^3R^4$, $S(O)_2NR^3R^4$, and $S(O)_2R^5$;

$Z^3$ is selected from the group consisting of $OR^3$, $SR^3$, and $NR^3R^4$;

$Z^4$ is selected from the group consisting of H, halo, $C_1-C_4$ alkyl, $C_3-C_6$ cycloalkyl, CN, $CF_3$, heterocycle, $NO_2$, $C(O)R^3$, $C(O)_2R^3$, $C(O)NR^3R^4$, $S(O)_2NR^3R^4$, and $S(O)_2R^5$;

$Z^5$ is selected from the group consisting of halo, CN, $CF_3$, heterocycle, $NO_2$, $C(O)R^3$, $C(O)_2R^3$, $C(O)NR^3R^4$, $S(O)_2NR^3R^4$, and $S(O)_2R^5$;

$Z^6$ is selected from the group consisting of H, C(O)H, $C(O)R^3$, $C(O)OR^5$, $C(O)NR^3R^4$, $S(O)R^5$ and $S(O)_2R^5$;

$Z^7$ is selected from the group consisting of OH, $OR^3$ and $NR^3R^4$;

$R^{10}$ is selected from hydrogen, $(C_1-C_4)$ alkyl, $(C_2-C_4)$alkenyl or alkynyl, aryl, heterocyclic, and cycloalkyl, and each $R^{10}$ optionally comprises up to 3 substituents selected from $R^{11}$ or $R^{12}$;

$R^{11}$ is selected from the group consisting of H, halogen, $NO_2$, CN, $C_1-C_4$ alkyl, $C_3-C_{10}$ cycloalkyl, $C_2-C_6$ alkenyl, $C_2-C_6$ alkynyl, haloalkyl, haloalkoxy, OH, $C_1-C_4$ alkoxy, $C_1-C_4$ alkylcarbonyl, $NH_2$, $(C_0-C_4$ alkyl$)_0$-2 alkylamino, $C_0-C_4$ alkylthio, $C_1-C_4$ alkylsulfonyl, aryl $C_0-C_4$ alkylsulfonyl, $(C_0-C_4$ alkyl$)_0$-2 alkylaminosulfonyl-, $(C_0-C_4$ alkylcarbonylaminosulfonyl-, aryl$C_0-C_4$ alkylsulfonylaminocarbonyl, $C_1-C_4$ alkylsulfonylaminocarbonyl carboxylate, $C_1-C_4$ alkyloxycarbonyl, $(C_0-C_4$ alkyl$)_0$-2 aminocarbonyl-, and $(C_0-C_4$ alkyl$)$tetrazol-5-yl;

$R^{12}$ is selected from H, alkyl, $(C_1-C_6)$ alkyloxy, $C_3-C_6$ cycloalkyl, heterocycle and aryl, and pharmaceutically acceptable salts thereof.

In some embodiments, the compounds of formula (XXI) have a structure represented by the formula:

$$A\underset{H}{\overset{}{\underset{N}{\bigvee}}}\overset{V}{\underset{H}{\overset{}{\underset{N}{\bigvee}}}}M \quad (XXII)$$

wherein:

V is $-C(NZ^2)-$ or $-C(CZ^9Z^{10})-$;

$Z^2$ is selected from the group consisting of lower alkyl, cycloalkyl, CN, $CF_3$, heterocycle, $NO_2$, $C(O)R^3$, $C(O)_2R^3$, $C(O)NR^3R^4$, $S(O)_2NR^3R^4$, and $S(O)_2R^5$;

$Z^9$ is selected the group consisting of H, lower alkyl, cycloalkyl, CN, $CF_3$, heterocycle, $NO_2$, $C(O)R^3$, $C(O)_2R^4$, $C(O)NR^3R^4$, $S(O)_2NR^3R^4$, and $S(O)_2R^5$;

$Z^{10}$ is selected the group consisting of CN, $CF_3$, heterocycle, $NO_2$, $C(O)R^3$, $C(O)_2R^3$, $C(O)NR^3R^4$, $S(O)_2NR^3R^4$, and $S(O)_2R^5$;

A is $$\begin{array}{c}A^4-A^2\\ \mid \quad \quad \mid \\ A^6 \quad \quad A^1- \\ \mid \quad \quad \mid \\ A^5-A^3\end{array} \quad \text{and}$$

$A^1$ is C or $CS^1$;

$A^2$ is selected from the group consisting of
1) a heteroatom selected from the group consisting of nitrogen, oxygen and sulfur,
2) $CS^2$,
3) CO,
4) $NS^7$,
5) $S(O)_2$;

$A^3$ is selected from the group consisting of
1) a heteroatom selected from the group consisting of nitrogen, oxygen and sulfur,
2) $CS^3$,
3) CO,
4) $NS^7$,
5) $S(O)_2$;

$A^4$ is selected from the group consisting of
1) a heteroatom selected from the group consisting of nitrogen, oxygen and sulfur, 2) CS$^4$,
3) CO,
4) NS$^7$,
5) S(O)$_2$,
6) a bond;
A$^5$ is selected from the group consisting of
1) a heteroatom selected from the group consisting of nitrogen, oxygen and sulfur,
2) CS$^5$,
3) CO,
4) NS$^7$,
5) S(O)$_2$;
A$^6$ is selected from the group consisting of
1) a heteroatom selected from the group consisting of nitrogen, oxygen and sulfur,
2) CS$^6$,
3) CO,
4) NS$^7$,
5) S(O)$_2$;
A$^4$, A$^6$ and the atoms to which they are attached together may form a bicyclic ring system containing 0-2 additional heteroatoms selected from nitrogen, oxygen and sulphur;
A$^5$, A$^6$ and the atoms to which they are attached together may form a bicyclic ring system containing 0-2 additional heteroatoms selected from nitrogen, oxygen and sulphur;
wherein, A$^2$, A$^3$, A$^4$, A$^5$, and A$^6$, are chosen such that the total number of heteroatoms in the monocyclic or bicyclic ring system does not exceed four, and the attached substituents S$^1$, S$^2$, S$^3$, S$^4$, S$^5$, S$^6$, and S$^7$ are chosen such that the total number of non-hydrogen substituents does not exceed four;
S$^1$ is selected from H, C$_1$-C$_3$ alkyl and halo;
S$^2$ is selected from H, C$_1$-C$_3$-alkyl and halo;
S$^3$ is selected from H, C$_1$-C$_3$ alkyl and halo;
S$^4$ is selected from H, R$^1$, R$^2$ or R$^3$;
S$^5$ is selected from H, R$^1$, R$^2$ or R$^3$;
S$^6$ is selected from R$^1$, R$^2$ or R$^5$;
S$^7$ is selected from R$^3$, or R$^4$;
R$^1$ is a monocyclic ring system comprising 4 to 6 members per ring, wherein said ring system optionally comprises up to 4 heteroatoms selected from N, O, or S, and wherein a CH$_2$ adjacent to any of said N, O, or S heteroatoms is optionally substituted with oxo (=O); and each R$^1$ optionally comprises up to 3 substituents selected from R$^2$ or R$^3$;
R$^2$ is selected from halogen, CN, NO$_2$, CF$_3$, (C$_0$-C$_4$ alkyl) OR$^3$, OCF$_3$, OC(O)R$^3$, OC(O)OR$^3$, O(C)NR$^3$R$^4$, (C$_0$-C$_4$ alkyl)C(O)R$^3$, (C$_0$-C$_4$ alkyl)C(O)OR$^3$, C$_0$-C$_4$ alkyl)C(O) OR$^3$, (C$_4$-C$_4$ alkyl)C(O)NR$^3$R$^4$, (C$_0$-C$_4$ alkyl)CONR$^3$S(O)$_2$ R$^5$, (C$_0$-C$_4$ alkyl)C(O)N(OR$^3$)R$^3$, (C$_0$-C$_4$ alkyl)SR$^3$, (C$_0$-C$_4$ alkyl)SR$^3$, (C$_0$-C$_4$ alkyl)S(O)R$^5$, (C$_{04}$ alkyl)S(O)$_2$R$^5$, (C$_0$-C$_4$ alkyl)S(O)R$^5$, (C$_0$-C$_4$ alkyl)S(O)$_2$R$^5$, (C$_0$-C$_4$ alkyl)S(O)$_2$ NR$^3$R$^4$, (C$_0$-C$_4$ alkyl)S(O)$_2$NR$^3$C(O)R$^4$, (C$_0$-C$_4$ alkyl) NR$^3$R$^4$, (C$_0$-C$_4$ alkyl)NR$^3$C(O)NR$^4$, (C$_0$-C$_4$ alkyl)NR$^3$C(O) R$^4$, (C$_0$-C$_4$ alkyl)NR$^3$C(O)OR$^5$, (C$_1$-C$_4$ alkyl)NR$^3$C(O) NR$_3$R$^5$a, (C$_0$-C$_4$ alkyl)NR$^3$S(O)$_2$R$^5$, (C$_0$-C$_4$ alkyl)S(O)$_2$ OR$^3$, (C$_0$-C$_4$ alkyl)P(O)(OH)OR$^3$, -J-(C$_0$-C$_4$ alkyl)OR$^3$, -J-(C$_1$-C$_4$ alkyl)C(O)OR$^3$, -J-(C$_1$-C$_4$ alkyl)CONR$^3$S(O)$_2$R$^5$, -J-(C$_1$-C$_4$ alkyl)S(O)$_2$NR$^3$R$^4$, -J-(C$_1$-C$_4$ alkyl)S(O)$_2$NR$^3$C(O) R$^4$, (C$_0$-C$_4$ alkyl)tetrazol-5-yl, and -J-(C$_1$-C$_4$ alkyl)tetrazol-5-yl, wherein J is chosen from O, S, and NR$^3$;
R$^3$ is selected from hydrogen, (C$_1$-C$_4$) alkyl; (C$_2$-C$_4$)alkenyl, (C$_2$-C$_4$)alkynyl, aryl(C$_0$-C$_4$) alkyl-, heterocyclic(C$_0$-C$_4$) alkyl-, and cycloalkyl(C$_0$-C$_4$) alkyl-, wherein said groups are substituted with 0-2 substituents independently selected from R$^6$;
R$^4$ is selected from hydrogen, (C$_1$-C$_4$) alkyl, (C$_2$-C$_4$)-alkenyl, (C$_2$-C$_4$)alkynyl, aryl(C$_0$-C$_4$)alkyl-, heterocyclic(C$_0$-C$_4$) alkyl-, cycloalkyl, (C$_0$-C$_4$)alkylcarbonyl, aryl(C$_0$-C$_4$)alkylcarbonyl, heterocyclic(C$_0$-C$_4$)alkylcarbonyl, (C$_1$-C$_4$) alkyloxycarbonyl, aryl(C$_1$-C$_4$)alkyloxycarbonyl, and heterocyclic(C$_1$-C$_4$)alkyloxycarbonyl, wherein said groups are substituted with 0-2 substituents independently selected from R$^6$;
alternatively, R$^3$ and R$^4$, when both substituents are on the same nitrogen atom, as in (—NR$^3$R$^4$), can be taken together with the nitrogen atom to which they are attached to form a heterocycle selected from the group consisting of 1-aziridinyl, 1-azetidinyl, 1-piperidinyl, 1-morpholinyl, 1-pyrrolidinyl, thiamorpholinyl, thiazolidinyl, and 1-piperazinyl, said heterocycle being optionally substituted with 0-3 groups selected from the group consisting of oxo, R$^6$, C$_1$-C$_6$ alkyl, C$_3$-C$_7$ cycloalkyl(C$_0$-C$_4$ alkyl)-, C$_1$-C$_6$ alkylcarbonyl, C$_3$-C$_7$ cycloalkyl(C$_0$-C$_5$ alkyl)carbonyl, C$_1$-C$_6$ alkoxycarbonyl, C$_3$-C$_7$ cycloalkyl(C$_0$-C$_5$ alkoxy)carbonyl, aryl(C$_0$-C$_5$ alkyl), heterocyclic(C$_0$-C$_5$ alkyl), aryl(C$_1$-C$_5$ alkoxy)carbonyl, heterocyclic(C$_1$-C$_5$ alkoxy)carbonyl, C$_1$-C$_6$ alkylsulfonyl, arylsulfonyl, and heterocyclicsulfonyl,
wherein said aryl or heterocyclic groups are substituted with 0-2 substituents independently selected from the group consisting of C$_1$-C$_4$ alkyl, C$_1$-C$_4$ alkoxy, F, Cl, Br, CF$_3$, CN, and NO$_2$;
R$^5$ is selected from (C$_1$-C$_4$)alkyl, (C$_2$-C$_4$)alkenyl, (C$_2$-C$_4$) alkynyl, aryl(C$_0$-C$_4$) alkyl-, heterocyclic(C$_0$-C$_4$) alkyl-, or cycloalkyl(C$_0$-C$_4$) alkyl-, and each R$^3$ optionally comprises up to 2 different or identical substituents selected from R$^6$;
R$^5$a is selected from (C$_1$-C$_4$)alkyl, (C$_2$-C$_4$)alkenyl, (C$_2$-C$_4$) alkynyl, aryl(C$_1$-C$_4$) alkyl-, heterocyclic(C$_1$-C$_4$) alkyl-, or cycloalkyl(C$_1$-C$_4$) alkyl-, and each R$^3$ optionally comprises up to 2 different or identical substituents selected from R$^6$;
R$^6$ is selected from H, halogen, NO$_2$, CN, C$_1$-C$_4$ alkyl, C$_3$-C$_{10}$ cycloalkyl, C$_2$-C$_6$ alkenyl, C$_2$-C$_6$ alkynyl, haloalkyl, haloalkoxy, OH, hydroxy C$_1$-C$_4$ alkyl, C$_1$-C$_4$ alkoxy, C$_1$-C$_4$ alkylcarbonyl, NH$_2$, (C$_0$-C$_4$ alkyl)$_0$-2 alkylamino, C$_{0-4}$ alkylthio, C$_1$-C$_4$ alkylsulfonyl, aryl C$_0$-C$_4$ alkylsulfonyl, (C$_{0-4}$ alkyl)$_0$-2 alkylaminosulfonyl-, (C$_0$-C$_4$ alkylcarbonylaminosulfonyl-, arylC$_0$-C$_4$ alkylsulfonylaminocarbonyl, C$_1$-C$_4$ alkylsulfonylaminocarbonyl carboxylate, C$_1$-C$_4$ alkyloxycarbonyl, (C$_0$-C$_4$ alkyl)$_0$-2 aminocarbonyl-, and (C$_0$-C$_4$ alkyl) tetrazol-5-yl;
M is selected from the group consisting of:
(i) (C$_1$-C$_6$)alkyl, (C$_2$-C$_6$)alkenyl, (C$_2$-C$_6$)alkynyl, and cycloalkyl(C$_1$-C$_4$)alkyl, optionally comprising up to 3 substituents selected from the group consisting of R$^1$, R$^2$, or R$^4$, wherein any CH$_2$ is optionally substituted with oxo (=O); and
(ii)

$$\begin{array}{c} M^4-M^2 \\ / \quad \backslash \\ M^6 \quad \quad M^1- \\ \backslash \quad / \\ M^5-M^3 \end{array} \text{ and}$$

M$^1$ is C or CP$^1$;
M$^2$ is selected from the group consisting of
1) a heteroatom selected from the group consisting of nitrogen, oxygen and sulfur,
2) C(P$^2$)$_1$-2,
3) CO,
4) NP$^7$,
5) S(O)$_2$;
M$^3$ is selected from the group consisting of
1) a heteroatom selected from the group consisting of nitrogen, oxygen and sulfur,

2) C(P³)₁₋₂,
3) CO,
4) NP⁷,
5) S(O)₂

M⁴ is selected from the group consisting of
1) a heteroatom selected from the group consisting of nitrogen, oxygen and sulfur,
2) CP⁴,
3) CP⁵,
4) C(P⁵)₁₋₂,
5) CO,
6) NP⁷,
7) S(O)₂;

M⁵ is selected from the group consisting of
1) a heteroatom selected from the group consisting of nitrogen, oxygen and sulfur,
2) C(P⁵)₁₋₂,
3) CO,
4) NP⁷,
5) S(O)₂;

M⁶ is selected from the group consisting of
1) a heteroatom selected from the group consisting of nitrogen, oxygen and sulfur,
2) C(P⁶)₁₋₂,
3) CO,
4) NP⁷,
5) S(O)₂,
6) a bond;

M⁴, M⁶ and the atoms to which they are attached together may form a bicyclic ring system containing 0-2 additional heteroatoms selected from nitrogen, oxygen and sulphur;

M⁵, M⁶ and the atoms to which they are attached together may form a bicyclic ring system containing 0-2 additional heteroatoms selected from nitrogen, oxygen and sulphur;

wherein, M², M³, M⁴, M⁵, and M⁶, are chosen such that the total number of heteroatoms in the monocyclic or bicyclic ring system does not exceed four, and the attached substituents P¹, P², P³, P⁴, P⁵, P⁶, and P⁷ are chosen such that the total number of non-hydrogen substituents does not exceed four;

P¹ is selected from H, C₁-C₃ alkyl or halo;
P² is selected from H, C₁-C₃ alkyl or halo;
P³ is selected from H, C₁-C₃ alkyl or halo;
P⁴ is selected from R², R⁵, R⁷, R⁸ or R⁹;
P⁵ is selected from H, R² or R³
P⁶ is selected from H, R³, R⁴, R⁷, R⁸ or R⁹;
P⁷ is selected from R³ or R⁴;

R⁷ is selected from (C₀-C₆) alkyl, (C₂-C₆) alkenyl or (C₂-C₆)alkynyl and R⁷ is substituted with:

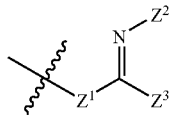

R⁸ is elected from (C₀-C₆) alkyl, (C₂-C₆) alkenyl or (C₂-C₆)alkynyl and R⁸ is substituted with:

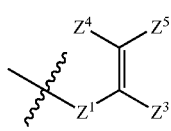

R⁹ is selected from (C₀-C₆) alkyl or (C₂-C₆) alkenyl or alkynyl and R⁹ is substituted with:

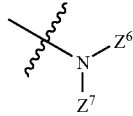

Z¹ is selected from the group consisting of O, S, and NR³;
Z² is selected from the group consisting of H, C₁-C₄ alkyl, C₃-C₆ cycloalkyl, CN, CF₃, OR³, heterocycle, NO₂, C(O)R³, C(O)₂R³, C(O)NR³R⁴, S(O)₂NR³R⁴, and S(O)₂R⁵;
Z³ is selected from the group consisting of OR³, SR³, and NR³R⁴;
Z⁴ is selected from the group consisting of H, halo, C₁-C₄ alkyl, C₃-C₆ cycloalkyl, CN, CF₃, heterocycle, NO₂, C(O)R³, C(O)₂R³, C(O)NR³R⁴, S(O)₂NR³R⁴, and S(O)₂R⁵;
Z⁵ is selected from the group consisting of halo, CN, CF₃, heterocycle, NO₂, C(O)R³, C(O)₂R³, C(O)NR³R⁴, S(O)₂NR³R⁴, and S(O)₂R⁵;
Z⁶ is selected from the group consisting of H, C(O)H, C(O)R³, C(O)OR⁴, C(O)NR³R⁴, S(O)R⁵ and S(O)₂R⁵;
Z⁷ is selected from the group consisting of OH, OR³ and NR³R⁴, R¹⁰ is selected from hydrogen, (C₁-C₄) alkyl, (C₂-C₄)alkenyl or alkynyl, aryl, heterocyclic, and cycloalkyl, wherein said groups are substituted with 0-2 substituents independently selected from R¹¹ or R¹²;

R¹¹ is selected from the group consisting of H, halogen, NO₂, CN, C₁-C₄ alkyl, C₃-C₁₀ cycloalkyl, C₂-C₆ alkenyl, C₂-C₆ alkynyl, haloalkyl, haloalkoxy, OH, C₁-C₄ alkoxy, C₁-C₄ alkylcarbonyl, NH₂, (C₀-C₄ alkyl)₀₋₂ alkylamino, C₀-C₄ alkylthio, C₁-C₄ alkylsulfonyl, aryl C₀-C₄ alkylsulfonyl, (C₀-C₄ alkyl)₀₋₂ alkylaminosulfonyl-, (C₀-C₄ alkylcarbonylaminosulfonyl-, arylC₀-C₄ alkylsulfonylaminocarbonyl, C₁-C₄ alkylsulfonylaminocarbonyl carboxylate, C₁-C₄ alkyloxycarbonyl, (C₀₋₄ alkyl)₀₋₂ aminocarbonyl-, and (C₀-C₄ alkyl)tetrazol-5-yl;

R¹² is selected from H, alkyl, (C₁-C₆) alkyloxy, C₃-C₆ cycloalkyl, heterocyclic and aryl.

Representative compounds falling within the scope of formula (XXII) include, but are not limited to: N-[3-[[[(cyanoamino)phenoxymethylene]amino]methyl]phenyl]-N'-[3-methoxy-4-(5-oxazolyl)phenyl]urea; N-[3-[[[Amino(cyanoamino)methylene]amino]methyl]phenyl]-N'-[3-methoxy-4-(5-oxazolyl)phenyl]urea; N-[3-[[[(cyanoamino)(4-morpholinyl)methylene]amino]methyl]phenyl]-N'-[3-methoxy-4-(5-oxazolyl)phenyl]urea; N-[3-[[[(cyanoamino)[[2-(1H-imidazol-4-yl)ethyl]amino]methylene]-amino]methyl]phenyl]-N'-[3-methoxy-4-(5-oxazolyl)phenyl]urea; N-[3-[[[(cyanoamino)(4-hydroxy-1-piperidinyl)methylene]amino]-methyl]phenyl]-N-[3-methoxy-4-(5-oxazoly)phenyl]area; N-[3-[[[(cyanoamino)(3-hydroxy-1-piperidinyl)methylene]amino]-methyl]phenyl]-N'-[3-methoxy-4-(5-oxazolyl)phenyl]urea; N-[3-[[[(cyanoamino)(cyclohexylamino)methylene]amino]methyl]-phenyl]-N'-[3-methoxy-4-(5-oxazolyl)phenyl]urea; N-[3-[[[(cyanoamino)[(4-pyridinylmethyl)amino]methylene]amino]-methyl]phenyl]-N'-[3-methoxy-4-(5-oxazolyl)phenyl]urea; N-[3-[[[(cyanoamino)[[(tetrahydro-2-fuaranyl)methyl]amino]methylene]-amino]methyl]phenyl]-N'-[3-methoxy-4-(5-oxazolyl)phenyl]urea; N-[3-[[[(cyanoamino)[4-(2-hydroxyethyl)-1-piperazinyl]methylene]-amino]methyl]phenyl]-N'-[3-methoxy-4-(5-oxazolyl)phenyl]urea; N-[3-[[[(cyanoamino)(methylamino)methylene]amino]methyl]phenyl]-N'-[3-methoxy-4-(5-oxazolyl)phenyl]urea; (S)-N-[3-[[[(cyanoamino)[(tetrahydro-2-furanylmethyl)amino]-methylene]amino]methyl]phenyl]-N'-[3-methoxy-4-(5-oxazolyl)phenyl]urea; (R)-N-[3-[[[(cyanoamino)[(tetrahydro-2-furanylmethyl)amino]-methylene]amino]methyl] phenyl]-N'-[3-methoxy-4-(5-oxazolyl)phenyl]urea; N-[3-[[[(cyanoamino)[(tetrahydro-2-furanyl)methoxy]methylene]amino]-methyl]phenyl]-N'-[3-methoxy-4-(5-oxazolyl)phenyl]urea; N-cyano-N'-cyclohexyl-N"-[3-methoxy-4-(5-oxazolyl)phenyl]guanidine; (R)-N-cyano-N'-(1-cyclohexylethyl)-N"-[3-methoxy-4-(5-oxazolyl)-phenyl]guanidine; N-cyano-N'-[3-methoxy-4-(5-oxazolyl)phenyl]-N"-propylguanidine; N-cyano-N'-(2,3-dihydro-1H-inden-2-yl)-N"-[3-methoxy-4-(5-oxazolyl)-phenyl]guanidine; N-cyano-N'-cyclopentyl-N"-[3-methoxy-4-(5-oxazolyl)phenyl]guanidine; N-cyano-N'-[3-methoxy-4-(5-oxazolyl)phenyl]-N"-[(5-methyl-2-furanyl)methyl]guanidine; N-cyano-N'-[3-methoxy-4-(5-oxazolyl)phenyl]-N"-(2-thienylmethyl)guanidine; N-cyano-N'-[3-methoxy-4-(5-oxazolyl)phenyl]-N"-[(2-methylphenyl)methyl]guanidine; N-cyano-N'-[3-methoxy-4-(5-oxazolyl)phenyl]-N'-[(3-methylphenyl)methyl]guanidine; N-[(2-Bromophenyl)methyl]-N'-cyano-N"-[3-methoxy-4-(5-oxazolyl)phenyl]guanidine; N-[(4-Chlorophenyl)methyl]-N'-cyano-N"-[3-methoxy-4-(5-oxazolyl)phenyl]guanidine; N-(bicyclo[2.2.1]heptan-2-yl)-N'-cyano-N"-[3-methoxy-4-(5-oxazolyl)-phenyl]guanidine; N-cyano-N'-[3-methoxy-4-(5-oxazolyl)phenyl]-N"-(4-methylcyclohexyl)-guanidine; N-cyano-N'-[3-methoxy-4-(5-oxazolyl)phenyl]-N"-(3-methylbutyl)guanidine; N-[(4-Aminophenyl)methyl]-N'-cyano-N'-[3-methoxy-4-(5-oxazolyl)phenyl]guanidine; N-cyano-N'-(cyclopropylmethyl)-N"-[3-methoxy-4-(5-oxazolyl)phenyl]-guanidine; N-Butyl-N'-cyano-N"-[3-methoxy-4-(5-oxazolyl)phenyl]guanidine; N-[(3-Chlorophenyl)methyl]-N'-cyano-N"-[3-methoxy-4-(5-oxazolyl)phenyl]guanidine; N-cyano-N'-[4-(1,1-dimethylethyl)cyclohexyl]-N"-[3-methoxy-4-(5-oxazolyl)phenyl]guanidine; N-cyano-N'-(3-methoxy-4-(5-oxazolyl)phenyl)-N"-phenylguanidine; N-cyano-N'-(3-methoxy-4-(5-oxazolyl)phenyl)-N"-(2-methylphenyl)guanidine; N-cyano-N'-(3-methoxy-4-(5-oxazolyl)phenyl)-N"-(4-methylphenyl)guanidine; N-cyano-N'-[3-methoxy-4-(5-oxazolyl)phenyl]-N"-[3-(1-methylethyl)phenyl]guanidine; N-cyano-N'-[3-methoxy-4-(5-oxazolyl)phenyl]-N"-[3-(trifluoromethoxy)-phenyl]guanidine; N-cyano-N'-[3-(1,1-dimethylethyl)phenyl]-N"-[3-methoxy-4-(5-oxazolyl)phenyl]guanidine; N-cyano-N'-[3-methoxy-4-(5-oxazolyl)phenyl]-N"-[3-(2-phenoxyethoxy)phenyl]guanidine; N-cyano-N'-[3-(hydroxymethyl)phenyl]-N"-[3-methoxy-4-(5-oxazolyl)phenyl]guanidine; Trans-N-cyano-N'-[3-methoxy-4-(5-oxazolyl)phenyl]-N"-(2-phenylcyclopropyl) guanidine; N-cyano-N'-[3-methoxy-4-(5-oxazolyl)phenyl]-N"-3-pyridinylguanidine; (S)-[[3-[[(cyanoamino)[[3-methoxy-4-(5-oxazolyl)phenyl]amino]methylene]amino]phenyl]methyl] carbamic acid tetrahydro-3-furanyl ester; [[3-[[(cyanoamino)[[3-methoxy-4-(5-oxazolyl)phenyl]amino]methylene]-amino]phenyl]methyl]carbamic Acid Tetrahydro-3-furanylmethyl ester; N-[[3-[[(cyanoamino)[[3-methoxy-4-(5-oxazolyl)phenyl]amino]methylene]amino]phenyl] methyl]-N'-[(tetrahydro-3-furanyl)methyl]urea; N-[3-[[[(cyanoamino)methoxymethylene]amino]methyl]phenyl]-N'-[3-methoxy-4-(5-oxazolyl)phenyl]urea; N-[3-[[[(cyanoamino)[(tetrahydro-3-furanyl)methoxy]methylene]amino]-methyl]phenyl]-N'-[3-methoxy-4-(5-oxazolyl)phenyl]urea; and N-[3-[[amino(cyanoamino)methylene]amino]phenyl]-N'-[3-methoxy-4-(5-oxazoly)phenyl]urea.

The above compounds and methods for their preparation are disclosed in U.S. Pat. No. 6,420,403.

In other embodiments, the IMPDH antagonist is selected from compounds with structures represented by formula (XXIII):

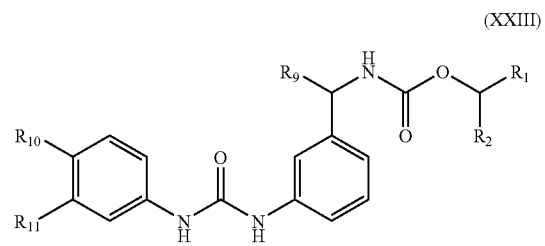

(XXIII)

wherein:

each of $R_1$ and $R_2$ is independently selected from hydrogen; —$CF_3$; $C_1$-$C_6$-straight or branched alkyl; $C_2$-$C_6$-straight or branched alkenyl or alkynyl; $C_1$-$C_6$-straight or branched alkyl-$R_7$; —[($C_2$-$C_6$)-straight or branched alkenyl or alkynyl]-$R_7$ or —$R_7$; and wherein at least one of $R_1$ or $R_2$ is $C_1$-$C_6$-straight or branched alkyl-$R_7$; —[($C_2$-$C_6$)-straight or branched alkenyl or alkynyl]-$R_7$ or —$R_7$ wherein up to 4 hydrogen atoms in any of said alkyl, alkenyl or alkynyl are optionally and independently replaced by $R_3$; or wherein $R_1$ and $R_2$ are alternatively taken together to form tetrahydrofuranyl, wherein when $R_9$ is hydrogen, (R)-methyl, (R)-ethyl or (R)-hydroxymethyl, one hydrogen atom in said tetrahydrofuran is replaced by —$OR_6$ or —$R_7$, and wherein when $R_9$ is (S)-methyl, (S)-ethyl or (S)-hydroxymethyl, one hydrogen atom in said tetrahydrofuran is optionally replaced by —$OR_6$ or —$R_7$;

wherein when $R_9$ is hydrogen, (R)-methyl, (R)-ethyl or (R)-hydroxymethyl and each of $R_1$ and $R_2$ are independently hydrogen, unsubstituted —($C_1$-$C_6$)-straight or branched alkyl, or unsubstituted —($C_2$-$C_6$)-straight or branched alkenyl or alkynyl, then the portion of the compound represented by —$CH(R_1)R_2$ is a $C_5$-$C_{12}$ straight or branched alkyl, alkenyl or alkynyl;

each $R_3$ is independently selected from halo, CN, —$OR_4$, or —$N(R_5)_2$;

$R_4$ is selected from hydrogen, —($C_1$-$C_6$)-straight or branched alkyl, —($C_2$-$C_6$)-straight or branched alkenyl or alkynyl, —[($C_1$-$C_6$)-straight or branched alkyl]-$R_7$, —[($C_2$-$C_6$)-straight or branched alkenyl or alkynyl]-$R_7$, —C(O)[($C_1$-$C_6$)-straight or branched alkyl], —C(O)[($C_2$-$C_6$)-straight or branched alkenyl or alkynyl], —C(O)[($C_1$-$C_6$)-straight or branched alkyl]-$N(R_8)_2$, —C(O)—[($C_2$-$C_6$)-straight or branched alkenyl or alkynyl]-$N(R_8)_2$, —P(O)($OR_8$)$_2$, —P(O)($OR_8$)($R_8$), —C(O)—$R_7$, —[($C_1$-$C_6$)-straight or branched alkyl]-CN, —$S(O)_2N(R_5)_2$ or —[($C_2$-$C_6$)-straight or branched alkenyl or alkynyl]-CN;

each $R_5$ is independently selected from hydrogen, —($C_1$-$C_6$)-straight or branched alkyl, —($C_2$-$C_6$)-straight or branched alkenyl or alkynyl, —[($C_1$-$C_6$)-straight or branched alkyl]-$R_7$, —[($C_2$-$C_6$)-straight or branched alkenyl or alkynyl]-$R_7$, —[($C_1$-$C_6$)-straight alkyl]-CN, —[($C_2$-$C_6$)-straight or branched alkenyl or alkynyl]-CN, —[($C_1$-$C_6$)-straight or branched alkyl]-$OR_4$, —[($C_2$-$C_6$)-straight or branched alkenyl or alkynyl]-$OR_4$, —C(O)—($C_1$-$C_6$)-straight or branched alkyl, —C(O)—[($C_2$-$C_6$)-straight or branched alkenyl or alkynyl], —C(O)—$R_7$, —C(O)O—$R_7$, —C(O)O—($C_1$-$C_6$)-straight or branched alkyl, —C(O)O—[($C_2$-$C_6$)-straight or branched alkenyl or alkynyl], —$S(O)_2$—($C_1$-$C_6$)-straight or branched alkyl, or —$S(O)_2$—$R_7$; or two $R_5$ moieties, when bound to the same nitrogen atom, are taken together with said nitrogen atom to form a 3 to 7-membered heterocyclic ring, wherein said heterocyclic ring optionally contains 1 to 3 additional heteroatoms independently selected from N, O, S, S(O) or S(O)$_2$;

$R_6$ is selected from —C(O)—CH$_3$, —CH$_2$—C(O)—OH, —CH$_2$—C(O)—O-tBu, —CH$_2$—CN, or —CH$_2$—C.ident.CH;

each $R_7$ is a monocyclic or bicyclic ring system wherein in said ring system:
  i. each ring comprises 3 to 7 ring atoms independently selected from C, N, O or S;
  ii. no more than 4 ring atoms are selected from N, O or S;
  iii. any CH$_2$ is optionally replaced with C(O);
  iv. any S is optionally replaced with S(O) or S(O)$_2$;

each $R_8$ is independently selected from hydrogen or —[C$_1$-C$_4$]-straight or branched alkyl;

wherein in any ring system in said compound up to 3 hydrogen atoms bound to the ring atoms are optionally and independently replaced with halo, hydroxy, nitro, cyano, amino, (C$_1$-C$_4$)-straight or branched alkyl; O—(C$_1$-C$_4$)-straight or branched alkyl, (C$_2$-C$_4$)-straight or branched alkenyl or alkynyl, or O—(C$_2$-C$_4$)-straight or branched alkenyl or alkynyl; and wherein any ring system is optionally benzofused;

$R_9$ is selected from hydrogen, (R)-methyl, (S)-methyl, (R)-ethyl, (S)-ethyl, (R)-hydroxymethyl or (S)-hydroxymethyl;

$R_{10}$ is selected from —C≡N or 5-oxazolyl; and $R_{11}$ is selected from halo, —O—(C$_1$-C$_3$) straight alkyl, or —O—(C$_2$-C$_3$) straight alkenyl or alkynyl.

In some embodiments, the compounds of formula (XXIII) have a structure represented by the formula:

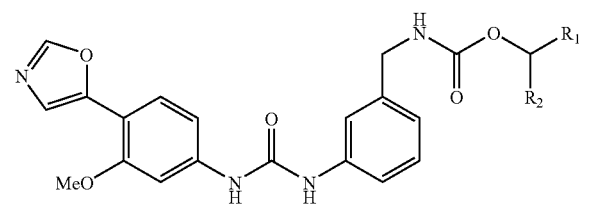

(XXIV)

wherein:
$R_1$ and $R_2$ are as defined above for formula (XXIII).

In other embodiments, the compounds of formula (XXIII) have a structure represented by the formula:

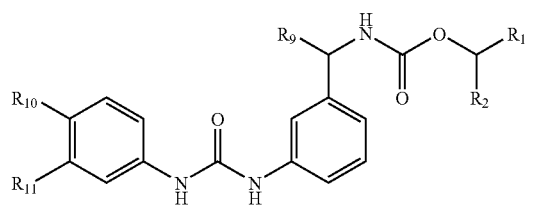

(XXIIIa)

wherein:
$R_9$ is selected from (R)-methyl, (S)-methyl, (R)-ethyl, (S)-ethyl, (R)-hydroxymethyl or (S)-hydroxymethyl; and
$R_1$, $R_2$, $R_{10}$ and $R_{11}$ are as defined above for formula (XXIII).

In specific embodiments of compounds according to formula (XXIIIa), $R_9$ is selected from (S)-methyl, (S)-ethyl, or (S)-hydroxymethyl methyl. More suitably, $R_9$ is (S)-methyl. Compounds wherein $R_9$ is selected from (S)-methyl, (S)-ethyl, or (S)-hydroxymethyl methyl and wherein the portion of the compound represented by —CH(R$_1$)R$_2$ is a C$_1$-C$_4$ straight or branched alkyl, or a C$_2$-C$_4$ straight or branched alkenyl or alkynyl fall within the genus of compounds described in International Publication WO 97/40028.

In other embodiments of compounds according to formulae (XXIII) and (XXIIIa), at least one of $R_1$ or $R_2$ is selected from hydrogen, methyl, ethyl, n-propyl, isopropyl, n-butyl, t-butyl, n-pentyl, phenyl, pyridyl, —CH$_2$OCH$_3$, —CH$_2$CN, —CH$_2$OCH$_2$CH$_2$CN, —CH$_2$C(CH$_3$)$_2$CH$_2$CH$_2$CN, —CH$_2$C(CH$_2$CH$_3$)$_2$CH$_2$CH$_2$CN, —CH$_2$CH$_2$CN, —CH$_2$N(CH$_2$CH$_2$CN)$_2$, —CH$_2$N(CH$_3$)CH$_2$CH$_2$CN, —CH(NH$_2$)CH$_2$CN, —CH$_2$Cl, —CH$_2$OH, —CH$_2$CH$_2$OH, —CH$_2$CH$_2$OH, —CH$_2$CH$_2$CH$_2$OH, —CH$_2$CH$_2$OC(O)CH$_3$, —CH$_2$CH$_2$OC(O)CH$_2$NH$_2$, —CH$_2$CH$_2$NHCH$_3$, —CH$_2$CH$_2$N(CH$_3$)$_2$, —CH$_2$CH$_2$N(CH$_2$CH$_3$)$_2$, —CH$_2$N(CH$_2$CH$_3$)$_2$, —CH$_2$CH$_2$CH$_2$N(CH$_3$)$_2$, —CH$_2$CH$_2$CH$_2$N$^+$(CH$_3$)$_2$, —CH$_2$OCH$_2$CH(CH$_3$)$_2$, —CH$_2$N(CH$_3$)C(O)OC(CH$_3$)$_3$, —CH$_2$N(CH$_2$CH$_2$CN)CH$_2$CH(CH$_3$)$_2$, —CH(CH$_2$CN)N(CH$_3$)$_2$, —CH$_2$CH(CH$_2$CN)NHC(O)OC(CH$_3$)$_3$,

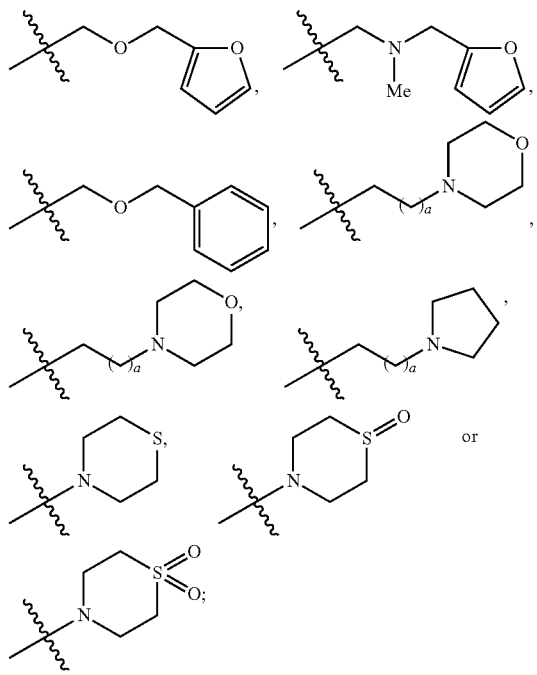

wherein:
n is 0 or 1.

In some embodiments of compounds according to formula (XXIIIa), one of $R_1$ or $R_2$ is selected from hydrogen, ethyl or phenyl; and the other of $R_1$ or $R_2$ is selected from —CH$_2$OH, —CH$_2$CN, —CH$_2$CH$_2$CN or CH$_2$N(CH$_2$CH$_3$)$_2$; or $R_1$ and $R_2$ are taken together to form a 3-tetrahydrofuranyl moiety.

According to alternate embodiments of formula (XXIII), $R_1$ and $R_2$ are taken together to form a 3-tetrahydrofuranyl moiety that is substituted by —OR$_6$.

Representative compounds falling within the scope of formula (XXIII) include, but are not limited to:

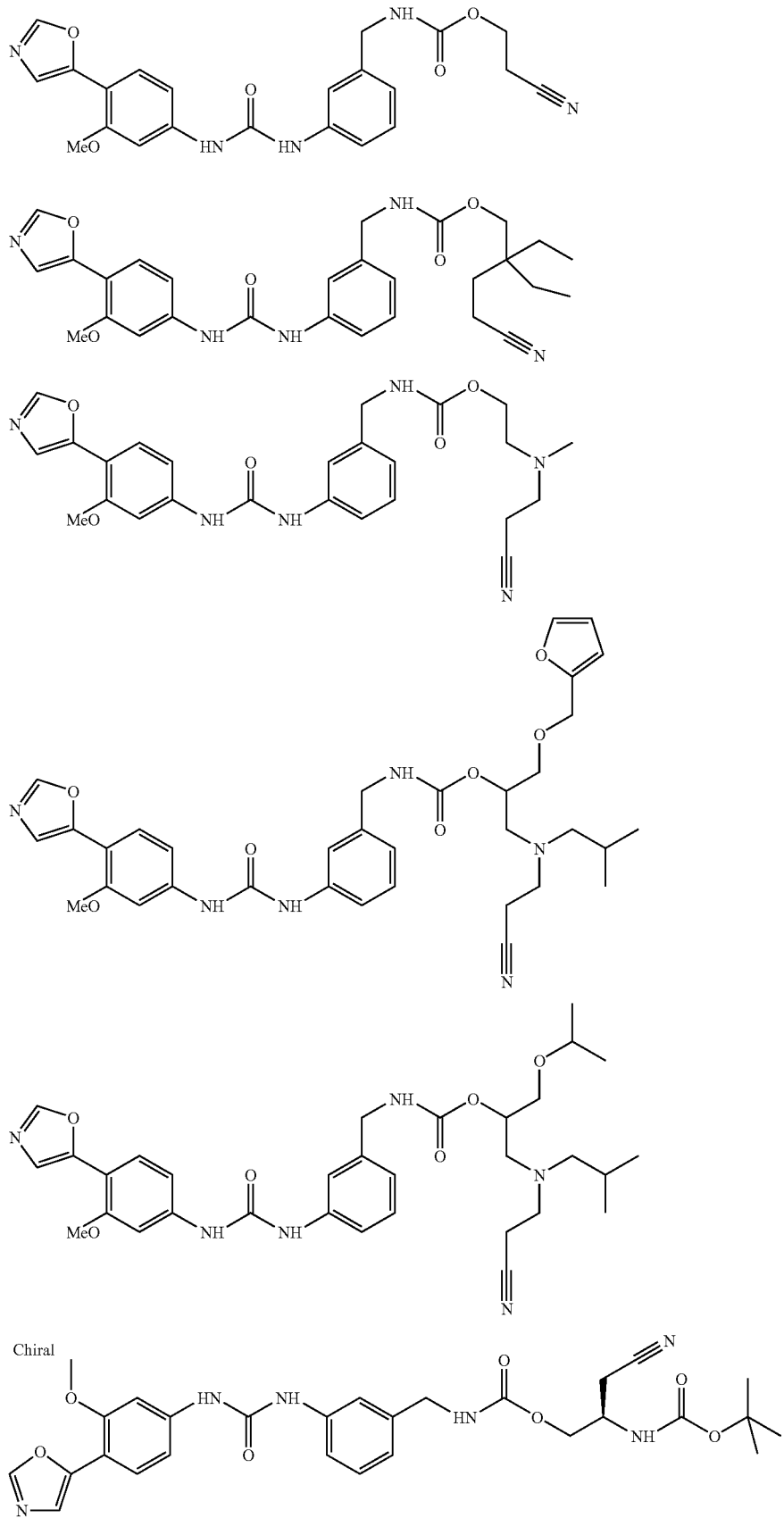

-continued
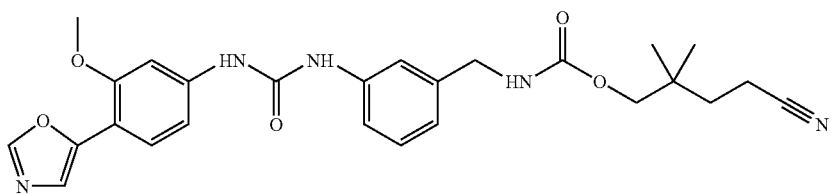
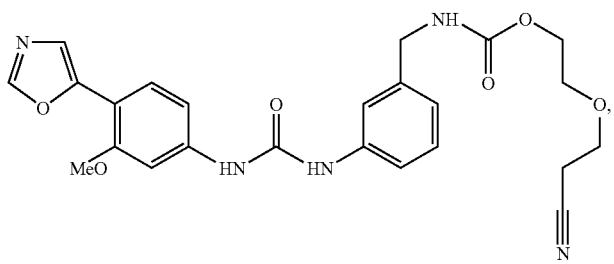
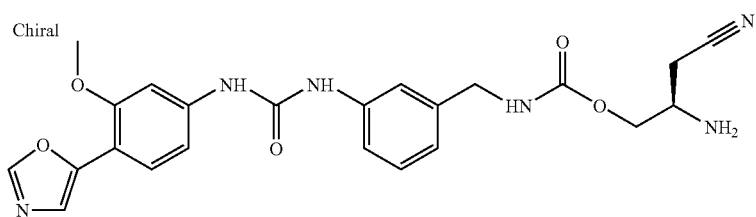
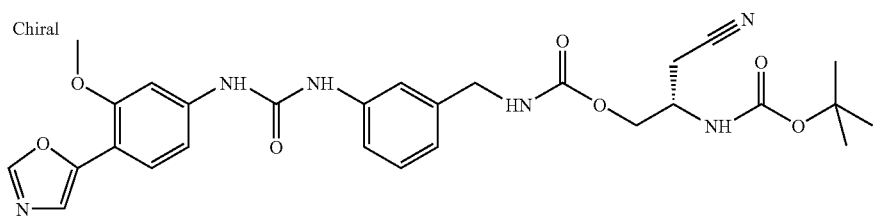
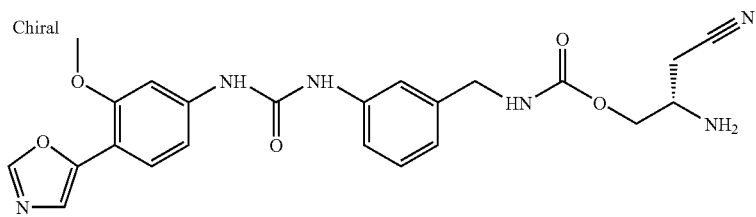
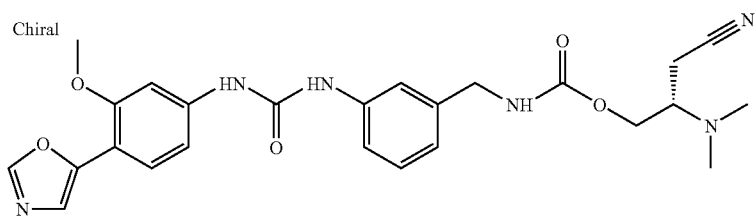
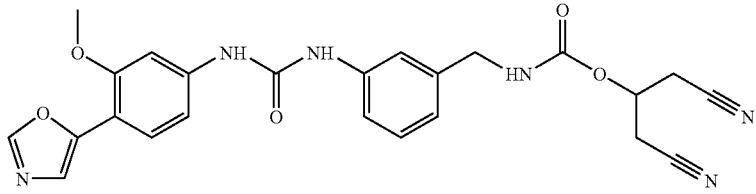

-continued
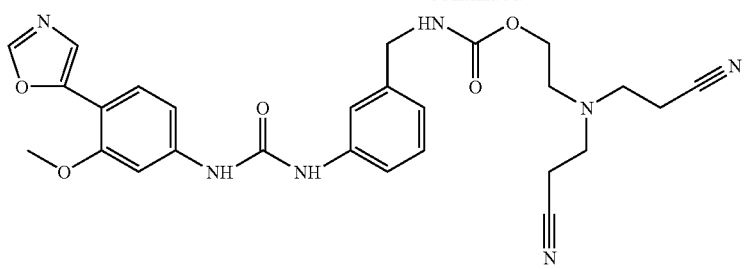
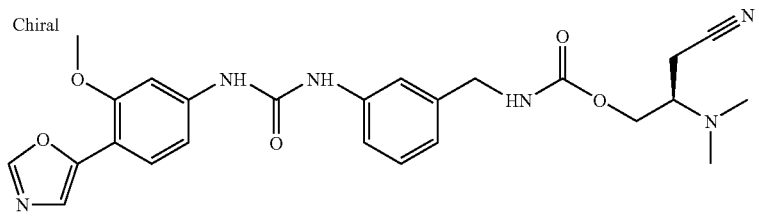
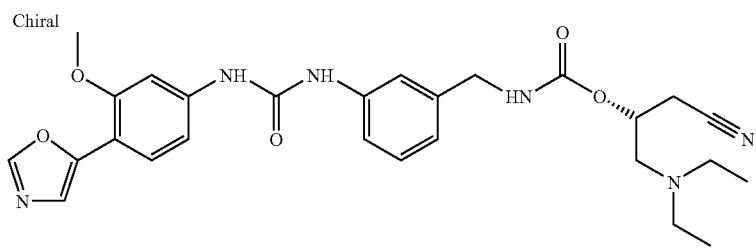
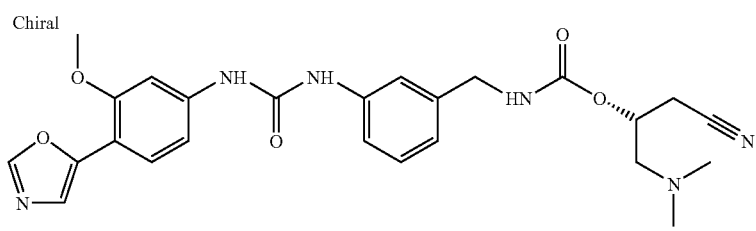
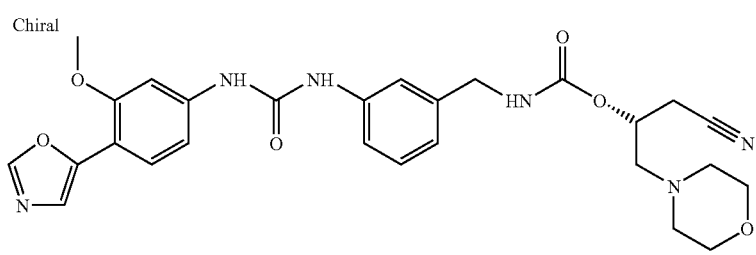
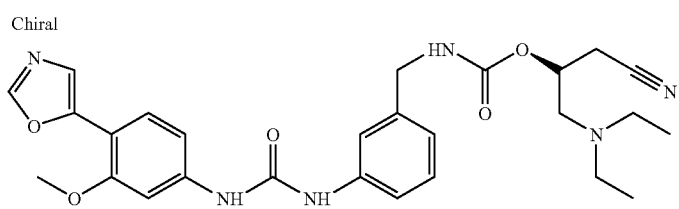
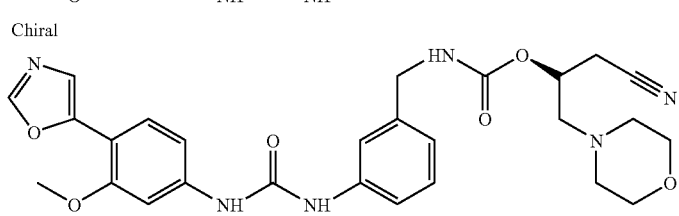

-continued
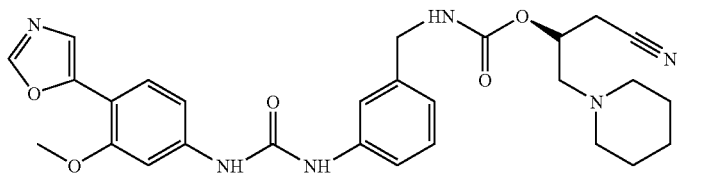
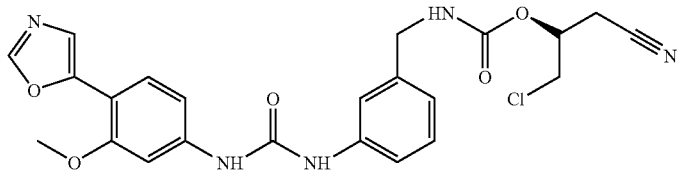
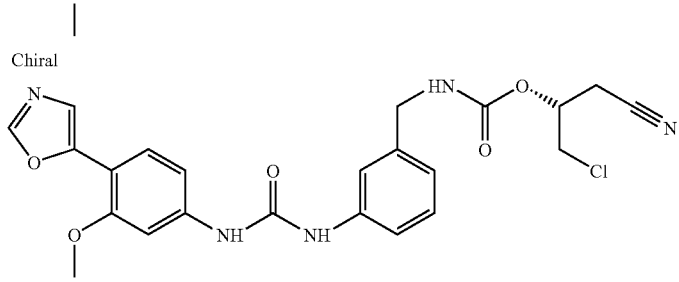
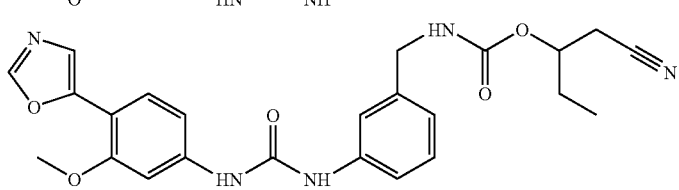
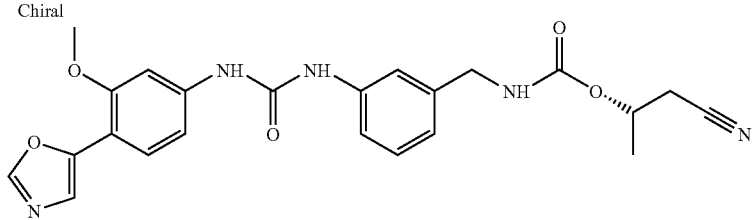

-continued
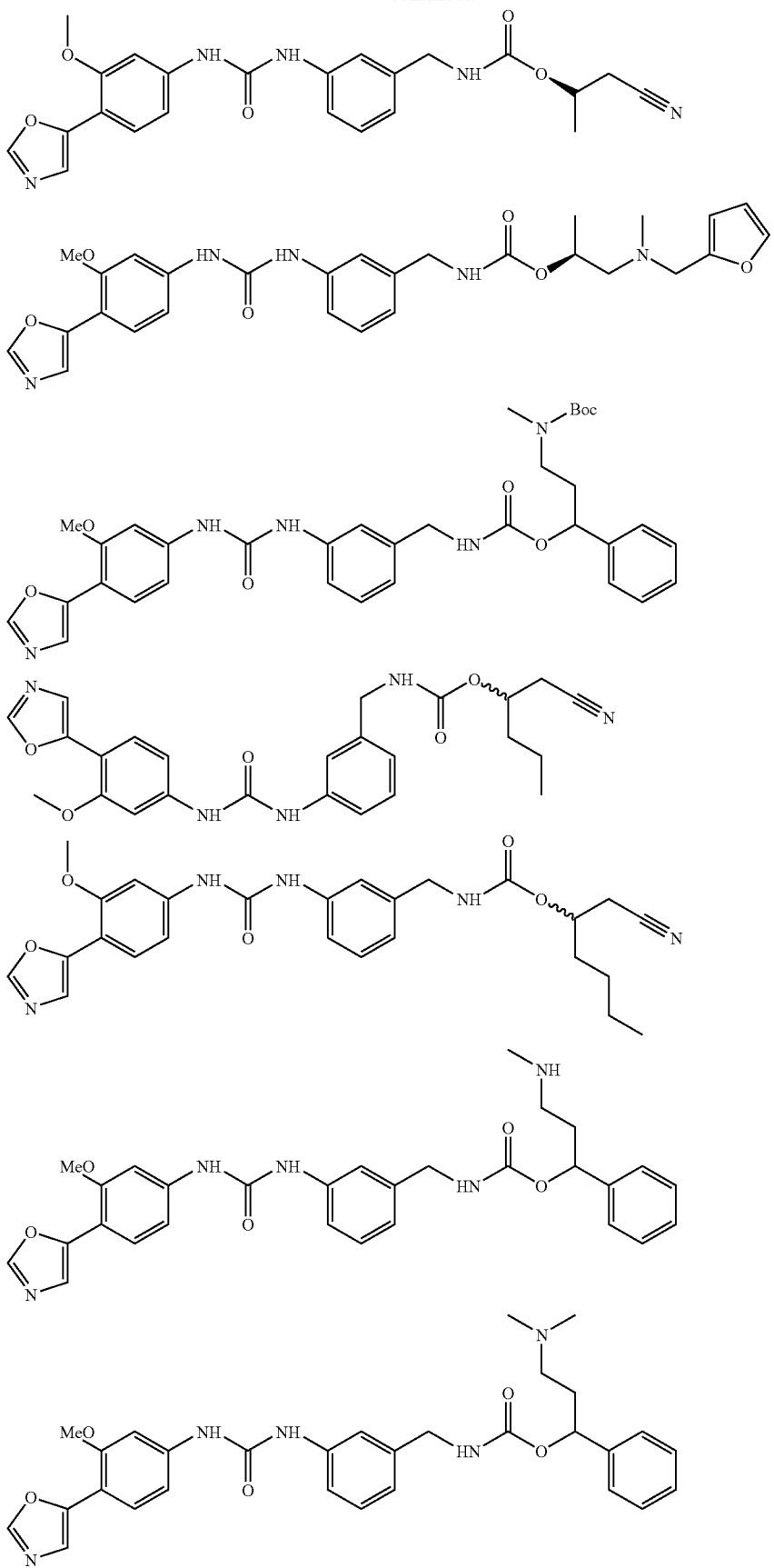

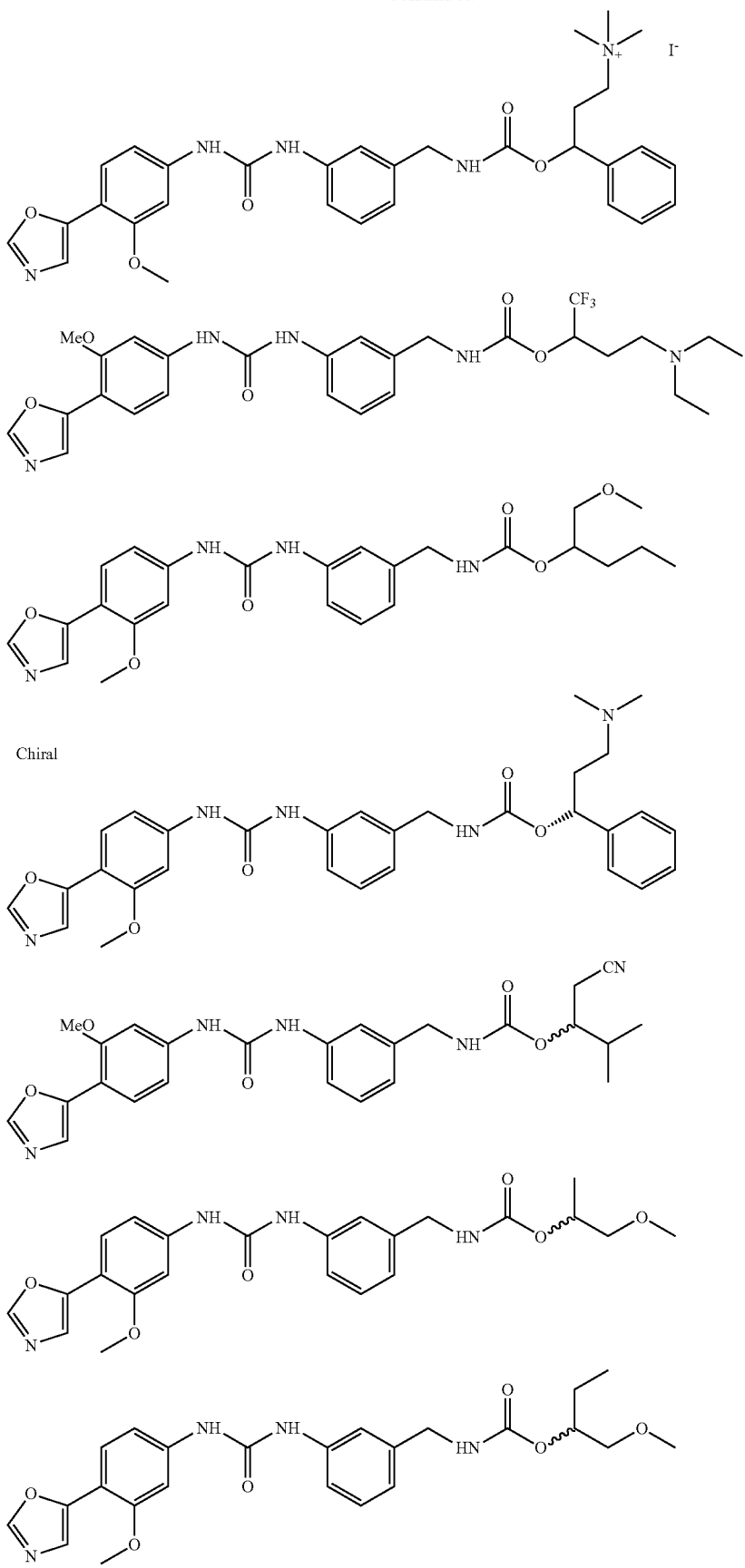

-continued
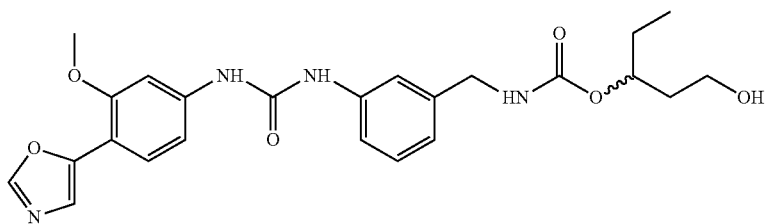
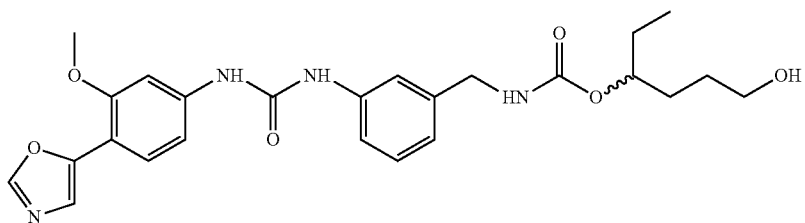
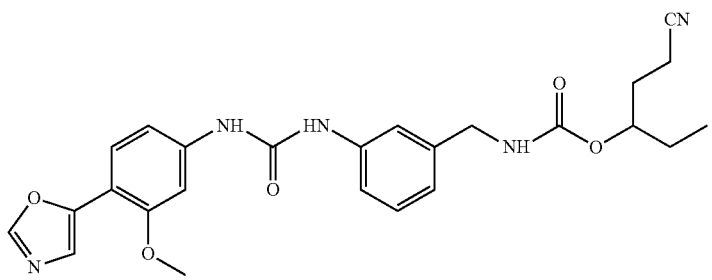
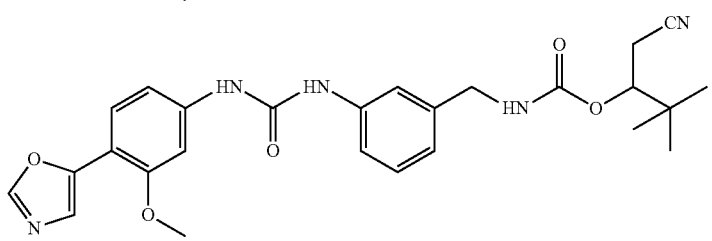
Chiral
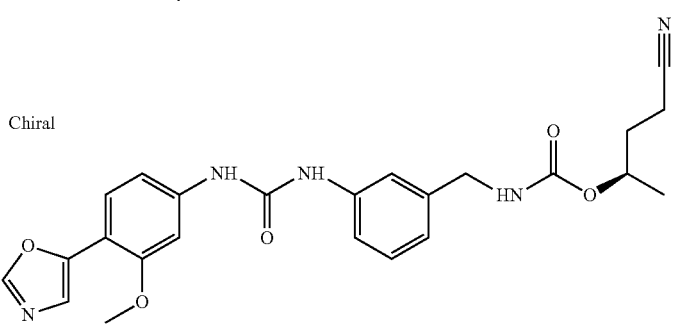
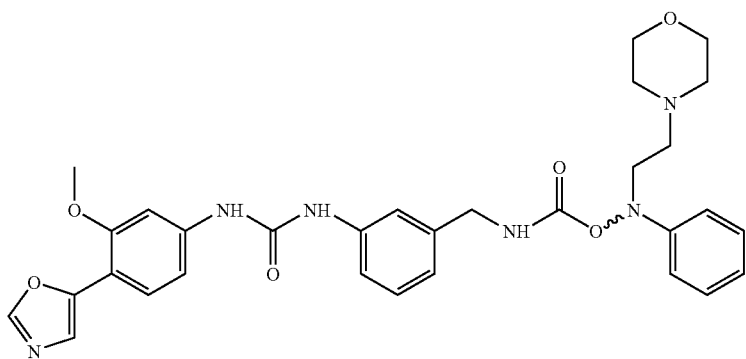

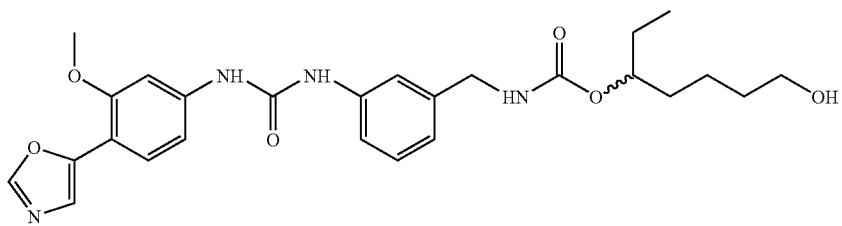
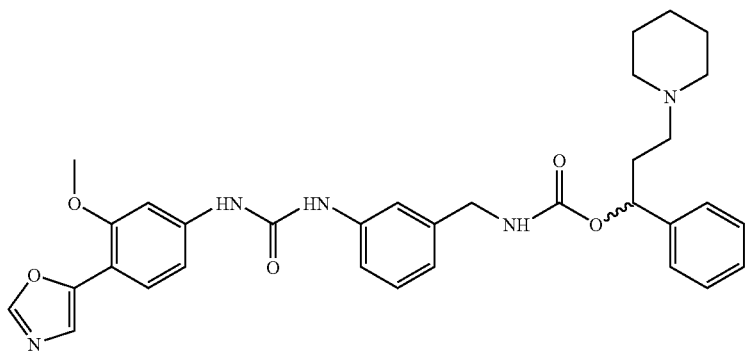
Chiral
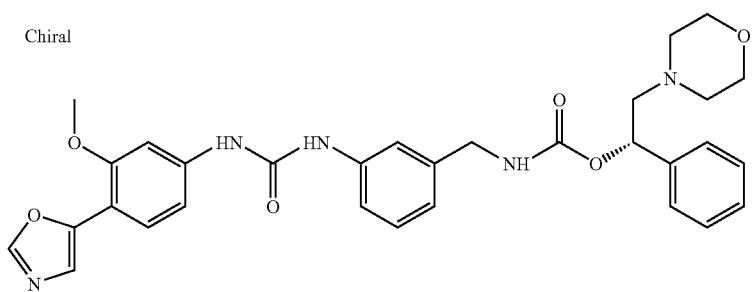
Chiral
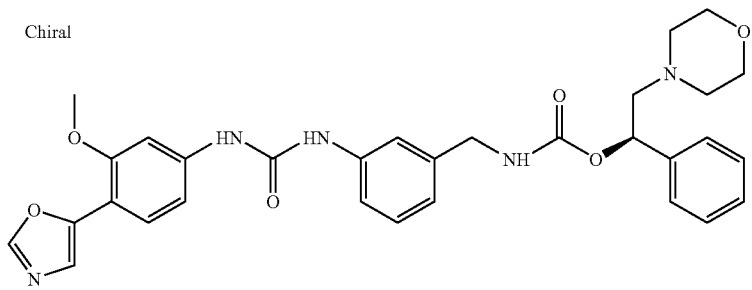
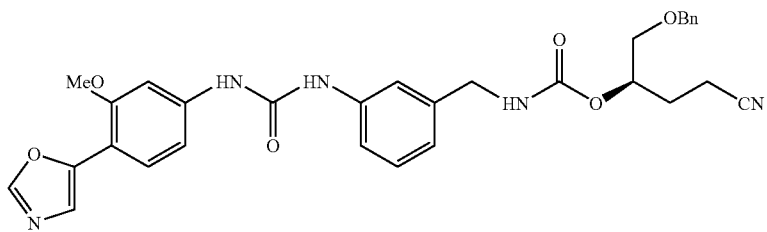
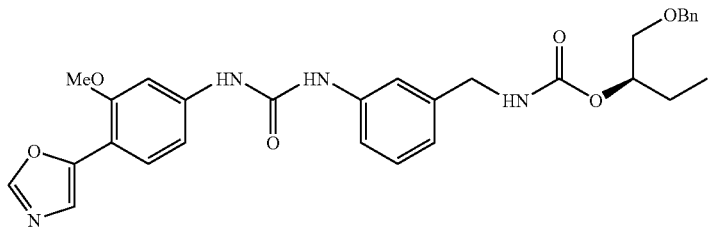

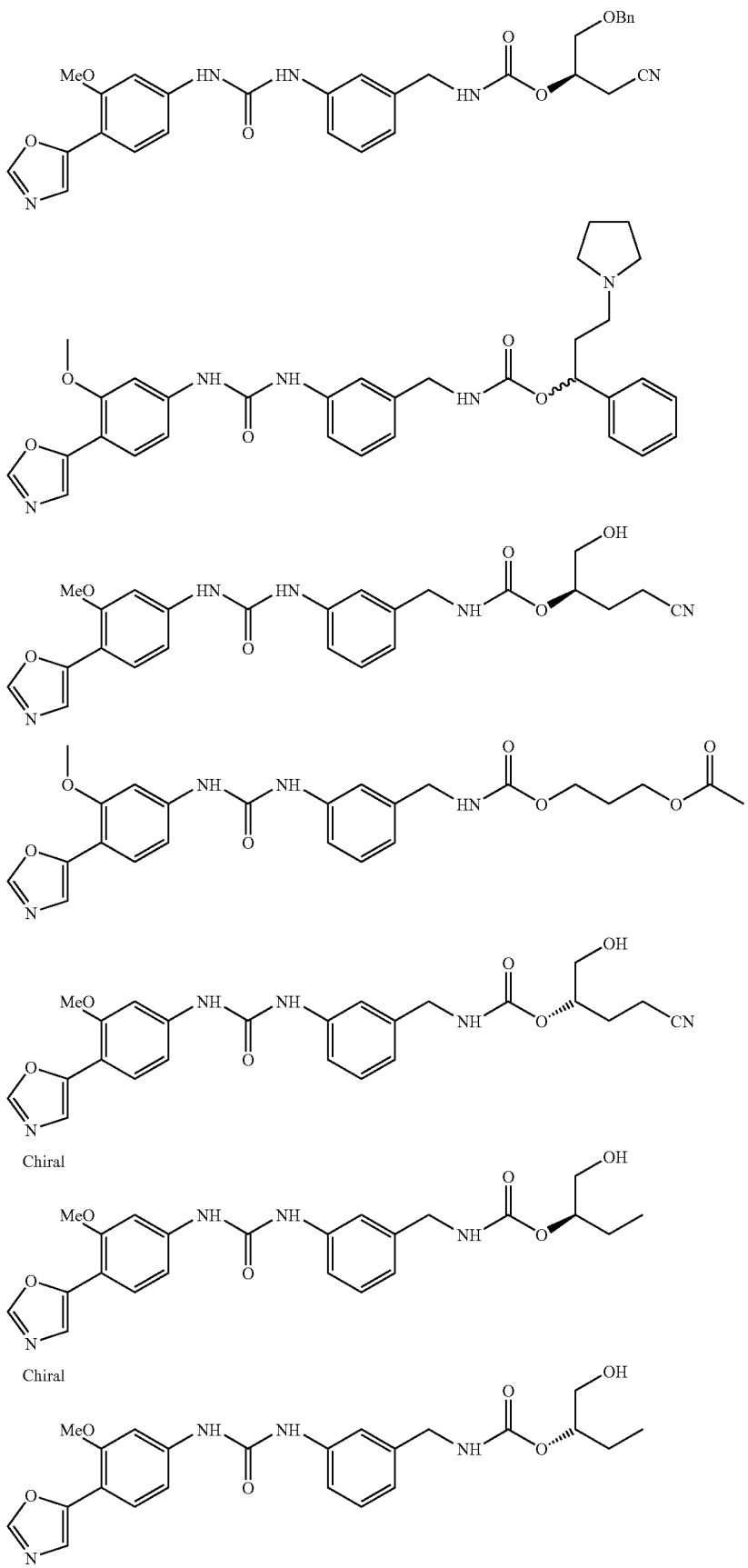

-continued
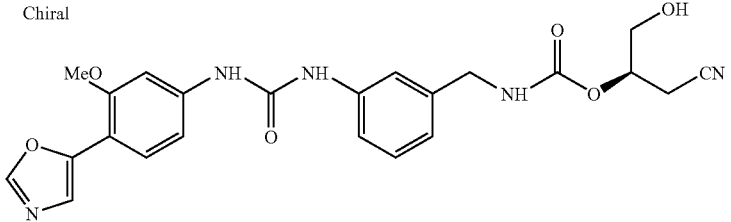
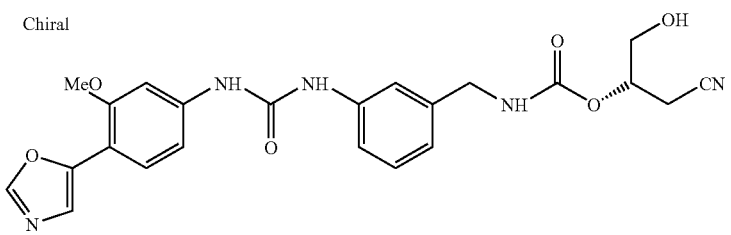
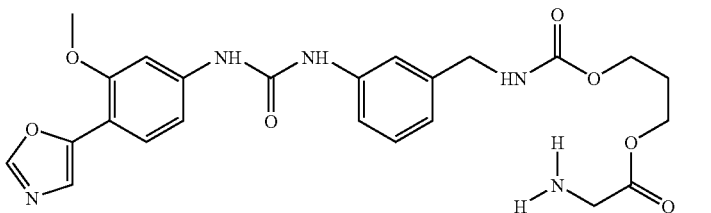
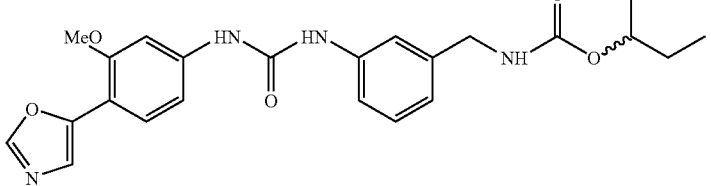
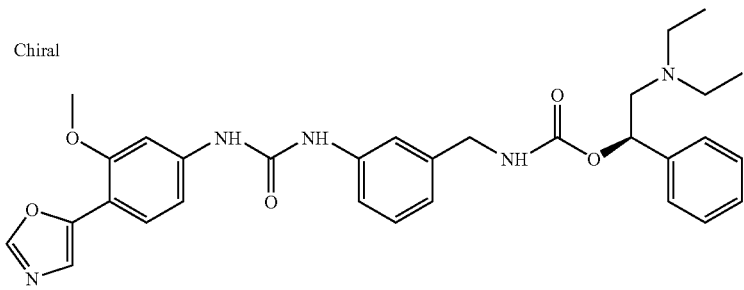
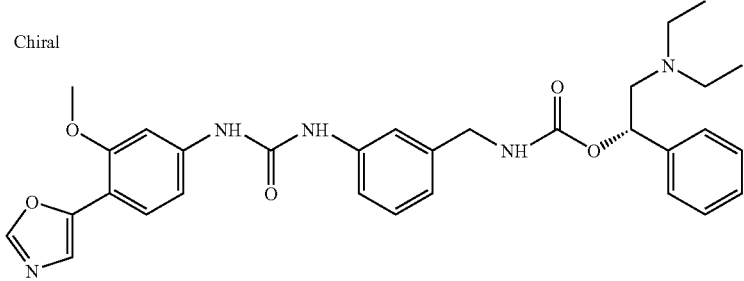

-continued
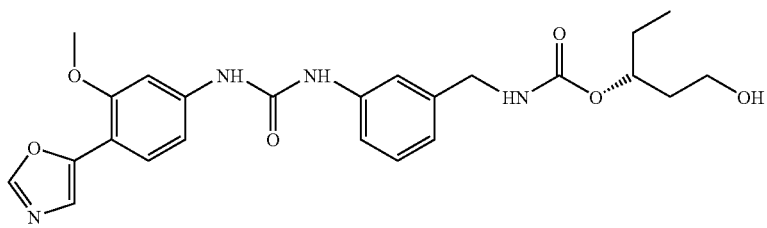
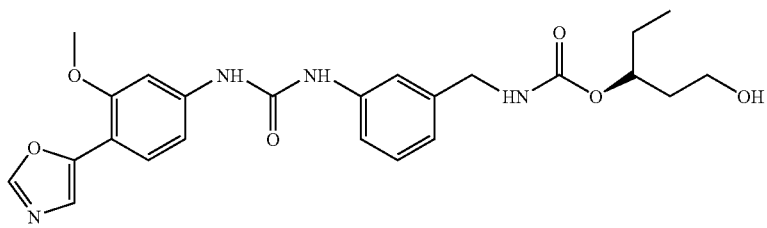
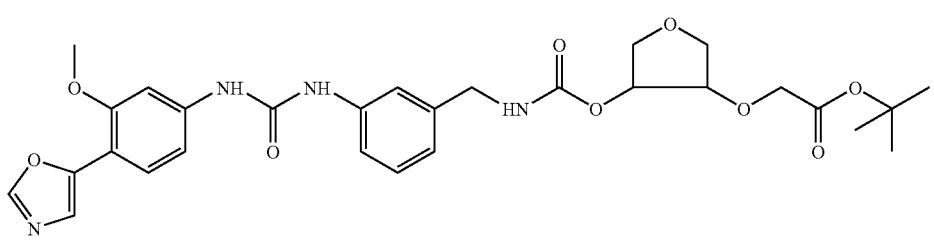
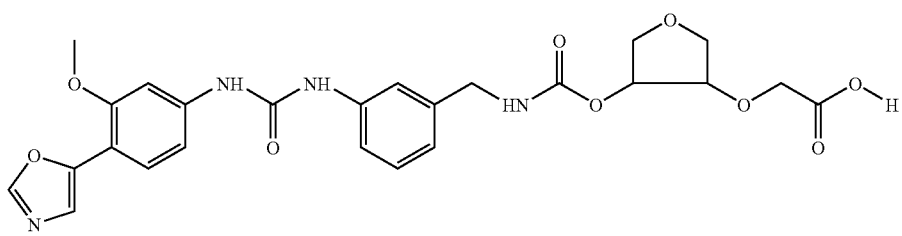
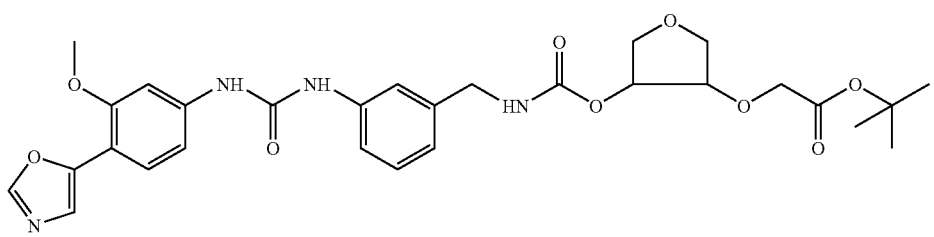
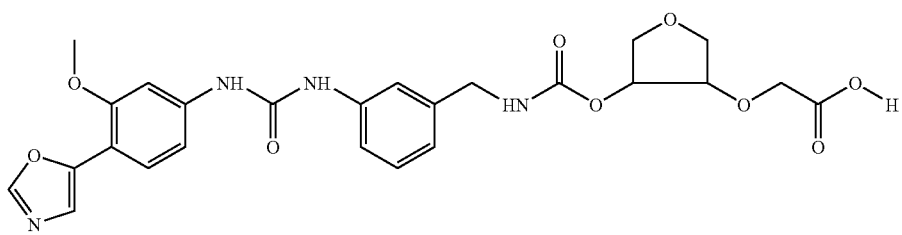
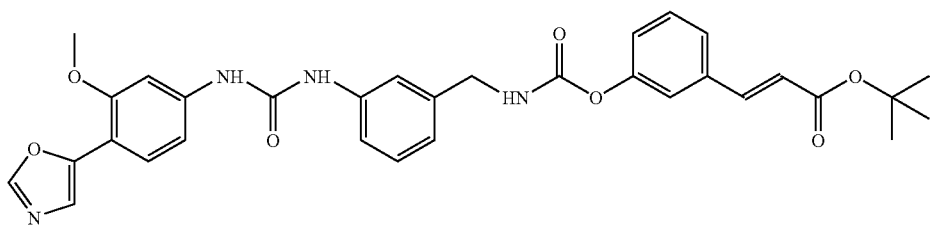

-continued
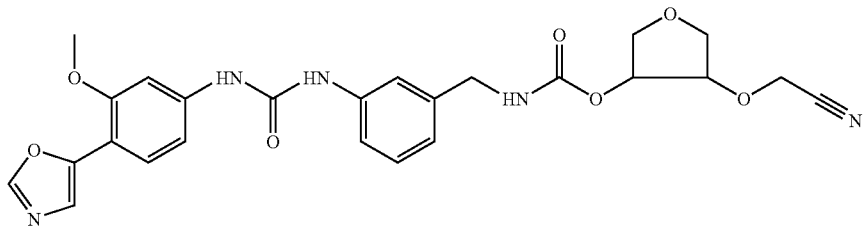
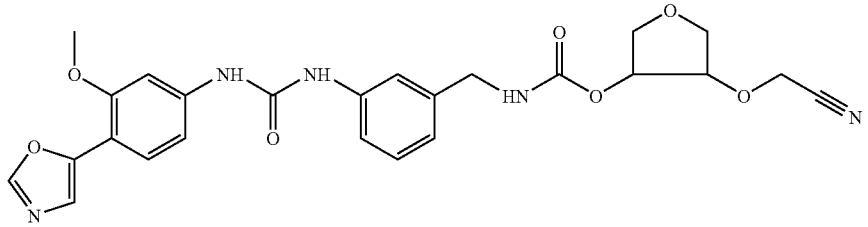
Chiral
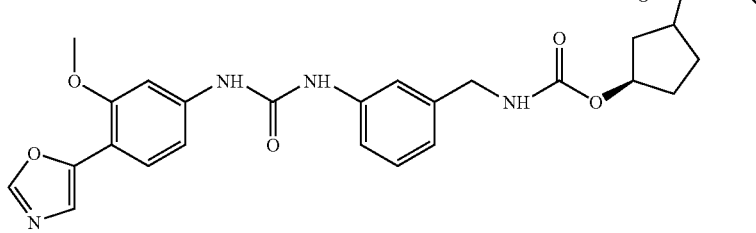
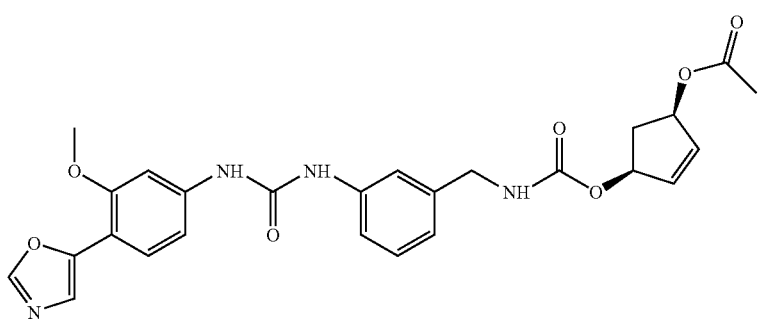
Chiral
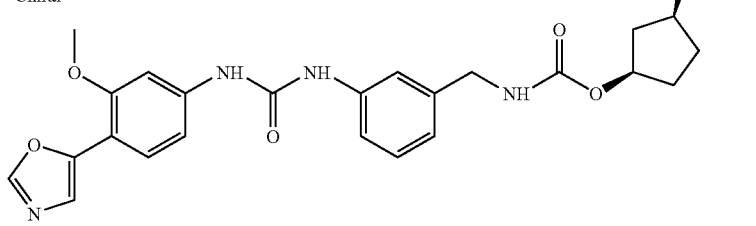
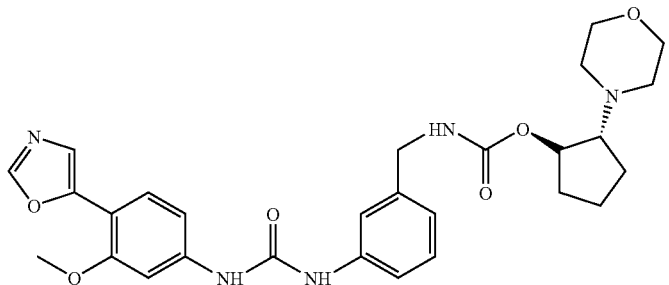

-continued
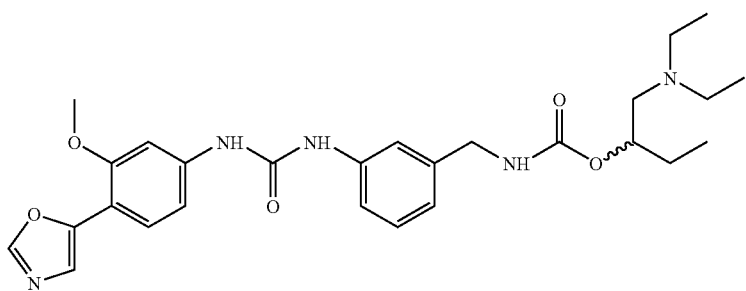
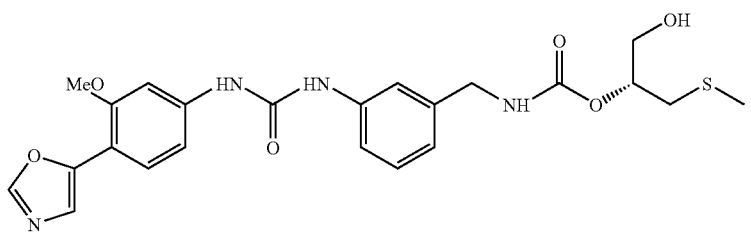
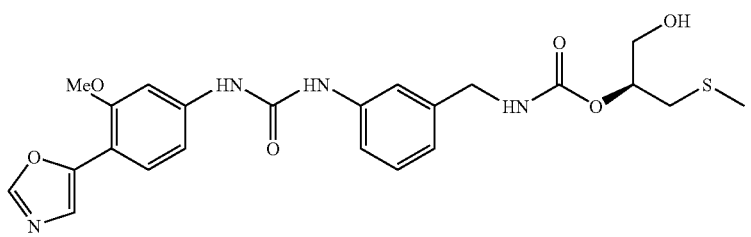
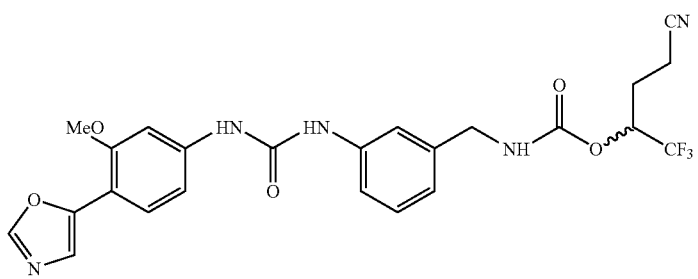
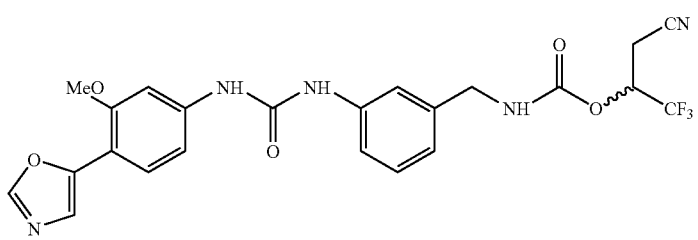
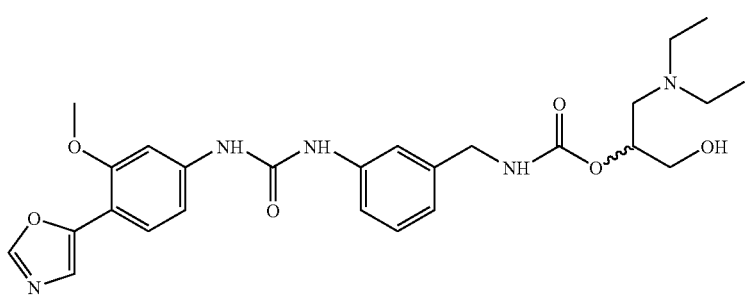

-continued
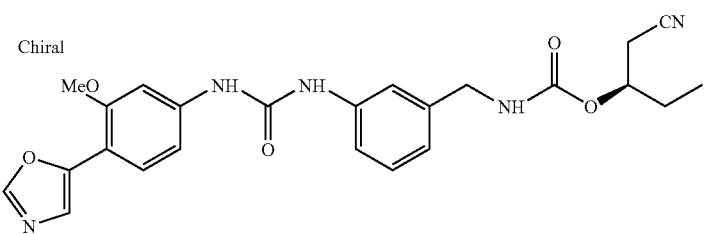
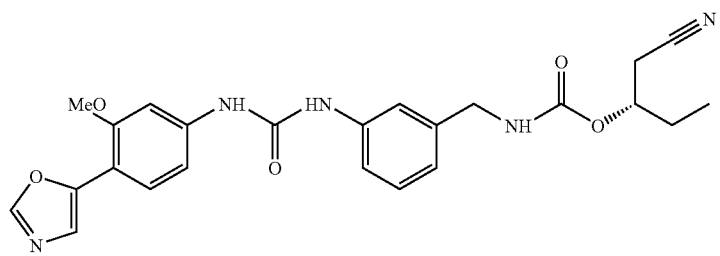
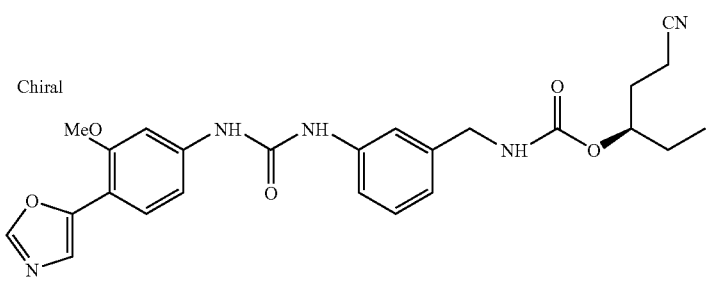
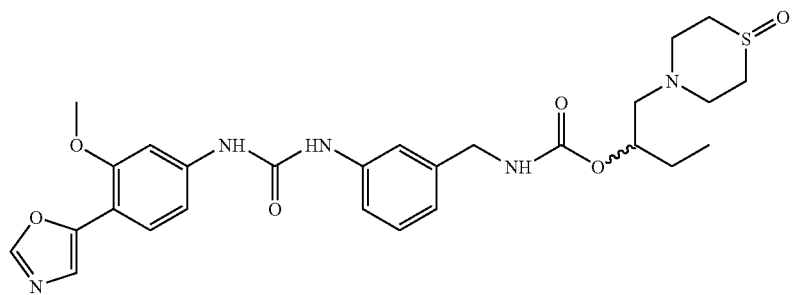
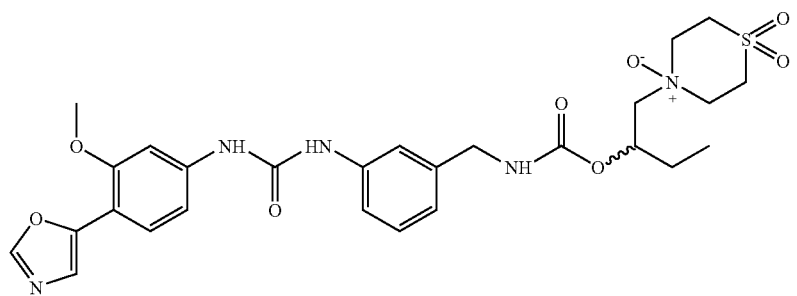
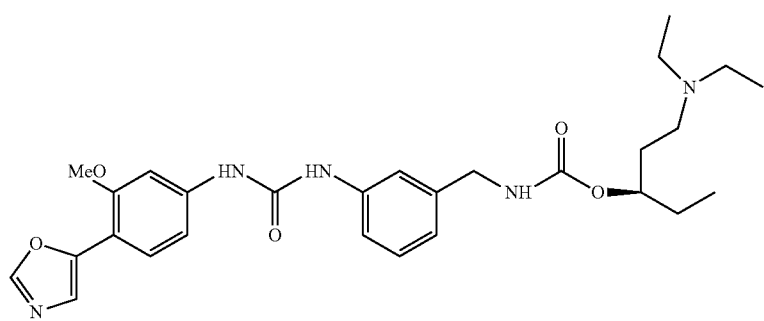

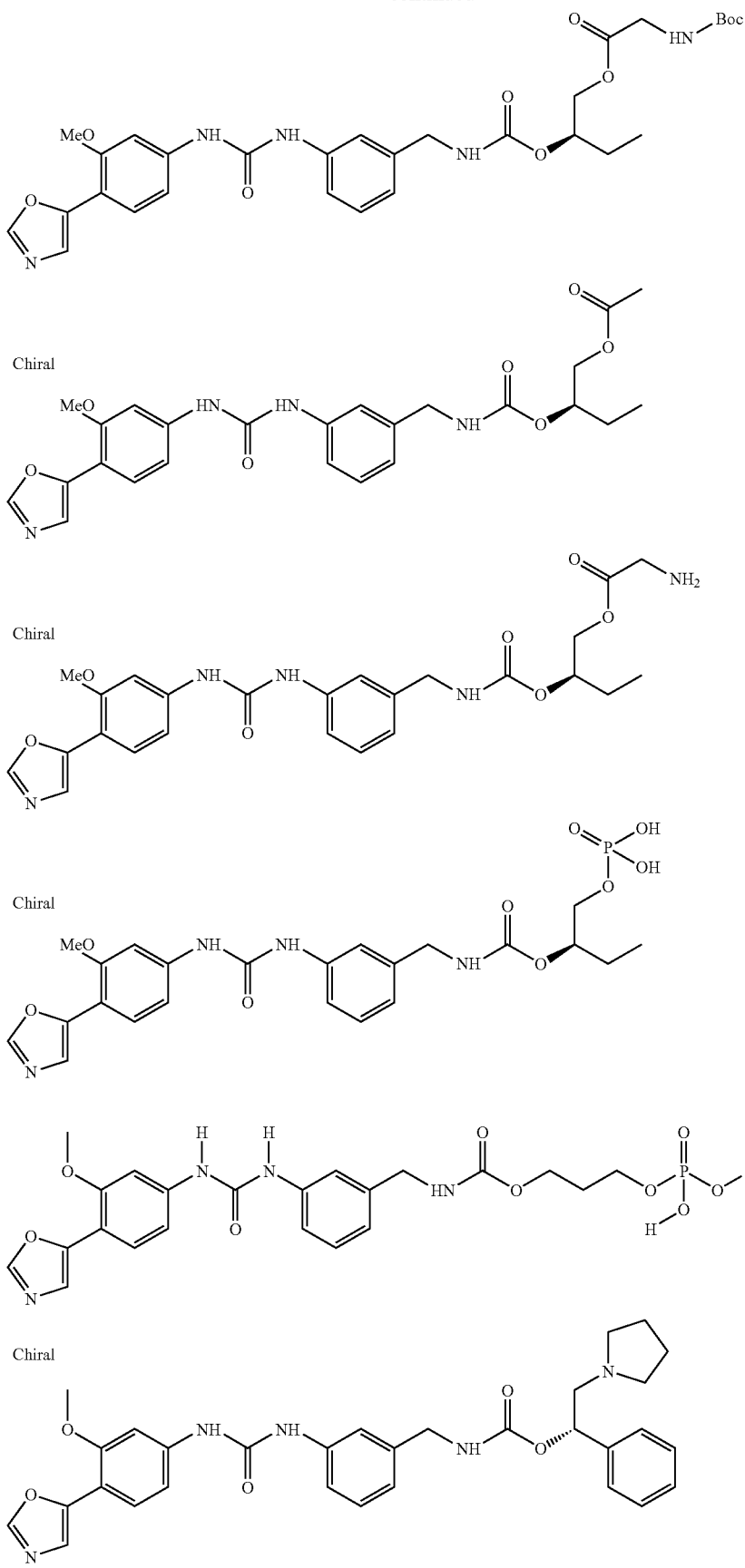

-continued
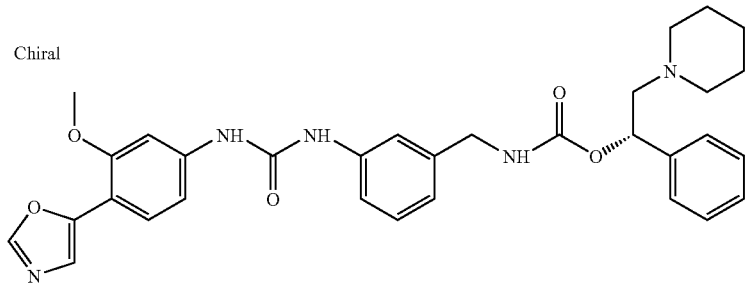
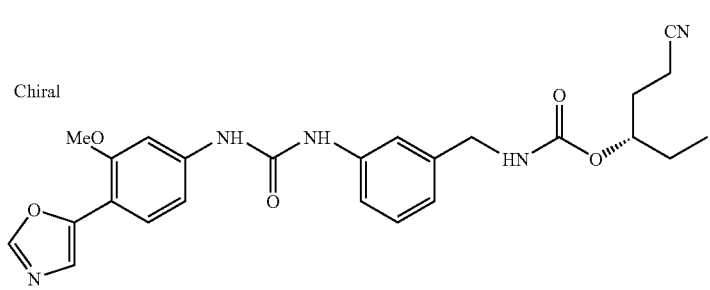
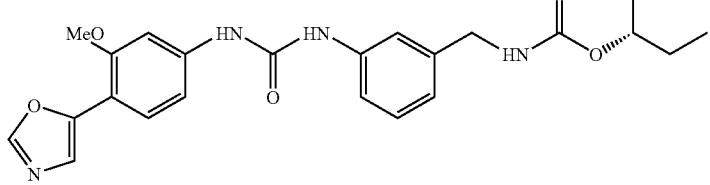
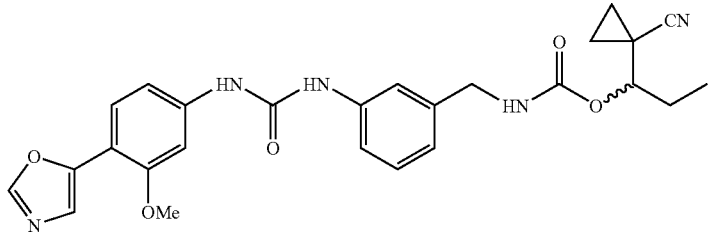
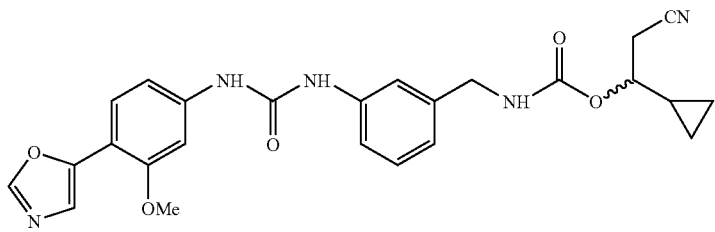

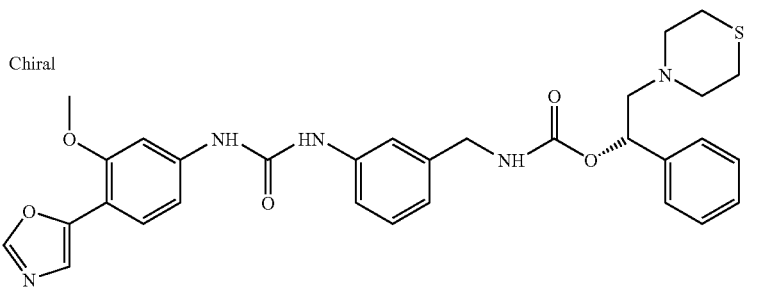
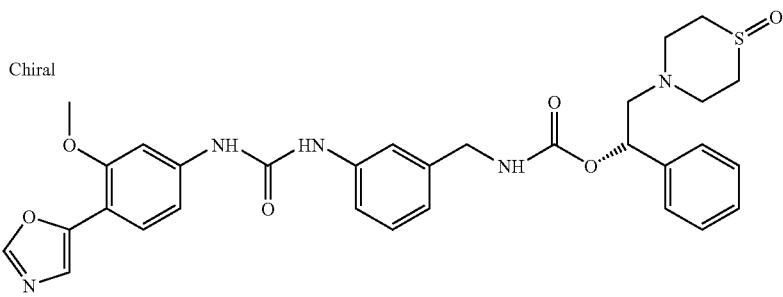
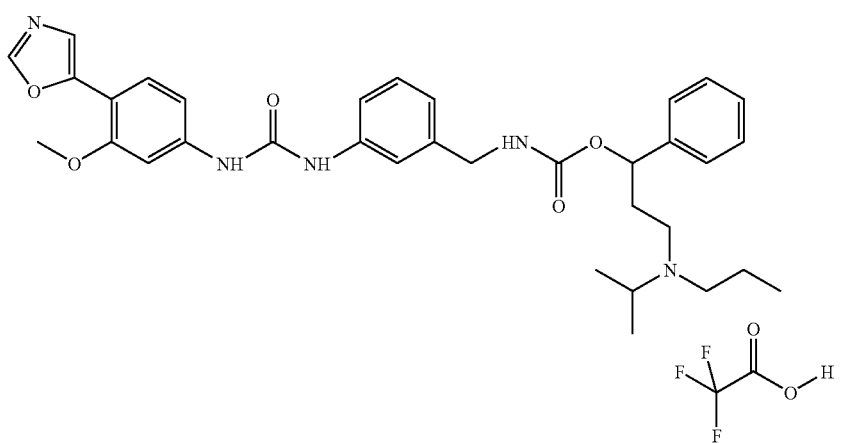
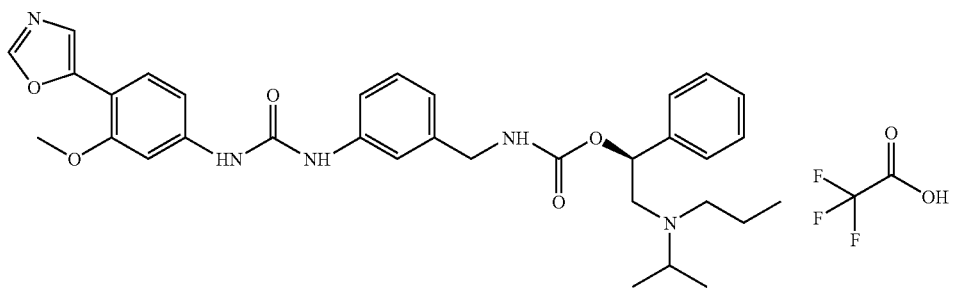
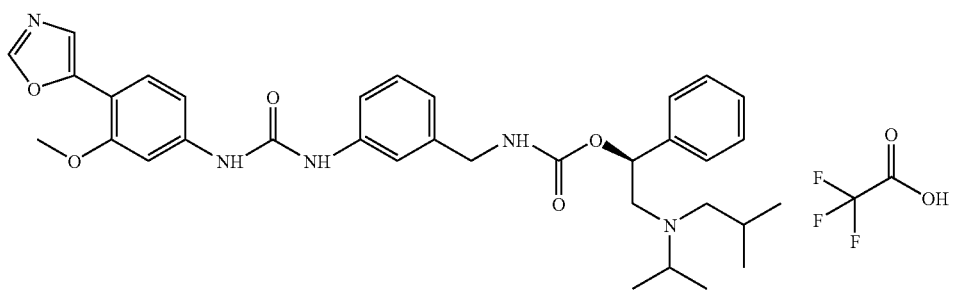

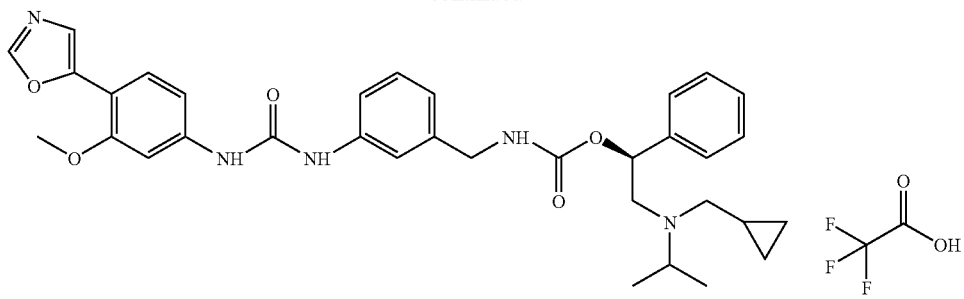
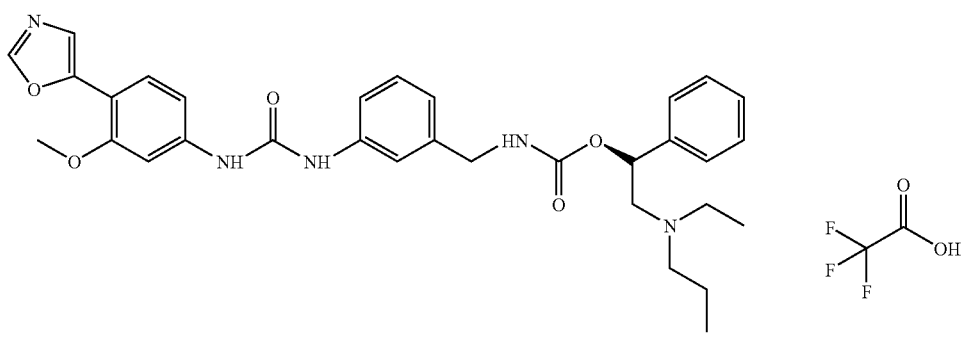
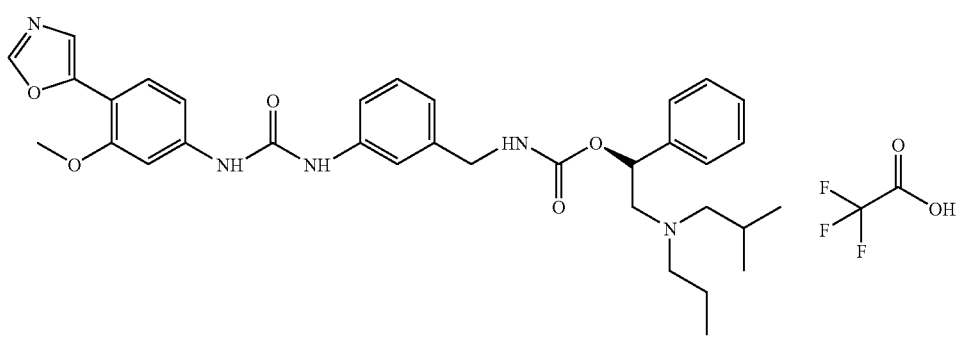
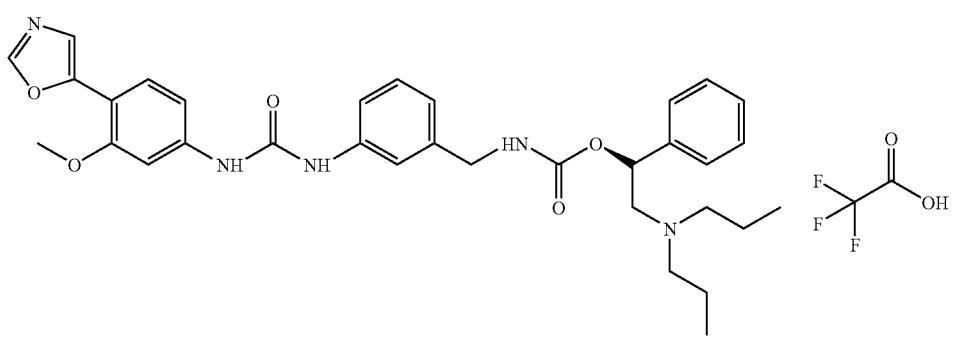
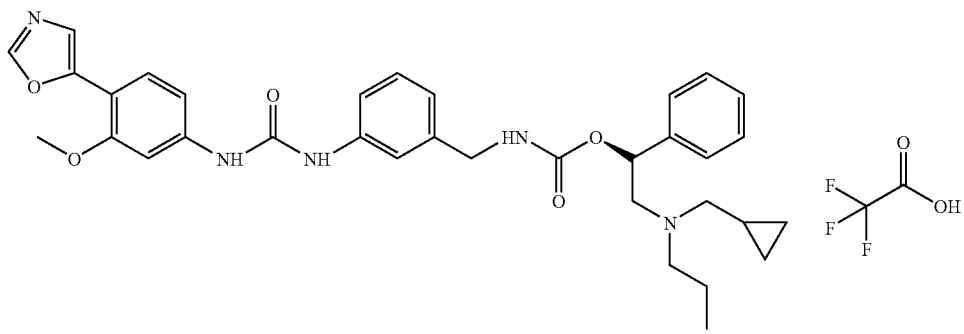

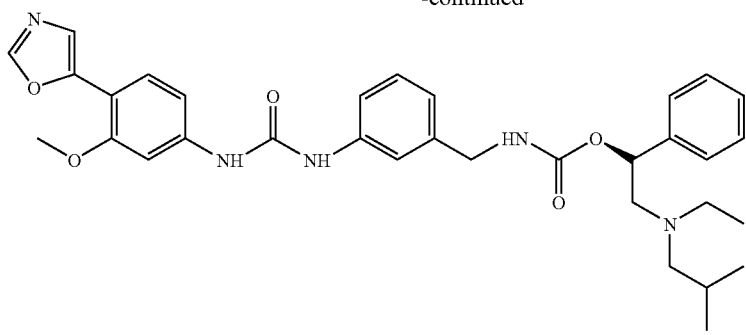
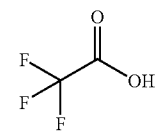
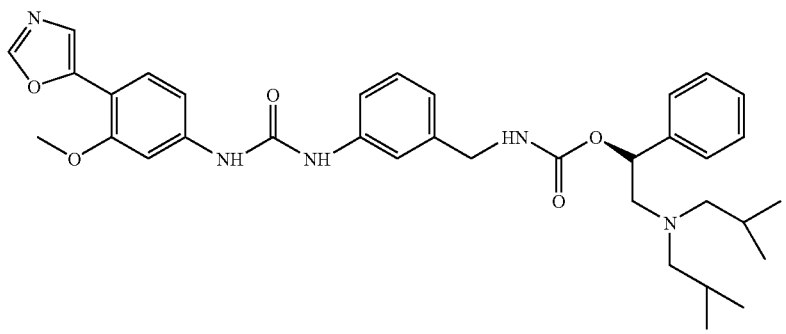
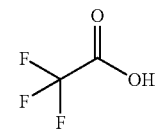
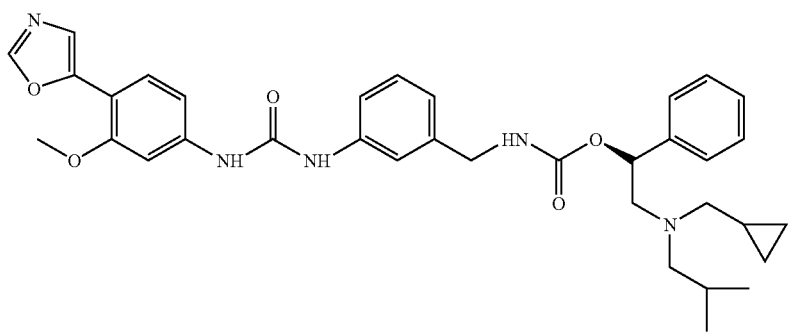
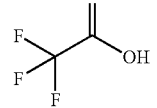
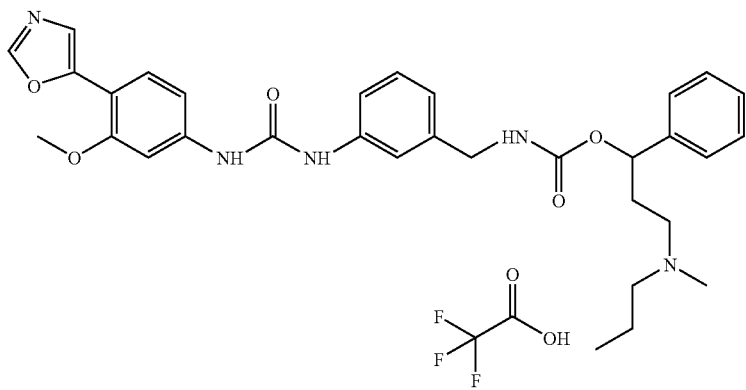
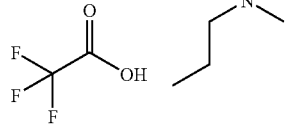

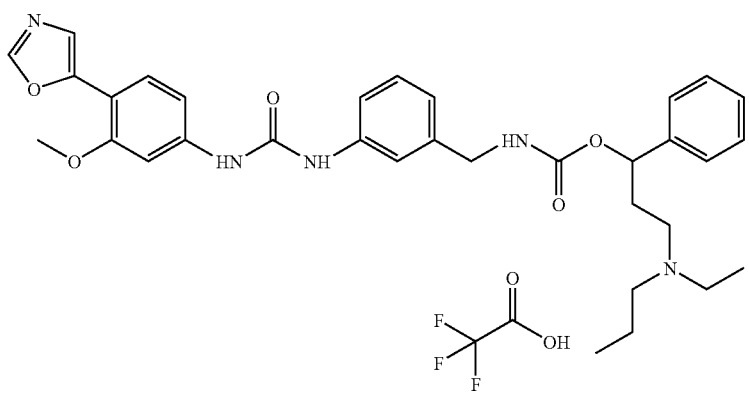
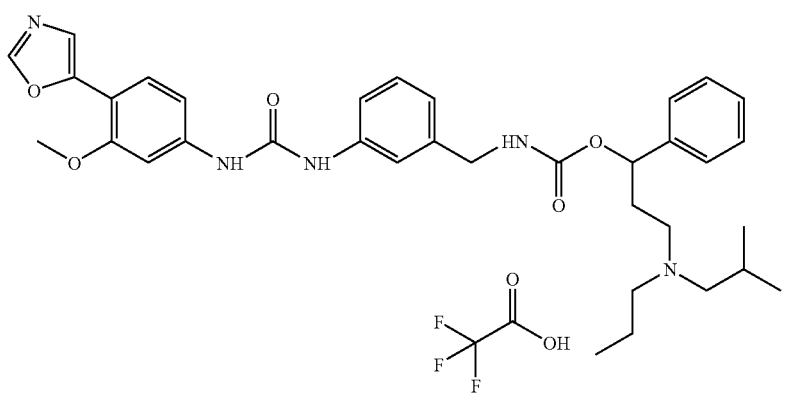
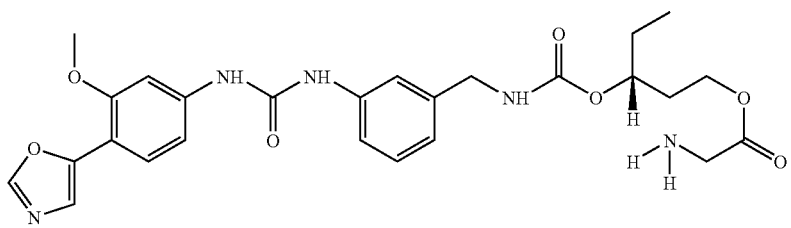
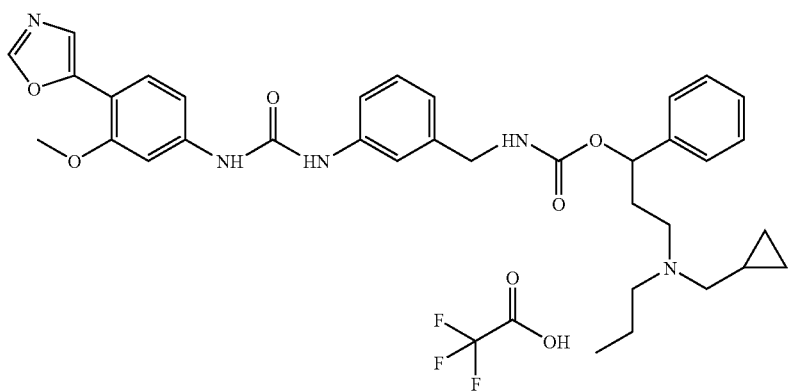

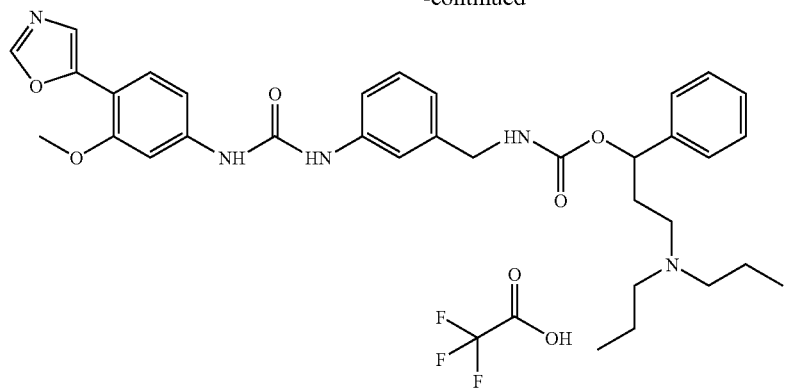
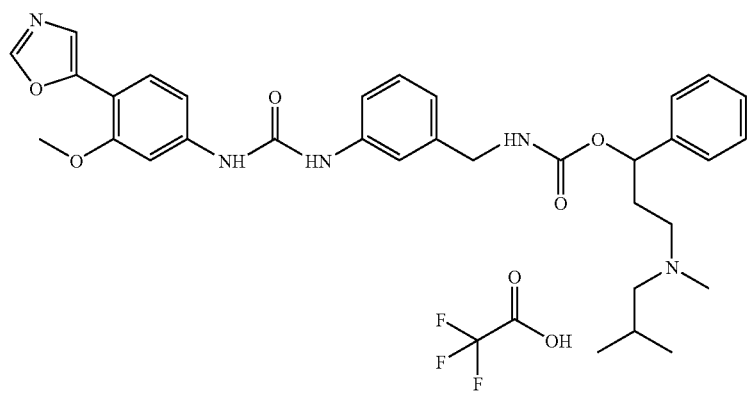
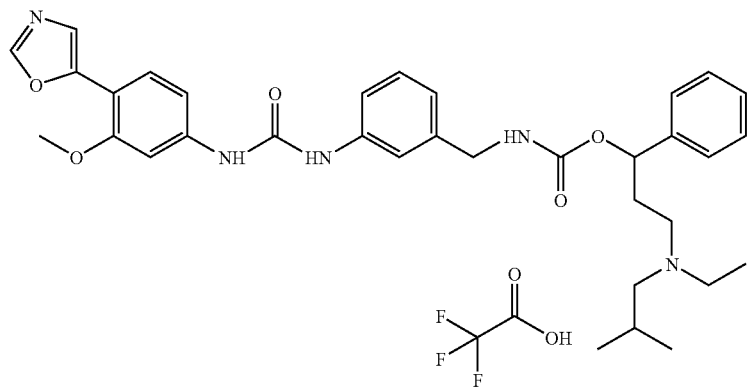
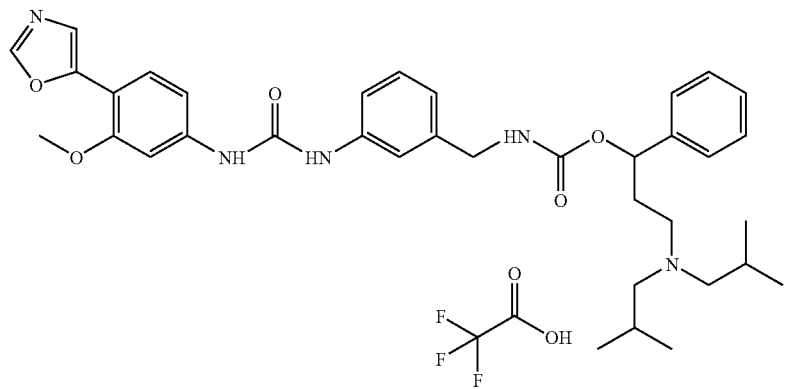

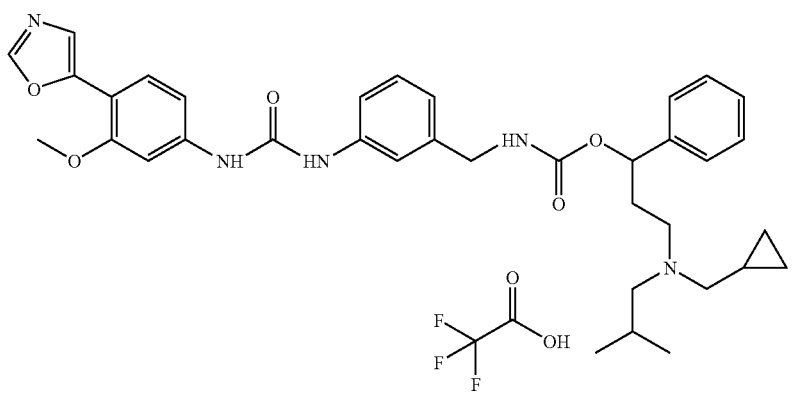
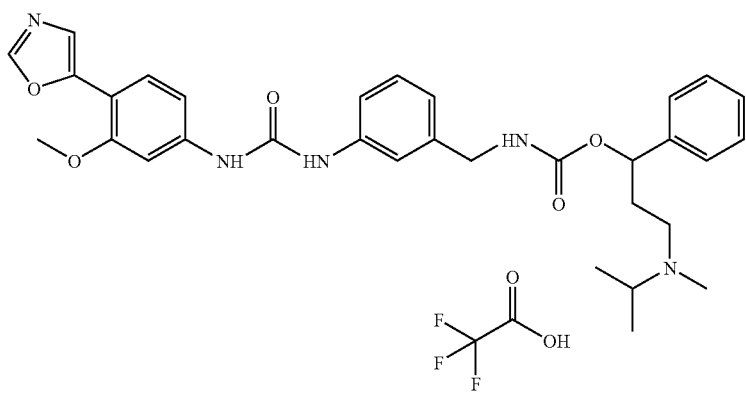
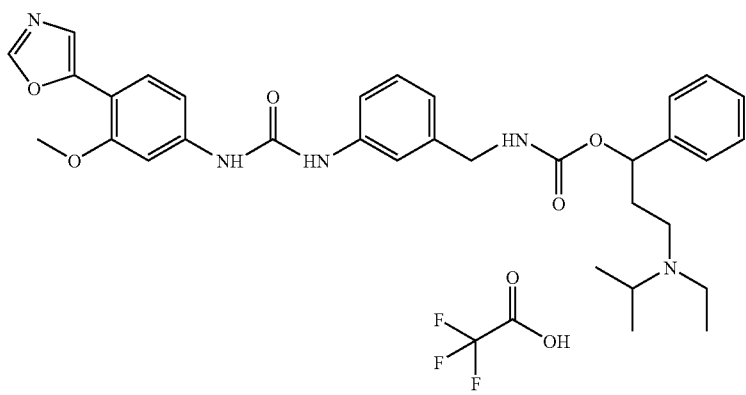
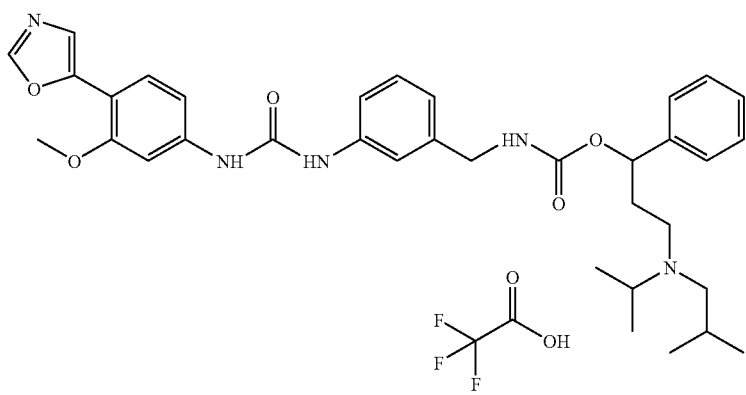

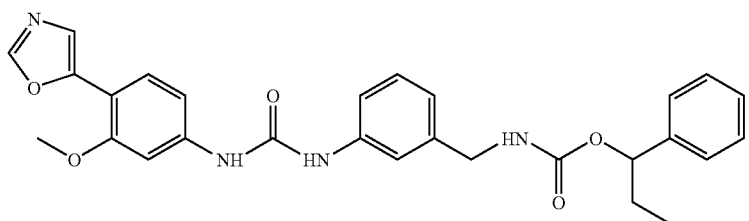
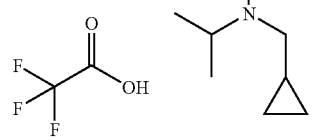
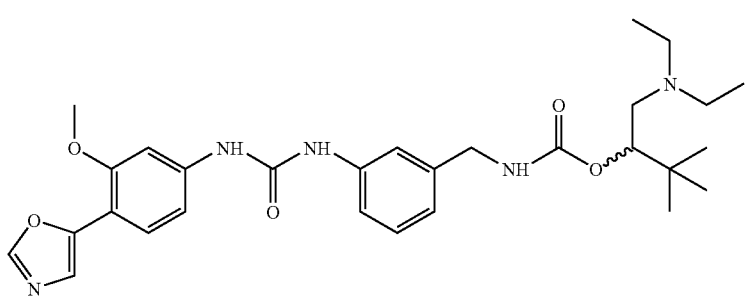
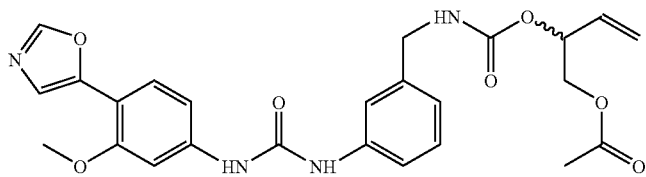
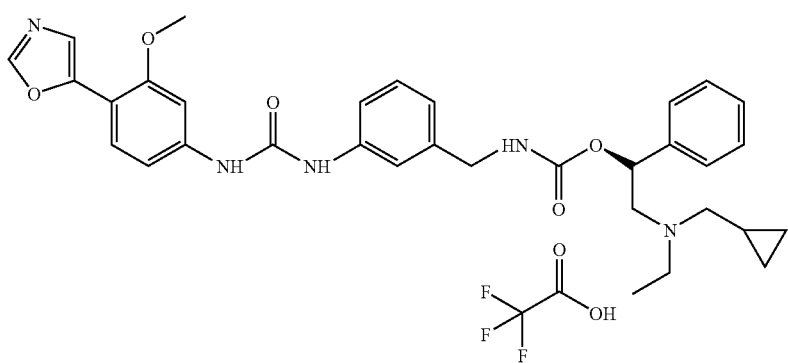
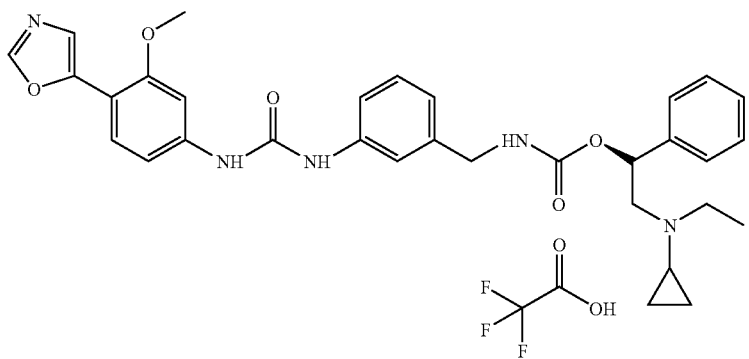

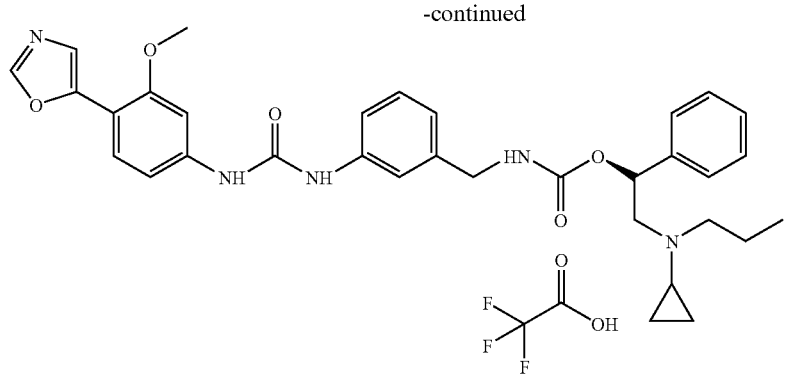
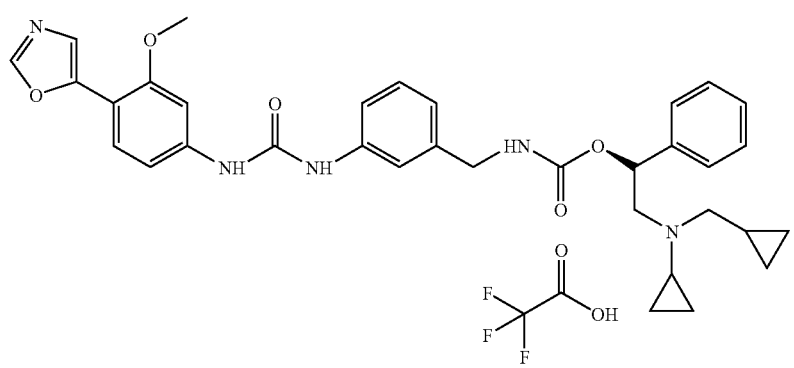
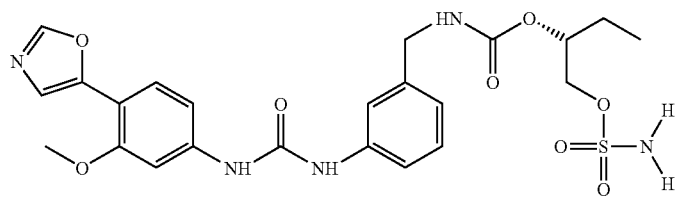
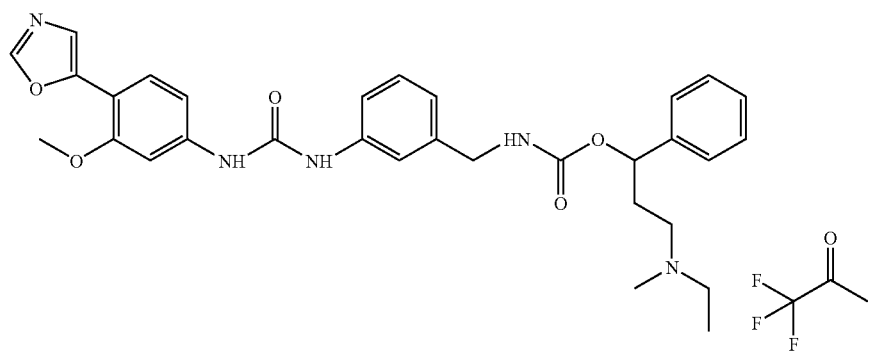
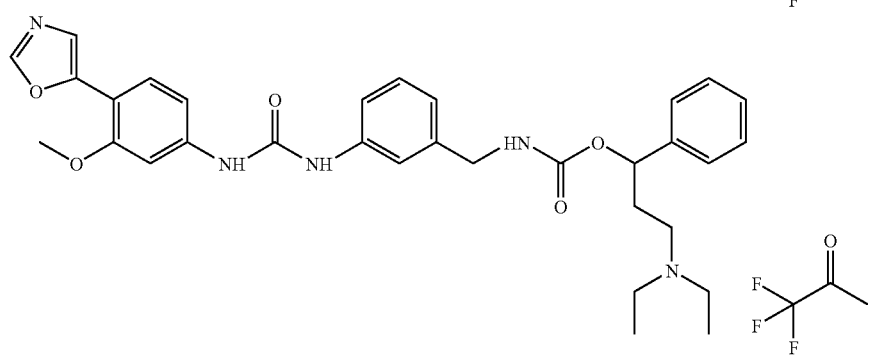

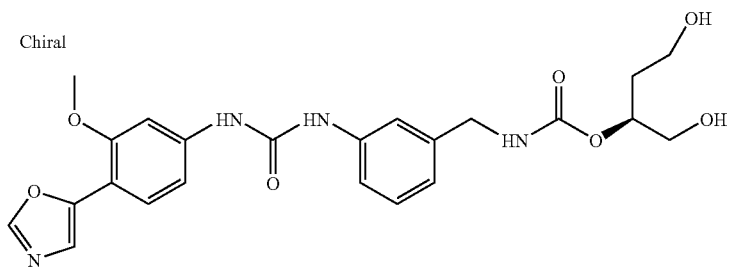
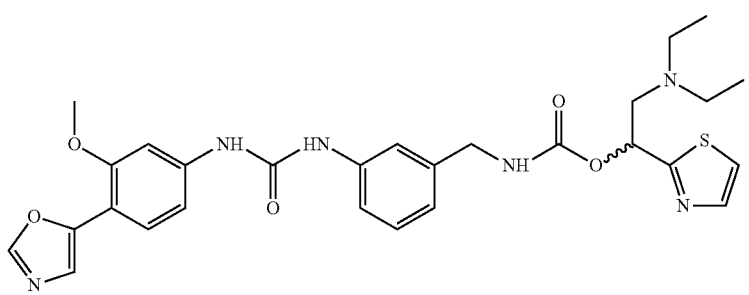
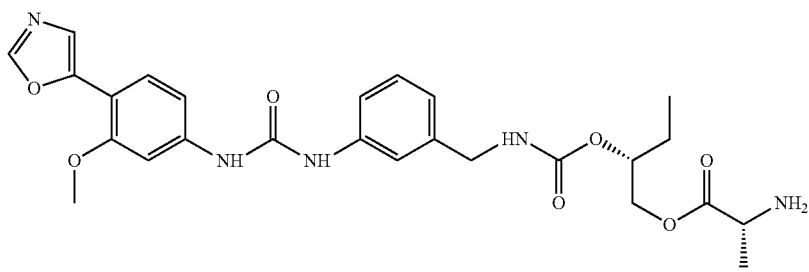
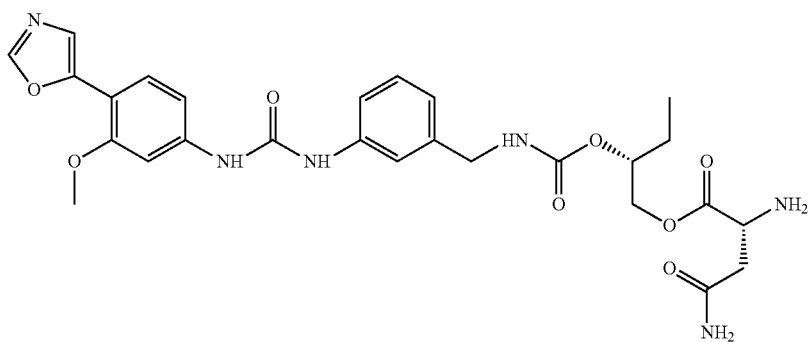
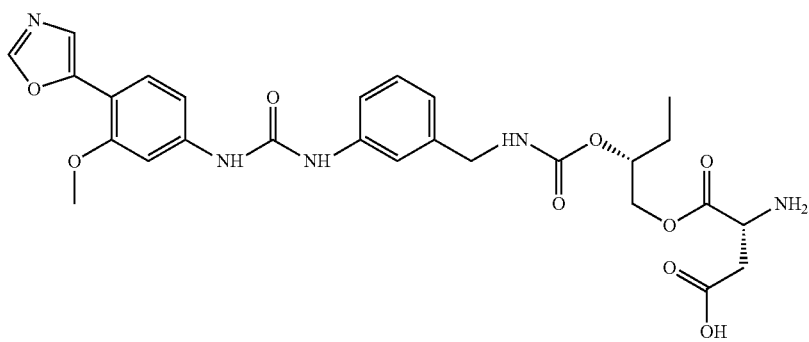

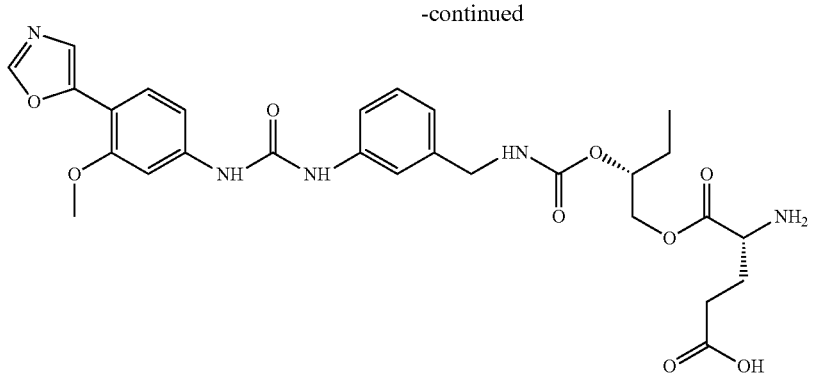
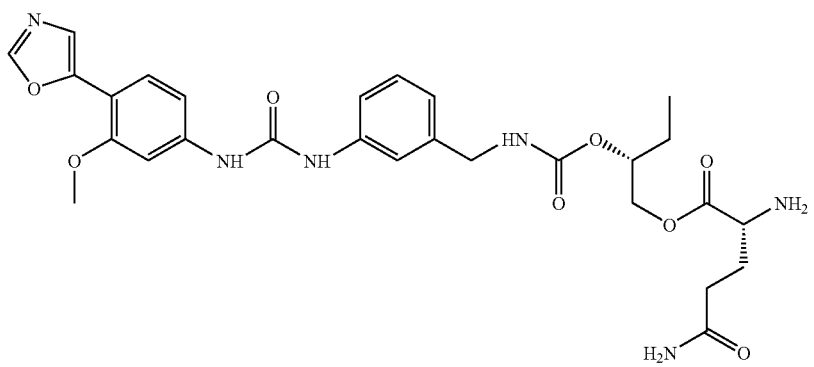
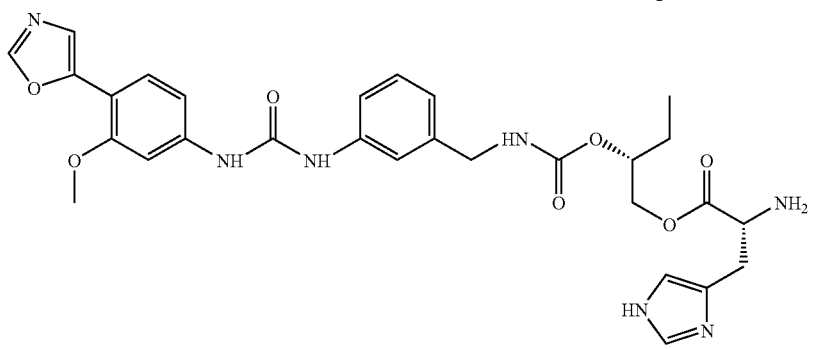
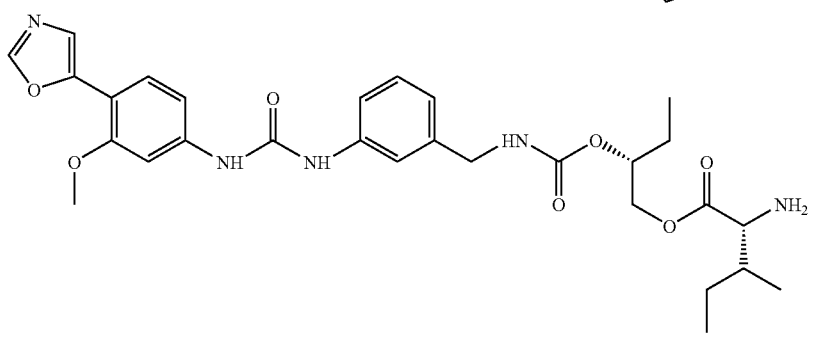
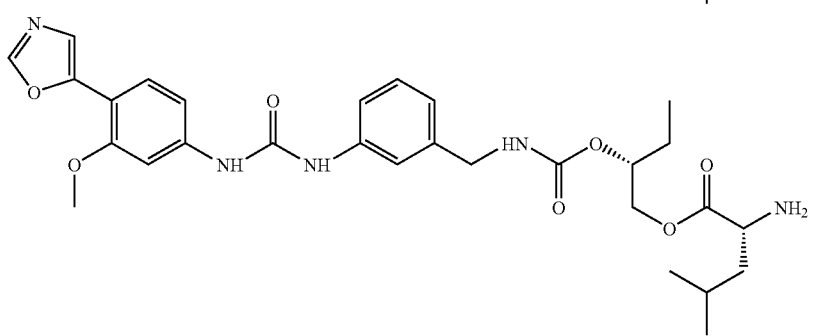

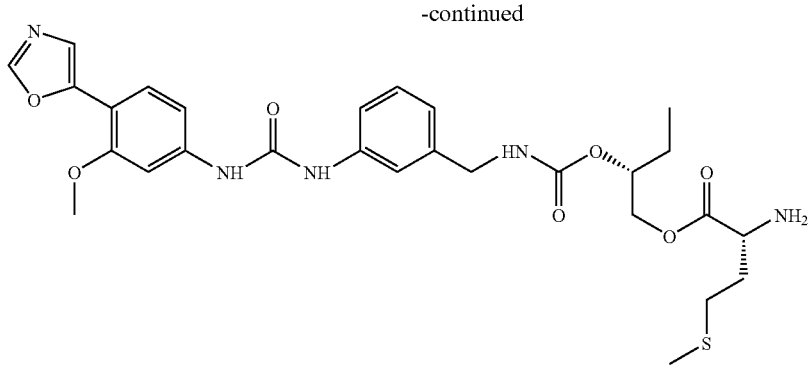
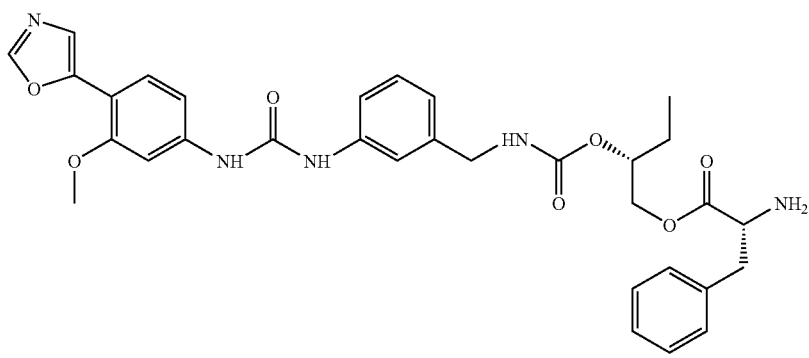
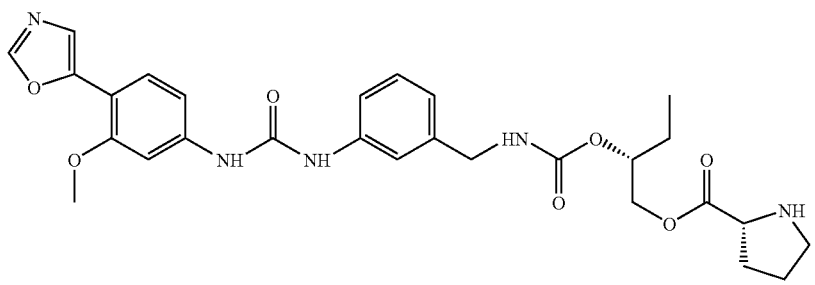
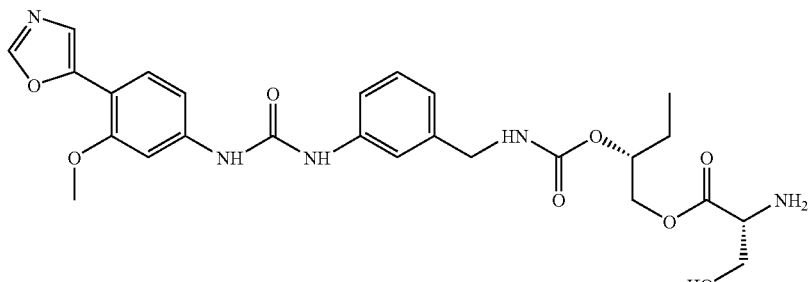
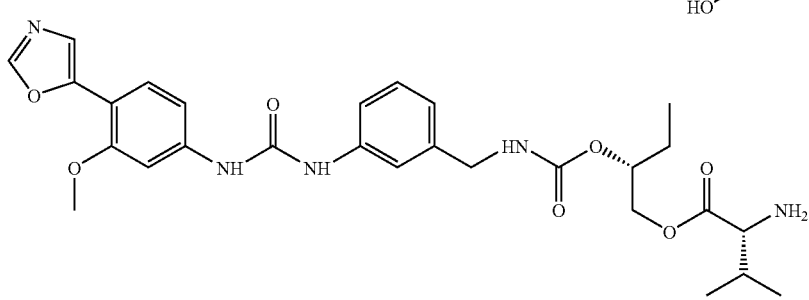

-continued
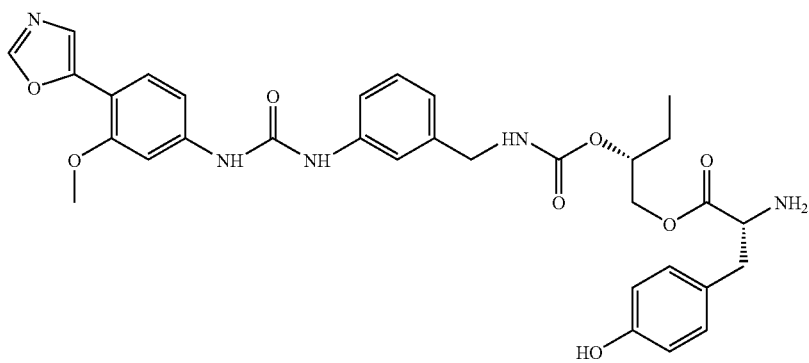
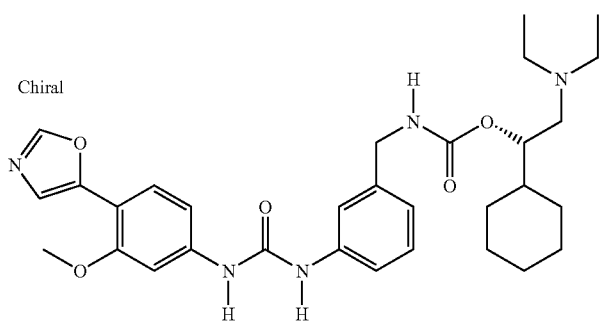
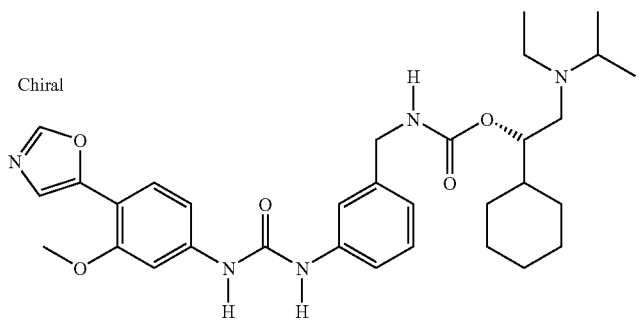
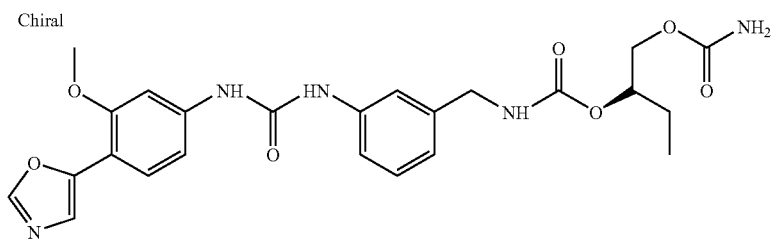
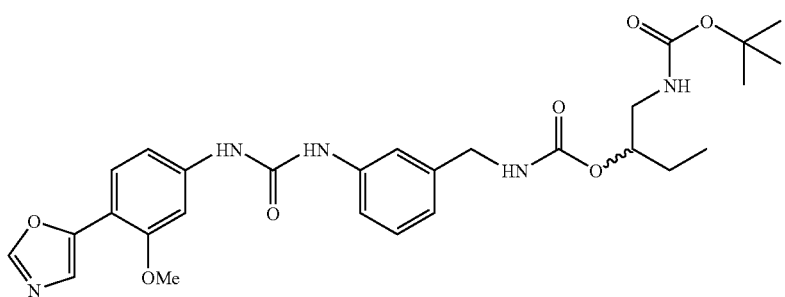

-continued
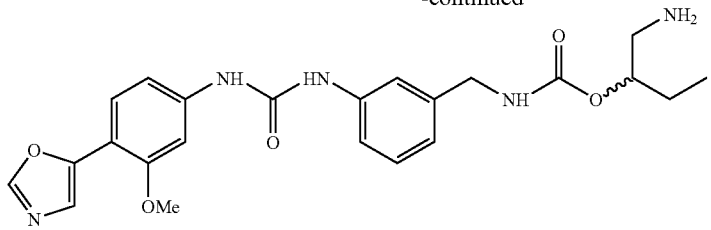
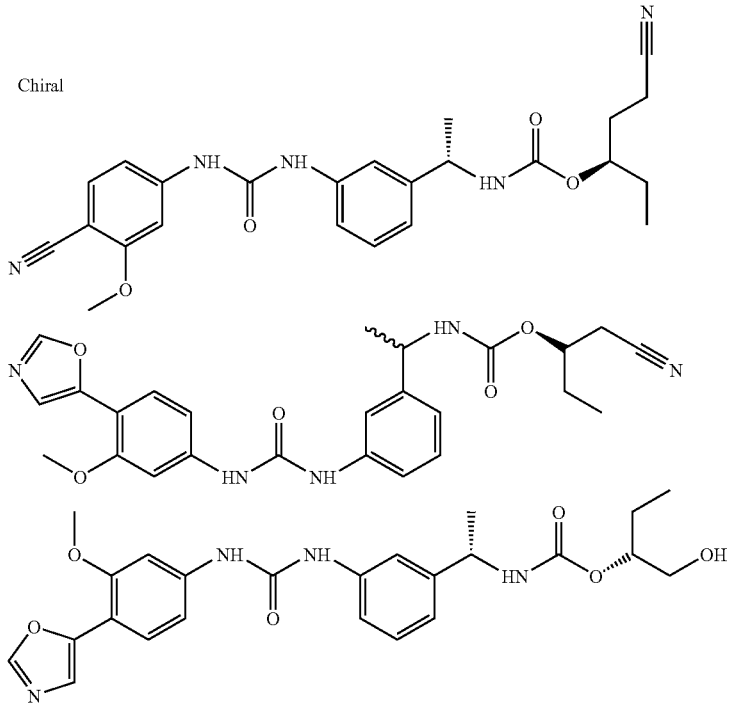
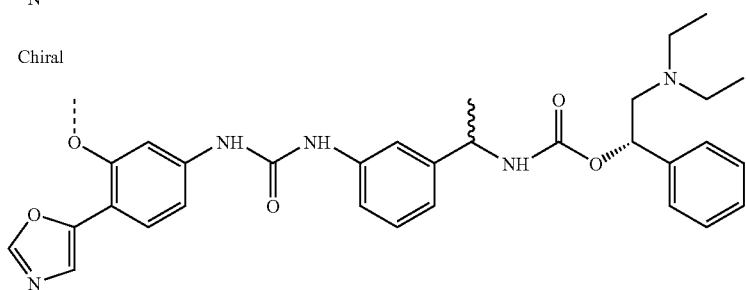
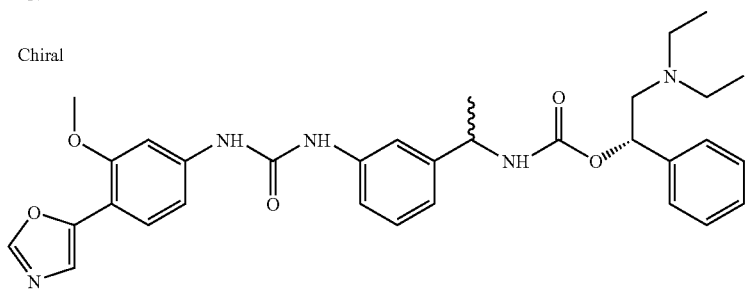

-continued
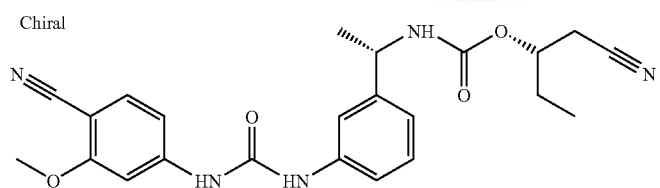
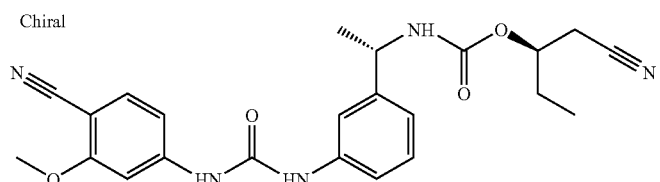
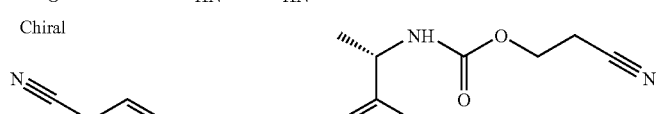
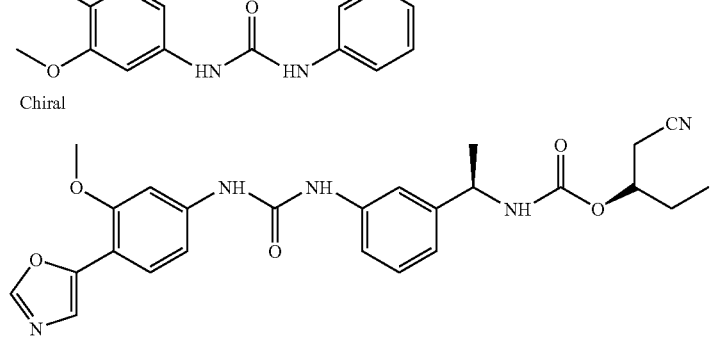
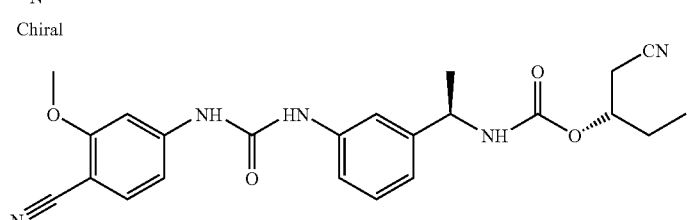
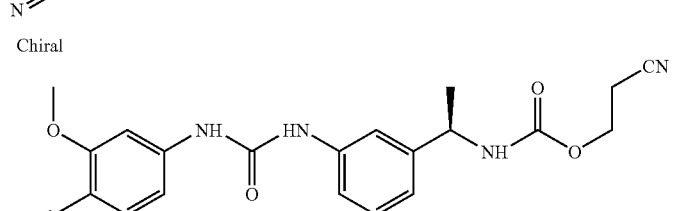
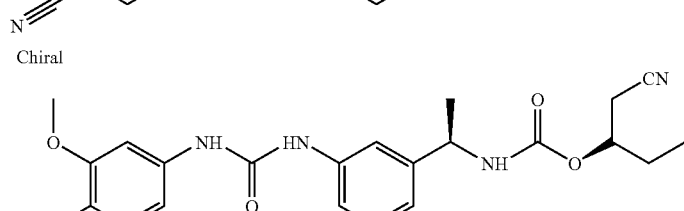
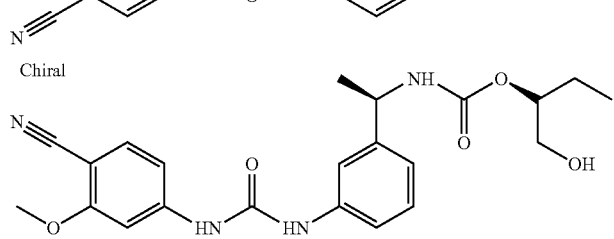

-continued
Chiral
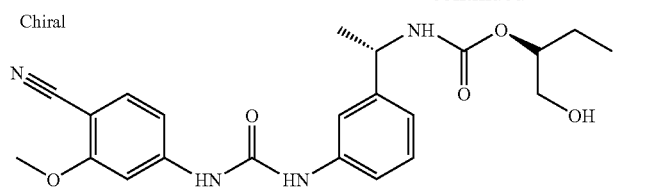
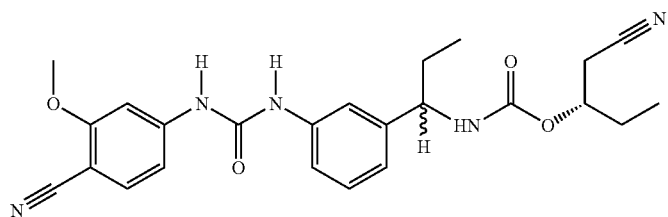
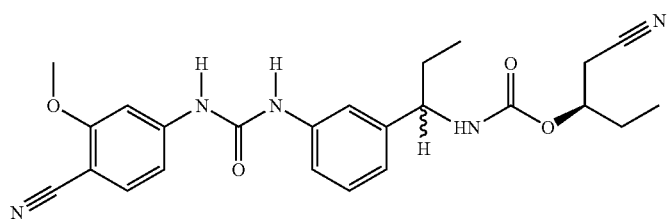
Chiral
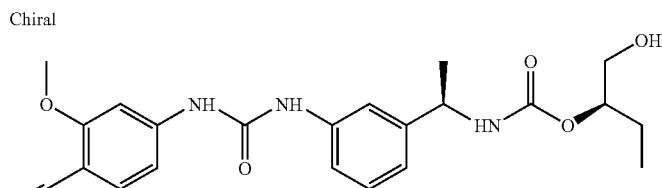
Chiral
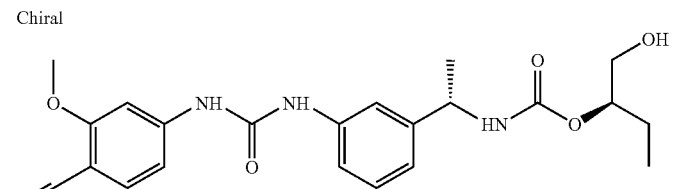
Chiral
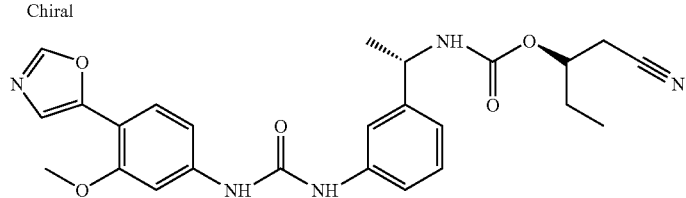
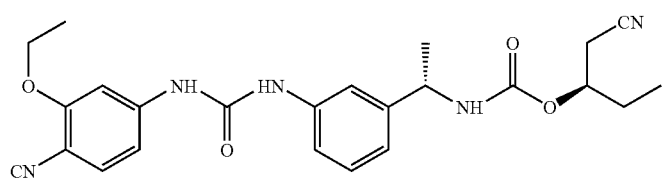
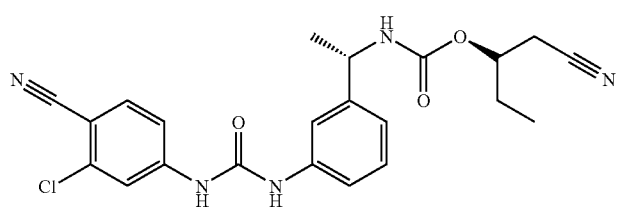

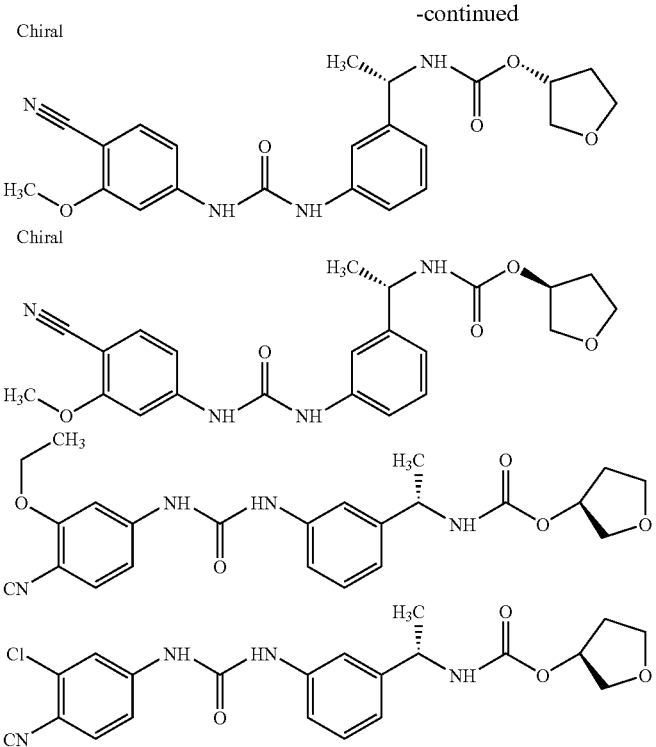

The above compounds and methods for their preparation are disclosed in U.S. Pat. No. 6,498,178.

In still other embodiments, the IMPDH antagonist is selected from compounds with structures represented by formula (XXIV):

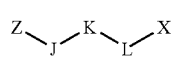

(XXIV)

wherein:

Z is a monocyclic or bicyclic ring system optionally containing up to 4 heteroatoms selected from N, O, and S, and wherein a $CH_2$ adjacent to any of the said N, O or S heteroatoms is optionally substituted with oxo (=O), and wherein Z is optionally substituted with 0-5 substituents chosen from $R^1$, $R^2$, $R^3$ or $R^4$;

$R^1$ and $R^2$ are each independently selected from the group consisting of H, F, Cl, Br, I, $NO_2$, $CF_3$, CN, $OCF_3$, OH, $C_1$-$C_4$ alkoxy-, $C_1$-$C_4$ alkylcarbonyl-, $C_1$-$C_6$ alkyl, hydroxy $C_1$-$C_4$ alkyl-, $C_3$-$C_6$ alkenyl, $C_3$-$C_6$ alkynyl, $C_3$-$C_{10}$ cycloalkyl($C_0$-$C_4$ alkyl)-, $H_2N(C_0$-$C_4)$alkyl-, $R^6HN(C_0$-$C_4)$alkyl-, $R^6R^7N(C_0$-$C_4)$alkyl-, $R^7S(C_0$-$C_4)$alkyl-, $R^7S(O)$ $(C_0$-$C_4)$alkyl-, $R^7SO_2(C_0$-$C_4)$alkyl-, $R^6R^7NSO_2(C_0$-$C_4)$alkyl-, $HSO_3$, $HO_2C(C_0$-$C_4)$alkyl-, $R^6O_2C(C_0$-$C_4)$alkyl-, and $R^6R^7NCO(C_0$-$C_4)$alkyl-, or Alternatively, $R^1$ and $R^2$, when on adjacent carbon atoms, and when taken together are methylenedioxy or ethylenedioxy;

$R^3$ is a 5- or 6-membered heterocyclic ring system containing up to 4 heteroatoms selected from N, O, and S, said heterocyclic ring system being optionally substituted with 0-3 $R^5$, wherein when Rs is hydroxy the heterocycle may undergo tautomerisation to an oxo species or may exist as an equilibrium mixture of both tautomers;

$R^4$ is selected from F, Cl, Br, I, $NO_2$, $CF_3$, CN, $C_1$-$C_4$ alkoxy-, OH, oxo, $CF_3O$, haloalkyloxy, $C_0$-$C_4$ alkylhydroxy, $C_1$-$C_4$ alkyl-, $C_1$-$C_4$ alkylcarbonyl-, $C_0$-$C_4$ alkylOCOR$^6$, $C_0$-$C_4$ alkylOC(=O)OR$^6$, $C_0$-$C_4$ alkylOC(=O)NR$^6R^7$, $NH_2$, NHR$^6$, $C_0$-$C_4$ alkylN$^6R^7$, $C_0$-$C_4$ alkylNR$^7$C(=O)OR$^6$, $C_0$-$C_4$ alkylNR$^6$SO$_2$NR$^6R^7$, $C_0$-$C_4$ alkylNR$^7$SO$_2R^6$, $C_0$-$C_4$ alkylSR$^6$, $C_0$-$C_4$ alkylS(O)R$^6$, $C_0$-$C_4$ alkylSO$_2R^6$, $SO_3R^7$, $C_0$-$C_4$ alkylSO$_2$NR$^6R^7$, $C_0$-$C_4$ alkyl SO$_2$NR$^7$CO(CR$^9R^{10}$)$_0$-$3R^6$, $C_0$-$C_4$ alkylCO$_2$H, $C_0$-$C_4$ alkylCO$_2R^6$, $C_0$-$C_4$ alkylCONR$^6R^7$, and $C_0$-$C_4$ alkylCONR$^7$SO$_2$(CR$^9R^{10}$)$_0$-$3R^6$;

$R^5$ is selected from the group consisting of H, $C_1$-$C_4$ alkyl, $C_3$-$C_7$ cycloalkyl, F, Cl, Br, I, $NO_2$, CN, $CF_3$, $OCF_3$, OH, oxo, $C_1$-$C_4$ alkoxy-, hydroxy$C_1$-$C_4$ alkyl-, $C_1$-$C_4$ alkylcarbonyl-, $CO_2$H, $CO_2R^6$, CONR$^6R^7$, NHR$^6$, and NR$^6R^7$;

$R^6$ is selected from the group consisting of H, $C_1$-$C_8$ alkyl, $C_3$-$C_6$ alkenyl, $C_3$-$C_6$ alkynyl, $C_3$-$C_{10}$ cycloalkyl($C_0$-$C_4$ alkyl)-, aryl($C_0$-$C_4$ alkyl)-, and heterocyclic ($C_0$-$C_4$ alkyl)-, wherein said aryl or heterocyclic groups are substituted with 0-2 substituents independently selected from the group consisting of $C_1$-$C_4$ alkyl, $C_1$-$C_4$ alkoxy, hydroxy $C_0$-$C_4$ alkyl, oxo, F, Cl, Br, $CF_3$, $NO_2$, CN, $OCF_3$, $NH_2$, NHR$^7$, NR$^7R^8$, SR$^7$, S(O)R$^7$, SO$_2R^7$, SO$_2$NR$^7R^8$, $CO_2$H, $CO_2R^7$, and CONR$^7R^8$;

$R^7$ and $R^8$ are each independently selected from the group consisting of H, $C_1$-$C_8$ alkyl, $C_3$-$C_6$ alkenyl, $C_3$-C, alkynyl, $C_3$-$C_{10}$ cycloalkyl($C_0$-$C_4$ alkyl)-, $C_1$-$C_6$ alkylcarbonyl, $C_3$-$C_7$ cycloalkyl($C_0$-$C_5$ alkyl)carbonyl, $C_1$-$C_6$ alkoxycarbonyl, $C_3$-$C_7$ cycloalkyl($C_0$-$C_5$ alkoxy)carbonyl, aryl($C_1$-$C_5$ alkoxy)carbonyl, arylsulfonyl, aryl($C_0$-$C_4$ alkyl)-, heterocyclic($C_1$-$C_5$ alkoxy)carbonyl, heterocyclic sulfonyl and heterocyclic ($C_0$-$C_4$ alkyl)-, wherein said aryl or heterocyclic groups are substituted with 0-2 substituents independently selected from the group consisting of $C_1$-$C_4$ alkyl, $C_1$-$C_4$ alkoxy, F, Cl, Br, $CF_3$, CN, and $NO_2$;

alternatively, $R^6$ and $R^7$, or $R^6$ and $R^8$, or $R^7$ and $R^8$, when both substituents are on the same nitrogen atom [as in (—NR$^6$R$^7$) or (—NR$^7$R$^8$)], can be taken together with the nitrogen atom to which they are attached to form a heterocycle selected from the group consisting of 1-aziridinyl, 1-azetidinyl, 1-piperidinyl, 1-morpholinyl, 1-pyrrolidinyl, thiamorpholinyl, thiazolidinyl, and 1-piperazinyi, said heterocycle being optionally substituted with 0-3 groups selected from the group consisting of oxo, C$_1$-C$_6$ alkyl, C$_3$-C$_7$ cycloalkyl(C$_0$-C$_4$ alkyl)-, C$_1$-C$_6$ alkylcarbonyl, C$_3$-C$_7$ cycloal (C$_0$-C$_5$ alkyl)carbonyl, C$_1$-C$_6$ alkoxycarbonyl, C$_3$-C$_7$ cycloalkyl(C$_0$-C$_5$ alkoxy)carbonyl, aryl(C$_0$-C$_5$ alkyl), heterocyclic(C$_0$-C$_5$ alkyl), aryl(C$_1$-C$_5$ alkoxy)carbonyl, heterocyclic(C$_1$-C$_5$ alkoxy)carbonyl, C$_1$-C$_6$ alkylsulfonyl, arylsulfonyl, and heterocyclicsulfonyl, wherein said aryl or heterocyclic groups are substituted with 0-2 substituents independently selected from the group consisting of C$_1$-C$_4$ alkyl, C$_1$-C$_4$ alkoxy, F, Cl, Br, CF$_3$, CN, and NO$_2$;

J is selected from the group consisting of —NR$^7$— and —(=O)—;

K is selected from the group consisting of —NR$^7$—, —C(=O)—, and —CHR$^9$—;

L is selected from the group consisting of a single bond, —C(=O), —CR$^{10}$R$^{11}$—, —C(=O)CR$^{10}$R$^{11}$—, —CR$^{10}$R$^{11}$C(=O)—, —CR$^{10}$R$^{11}$C(=O)—, —HR$^{15}$C—CHR$^{16}$—, and —R$^{15}$C=CR$^{16}$;

R$^9$ is selected from the group consisting of H, C$_1$-C$_8$ alkyl, C$_3$-C$_6$ alkenyl, C$_3$-C$_{10}$ cycloalkyl(C$_0$-C$_4$ alkyl)-, aryl(C$_0$-C$_4$ alkyl)-, and heterocyclic(C$_0$-C$_4$ alkyl)-, wherein said aryl or heterocyclic groups are substituted with 0-2 substituents dependently selected from the group consisting of C$_1$-C$_4$ alkyl, C$_1$-C$_4$ alkoxy, F, Cl, Br, CF$_3$, and NO$_2$;

R$^{10}$ is selected from the group consisting of H, F, Cl, Br, C$_1$-C$_6$ alkoxy, C$_1$-C$_8$ alkyl, C$_3$-C$_6$ alkenyl, C$_3$-C$_{10}$ cycloalkyl (C$_0$-C$_4$ alkyl)-, aryl(C$_0$-C$_4$ alkyl)-, and terocyclic(C$_0$-C$_4$ alkyl)-, wherein said aryl or heterocyclic groups are substituted with 0-2 substituents independently selected from the group consisting of C$_1$-C$_4$ alkyl, C$_1$-C$_4$ alkoxy, F, Cl, Br, CF$_3$, CN, and NO$_2$;

R$^{11}$ is selected from the group consisting of H, F, Cl, Br, OMe, C$_1$-C$_8$ alkyl, C$_3$-C$_6$ alkenyl, C$_3$-C$_{10}$ cycloalkyl(C$_0$-C$_4$ alkyl)-, aryl(C$_0$-C$_4$ alkyl)-, and heterocyclic(C$_0$-C$_4$ alkyl)-, wherein said aryl or heterocyclic groups are substituted with 0-2 substituents independently selected from the group consisting of C$_1$-C$_4$ alkyl, C$_1$-C$_4$ alkoxy, F, Cl, Br, CF$_3$, CN, and NO$_2$;

alternatively, R$^{10}$ and R$^{11}$, when on the same carbon atom [as in (—CR$^{10}$R$^{11}$—)], can be taken together with the carbon atoms to which they are attached to form a 3-7 membered carbocyclic or 3-7 membered heterocyclic non-aromatic ring system, said carbocyclic or heterocyclic ring being optionally substituted with 0-2 substituents independently selected from the group consisting of C$_1$-C$_4$ alkyl, C$_1$-C$_4$ alkoxy, hydroxy C$_0$-C$_4$ alkyl, oxo, F, Cl, Br, CF$_3$, and NO$_2$;

X is selected from the group consisting of OR$^{12}$, NR$^{12}$R$^{13}$, C$_1$-C$_8$ alkyl, C$_3$-C$_6$ alkenyl, C$_3$-C$_{10}$ cycloalkyl(C$_0$-C$_4$ alkyl)-, C$_6$-C$_{10}$ aryl(C$_0$-C$_4$ alkyl)-, and heterocyclic(C$_0$-C$_4$ alkyl)-, wherein said aryl or heterocyclic groups are substituted with 0-3 substituents independently selected from R$^{14}$, with the proviso that when L is a single bond, X cannot be NR$^{12}$R$^{13}$;

R$^{12}$ is selected from the group consisting of H, C$_1$-C$_8$ alkyl, C$_3$-C$_6$ alkenyl, C$_3$-C$_{10}$ cycloalkyl(C$_0$-C$_4$ alkyl)-, monocyclic or bicyclic aryl(C$_0$-C$_4$ alkyl)-, and monocyclic or bicyclic 5-10 membered heterocyclic(C$_0$-C$_4$ alkyl)-, and —CZ$^1$Z$^2$Z$^3$, wherein said aryl or heterocyclic groups are substituted with 0-3 substituents independently selected from R$^{14}$;

Z$^1$ is selected from the group consisting of C$_1$-C$_8$ alkyl, C$_2$-C$_6$ alkenyl, C$_2$-C$_6$ alkynyl, C$_1$-C$_6$ hydroxyalkyl, C$_1$-C$_4$ alkoxy C$_1$-C$_4$ alkyl, aryl(C$_0$-C$_4$ alkyl)-, and 4-10 membered heterocyclic (C$_0$-C$_4$ alkyl)-, wherein said aryl or heterocyclic groups are substituted with 0-3 substituents independently selected from R$^{14}$;

Z$^2$ is selected from the group consisting of C$_1$-C$_8$ alkyl, C$_2$-C$_6$ alkenyl, C$_2$-C$_6$ alkynyl, C$_1$-C$_6$ hydroxyalkyl, C$_1$-C$_4$ alkoxy C$_1$-C$_4$ alkyl, C$_1$-C$_6$ NR$^1$$^7$R$^1$$^8$, aryl(C$_0$-C$_4$ alkyl)-, and 4-10 membered heterocyclic (C$_0$-C$_4$ alkyl)-, wherein said aryl or heterocyclic groups are substituted with 0-3 substituents independently selected from R$^{14}$;

Z$^3$ is selected from the group consisting of C$_1$-C$_8$ alkyl, R$^{14}$(C$_2$-C$_4$ alkyl)-, C$_2$-C$_6$ alkenyl, C$_2$-C$_6$ alkynyl, C$_1$-C$_6$ hydroxyalkyl, C$_1$-C$_4$ alkoxy C$_1$-C$_4$ alkyl, aryl(C$_0$-C$_4$ alkyl)-, 4-10 membered heterocyclic (C$_0$-C$_4$ alkyl)-, R$^1$$^7$O=C(C$_0$-C$_4$ alkyl)-, R$^1$$^7$OO=C(C$_0$-C$_4$ alkyl)-, and R$^1$$^7$R$^1$$^8$NO=C (C$_0$-C$_4$ alkyl)-, wherein said aryl or heterocyclic groups are substituted with 0-3 substituents independently selected from R$^{14}$;

alternatively, Z$^1$ and Z$^2$, when on the same carbon atom [as in (—CZ$^1$Z$^2$—)], can be taken together with the carbon atoms to which they are attached to form a 3-7 membered carbocyclic or 3-7 membered heterocyclic non-aromatic ring system, said carbocyclic or heterocyclic ring being optionally substituted with 0-2 substituents independently selected from R$^{14}$.

R$^{13}$ is selected from the group consisting of H, C$_1$-C$_8$ alkyl, C$_3$-C$_6$ alkenyl, C$_3$-C$_{10}$ cycloalkyl(C$_0$-C$_4$ alkyl)-, C$_1$-C$_6$ alkylcarbonyl, C$_1$-C$_6$ alkylsulfonyl, C$_3$-C$_7$ cycloalkyl(C$_0$-C$_5$ alkyl)carbonyl, C$_1$-C$_6$ alkoxycarbonyl, C$_3$-C$_7$ cycloalkyl(C$_0$-C$_5$ alkoxy)carbonyl, aryl(C$_0$-C$_4$ alkyl)-, aryl(C$_1$-C$_5$ alkoxy)carbonyl, arylsulfonyl, heterocyclic(C$_0$-C$_4$ alkyl), heterocyclic (C$_1$-C$_5$ alkoxy)carbonyl, and heterocyclicsulfonyl, wherein said aryl or heterocyclic groups are substituted with 0-2 substituents independently selected from the group consisting of C$_1$-C$_4$ alkyl, C$_1$-C$_4$ alkoxy, F, Cl, Br, CF$_3$, CN, and NO$_2$;

alternatively, R$^{12}$ and R$^{13}$, when both are on the same nitrogen atom [as in (—NR$^{12}$R$^{13}$)] can be taken together with the nitrogen atom to which they are attached to form a heterocycle selected from 1-aziridinyl, 1-azetidinyl, 1-piperidinyl, 1-morpholinyl, 1-pyrrolidinyl, thiamorpholinyl, thiazolidinyl, and 1-piperazinyl, said heterocycle being optionally substituted with 0-3 groups independently selected from oxo, C$_1$-C$_6$ alkyl, C$_3$-C$_7$ cycloalkyl(C$_0$-C$_4$ alkyl)-, C$_1$-C$_6$ alkylcarbonyl, C$_3$-C$_7$ cycloalkyl(C$_0$-C$_5$ alkyl)carbonyl, C$_1$-C$_6$ alkoxycarbonyl, C$_3$-C$_7$ cycloalkyl(C$_0$-C$_5$ alkoxy)carbonyl, aryl(C$_0$-C$_5$ alkyl), heterocyclic(C$_0$-C$_5$ alkyl), aryl(C$_1$-C$_5$ alkoxy)carbonyl, heterocyclic(C$_1$-C$_5$ alkoxy)carbonyl, C$_1$-C$_6$ alkylsulfonyl arylsulfonyl and heterocyclicsulfonyl, wherein said aryl or heterocyclic groups are substituted with 0-2 substituents independently selected from the group consisting of CH$_3$—, alkoxy, F, Cl, Br, CF$_3$, CN, and NO$_2$;

R$^{14}$ is selected from the group consisting of H, C$_1$-C$_{10}$ alkyl, NO$_2$, CF$_3$, CN, F, Cl, Br, C$_1$-C$_{10}$ alkylcarbonyl, haloalkyl, haloalkoxy, OH, NR$^6$R$^7$(C$_0$-C$_4$ alkyl)-, R$^6$C(=O) O(C$_0$-C$_4$ alkyl)-, R$^6$OC(=O)O(C$_0$-C$_4$ alkyl)-, R$^6$O(C$_0$-C$_4$ alkyl), R$^6$R$^7$NC(=O)O(C$_0$-C$_4$ alkyl)-, R$^6$R$^7$NC(=O)(C$_0$l-C$_4$ alkyl)-, R$^6$O(CR$^{10}$R$^{11}$)$_2$-6R$^6$NC(=O)(C$_0$-C$_4$ alkyl)-, R$^6$R$^7$N(CR$^{10}$R$^{11}$)$_2$-6R$^6$NC(=O)(C$_0$-C$_4$ alkyl)-, R$^6$O$_2$C (CH$_2$), $_1$-4O(C$_0$-C$_4$ alkyl)-, R$^6$OOC(C$_1$-C$_4$ alkoxy), —R$^6$OOC(C$_0$-C$_4$ alkyl)-, R$^6$C(=O)(C$_0$-C$_4$ alkyl)-, R$^6$C (=O)NR$^7$(C$_0$-C$_4$ alkyl)-, R$^6$OC(=O)NR$^7$(C$_0$-C$_4$ alkyl)-, R$^6$OC(=NCN)NR$^7$(C$_0$-C$_4$ alkyl)-, R$^6$R$^7$NC(=O)NR$^8$(C$_0$-C$_4$ alkyl)-, R$^6$OC(=NC)NR$^7$(C$_0$-C$_4$ alkyl)-, R$^6$(CR$^{10}$R$^{11}$)$_1$-4 NR$^7$C=O—, R$^6$O(CR$^{10}$R$^{11}$)$_1$-4O=CR$^7$N—, NR$^6$R$^7$ $(CR^{10}R^{11})_1-4C=OR^7N-$, $R^6O(CR^{10}R^{11})_2-4R^7N-$, $R^6O_2C(CR^{10}R^{11})_1-4R^7N$, $R^6R^7N(CR^{10}R^{11})_2-4R^7N-$, $R^6R^7NC(=NCN)NR^7(C_0-C_4\ alkyl)-$, $R^6R^7NC(=C(H)(NO_2))NR^7(C_0-C_4\ alkyl)-$, $R^7R^8NC(=NR^7)NR^7(C_0-C_4\ alkyl)-$, $R^6R^1NSO_2NR^8(C_0-C_4\ alkyl)-$, $R^6SO_2NR^7(C_0-C_4\ alkyl)-$, $R^6R^7N(C_1-C_4)CO-$, $R^6R^7N(C_2-C_6\ alkyl)O-$, $R^6CO(CR^{10}R^{11})_0-2R^7N(O_2)S(C_0-C_4\ alkyl)$, $R^6(O_2)SR^7NC(=O)(C_0-C_4\ alkyl)-$, $R^6S(C_0-C_4\ alkyl)-$, $R^6S(=O)(C_0-C_4\ alkyl)-$, $R^6SO_2(C_0-C_4\ alkyl)-$, $SO_2N^6R^7$, $SiMe_3$, $R^6R^7N(C_2-C_4\ alkyl)-$, $R^6R^7N(C_2-C_4\ alkoxy)-$, $HSO_3$, $HONH-$, $R^6ONH-$, $R^8R^7NNR^6-$, $HO(COR^6)N-$, $HO(R^6O_2C)N$, $C_2-C_6$ alkenyl, $C_3-C_{10}$ cycloalkyl, $C_3-C_{10}$ cycloalkylmethyl, aryl($C_0-C_4$ alkyl)-, heteroaryl($C_0-C_4$ alkyl)-, aryl($C_0-C_4$ alkyl)O—, and heteroaryl($C_0-C_4$ alkyl)O—, wherein said aryl groups are substituted with 0-2 substituents independently selected from a group consisting of $C_1-C_4$ alkyl, $C_1-C_4$ alkoxy, F, Cl, Br, $CF_3$, and $NO_2$;

$R^{15}$ is selected from the group consisting of H, halo, cyano, $C_1-C_8$ alkyl, $C_3-C_6$ alkenyl, and $C_3-C_{10}$ cycloalkyl($C_0-C_4$ alkyl)-, aryl($C_0-C_4$ alkyl)-, and heterocyclic($C_0-C_4$ alkyl)-, wherein said aryl or heterocyclic groups are substituted with 0-2 substituents independently selected from $R^{14}$;

$R^{16}$ is selected from the group consisting of H, halo, cyano, $C_1-C_8$ alkyl, $C_3-C_6$ alkenyl, $C_3-C_{10}$ cycloalkyl($C_0-C_4$ alkyl)-, aryl($C_0-C_4$ alkyl)-, and heterocyclic($C_0-C_4$ alkyl)-, wherein said aryl or heterocyclic groups are substituted with 0-2 substituents independently selected from $R^{14}$;

alternatively, when $R^{15}$ and $R^{16}$ are on adjacent carbon atoms [as in $-HR^{15}C-CHR^{16}-$], or when $R^{15}$ and $R^{16}$ are oriented on the same side of the double bond, as in the following structure (XXV):

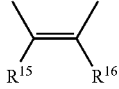

(XXV)

$R^{15}$ and $R^{16}$ can be taken together with the carbon atoms to which they are attached to form a 3-7 membered carbocyclic aromatic or nonaromatic ring system, or a 3-7 membered heterocyclic aromatic or nonaromatic ring system, said carbocyclic or heterocyclic ring being optionally substituted with 0-2 substituents independently selected from the group consisting of $C_1-C_4$ alkyl, $C_1-C_4$ alkoxy, F, Cl, Br, $CF_3$, $NO_2$;

$R^{17}$ is selected from the group consisting of H, $C_1-C_8$ alkyl, $C_3-C_6$ alkenyl, $C_3-C_{10}$ cycloalkyl($C_0-C_4$ alkyl)-, $C_1-C_6$ alkylcarbonyl, $C_1-C_6$ alkylsulfonyl, $C_3-C_7$ cycloalkyl($C_0-C_5$ alkyl)carbonyl, $C_1-C_6$ alkoxycarbonyl, $C_3-C_7$ cycloalkyl($C_0-C_5$ alkoxy)carbonyl, hydroxy($C_2-C_4$)alkyl-, $C_1-C_3$ alkoxy($C_2-C_4$)alkyl-, ($C_0-C_4$ alkyl) ($C_0-C_4$ alkyl) amino($C_2-C_4$)alkyl-, aryl($C_0-C_4$ alkyl)-, aryl($C_1-C_5$ alkoxy)carbonyl, arylsulfonyl, heterocyclic($C_0-C_4$ alkyl), heterocyclic($C_1-C_5$ alkoxy)carbonyl, and heterocyclicsulfonyl, wherein said aryl or heterocyclic groups are substituted with 0-2 substituents independently selected from the group consisting of $C_1-C_4$ alkyl, $C_1-C_4$ alkoxy, $C_1-C_4$ alkoxy $C_1-C_4$ alkyl, oxo, F, Cl, Br, $CF_3$, CN, and $NO_2$;

$R^{18}$ is selected from the group consisting of H, $C_1-C_8$ alkyl, $C_3-C_6$ alkenyl, $C_3-C_{10}$ cycloalkyl($C_0-C_4$ alkyl)-, aryl($C_0-C_4$ alkyl)-, and heterocyclic($C_0-C_4$ alkyl), wherein said aryl or heterocyclic groups are substituted with 0-2 substituents independently selected from the group consisting of $C_1-C_4$ alkyl, $C_1-C_4$ alkoxy, F, Cl, Br, $CF_3$, CN, and $NO_2$; and alternatively, $R^{17}$ and $R^{18}$, when both are on the same nitrogen atom [as in ($-NR^{12}R^{13}$)] can be taken together with the nitrogen atom to which they are attached to form a heterocycle selected from 1-aziridinyl, 1-azetidinyl, 1-piperidinyl, 1-morpholinyl, 1-pyrrolidinyl, thiamorpholinyl, thiazolidinyl, and 1-piperazinyl, said heterocycle being optionally substituted with 0-3 groups selected from oxo, $C_1-C_6$ alkyl, $C_3-C_7$ cycloalkyl($C_0-C_4$ alkyl)-, $C_1-C_6$ alkylcarbonyl, ($C_1-C_6$ alkylcarbonyl)($C_0-C_4$ alkyl)amino-, $C_3-C_7$ cycloalkyl($C_0-C_5$ alkyl)carbonyl, $C_1-C_6$ alkoxycarbonyl, $C_3-C_7$ cycloalkyl($C_0-C_5$ alkoxy)carbonyl, aryl($C_0-C_5$ alkyl), heterocyclic($C_0-C_5$ alkyl), aryl($C_1-C_5$ alkoxy)carbonyl, heterocyclic($C_1-C_5$ alkoxy)carbonyl, $C_1-C_6$ alkylsulfonyl arylsulfonyl and heterocyclicsulfonyl, wherein said aryl or heterocyclic groups are substituted with 0-2 substituents independently selected from the group consisting of $CH_3-$, alkoxy, F, Cl, Br, $CF_3$, CN, and $NO_2$.

Representative compounds falling within the scope of formula (XIV) include, but are not limited to: N-(4-fluorophenyl)-N-2-[3-methoxy-4-(5-oxazolyl)phenyl]glycinamide; N-[3-methoxy-4-(5-oxazolyl)phenyl]-N-2-phenylglycinamide; N-[3-methoxy-4-(5-oxazolyl)phenyl]-N-2-(3-methylphenyl)glycinamide; [[3-methoxy-4-(5-oxazolyl)phenyl]amino]oxoacetic acid Ethyl Ester; N-[3-methoxy-4-(5-oxazolyl)phenyl]-N'-phenylethanediamide; N-[3-methoxy-4-(5-oxazolyl)phenyl]-N'-(2-methylphenyl)ethanediamide; N-[3-methoxy-4-(5-oxazolyl)phenyl]-N'-(3-methylphenyl)ethanediamide; N-[3-methoxy-4-(5-oxazolyl)phenyl]-N'-(4-methylphenyl)ethanediamide; (S)-[[3-[[[[3-methoxy-4-(5-oxazolyl)phenyl]amino]oxoacetyl]-amino]phenyl]methyl] carbamic acidtetrahydro-3-furanyl ester; N-[3-methoxy-4-(5-oxazolyl)phenyl]-N'-(3-methoxyphenyl)ethanediamide; N-[3-methoxy-4-(5-oxazolyl)phenyl]-N'-(phenylmethyl)ethanediamide; N-(4-cyanophenyl)-N'-[3-methoxy-4-(5-oxazolyl)phenyl]ethanediamide; N-(1,1-dimethylethyl)-N'-[3-methoxy-4-(5-oxazolyl)phenyl]ethanediamide; N-[1,1-bis(hydroxymethyl)propyl]-N'-[3-methoxy-4-(5-oxazolyl)phenyl]ethanediamide; N-(2-hydroxy-1,1-dimethylethyl)-N'-[3-methoxy-4-(5-oxazolyl)phenyl]ethanediamide; N-[[[3-methoxy-4-(5-oxazolyl)phenyl]amino]oxoacetyl]-2-methylalanine 1,1-dimethylethyl ester; N-(2-hydroxy-1,1-dimethylpentyl)-N'-[3-methoxy-4-(5-oxazolyl)phenyl]ethanediamide; N-[2-[(2-hydroxy-1,1-dimethylethyl)amino]-1,1-dimethylethyl]-N'-[3-methoxy-4-(5-oxazolyl)phenyl]ethanediamide; N-[2-(dimethylamino)-1,1-dimethylethyl]-N'-[3-methoxy-4-(5-oxazolyl)phenyl]ethanediamide; N-(1,1-diethyl-2-propynyl)-N'-[3-methoxy-4-(5-oxazolyl)phenyl]ethanediamide; N-[3-methoxy-4-(5-oxazolyl)phenyl]-N'-(1,1,3,3-tetramethylbutyl)ethanediamide; N-(1,1-dimethylpropyl)-N'-[3-methoxy-4-(5-oxazolyl)phenyl]ethanediamide; N-[1-(hydroxymethyl)cyclopentyl]-N'-[3-methoxy-4-(5-oxazolyl)phenyl]ethanediamide; N-[2-(4-fluorophenyl)-1,1-dimethylethyl]-N'-[3-methoxy-4-(5-oxazolyl)phenyl]ethanediamide; N-[[[3-methoxy-4-(5-oxazolyl)phenyl]amino]oxoacetyl]-□-methyltyrosine methyl ester; N-[[[3-methoxy-4-(5-oxazolyl)phenyl]amino]oxoacetyl]-□-methyltryptophan methyl ester; N-[1,1-bis(hydroxymethyl)ethyl]-N'-[3-methoxy-4-(5-oxazolyl)phenyl]-N-methylethanediamide; N-[1,1-dimethyl-3-oxobutyl)-N'-[3-methoxy-4-(5-oxazolyl)phenyl]ethanediamide; N-[3-methoxy-4-(5-oxazolyl)phenyl]-N'-(1-methyl-1-phenylethyl)ethanediamide; N-(2-hydroxy-1,2-dimethyl-1-phenylpropyl)-N'-[3-methoxy-4-(5-oxazolyl)phenyl]ethanediamide; N-[[[3-methoxy-4-(5-oxazolyl)phenyl]amino]oxoacetyl]-2-methylalanine methyl ester; 1-[[[[3-methoxy-4-(5-oxazolyl)phenyl]amino]oxoacetyl]-amino]cyclopropanecarboxylic acid methylester;

N-(1-Ethynylcyclohexyl)-N'-[3-methoxy-4-(5-oxazolyl)phenyl]ethanediamide; (R)-N-[1-(hydroxymethyl)-1-methylpropyl]-N'-[3-methoxy-4-(5-oxazolyl)phenyl]-N-methylethanediamide; N-[[[3-methoxy-4-(5-oxazolyl)phenyl]amino]oxoacetyl]-2-methylalanine; N-[1,1-dimethyl-2-oxo-2-(1-piperidinyl)ethyl]-N'-[3-methoxy-4-(5-oxazolyl)phenyl]ethanediamide; N-[1,1-dimethyl-2-(4-methyl-1-piperazinyl)-2-oxoethyl]-N'-[3-methoxy-4-(5-oxazolyl)phenyl]ethanediamide; N-[1,1-dimethyl-2-(4-morpholinyl)-2-oxoethyl]-N'-[3-methoxy-4-(5-oxazolyl)phenyl]ethanediamide; 4-[2-[[[[3-methoxy-4-(5-oxazolyl)phenyl]amino]oxoacetyl]amino]-2-methyl-1-oxopropyl]-1-piperazinecarboxylic acid ethyl ester; N-[2-[3-(acetylmethylamino)-1-pyrrolidinyl]-1,1-dimethyl-2-oxoethyl]-N'-[3-methoxy-4-(5-oxazolyl)phenyl]ethanediamide; N-[1,1-dimethyl-2-[methyl[2-(methylamino)ethyl]amino]-2-oxoethyl]-N'-[3-methoxy-4-(5-oxazolyl)phenyl]ethanediamide; N-[1,1-dimethyl-2-oxo-2-(propylamino)ethyl]-N'-[3-methoxy-4-(5-oxazolyl)phenyl]ethanediamide; N-[1,1-dimethyl-2-[[2-(methylamino)ethyl]amino]-2-oxoethyl]-N'-[3-methoxy-4-(5-oxazolyl)phenyl]ethanediamide; N-[1,1-dimethyl-2-[[2-(4-morpholinyl)ethyl]amino]-2-oxoethyl]-N'-[3-methoxy-4-(5-oxazolyl)phenyl]ethanediamide; N-[1,1-dimethyl-2-oxo-2-[[3-(2-oxo-1-pyrrolidinyl)propyl]amino]ethyl]-N'-[3-methoxy-4-(5-oxazolyl)phenyl]ethanediamide; N-[2-[[2-(1h-Imidazol-4-yl)ethyl]amino]-1,1-dimethyl-2-oxoethyl]-N'-[3-methoxy-4-(5-oxazolyl)phenyl]ethanediamide; N-[2-[[2-(acetylamino)ethyl]amino]-1,1-dimethyl-2-oxoethyl]-N'-[3-methoxy-4-(5-oxazolyl)phenyl]ethanediamide; N-[2-[[2-(1 h-Imidazol-1-yl)ethyl]amino]-1,1-dimethyl-2-oxoethyl]-N'-[3-methoxy-4-(5-oxazolyl)phenyl]ethanediamide; N-[1,1-dimethyl-2-oxo-2-[[2-(4-pyridinyl)ethyl]amino]ethyl]-N'-[3-methoxy-4-(5-oxazolyl)phenyl]ethanediamide; N-[1,1-dimethyl-2-oxo-2-[[(tetrahydro-2-furanyl)methyl]amino]ethyl]-N'-[3-methoxy-4-(5-oxazolyl)phenyl]ethanediamide; N-[2-[(2-methoxyethyl)amino]-1,1-dimethyl-2-oxoethyl]-N'-[3-methoxy-4-(5-oxazolyl)phenyl]ethanediamide; N-[2-(dimethylamino)-1,1-dimethyl-2-oxoethyl]-N'-[3-methoxy-4-(5-oxazolyl)phenyl]ethanediamide; N-[2-[4-(2-methoxyethyl)-1-piperazinyl]-1,1-dimethyl-2-oxoethyl]-N'-[3-methoxy-4-(5-oxazolyl)phenyl]ethanediamide; N-[1,1-dimethyl-2-oxo-2-(2-pyridinylamino)ethyl]-N'-[3-methoxy-4-(5-oxazolyl)phenyl]ethanediamide; 3-[[3-methoxy-4-(5-oxazolyl)phenyl]amino]-3-oxopropanoic acid Ethyl Ester; N-[3-methoxy-4-(5-oxazolyl)phenyl]-N'-(3-methylphenyl)propanediamide; N-[3-methoxy-4-(5-oxazolyl)phenyl]-N'-(phenyl)propanediamide; (S)-[[3-[[3-methoxy-4-(5-oxazolyl)phenyl]amino]-1,3-dioxopropyl]amino]-phenyl]methyl]carbamic acid tetrahydro-3-furanyl ester; N-[3-methoxy-4-(5-oxazolyl)phenyl]benzeneacetamide; N-[3-methoxy-4-(5-oxazolyl)phenyl]-1-oxobenzeneacetamide; N-[3-methoxy-4-(5-oxazolyl)phenyl]-1 h-indole-2-carboxamide; N-[3-methoxy-4-(5-oxazolyl)phenyl]-1-methyl-1 h-indole-2-carboxamide; N-[3-methoxy-4-(5-oxazolyl)phenyl]-2-benzofurancarboxamide; N-[3-methoxy-4-(5-oxazolyl)phenyl]benzo[b]thiophene-2-carboxamide; N-[3-methoxy-4-(5-oxazolyl)phenyl]-1,3-benzodioxole-5-carboxamide; N-[3-methoxy-4-(5-oxazolyl)phenyl]-1-methyl-1 h-pyrrole-2-carboxamide; 5-(1,1-dimethylethyl)-N-[3-methoxy-4-(5-oxazolyl)phenyl]-2-furancarboxamide; N-[3-methoxy-4-(5-oxazolyl)phenyl]-4,5-dimethyl-2-furancarboxamide; N-[3-methoxy-4-(5-oxazolyl)phenyl]-5-methyl-2-thiophenecarboxamide; N-[3-methoxy-4-(5-oxazolyl)phenyl]-5-(2-pyridinyl)-2-thiophenecarboxamide; N-[3-methoxy-4-(5-oxazolyl)phenyl]-2,4-dimethyl-5-thiazolecarboxamide; 5-hydroxy-N-[3-methoxy-4-(5-oxazolyl)phenyl]-1h-indole-2-carboxamide; 7-methoxy-N[3-methoxy-4-(5-oxazolyl)phenyl]-2-benzofurancarboxamide; 8-hydroxy-N-[3-methoxy-4-(5-oxazolyl)phenyl]-2-guinolinecarboxamide; (E)-N-[3-methoxy-4-(5-oxazolyl)phenyl]-3-phenyl-2-propenamide; N-[3-methoxy-4-(5-oxazolyl)phenyl]benzamide; (E)-N-[3-methoxy-4-(5-oxazolyl)phenyl]-3-(2-methylphenyl)-2-propenamide; (E)-N-[3-methoxy-4-(5-oxazolyl)phenyl]-3-(4-methylphenyl)-2-propenamide; (E)-3-(2-fluorophenyl)-N-[3-methoxy-4-(5-oxazolyl)phenyl]-2-propenamide; (E)-3-(3-fluorophenyl)-N-[3-methoxy-4-(5-oxazolyl)phenyl]-2-propenamide; (E)-3-(4-fluorophenyl)-N-[3-methoxy-4-(5-oxazolyl)phenyl]-2-propenamide; (E)-3-(2-chlorophenyl)-N-[3-methoxy-4-(5-oxazolyl)phenyl]-2-propenamide; (E)-3-(3-chlorophenyl)-N-[3-methoxy-4-(5-oxazolyl)phenyl]-2-propenamide; (E)-3-(4-chlorophenyl)-N-[3-methoxy-4-(5-oxazolyl)phenyl]-2-propenamide; (E)-N-[3-methoxy-4-(5-oxazolyl)phenyl]-3-[2-(trifluoromethyl)phenyl]-2-propenamide; (E)-3-(3-cyanophenyl)-N-[3-methoxy-4-(5-oxazolyl)phenyl]-2-propenamide; (E)-3-[4-(acetylamino)phenyl]-N-[3-methoxy-4-(5-oxazolyl)phenyl]-2-propenamide; (E)-3-(2,3-dimethoxyphenyl)-N-[3-methoxy-4-(5-oxazolyl)phenyl]-2-propenamide; (E)-3-(2,6-difluorophenyl)-N-[3-methoxy-4-(5-oxazolyl)phenyl]-2-propenamide; (E)-N-[3-methoxy-4-(5-oxazolyl)phenyl]-3-(2,3,4-trimethoxyphenyl)-2-propenamide; (E)-2-fluoro-N-[3-methoxy-4-(5-oxazolyl)phenyl]-3-phenyl-2-propenamide; (E)-3-(2-furanyl)-N-[3-methoxy-4-(5-oxazolyl)phenyl]-2-propenamide; (E)-N-[3-methoxy-4-(5-oxazolyl)phenyl]-3-(2-thienyl)-2-propenamide; (E)-N-[3-methoxy-4-(5-oxazolyl)phenyl]-3-(3-pyridinyl)-2-propenamide; (E)-N-[3-methoxy-4-(5-oxazolyl)phenyl]-3-(4-pyridinyl)-2-propenamide; (E)-N-[3-methoxy-4-(5-oxazolyl)phenyl]-3-(1-naphthalenyl)-2-propenamide; N-[3-methoxy-4-(5-oxazolyl)phenyl]-3,4-dimethylbenzamide; N-[3-methoxy-4-(5-oxazolyl)phenyl]-2-indolizinecarboxamide; (E)-N-[3-methoxy-4-(5-oxazolyl)phenyl]-3-[3-methoxy-4-(phenylmethoxy)phenyl]-2-propenamide; and 3-aminophenyl)-(+)-tetrahydrofuranylcarbamate.

The above compounds and methods for their preparation are disclosed in U.S. Pat. No. 6,624,184.

In still other embodiments, the IMPDH antagonist is selected from compounds with structures represented by formula (XXVI):

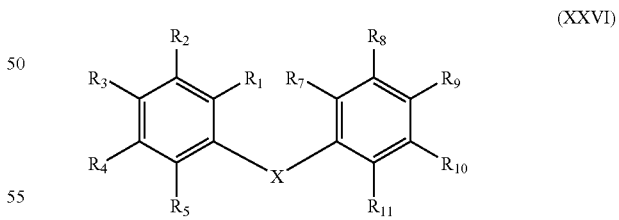

(XXVI)

wherein:

X is selected from —C(O)—N($R_6$)—, —N($R_6$)—C(O)—, —CH$_2$—N($R_6$)—, —N($R_6$)—CH$_2$—, —N($R_6$)—S(O)$_2$—, —S(O)$_2$—N($R_6$)—, —C($R_{12}$)($R_{12}$)—C(O)—, —C(O)—C($R_{12}$)($R_{12}$)—, —C($R_{12}$)($R_{12}$)—S(O)$_2$—, —S(O)$_2$—C($R_{12}$)($R_{12}$)—, —S(O)$_2$(O)$_2$—O—, —S(O)$_2$—O—, —O—S(O)$_2$—, —NR$_6$—C(O)—Y—, or Y—C(O)—NR$_6$—; wherein each $R_6$ is independently selected from hydrogen, $C_1$-$C_4$ straight or branched alkyl, $C_1$-$C_4$ straight or branched alkenyl or alkynyl, Ar-substituted-$C_1$-$C_4$ straight or branched alkyl, or Ar-substituted-$C_2$-$C_4$ straight or branched alkenyl or alkynyl; wherein $R_6$ is optionally substituted with up to 3 substituents independently selected from halo, hydroxy, nitro, cyano or amino;

each $R_{12}$ is independently selected from $R_6$, W—[$C_1$-$C_4$ straight or branched alkyl], W—[$C_2$-$C_4$ straight or branched alkenyl or alkynyl], Ar-substituted-[W—$C_1$-$C_4$ straight or branched alkyl], Ar-substituted-[W—[$C_2$-$C_4$ straight or branched alkenyl or alkynyl], O—Ar, N($R_6$)—Ar, S—Ar, S(O)—Ar, S(O)$_2$—Ar, S—C(O)H, N($R_6$)—C(O)H, or O—C(O)H;

wherein W is O—, O—C(O)—, S—, S(O)—, S(O)$_2$—, S—C(O)—, N($R_6$)—, or N($R_6$)—C(O)—; and wherein each $R_{12}$ is optionally and independently substituted with up to 3 substituents independently selected from halo, hydroxy, nitro, cyano or amino and Y is selected from —O—, —S—, —C≡C—, —C($R_{12}$)$_2$—C($R_{12}$)$_2$—, —C($R_{12}$)$_2$— or —C($R_{12}$)=C($R_{12}$)—;

wherein:

each of $R_1$, $R_2$, $R_3$, $R_4$, $R_5$, $R_7$, $R_8$, $R_9$, $R_{10}$ and $R_{11}$ is independently selected from hydrogen, halo, hydroxy, cyano, nitro, amino, —C(O)NH$_2$, Z-($C_1$-$C_4$)-straight or branched alkyl], Z-[($C_2$-$C_4$)-straight or branched alkenyl or alkynyl], Ar-substituted-[($C_1$-$C_4$)-straight or branched alkyl], Ar-substituted-[($C_2$-$C_4$)-straight or branched alkenyl or alkynyl], Ar, Q-Ar, [($C_1$-$C_4$)-straight or branched alkyl]-Q-Ar, [($C_2$-$C_4$)-straight or branched alkenyl or alkynyl]-Q-Ar, O—[($C_1$-$C_4$)-straight or branched alkyl]-Q-Ar, O—[($C_2$-$C_4$)-straight or branched alkenyl or alkynyl]-Q-Ar, or any two adjacent R groups may be taken together with the carbon atoms to which they are bound to form a 5 to 6-membered aromatic carbocyclic or heterocyclic ring; wherein Z is selected from a bond, O—, S—, S(O)$_2$—, C(O)—, OC(O)—, or N(H)C(O)—;

Q is selected from O, —O—C(O)—, —C(O)—O—, —N(H)—C(O)—O—, —O—N(H)—C(O)—, —N(H)—C(O)—, —C(O)—N(H)—, —O—C(O)—N(H)—, or —C(O)—N(H)—O;

Ar is selected from phenyl, 1-naphthyl, 2-naphthyl, indenyl, azulenyl, fluorenyl, anthracenyl, 2-furyl, 3-furyl, 2-thienyl, 3-thienyl, 2-pyridyl, 3-pyridyl, 4-pyridyl, pyrrolyl, oxazolyl, thiazolyl, imidazolyl, pyraxolyl, 2-pyrazolinyl, pyrazolidinyl, isoxazolyl, isotriazolyl, 1,2,3-oxadiazolyl, 1,2,3-triazolyl, 1,3,4-thiadiazolyl, pyridazinyl, pyrimidinyl, pyrazinyl, 1,3,5-triazinyl, 1,3,5-trithianyl, indolizinyl, indolyl, isoindolyl, 3H-indolyl, indolinyl, benzo[b]furanyl, benzo[b]thiophenyl, 1H-indazolyl, benzimidazolyl, benzthiazolyl, purinyl, 4H-quinolizinyl, quinolinyl, isoquinolinyl, 1,2,3,4-tetrahydro-isoquinolinyl, cinnolinyl, phthalazinyl, quinazolinyl, quinoxalinyl, 1,8-naphthyridinyl, peridinyl, carbazolyl, acridinyl, phenazinyl, phenothiazinyl orphenoxazinyl or other chemically feasible monocyclic, bicyclic or tricyclic ring systems, wherein each ring consists of 5 to 7 ring atoms and wherein each ring comprises 0 to 3 heteroatoms independently selected from N, O and S;

$R_{13}$ is selected from [$C_1$-$C_{12}$ straight or branched alkyl] or, [$C_2$-$C_{12}$ straight or branched alkenyl or alkynyl]; wherein $R_{13}$ is optionally substituted with 1 to 4 substituents independently selected from $R_{14}$ or $R_{15}$, wherein each $R_{14}$ is a monocyclic or a bicyclic ring system consisting of 3 to 7 members per ring, wherein said ring system optionally comprises up to 4 heteroatoms selected from N, O, and S; wherein a CH$_2$ adjacent to said N, O or S may be substituted with C(O); and wherein $R_{14}$ optionally comprises up to 2 substituents independently selected from ($C_1$-$C_4$)-straight or branched alkyl, ($C_2$-$C_4$)-straight or branched alkenyl, 1,-2-methylenedioxy, 1,2-ethylenedioxy, (CH$_2$)$_n$—$R_{16}$, —S—(CH$_2$)$_n$—$R_{16}$, —S(O)—(CH$_2$)$_n$—$R_{16}$, —S(O)$_2$—(CH$_2$)$_n$—$R_{16}$, —O—(CH$_2$)$_n$—$R_{16}$, or —N($R_{18}$)—(CH$_2$)$_n$—$R_{16}$ wherein n is 0, 1 or 2;

$R_{16}$ is selected from halogen, —CN, —NO$_2$, —CF$_3$, —OCF$_3$, —OH, —S—($C_1$-$C_4$)-alkyl, —S(O)—($C_1$-$C_4$)-alkyl, —S(O)$_2$—($C_1$-$C_4$)-alkyl, —NH$_2$, —NH—($C_1$-$C_4$)-alkyl, —N(($C_1$-$C_4$)-alkyl)$_2$, COOH, C(O)—O—($C_1$-$C_4$)-alkyl or O—($C_1$-$C_4$)-alkyl; and each $R_{15}$ is independently selected from —OR$_{17}$, or —N($R_{18}$)$_2$;

$R_{17}$ is selected from hydrogen, —($C_1$-$C_6$)-straight alkyl, —($C_1$-$C_6$)-straight alkyl-Ar, —C(O)—($C_1$-$C_6$)-straight or branched alkyl, —C(O)—Ar, or —($C_1$-$C_6$)-straight alkyl-CN; and each $R_{18}$ is independently selected from —($C_1$-$C_6$)-straight or branched alkyl, —($C_1$-$C_6$)-straight or branched alkyl-Ar, —($C_1$-$C_6$)-straight alkyl-CN, —($C_1$-$C_6$)-straight alkyl-OH, —($C_1$-$C_6$)-straight alkyl-OR$_{17}$, —C(O)—($C_1$-$C_6$)-straight or branched alkyl, —C(O)—Ar, —S(O)$_2$—($C_1$-$C_6$)-straight or branched alkyl, or —S(O)$_2$—Ar; wherein any alkyl, alkenyl or alkynyl group is optionally substituted with 1 to 3 independently selected halo groups; and any Ar, aromatic carbocyclic ring or heterocyclic ring is optionally substituted with 1 to 3 substituents independently selected from halo, hydroxy, nitro, cyano, amino, ($C_1$-$C_4$)-straight or branched alkyl; O—($C_1$-$C_4$-straight or branched alkyl, ($C_1$-$C_4$)-straight or branched alkenyl or alkynyl, or O—($C_2$-$C_4$)-straight or branched alkenyl or alkynyl; and any Ar, aromatic carbocyclic ring or heterocyclic ring is optionally benzofused.

In addition, in these compounds, at least two of $R_1$, $R_2$, $R_3$, $R_4$, or $R_5$ is hydrogen;

no more than two of $R_1$, $R_2$, $R_3$, $R_4$, or $R_5$ comprises Ar;

at least two of $R_7$, $R_8$, $R_9$, $R_{10}$ or $R_{11}$ is hydrogen; and no more than two of $R_7$, $R_8$, $R_9$, $R_{10}$ or $R_{11}$ comprises Ar.

In some embodiments, the compounds according to formula (XXVI) specifically exclude those wherein X is —NH—S(O)$_2$— or —S(O)$_2$—N(H)—, one of $R_1$, $R_2$, $R_3$, $R_4$, $R_5$, $R_7$, $R_8$, $R_9$, $R_{10}$ or $R_{11}$ is O—($C_1$-$C_4$)-straight or branched alkyl, seven of $R_1$, $R_2$, $R_3$, $R_4$, $R_5$, $R_7$, $R_8$, $R_9$, $R_{10}$ or $R_{11}$ is hydrogen and the remaining two of $R_1$, $R_2$, $R_3$, $R_4$, $R_5$, $R_7$, $R_8$, $R_9$, $R_{10}$ or $R_{11}$ are bound together to form a 5 to 6-membered aromatic carbocyclic or heterocyclic ring.

In some embodiments, the compounds according to formula (XXVI) specifically exclude those wherein X is —NH—S(O)$_2$— or —S(O)$_2$—N(H)—, two of $R_1$, $R_2$, $R_3$, $R_4$, $R_5$, $R_7$, $R_8$, $R_9$, $R_{10}$ or $R_{11}$ are O—($C_1$-$C_4$)-straight or branched alkyl, seven of $R_1$, $R_2$, $R_3$, $R_4$, $R_5$, $R_7$, $R_8$, $R_9$, $R_{10}$ or $R_{11}$ is hydrogen and the remaining one of $R_1$, $R_2$, $R_3$, $R_4$, $R_5$, $R_7$, $R_8$, $R_9$, $R_{10}$ or $R_{11}$ is —NO$_2$, —CN or —Ar.

In certain embodiments, the compounds according to formula (XXVI) specifically exclude those wherein X is —NH—S(O)$_2$— or —S(O)$_2$—N(H)—, two of $R_1$, $R_2$, $R_3$, $R_4$, $R_5$, $R_7$, $R_8$, $R_9$, $R_{10}$ or $R_{11}$ are O—($C_1$-$C_4$)-straight or branched alkyl, six of $R_1$, $R_2$, $R_3$, $R_4$, $R_5$, $R_7$, $R_8$, $R_9$, $R_{10}$ or $R_{11}$ is hydrogen and the remaining two of $R_1$, $R_2$, $R_3$, $R_4$, $R_5$, $R_7$, $R_8$, $R_9$, $R_{10}$ or $R_{11}$ are both halo.

In some embodiments, the compounds according to formula (XXVI) specifically exclude those wherein X is —NH—S(O)$_2$— or —S(O)$_2$—N(H)—, one of $R_1$, $R_2$, $R_3$, $R_4$, $R_5$, $R_7$, $R_8$, $R_9$, $R_{10}$ or $R_{11}$ is Ar and the remaining 9 of $R_1$, $R_2$, $R_3$, $R_4$, $R_5$, $R_7$, $R_8$, $R_9$, $R_{10}$ or $R_{11}$ are each hydrogen.

In certain embodiments, the compounds according to formula (XXVI) specifically exclude those wherein X is —N(H)—C(O)—S— or —S—C(O)—N(H)—, one of $R_1$, $R_2, R_3, R_4, R_5, R_7, R_8, R_9, R_{10}$ or $R_{11}$ is —OH, eight of $R_1, R_2, R_3, R_4, R_5, R_7, R_8, R_9, R_{10}$ or $R_{11}$ are hydrogen and the remaining one of $R_1, R_2, R_3, R_4, R_5, R_7, R_8, R_9, R_{10}$ or $R_{11}$ is halo; and those wherein X is —N(H)—C(O)—S— or —S—C(O)—N(H)—, one of $R_1, R_2, R_3, R_4, R_5, R_7, R_8, R_9, R_{10}$ or $R_{11}$ is —OH, seven of $R_1, R_2, R_3, R_4, R_5, R_7, R_8, R_9, R_{10}$ or $R_{11}$ are hydrogen, one of $R_1, R_2, R_3, R_4, R_5, R_7, R_8, R_9, R_{10}$ or $R_{11}$ is O—($C_1$-$C_4$)-straight or branched alkyl and the remaining one of $R_1, R_2, R_3, R_4, R_5, R_7, R_8, R_9, R_{10}$ or $R_{11}$ is halo or ($C_1$-$C_4$)-straight or branched alkyl.

Finally, in some embodiments, the compounds according to formula (XXVI) specifically exclude those wherein, when X is —C(O)—N($R_6$)— or —N($R_6$)—C(O)—, two adjacent groups selected from either $R_1, R_2, R_3, R_4$ and $R_5$, or from $R_7, R_8, R_9, R_{10}$ and $R_{11}$ may not be taken together with the carbon atoms to which they are bound to form a 6-membered aromatic carbocyclic ring.

In some embodiments, X is selected from —C(O)—N($R_6$)—, —N($R_6$)—C(O)—, —$CH_2$—N($R_6$)—, or —N($R_6$)—$CH_2$— or —N($R_6$)—C(O)—Y. More preferably, X is —N($R_6$)—C(O)—Y. Suitably, X is —N($R_6$)—C(O)—C($R_{12}$)=C($R_{12}$)—.

In some embodiments, $R_1$ is selected from H, ($C_1$-$C_4$)-straight or branched alkyl, OH, O—($C_1$-$C_4$)-straight or branched alkyl, O—Ar, $OCF_3$, halo, cyano or S—($C_1$-$C_4$)-straight or branched alkyl. In alternate embodiments, $R_1$ is H when $R_2$ is not H.

Suitably, $R_2$ is selected from H, ($C_1$-$C_4$)-straight or branched alkyl, Ar, O—($C_1$-$C_4$)-straight or branched alkyl, O—Ar, $OCF_3$, halo, cyano, $C(O)NH_2$ or $S(O)_2$—($C_1$-$C_4$)-straight or branched alkyl. In certain embodiments, $R_2$ is H.

$R_3$ is typically selected from H, Ar, cyano, O—($C_1$-$C_4$)-straight or branched alkyl, O—Ar, S—($C_1$-$C_4$)-straight or branched alkyl, $CF_3$ or $OCF_3$.

In some embodiments, $R_4$ is selected from H, ($C_1$-$C_4$)-straight or branched alkyl, OH, O—($C_1$-$C_4$)-straight or branched alkyl, O—Ar, $OCF_3$; halo, cyano or S—($C_1$-$C_4$)-straight or branched alkyl.

$R_5$ is suitably selected from H, ($C_1$-$C_4$)-straight or branched alkyl, Ar, O—($C_1$-$C_4$)-straight or branched alkyl, O—Ar, $OCF_3$, halo, cyano, $C(O)NH_2$ or $S(O)_2$—($C_1$-$C_4$)-straight or branched alkyl. In some embodiments, $R_5$ is H.

Typically, $R_7$ is selected from H, OH, OC(O)—($C_1$-$C_4$)-straight or branched alkyl, O—($C_1$-$C_4$)-straight or branched alkyl, O—Ar, amino, or N(H)C(O)—($C_1$-$C_4$)-straight or branched alkyl. Even more typically is when $R_7$ is OH.

$R_8$ is suitably H, ($C_1$-$C_4$)-straight or branched alkyl, O—($C_1$-$C_4$)-straight or branched alkyl, or ($C_1$-$C_4$)-straight or branched alkyl-N(H)C(O)O—Ar.

In some embodiments, $R_9$ is selected from H, ($C_1$-$C_4$)-straight or branched alkyl, O—($C_1$-$C_4$)-straight or branched alkyl, or $R_9$ is taken together with $R_{10}$ and the carbon atoms to which they are bound to form a fused benzene ring. More preferred is when $R_9$ and $R_{10}$ are taken together with the carbon atoms to which they are bound to form a fused benzene ring.

Desirably, $R_{10}$ is selected from H, ($C_1$-$C_4$)-straight or branched alkyl, O—($C_1$-$C_4$)-straight or branched alkyl, or $R_{10}$ is taken together with $R_9$ and the carbon atoms to which they are bound to form a fused benzene ring.

In some embodiments, $R_{11}$ is selected from H, OH, OC(O)—($C_1$-$C_4$)-straight or branched alkyl, O—($C_1$-$C_4$)-straight or branched alkyl, O—Ar, amino, or N(H)C(O)—($C_1$-$C_4$)-straight or branched alkyl. Suitably, $R_{11}$ is H.

Representative compounds falling within the scope of formula (XXVI) include, but are not limited to:

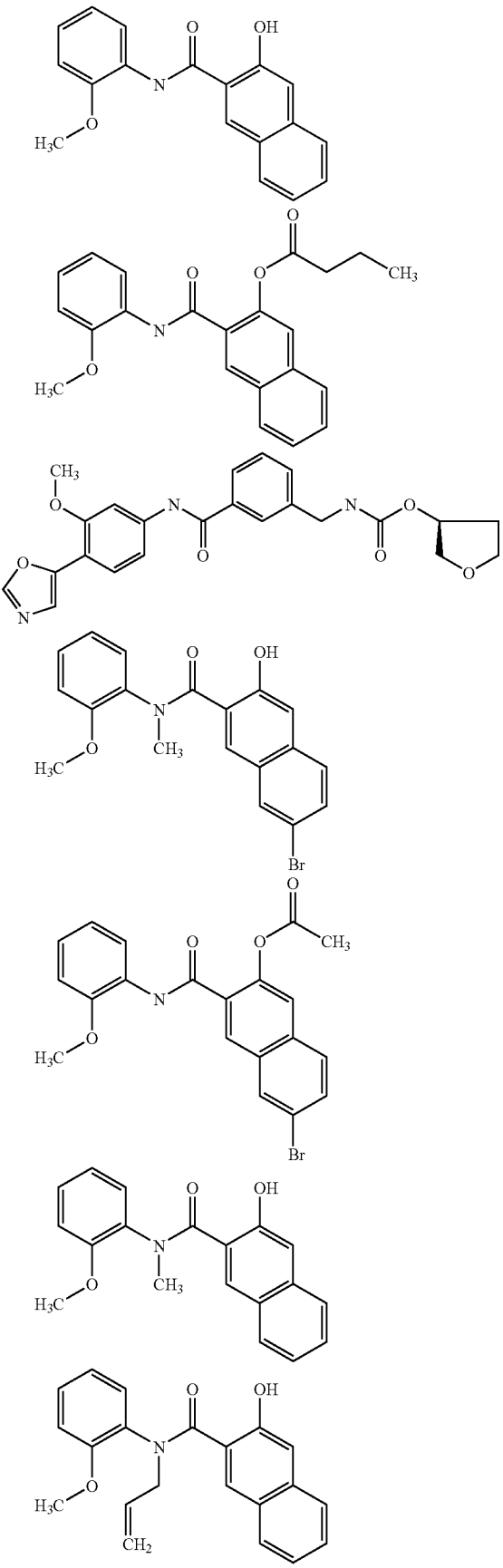

155
-continued
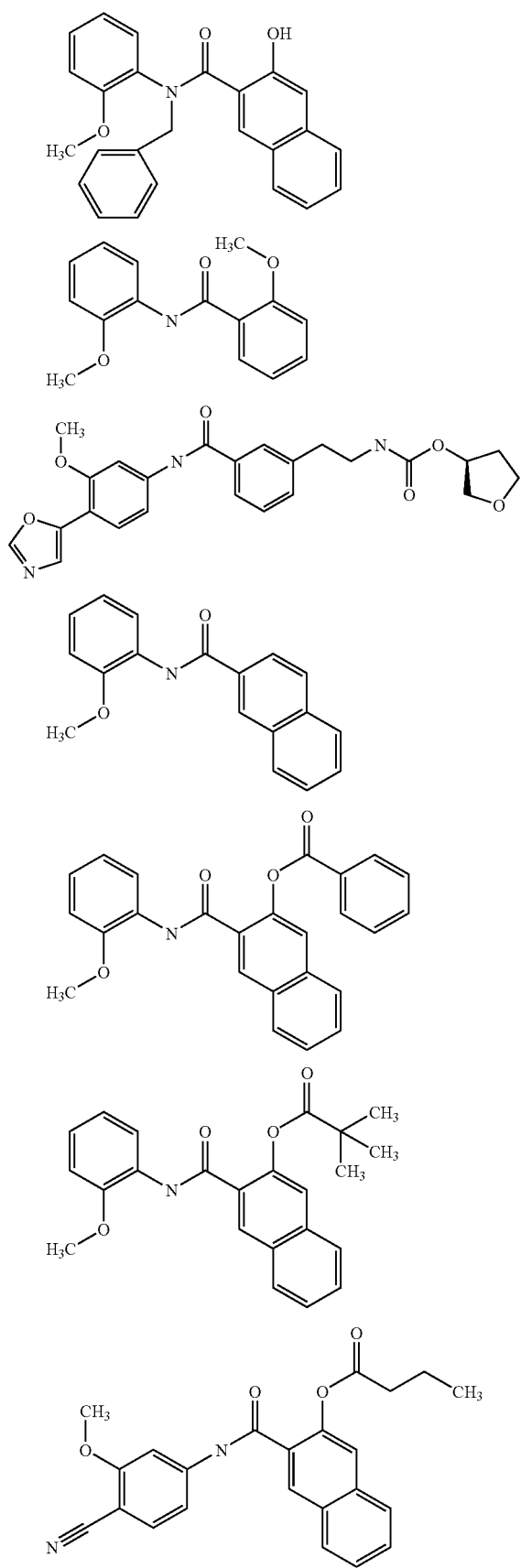
156
-continued
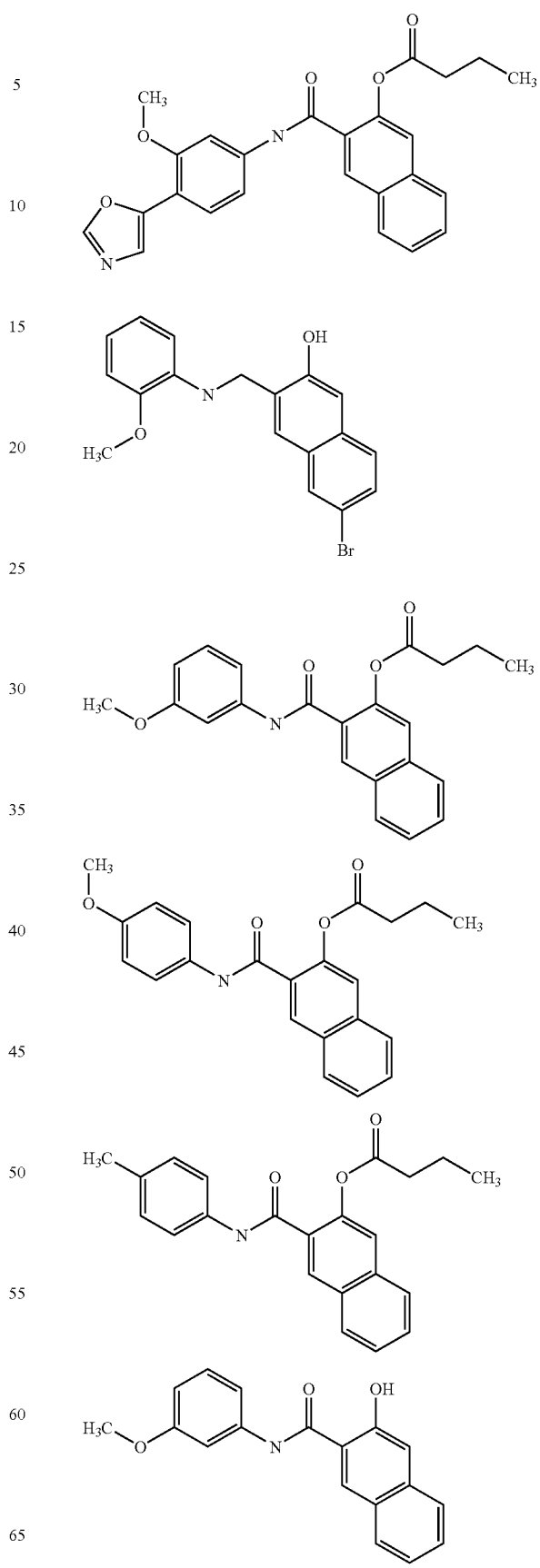

157
-continued
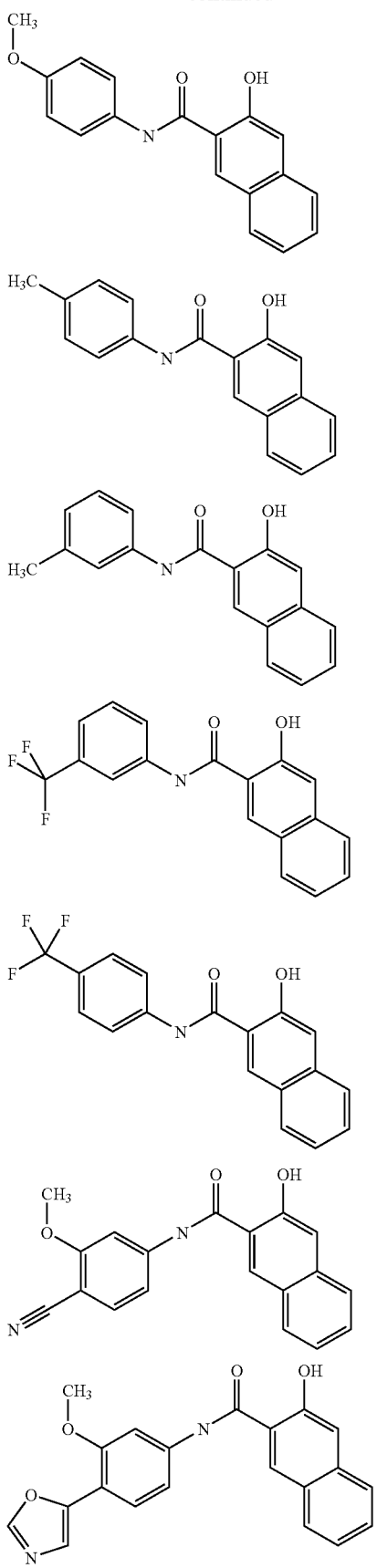
158
-continued
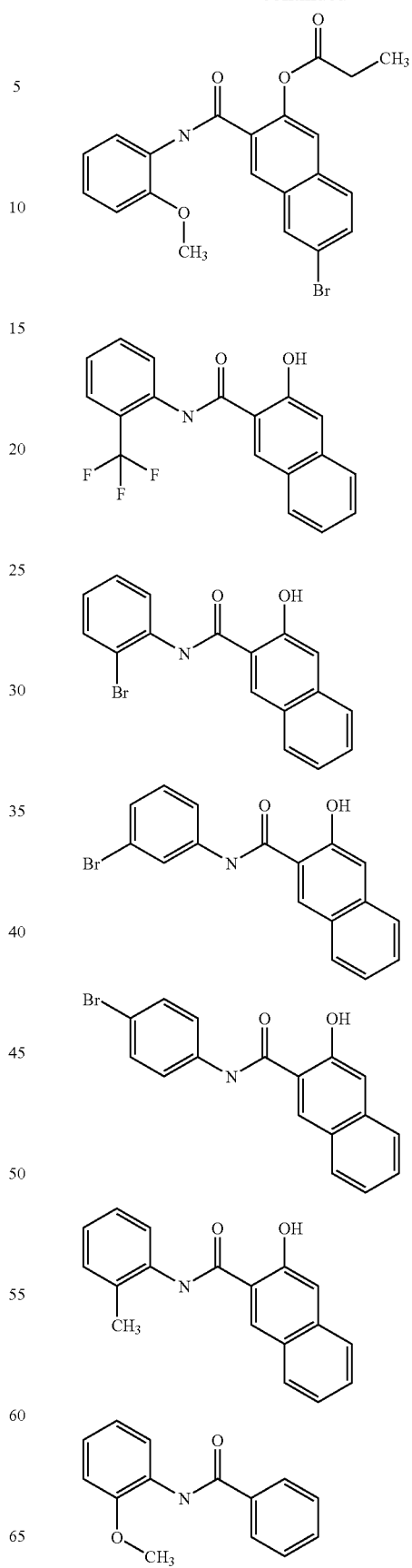

159
-continued
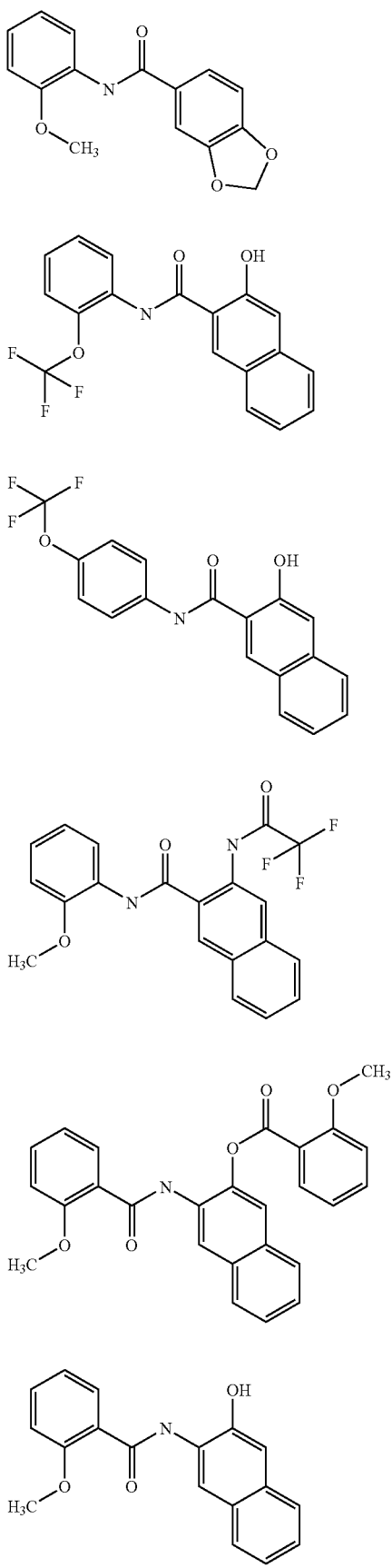
160
-continued
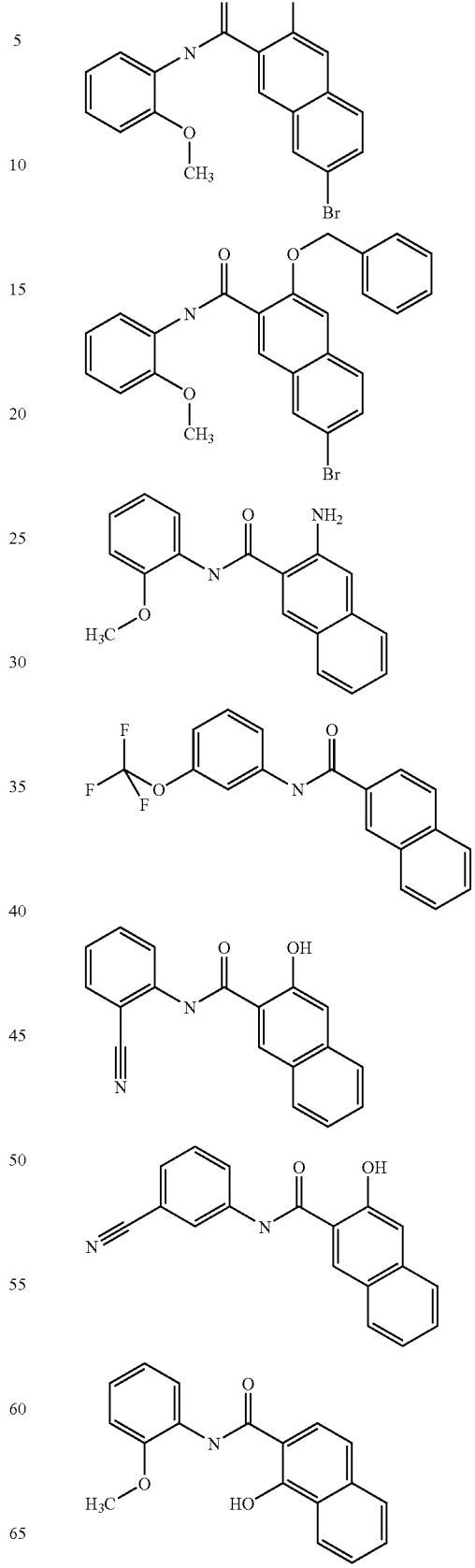

161
-continued
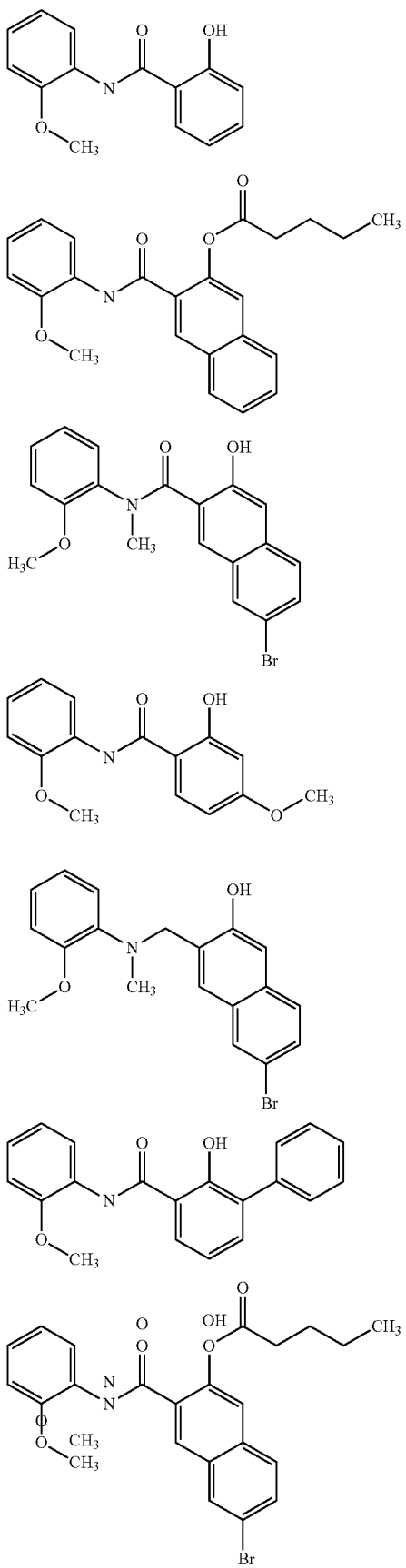
162
-continued
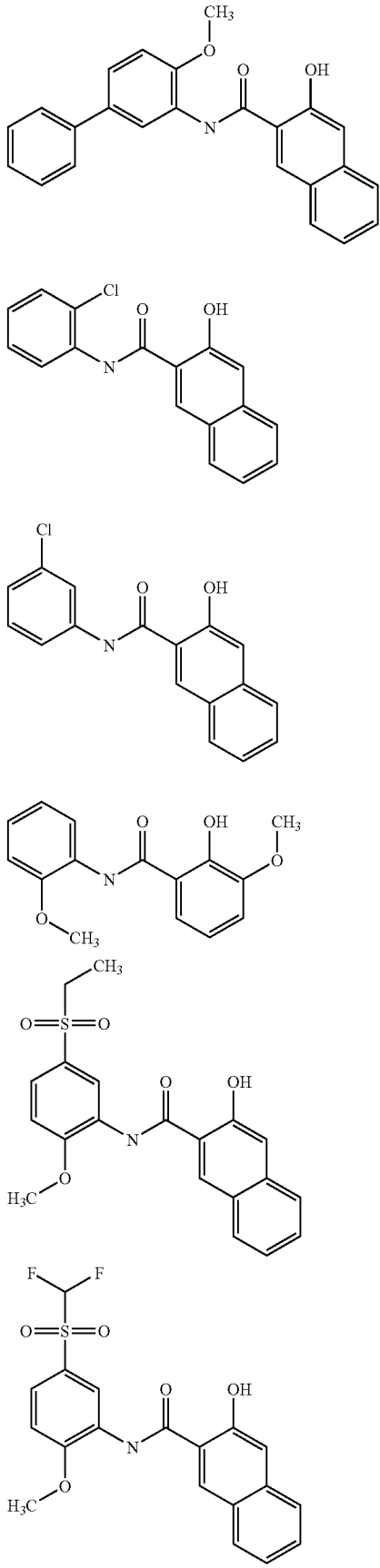

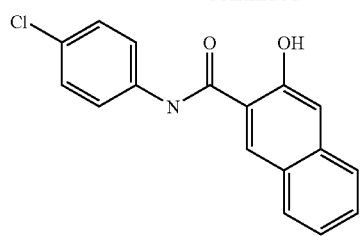
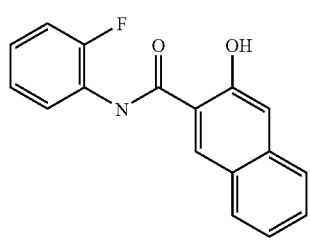
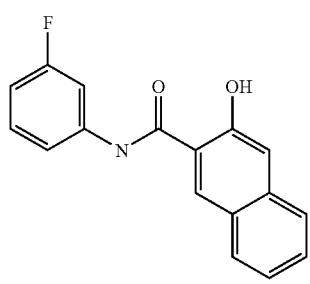
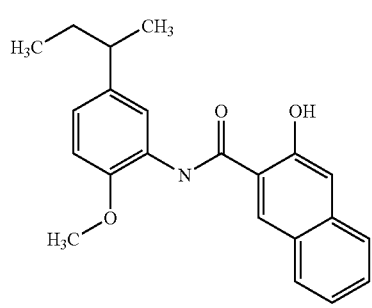
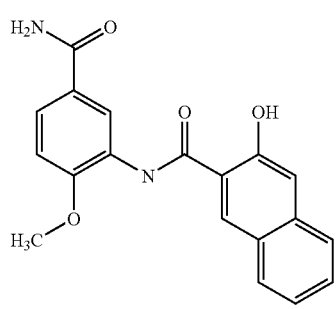
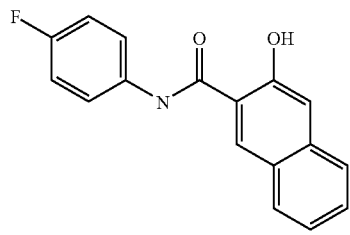
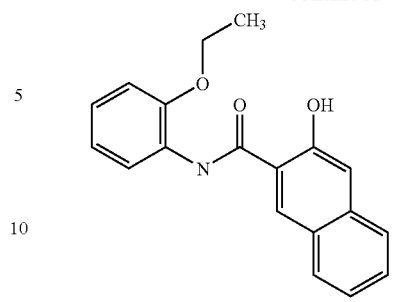
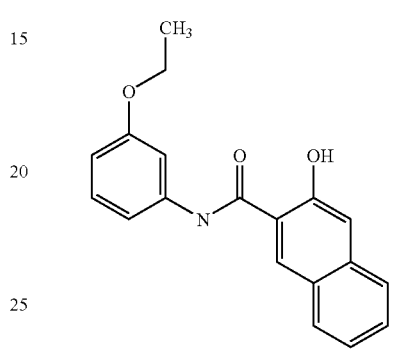
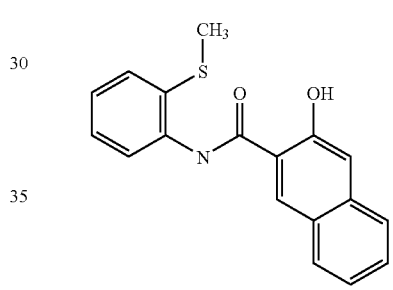
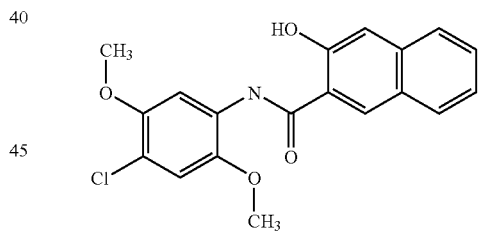
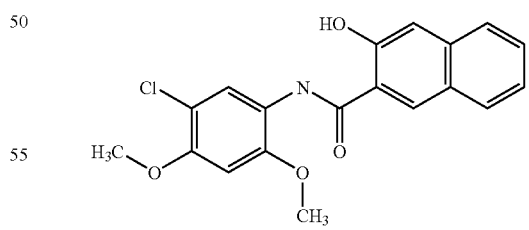
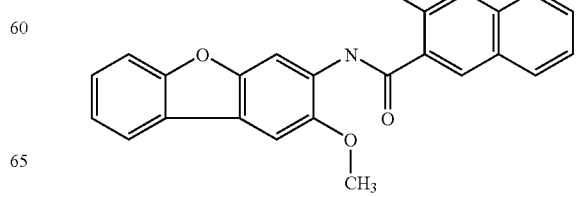

165
-continued
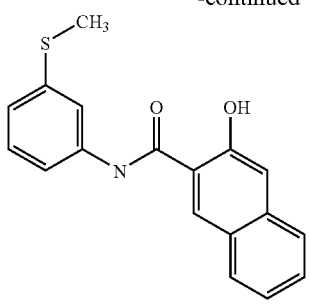
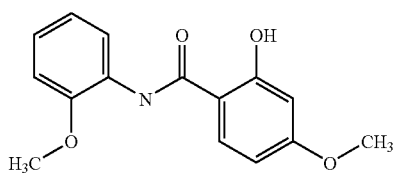
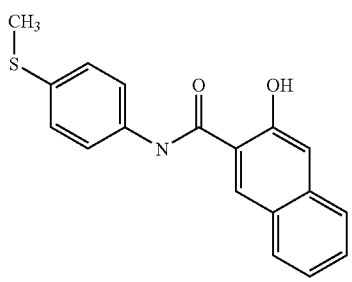
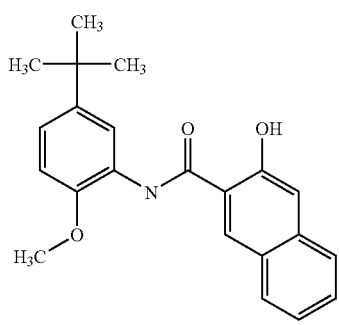
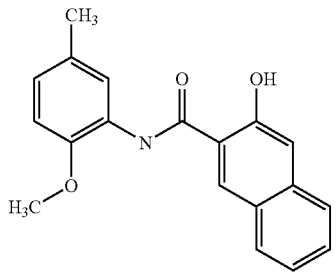
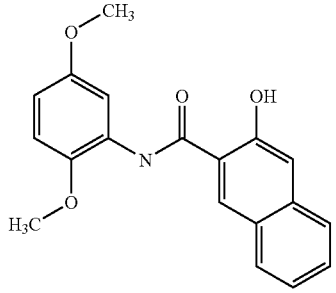
166
-continued
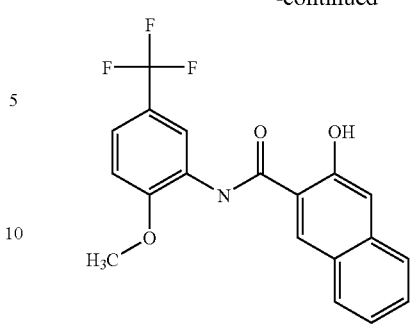
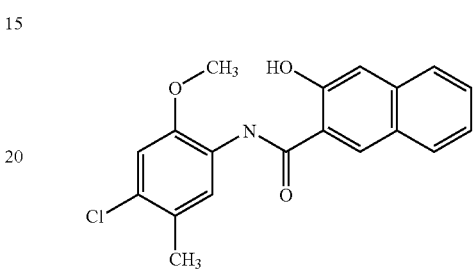
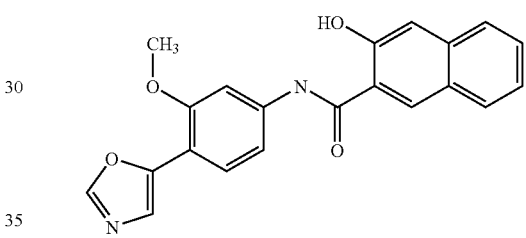
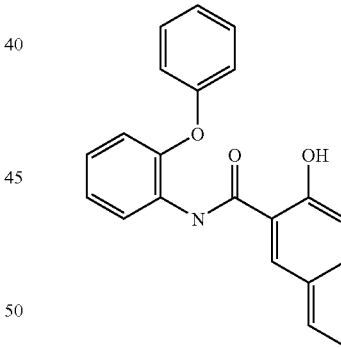
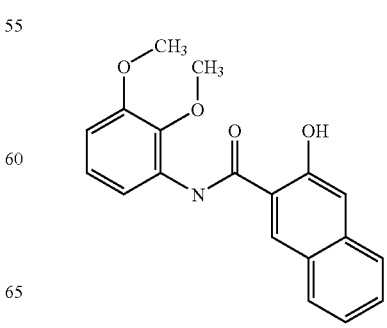

-continued
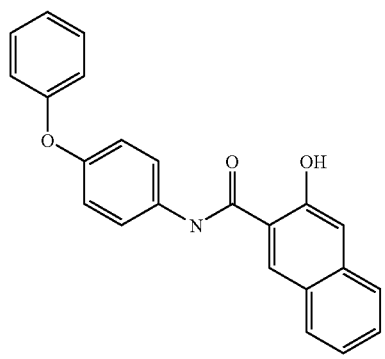
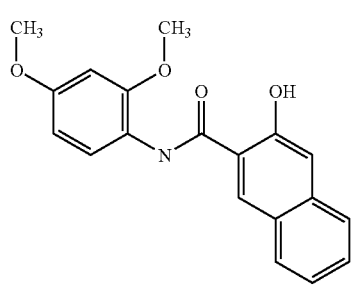
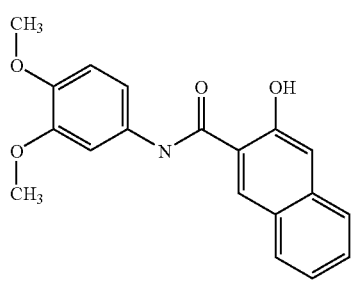
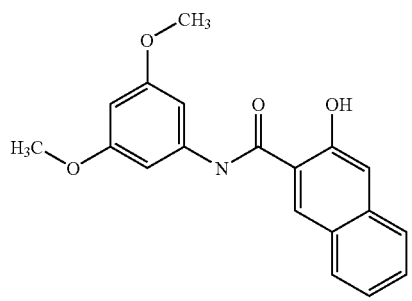
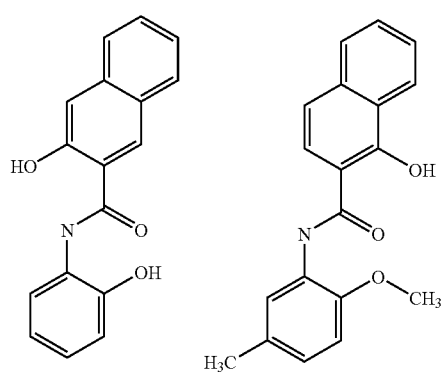
-continued
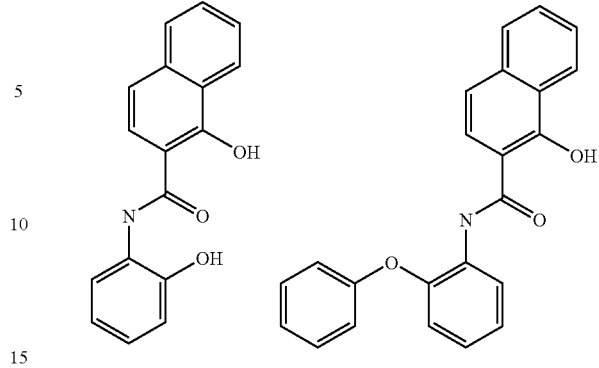
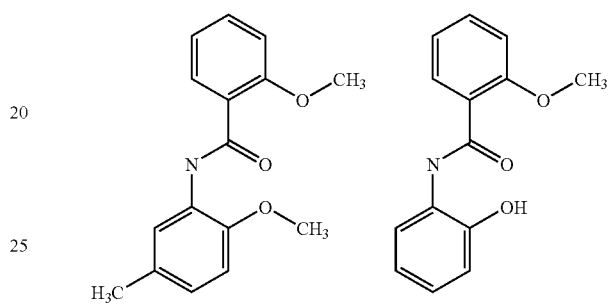
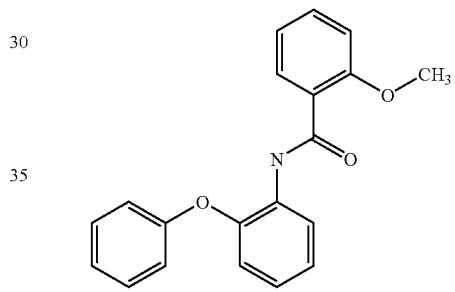
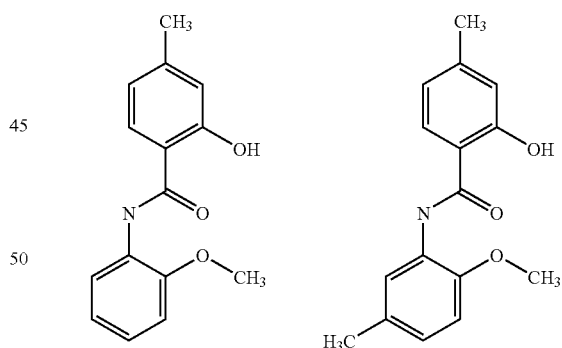
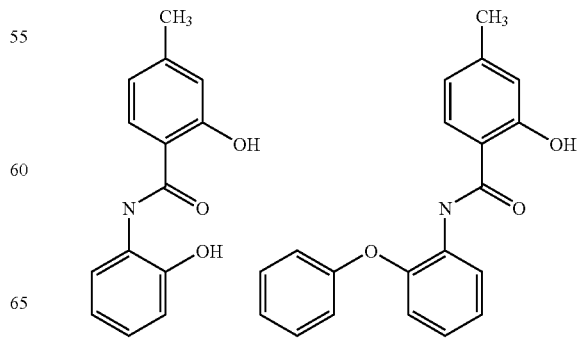

-continued
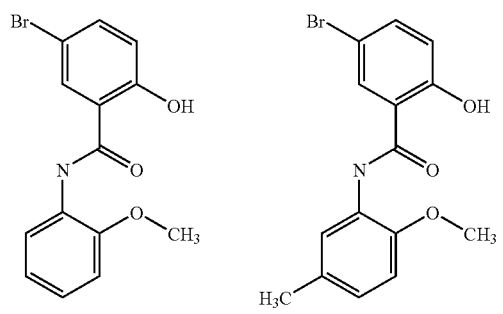
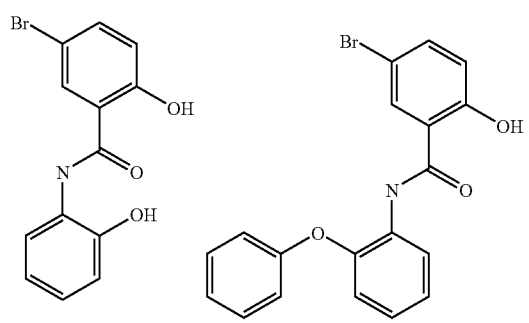
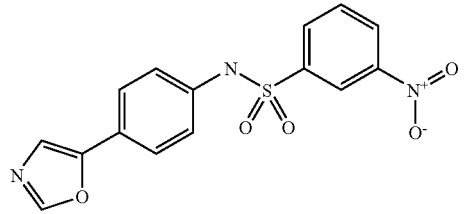
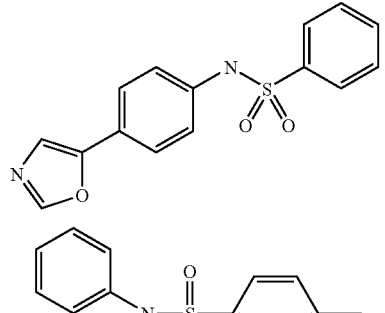
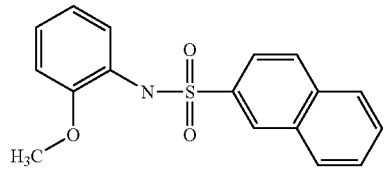
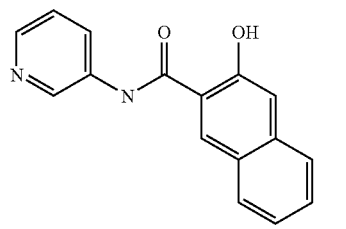
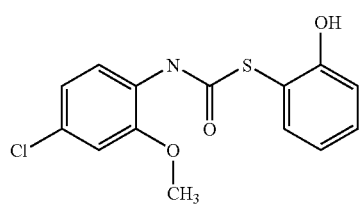
-continued
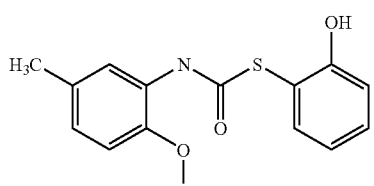
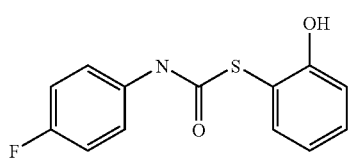
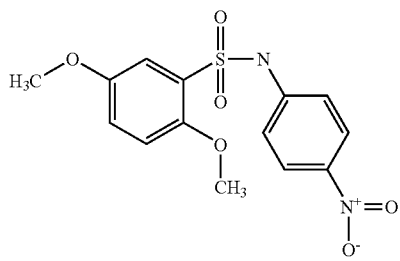
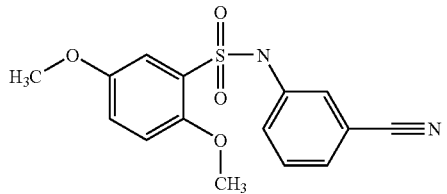
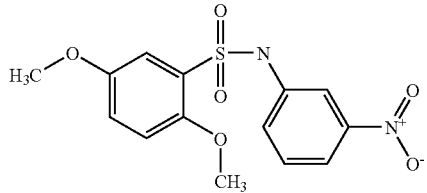
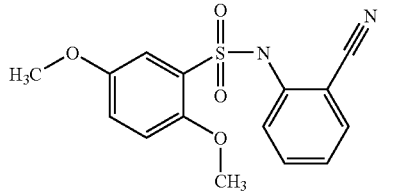
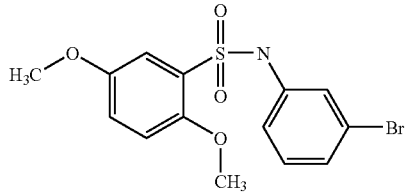
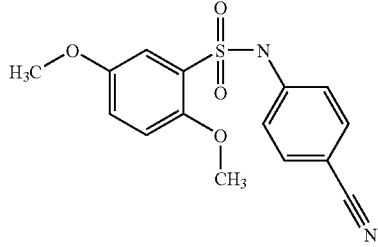

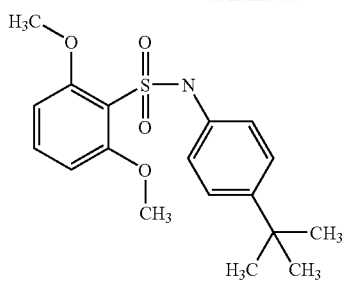
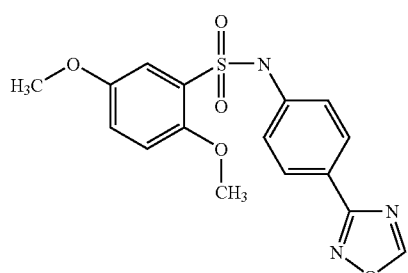
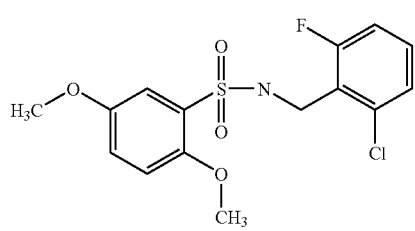
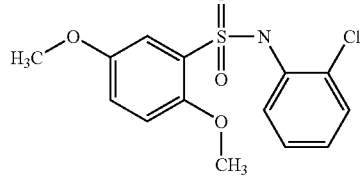
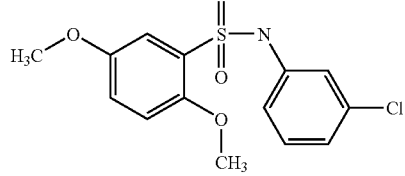
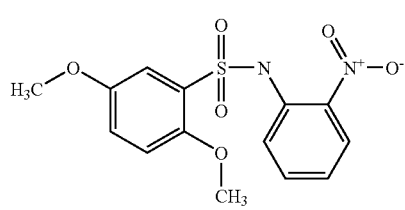
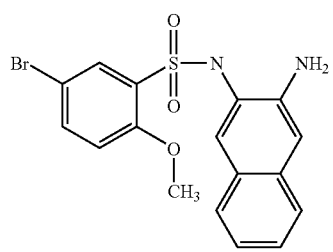

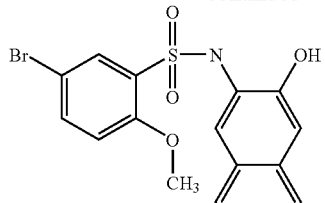
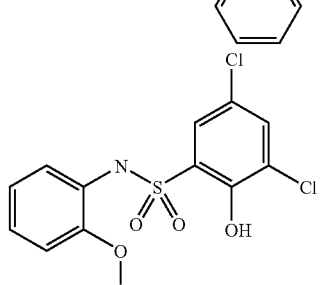
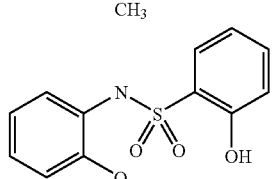
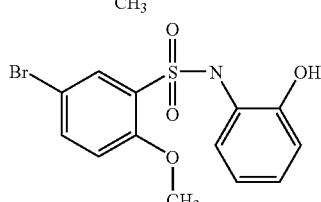
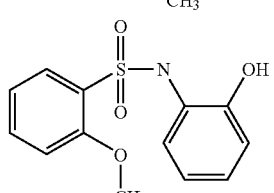
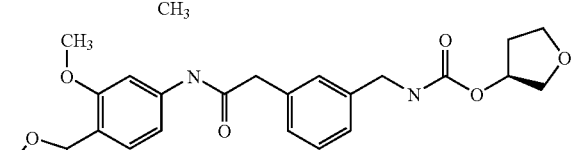
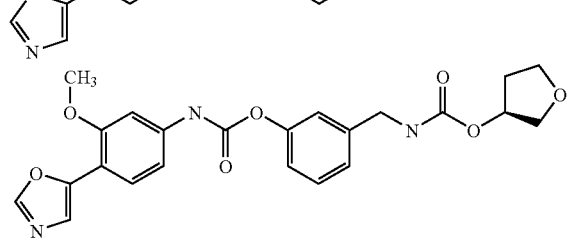

The above compounds and methods for their preparation are disclosed in U.S. Pat. No. 6,653,309.

In still other embodiments, the IMPDH antagonist is selected from mizoribine, mizoribine aglycone, mycophenolate mofetil, tiazoflirin, viramidine, and ribivarin, as described fro example in U.S. Patent Application Publication No. 20040127435 published Jul. 1, 2004.

Alternatively, the IMPDH antagonist may antagonise the function of a protein kinase that phosphorylates IMPDH (e.g., PI 3-kinase and PDK1) or an upstream activator of the protein kinase (e.g., a PDGF or a PDGF receptor). For example, illustrative PDGF receptor inhibitors and methods for their preparation are in particular generically and specifically disclosed in the patent applications EP 0 564 409 A1 and WO 99/03854, in particular in the compound claims and the final products of the working examples. A non-limiting example of such an inhibitor is a N-phenyl-2-pyrimidine-amine derivative of formula (XXVII):

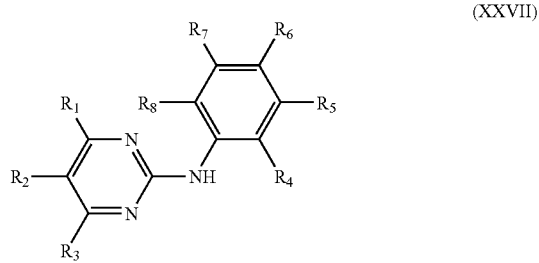

(XXVII)

wherein:

$R_1$ is 4-pyrazinyl; 1-methyl-1H-pyrrolyl; amino- or amino-lower alkyl-substituted phenyl, wherein the amino group in each case is free, alkylated or acylated; 1H-indolyl or 1H-imidazolyl bonded at a five-membered ring carbon atom; or unsubstituted or lower alkyl-substituted pyridyl bonded at a ring carbon atom and unsubstituted or substituted at the nitrogen atom by oxygen;

$R_2$ and $R_3$ are each independently of the other hydrogen or lower alkyl;

one or two of the radicals $R_4$, $R_5$, $R_6$, $R_7$ and $R_8$ are each nitro, fluoro-substituted lower alkoxy or a radical of formula XXVIII $$-N(R_9)-C(=X)-(Y)_n-R_{10}$$ (XXVIII)

wherein:

$R_9$ is hydrogen or lower alkyl, X is oxo, thio, imino, N-lower alkyl-imino, hydroximino or O-lower alkyl-hydroximino, Y is oxygen or the group NH, n is 0 or 1 and $R_{10}$ is an aliphatic radical having at least 5 carbon atoms, or an aromatic, aromatic-aliphatic, cycloaliphatic, cycloaliphatic-aliphatic, heterocyclic or heterocyclic-aliphatic radical, and the remaining radicals $R_4$, $R_5$, $R_6$, $R_7$ and $R_8$ are each independently of the others hydrogen, lower alkyl that is unsubstituted or substituted by free or alkylated amino, piperazinyl, piperidinyl, pyrrolidinyl or by morpholinyl, or lower alkanoyl, trifluoromethyl, free, etherified or esterified hydroxy, free, alkylated or acylated amino or free or esterified carboxy.

The present invention also contemplates the use, in the subject method of modulating adipogenesis, of gene or expression product inhibitors identified according to methods described for example in Section 4, infra.

3.2 IMPDH Agonists

Agents that may be used to enhance the activity of an IMPDH polypeptide include any suitable inducer or stabilising/activating agents which can be identified or produced by standard protocols as disclosed for example in Section 4 infra or using non-human animal models. For example, stimulation of IMPDH activity can be achieved by overexpression of the IMPDH, or through mutations that promote IMPDH tetramerisation/oligomerisation in the absence of ligand and subsequent constitutive activation. Alternatively, non-ligand molecules that induce IMPDH tetramerisation/oligomerisation can be used to produce a similar effect. In these embodiments, the agent is suitably selected from an IMPDH agonising antigen-binding molecule, a Impdh polynucleotide or an IMPDH polypeptide or a polynucleotide whose expression product enhances, promotes or otherwise capacitates the interaction between an IMPDH and a kinase, or the polypeptide expression product of the polynucleotide. Sequence information for producing Impdh polynucleotides and IMPDH polypeptides is available in publicly available databases such as GenBank and EMBL. Such molecules can be easily manufactured by persons of skill in the art using standard techniques.

The modulatory agents of the invention will suitably affect or modulate adipogenesis. Accordingly, the cells that are the subject of testing are typically adipocytes or preadipocytes. Preadipocytes are the cell type whose differentiation via adipogenesis creates new adipocytes. The proliferation of the latter cell type, and the lipid accumulation therein, leads to increases in adiposity which precede obesity, and conversely, excessive loss of adipocytes in the absence of adipogenesis leads to excessively low adiposity, as occurs in cachexia or conditions of localised deficiencies in adiposity. The ability of modulatory agents to inhibit or stimulate the differentiation potential of preadipocytes can be measured using cultured preadipocytes, including cell lines (e.g., 3T3-L1 cells) or primary cells (e.g., isolated from mouse, rat or human) or in vivo by administering molecules of the present invention to the appropriate animal model. Assays for measuring preadipocyte proliferation and differentiation are also well known in the art. For example, assays measuring proliferation include such assays as assessment of preadipocyte cell number following exposure to a proliferative growth medium using a formazan colorimetric assay (Promega). Preadipocyte differentiation potential is assessed by the measurement of glycerol-3-phosphate dehydrogenase (G3PDH) enzyme activity and triacylglycerol accumulation. Assays for measuring adipocyte proliferation and lipid accumulation are also well known. For example, adipocyte size and number can be determined using the method of Hirsch and Gallian (1968, *J. Lipid Res.* 9: 110-119) or modifications thereof as described, for example, by Cartwright (Determination of adipose cellularity. In: *Biology of the Adipocyte*, edited by G. J. Hausman, and R. J. Martin. New York: Van Nostrand Reinhold, 1987, p. 229-254). In addition, lipid accumulation in adipocytes can be measured using Oil Red-O staining, which stain neutral lipids in cells. The amount of staining is directly proportional to the amount of lipid in the cell and can be measured spectrophotometrically.

In vivo evaluation tools, which are well known to practitioners in the art, are available for evaluating the effect of IMPDH-modulatory agents as described herein on the differentiation potential of preadipocytes into adipocytes. Such differentiation results in the accumulation of adipose tissue, and assay means for measuring the amount of such tissue in a patient include skin fold measurements using an adipometer. This assay involves the integration of skin fold thicknesses from suitable areas (e.g., triceps, biceps, subscapular and suprailiac regions) to obtain a body fat percentage value. Other in vivo assays include underwater weighing, bioelectrical impedance, dual energy x-ray absorptiometry and radiological imaging (e.g., computerised tomography or magnetic resonance imaging).

IMPDH-modulatory agents as described herein may also have applications for enhancing adipogenesis in conditions where severe depletion of fat deposits occur, generally referred to herein by the terms cachexia and cachexia-related conditions. Other applications include in the clinical management of conditions where localised deficiencies in adipogenesis exist. Such conditions include lipodystrophy and regional loss of adipose tissue from physical injury, burns or atrophic disease. Such conditions may result from inter alia cancer, cardiac disease, malaria and advanced renal failure. The methods of the present invention may prevent or retard adipose tissue wastage associated with such pathological conditions.

4. Identification of Target Molecule Modulators

The invention also features methods of screening for agents that modulate the level or functional activity of an IMPDH. In some embodiments, the methods comprise: (1) contacting a preparation with a test agent, wherein the preparation contains (i) a polypeptide comprising an amino acid sequence corresponding to at least a biologically active fragment of an IMPDH polypeptide, or to a variant or derivative thereof; or (ii) a polynucleotide comprising at least a portion of a genetic sequence that regulates the level or functional activity of the IMPDH polypeptide, which is operably linked to a reporter gene; and (2) detecting a change in the level and/or functional activity of the IMPDH polypeptide, or an expression product of the reporter gene, relative to a normal or reference level and/or functional activity in the absence of the test agent, which indicates that the agent modulates the level or functional activity of the IMPDH.

Any suitable assay for detecting, measuring or otherwise determining modulation of adipogenesis (e.g., such as by detecting preadipocyte proliferation and differentiation potential or detecting adipocyte proliferation or lipid accumulation), is contemplated by the present invention. Assays of a suitable nature are known to persons of skill in the art and examples of these are described in Section 3 supra Modulators falling within the scope of the present invention include agonists and antagonists of the level or functional activity of IMPDH, including antagonistic antigen-binding molecules, and inhibitor peptide fragments, antisense molecules, ribozymes, RNAi molecules and co-suppression molecules and kinase inhibitors, as for example described in Section 3. Agonists include agonistic antigen-binding molecules, IMPDH polypeptides or their biologically active fragments, variants and derivatives, molecules which increase IMPDH promoter activity or interfere with negative regulatory mechanisms and molecules which overcome any negative regulatory mechanism.

Candidate agents encompass numerous chemical classes, though typically they are organic molecules, preferably small organic compounds having a molecular weight of more than 50 and less than about 2,500 Dalton. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agent often comprises cyclical carbon or heterocyclic structures or aromatic or polyaromatic structures substituted with one or more of the above functional groups. Candidate agents are also found among biomolecules including, but not limited to: peptides, saccharides, fatty acids, steroids, purines, pyrimidines, derivatives, structural analogues or combinations thereof.

Small (non-peptide) molecule modulators of a IMPDH polypeptide are particularly advantageous. In this regard, small molecules are desirable because such molecules are more readily absorbed after oral administration, have fewer potential antigenic determinants, or are more likely to cross the cell membrane than larger, protein-based pharmaceuticals. Small organic molecules may also have the ability to gain entry into an appropriate cell and affect the expression of a gene (eg by interacting with the regulatory region or transcription factors involved in gene expression); or affect the activity of a gene by inhibiting or enhancing the binding of accessory molecules.

Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc to produce structural analogues.

Screening may also be directed to known pharmacologically active compounds and chemical analogues thereof.

Screening for modulatory agents according to the invention can be achieved by any suitable method. For example, the method may include contacting a cell expressing a polynucleotide corresponding to an Impdh gene with an agent suspected of having the modulatory activity and screening for the modulation of the level or functional activity of a protein encoded by the polynucleotide, or the modulation of the level of a transcript encoded by the polynucleotide, or the modulation of the activity or expression of a downstream cellular target of the protein or of the transcript (hereafter referred to as target molecules). Detecting such modulation can be achieved utilising techniques including, but not restricted to, ELISA, cell-based ELISA, inhibition ELISA, Western blots, immunoprecipitation, slot or dot blot assays, immunostaining, RIA, scintillation proximity assays, fluorescent immunoassays using antigen-binding molecule conjugates or antigen conjugates of fluorescent substances such as fluorescein or rhodamine, Ouchterlony double diffusion analysis, immunoassays employing an avidin-biotin or a streptavidin-biotin detection system, and nucleic acid detection assays including reverse transcriptase polymerase chain reaction (RT-PCR).

It will be understood that a polynucleotide from which an IMPDH polypeptide is regulated or expressed may be naturally occurring in the cell which is the subject of testing or it may have been introduced into the host cell for the purpose of testing. In addition, the naturally-occurring or introduced polynucleotide may be constitutively expressed—thereby providing a model useful in screening for agents which down-regulate expression of an encoded product of the sequence wherein the down regulation can be at the nucleic acid or expression product level—or may require activation—thereby providing a model useful in screening for agents that up-regulate expression of an encoded product of the sequence. Further, to the extent that a polynucleotide is introduced into a cell, that polynucleotide may comprise the entire coding sequence that codes for an IMPDH polypeptide or it may comprise a portion of that coding sequence (e.g., the catalytic domain of an IMPDH, the DNA/RNA-binding domain of an IMPDH, or the tetramerisation/oligomerisation domain of an IMPDH) or a portion that regulates expression of an Impdh gene (e.g., an Impdh promoter). For example, the promoter that is naturally associated with the polynucleotide may be introduced into the cell that is the subject of testing. In this instance, where only the promoter is utilised, detecting modulation of the promoter activity can be achieved, for example, by operably linking the promoter to a suitable reporter polynucleotide including, but not restricted to, green fluorescent protein (GFP), luciferase, □-galactosidase and catecholamine acetyl transferase (CAT). Modulation of expression may be determined by measuring the activity associated with the reporter polynucleotide. In another example, the subject of detection could be a downstream regulatory target of an IMPDH, rather than the IMPDH itself or a reporter molecule operably linked to a promoter of a gene encoding a product the expression of which is regulated by an IMPDH.

These methods provide a mechanism for performing high throughput screening of putative modulatory agents such as proteinaceous or non-proteinaceous agents comprising synthetic, combinatorial, chemical and natural libraries. These methods will also facilitate the detection of agents which bind either the polynucleotide encoding the target molecule or which modulate the expression of an upstream molecule, which subsequently modulates the expression of the polynucleotide encoding the target molecule. Accordingly, these methods provide a mechanism of detecting agents that either directly or indirectly modulate the expression or activity of a target molecule according to the invention.

In a series of embodiments, the present invention provides assays for identifying small molecules or other compounds (i.e., modulatory agents) which are capable of inducing or inhibiting the level or functional activity of IMPDH. The assays may be performed in vitro using non-transformed cells, immortalised cell lines, or recombinant cell lines. In addition, the assays may detect the presence of increased or decreased expression of genes or production of proteins on the basis of increased or decreased mRNA expression (using, for example, nucleic acid probes that hybridise to an Impdh gene or coding sequence), increased or decreased levels of IMPDH (using, for example, antigen binding molecules that are immuno-interactive with an IMPDH polypeptide), or increased or decreased levels of expression of a reporter gene (e.g., GFP, β-galactosidase or luciferase) operably linked to an Impdh regulatory region (e.g., a promoter or enhancer) in a recombinant construct.

Thus, for example, one may culture cells which produce an IMPDH polypeptide and add to the culture medium one or more test compounds. After allowing a sufficient period of time (e.g., 6-72 hours) for the compound to induce or inhibit the level or functional activity of the IMPDH polypeptide, any change in the level from an established baseline may be detected using, for example, any of the techniques described herein or known in the art. In specific embodiments, the cells are preadipocytes or adipocytes. Using suitable nucleic acid probes or antigen-binding molecules, detection of changes in the level and or functional activity of an Impdh expression product, and thus identification of the compound as agonist or antagonist of the target molecule, requires only routine experimentation.

In some embodiments, recombinant assays are employed in which a reporter gene encoding, for example, GFP, β-galactosidase or luciferase is operably linked to the 5' regulatory regions of an IMPDH polypeptide. Such regulatory regions may be easily isolated and cloned by one of ordinary skill in the art. The reporter gene and regulatory regions are joined in-frame (or in each of the three possible reading frames) so that transcription and translation of the reporter gene may proceed under the control of the regulatory elements of the target molecule related gene. The recombinant construct may then be introduced into any appropriate cell type although mammalian cells are desirable, and human cells are more desirable. The transformed cells may be grown in culture and, after establishing the baseline level of expression of the reporter gene, test compounds may be added to the medium. The ease of detection of the expression of the reporter gene provides for a rapid, high throughput assay for the identification of IMPDH agonists or antagonists of the invention.

Compounds identified by this method will have potential utility in modifying the expression of Impdh in vivo. These compounds may be further tested in the animal models to identify those compounds having the most potent in vivo effects. In addition, as described above with respect to small molecules having target polypeptide binding activity, these molecules may serve as "lead compounds" for the further development of pharmaceuticals by, for example, subjecting the compounds to sequential modifications, molecular modelling, and other routine procedures employed in rational drug design.

In other embodiments, methods of identifying agents that inhibit IMPDH activity are provided in which a purified preparation of an IMPDH polypeptide is incubated in the presence and absence of a candidate agent under conditions in which the IMPDH is active, and the level of IMPDH activity is measured by a suitable assay. For example, an IMPDH inhibitor can be identified by measuring the ability of a candidate agent to decrease IMPDH activity in a cell (e.g., a preadipocyte or adipocyte). In illustrative examples of this method, a preadipocyte is exposed to, or cultured in the presence and absence of, a candidate agent under conditions in which the IMPDH is active in the preadipocytes, and an activity relating to adipogenesis such as the inhibition or reduction of the differentiation potential of the preadipocyte is detected. In other illustrative examples, an adipocyte is exposed to, or cultured in the presence and absence of, a candidate agent under conditions in which the IMPDH is active in the adipocyte, and an activity relating to adipogenesis such as the inhibition or reduction of lipid accumulation in or the proliferation of the adipocyte is detected. An agent tests positive if it inhibits any of these activities.

In still other embodiments, a method of identifying agents that increase IMPDH activity is provided in which a purified preparation of an IMPDH polypeptide is incubated in the presence and absence of a candidate agent under conditions in which the IMPDH is active, and the level of IMPDH activity is measured by a suitable assay. For example, an IMPDH stimulator or activator can be identified by measuring the ability of a candidate agent to increase IMPDH activity or activation in a cell (e.g., a preadipocyte or adipocyte). In illustrative examples of this method, a preadipocyte is exposed to, or cultured in the presence and absence of, a candidate agent under conditions in which the IMPDH is active in the preadipocytes, and an activity relating to adipogenesis such as the enhancement of the differentiation potential of the preadipocyte is detected. In other illustrative examples, an adipocyte is exposed to, or cultured in the presence and absence of, a candidate agent under conditions in which the IMPDH is active in the adipocyte, and an activity relating to adipogenesis such as the enhancement of lipid accumulation in or the proliferation of the adipocyte is detected. An agent tests positive if it enhances any of these activities.

In still other embodiments, random peptide libraries consisting of a large number of possible combinations of amino acids attached to a solid phase support may be used to identify peptides that are able to bind to an IMPDH polypeptide or to a functional domain thereof. Identification of molecules that are able to bind to an IMPDH polypeptide may be accomplished by screening a peptide library with a recombinant soluble IMPDH polypeptide. The IMPDH polypeptide may be purified, recombinantly expressed or synthesised by any suitable technique. Such polypeptides may be conveniently prepared by a person skilled in the art using standard protocols as for example described in Sambrook, et al., (1989, supra) in particular Sections 16 and 17; Ausubel et al., ("Current Protocols in Molecular Biology", John Wiley & Sons Inc, 1994-1998), in particular Chapters 10 and 16; and Coligan et al., ("Current Protocols in Immunology", (John Wiley & Sons, Inc, 1995-1997), in particular Chapters 1, 5 and 6. Alternatively, an IMPDH polypeptide may be synthesised using solution synthesis or solid phase synthesis as described, for example, in Chapter 9 of Atherton and Shephard (supra) and in Roberge et al (1995, *Science* 269: 202).

To identify and isolate the peptide/solid phase support that interacts and forms a complex with the IMPDH polypeptide it may be necessary to label or "tag" the IMPDH polypeptide. In this regard, the IMPDH polypeptide can be conjugated to any suitable reporter molecule, including enzymes such as alkaline phosphatase and horseradish peroxidase and fluorescent reporter molecules such as fluorescein isothiocynate (FITC), phycoerythrin (PE) and rhodamine. Conjugation of any given reporter molecule, with an IMPDH polypeptide, may be performed using techniques that are routine in the art. Alternatively, IMPDH expression vectors may be engineered to express a chimeric IMPDH polypeptide containing an epitope for which a commercially available antigen-binding molecule exists. The epitope specific antigen-binding molecule may be tagged using methods known in the art including labelling with enzymes, fluorescent dyes or coloured or magnetic beads.

For example, the "tagged" target polypeptide conjugate is incubated with the random peptide library for 30 minutes to one hour at 22° C. to allow complex formation between target polypeptide and peptide species within the library. The library is then washed to remove any unbound target polypeptide. If the target polypeptide has been conjugated to alkaline phosphatase or horseradish peroxidase the whole library is poured into a petri dish containing a substrate for either alkaline phosphatase or peroxidase, for example, 5-bromo-4-chloro-3-indoyl phosphate (BCIP) or 3,3',4,4"-diamnobenzidine (DAB), respectively. After incubating for several minutes, the peptide/solid phase-target polypeptide complex changes color, and can be easily identified and isolated physically under a dissecting microscope with a micromanipulator. If a fluorescently tagged target polypeptide has been used, complexes may be isolated by fluorescent activated sorting. If a chimeric target polypeptide having a heterologous epitope has been used, detection of the peptide/target polypeptide complex may be accomplished by using a labeled epitope specific antigen-binding molecule. Once isolated, the identity of the peptide attached to the solid phase support may be determined by peptide sequencing.

5. Methods of Detecting Expression of Impdh Genes

Since Impdh genes are considered to be associated with adipogenesis, and in particular, in differentiation of preadipocytes and/or in adipocyte lipid accumulation, it is proposed that aberrations in expression of such genes may underlie or contribute to dysfunctional adipogenesis including elevated adipogenesis that may be linked with a predisposition to developing obesity or obesity-related conditions, including but not limited to: familial obesity, atherosclerosis, hypertension and diabetes. Accordingly, the present invention contemplates a method for detecting the presence or diagnosing the risk of obesity in a patient, comprising determining the presence of an aberrant Impdh gene or an aberrant expression product of that gene in a biological sample obtained from the patient, wherein the aberrant gene or the aberrant expression product correlates with the presence of or predisposition to developing obesity or obesity-related conditions.

In some embodiments, the method comprises detecting a level and/or functional activity of an expression product of the Impdh gene, which is different than a normal reference level and/or functional activity of that expression product. For example, the presence of, or the probable affliction with, obesity is diagnosed when an Impdh gene product is expressed at a detectably higher level as compared to the level at which it is expressed in normal, non-obese patients or in non-affected patients. Alternatively, obesity is diagnosed by detecting a functional activity of an expression product of an Impdh gene, which is increased or elevated relative to a normal, non-obese reference functional activity of that gene.

Thus, it will be desirable to qualitatively or quantitatively determine protein levels or transcription levels of an Impdh gene. Alternatively or additionally, it may be desirable to search for aberrant structural Impdh genes and their regulatory regions.

The biological sample can be any suitable tissue (e.g., a biopsy of omental tissue, which desirably includes white adipose tissue) or fluid.

5.1 Genetic Diagnosis

One embodiment of the instant invention comprises a method for detecting an increase in the expression of an Impdh gene. For example, one may detect the expression of an Impdh gene by qualitatively or quantitatively determining the transcripts of the Impdh gene in a cell (e.g., a preadipocyte or adipocyte). Another embodiment of the instant invention comprises a method for detecting an increase in the expression or function of an Impdh gene by examining the genes and transcripts of a cell. In these embodiments, nucleic acid can be isolated from cells contained in the biological sample, according to standard methodologies (Sambrook, et al., "Molecular Cloning. A Laboratory Manual", Cold Spring Harbor Press, 1989; Ausubel et al., "Current Protocols in Molecular Biology", John Wiley & Sons Inc, 1994-1998). The nucleic acid may be genomic DNA or fractionated or whole cell RNA. Where RNA is used, it may be desired to convert the RNA to a complementary DNA. In one embodiment, the RNA is whole cell RNA; in another, it is poly-A RNA. In one embodiment, the nucleic acid is amplified by a nucleic acid amplification technique. Suitable nucleic acid amplification techniques are well known to the skilled person, and include the polymerase chain reaction (PCR) as for example described in Ausubel et al. (supra); strand displacement amplification (SDA) as for example described in U.S. Pat. No. 5,422,252; rolling circle replication (RCR) as for example described in Liu et al., (1996) and International application WO 92/01813 and Lizardi et al., (International Application WO 97/19193); nucleic acid sequence-based amplification (NASBA) as for example described by Sooknanan et al., (1994, *Biotechniques* 17:1077-1080); and Q-β replicase amplification as for example described by Tyagi et al., (1996, *Proc. Natl. Acad. Sci. USA* 93: 5395-5400).

Depending on the format, the specific nucleic acid of interest is identified in the sample directly using amplification or with a second, known nucleic acid following amplification. Next, the identified product is detected. In certain applications, the detection may be performed by visual means (e.g., ethidium bromide staining of a gel). Alternatively, the detection may involve indirect identification of the product via chemiluminescence, radioactive scintigraphy of radiolabel or fluorescent label or even via a system using electrical or thermal impulse signals (Affymax Technology; Bellus, 1994, *J Macromol. Sci. Pure, Appl. Chem.*, A31(1): 1355-1376).

Following detection, one may compare the results seen in a given patient with a control reaction or a statistically significant reference group of normal subjects. In this way, it is possible to correlate the amount of an expression product detected with the progression or severity of the obesity.

In addition to determining levels of transcripts, it also may prove useful to examine various types of defects. These defects could include deletions, insertions, point mutations and duplications. Point mutations result in stop codons, frameshift mutations or amino acid substitutions. Somatic mutations are those occurring in non-germline tissues. Germline tissue can occur in any tissue and are inherited. Mutations in and outside the coding region also may affect the amount of IMPDH produced, both by altering the transcription of the gene or in stabilising or otherwise altering the processing of either the transcript (mRNA) or protein.

A variety of different assays are contemplated in this regard, including but not limited to, fluorescent in situ hybridisation (FISH), direct DNA sequencing, pulse field gel electrophoresis (PFGE) analysis, Southern or Northern blotting, single-stranded conformation analysis (SSCA), RNase protection assay, allele-specific oligonucleotide (ASO), dot blot analysis, denaturing gradient gel electrophoresis, RFLP and PCR-SSCP. Also contemplated by the present invention are chip-based DNA technologies such as those described by Hacia et al. (1996, *Nature Genetics* 14: 441-447) and Shoemaker et al. (1996, *Nature Genetics* 14: 450456). Briefly, these techniques involve quantitative methods for analysing large numbers of genes rapidly and accurately. By tagging genes with oligonucleotides or using fixed probe arrays, one can employ chip technology to segregate target molecules as high density arrays and screen these molecules on the basis of hybridisation. See also Pease et al. (1994, *Proc. Natl. Acad. Sci. U.S.A.* 91: 5022-5026); Fodor et al. (1991, *Science* 251: 767-773).

5.2 Protein-Based Diagnostics 5.2.1 Antigen-Binding Molecules

Antigen-binding molecules that are immuno-interactive with an IMPDH polypeptide can be used in measuring an increase or decrease in the expression of Impdh genes. Thus, the present invention also contemplates antigen-binding molecules that bind specifically to an expression product of an Impdh gene. For example, the antigen-binding molecules may comprise whole polyclonal antibodies. Such antibodies may be prepared, for example, by injecting a target molecule of the invention into a production species, which may include mice or rabbits, to obtain polyclonal antisera. Methods of producing polyclonal antibodies are well known to those skilled in the art. Exemplary protocols which may be used are described for example in Coligan et al., "Current Protocols In Immunology", (John Wiley & Sons, Inc, 1991), and Ausubel et al., (1994-1998, supra), in particular Section III of Chapter 11.

In lieu of the polyclonal antisera obtained in the production species, monoclonal antibodies may be produced using the standard method as described, for example, by Köhler and Milstein (1975, *Nature* 256, 495497), or by more recent modifications thereof as described, for example, in Coligan et al., (1991, supra) by immortalising spleen or other antibody-producing cells derived from a production species which has been inoculated with target molecule of the invention.

The invention also contemplates as antigen-binding molecules Fv, Fab, Fab' and F(ab')$_2$ immunoglobulin fragments. Alternatively, the antigen-binding molecule may be in the form of a synthetic stabilised Fv fragment, a single variable region domain (also known as a dabs), a "minibody" and the like as known in the art.

Also contemplated as antigen binding molecules are humanised antibodies. Humanised antibodies are produced by transferring complementary determining regions from heavy and light variable chains of a non human (e.g., rodent, preferably mouse) immunoglobulin into a human variable domain. Typical residues of human antibodies are then substituted in the framework regions of the non human counterparts. The use of antibody components derived from humanised antibodies obviates potential problems associated with the immunogenicity of non human constant regions. General techniques for cloning non human, particular murine, immunoglobulin variable domains are described, for example, by Orlandi et al. (1989, *Proc. Natl. Acad. Sci. USA* 86: 3833). Techniques for producing humanised monoclonal antibodies are described, for example, by Jones et al. (1986, *Nature* 321:522), Carter et al. (1992, *Proc. Natl. Acad. Sci. USA* 89: 4285), Sandhu (1992, *Crit. Rev. Biotech.* 12: 437), Singer et al. (1993, *J. Immun.* 150: 2844), Sudhir (ed., *Antibody Engineering Protocols*, Humana Press, Inc. 1995), Kelley ("Engineering Therapeutic Antibodies", in *Protein Engineering: Principles and Practice* Cleland et al. (eds.), pages 399-434 (John Wiley & Sons, Inc. 1996), and by Queen et al., U.S. Pat. No. 5,693,762 (1997).

5.2.2 Immunodiagnostic Assays

The above antigen-binding molecules have utility in measuring directly or indirectly modulation of Impdh gene expression in healthy and diseased states, through techniques such as ELISAs and Western blotting. Illustrative assay strategies which can be used to detect a target polypeptide of the invention include, but are not limited to, immunoassays involving the binding of an antigen-binding molecule to the target polypeptide (e.g., an IMPDH polypeptide) in the sample, and the detection of a complex comprising the antigen-binding molecule and the target polypeptide. Exemplary immunoassays are those that can measure the level or functional activity of a target molecule of the invention. Typically, an antigen-binding molecule that is immuno-interactive with a target polypeptide of the invention is contacted with a biological sample suspected of containing the target polypeptide. The concentration of a complex comprising the antigen-binding molecule and the target polypeptide is measured and the measured complex concentration is then related to the concentration of target polypeptide in the sample. Consistent with the present invention, the presence of an aberrant concentration, especially an elevated concentration, of the target polypeptide is indicative of the presence of, or probable affliction with, adipogenic dysfunction including obesity.

Any suitable technique for determining formation of an antigen-binding molecule-target antigen complex may be used. For example, an antigen-binding molecule according to the invention, having a reporter molecule associated therewith may be utilised in immunoassays. Such immunoassays include, but are not limited to, radioimmunoassays (RIAs), enzyme-linked immunosorbent assays (ELISAs) and immunochromatographic techniques (ICTs), Western blotting which are well known to those of skill in the art. For example, reference may be made to Coligan et al. (1994, supra) which discloses a variety of immunoassays that may be used in accordance with the present invention. Immunoassays may include competitive assays as understood in the art or as for example described infra. It will be understood that the present invention encompasses qualitative and quantitative immunoassays.

Suitable immunoassay techniques are described for example in U.S. Pat. Nos. 4,016,043, 4,424,279 and 4,018,653. These include both single-site and two-site assays of the non-competitive types, as well as the traditional competitive binding assays. These assays also include direct binding of a labelled antigen-binding molecule to an IMPDH polypeptide antigen.

Two site assays are particularly favoured for use in the present invention. A number of variations of these assays exist, all of which are intended to be encompassed by the present invention. Briefly, in a typical forward assay, an unlabelled antigen-binding molecule such as an unlabelled antibody is immobilised on a solid substrate and the sample to be tested brought into contact with the bound molecule. After a suitable period of incubation, for a period of time sufficient to allow formation of an antibody-antigen complex, another antigen-binding molecule, suitably a second antibody specific to the antigen, labelled with a reporter molecule capable of producing a detectable signal is then added and incubated, allowing time sufficient for the formation of another complex of antibody-antigen-labelled antibody. Any un-reacted material is washed away and the presence of the antigen is determined by observation of a signal produced by the reporter molecule. The results may be either qualitative, by simple observation of the visible signal, or may be quantitated by comparing with a control sample containing known amounts of antigen. Variations on the forward assay include a simultaneous assay, in which both sample and labelled antibody are added simultaneously to the bound antibody. These techniques are well known to those skilled in the art, including minor variations as will be readily apparent. In accordance with the present invention, the sample is one that might contain an antigen including a tissue or fluid as described above.

In the typical forward assay, a first antibody having specificity for the antigen or antigenic parts thereof is either covalently or passively bound to a solid surface. The solid surface is typically glass or a polymer, the most commonly used polymers being cellulose, polyacrylamide, nylon, polystyrene, polyvinyl chloride or polypropylene. The solid supports may be in the form of tubes, beads, discs or microplates, or any other surface suitable for conducting an immunoassay. The binding processes are well known in the art and generally consist of cross-linking, covalently binding or physically adsorbing, the polymer-antibody complex to the solid support, which is then washed in preparation for the test sample. An aliquot of the sample to be tested is then added to the solid phase complex and incubated for a period of time sufficient and under suitable conditions to allow binding of any antigen present to the antibody. Following the incubation period, the antigen-antibody complex is washed and dried and incubated with a second antibody specific for a portion of the antigen. The second antibody has generally a reporter molecule associated therewith that is used to indicate the binding of the second antibody to the antigen. The amount of labelled antibody that binds, as determined by the associated reporter molecule, is proportional to the amount of antigen bound to the immobilised first antibody.

An alternative method involves immobilising the antigen in the biological sample and then exposing the immobilised antigen to specific antibody that may or may not be labelled with a reporter molecule. Depending on the amount of target and the strength of the reporter molecule signal, a bound antigen may be detectable by direct labelling with the antibody. Alternatively, a second labelled antibody, specific to the first antibody is exposed to the target-first antibody complex to form a target-first antibody-second antibody tertiary complex. The complex is detected by the signal emitted by the reporter molecule.

From the foregoing, it will be appreciated that the reporter molecule associated with the antigen-binding molecule may include the following: (a) direct attachment of the reporter molecule to the antigen-binding molecule; (b) indirect attachment of the reporter molecule to the antigen-binding molecule; i.e., attachment of the reporter molecule to another assay reagent which subsequently binds to the antigen-binding molecule; and (c) attachment to a subsequent reaction product of the antigen-binding molecule.

The reporter molecule may be selected from a group including a chromogen, a catalyst, an enzyme, a fluorochrome, a chemiluminescent molecule, a lanthanide ion such as Europium ($Eu^{34}$), a radioisotope and a direct visual label.

In the case of a direct visual label, use may be made of a colloidal metallic or non-metallic particle, a dye particle, an enzyme or a substrate, an organic polymer, a latex particle, a liposome, or other vesicle containing a signal producing substance and the like.

A large number of enzymes suitable for use as reporter molecules is disclosed in United States patent specifications U.S. Pat. No. 4,366,241, U.S. Pat. No. 4,843,000, and U.S. Pat. No. 4,849,338. Suitable enzymes useful in the present invention include alkaline phosphatase, horseradish peroxidase, luciferase, β-galactosidase, glucose oxidase, lysozyme, malate dehydrogenase and the like. The enzymes may be used alone or in combination with a second enzyme that is in solution.

Suitable fluorochromes include, but are not limited to, fluorescein isothiocyanate (FITC), tetramethylrhodamine isothiocyanate (TRITC), R-Phycoerythrin (RPE), and Texas Red. Other exemplary fluorochromes include those discussed by Dower et al. (International Publication WO 93/06121). Reference also may be made to the fluorochromes described in U.S. Pat. No. 5,573,909 (Singer et al), U.S. Pat. No. 5,326,692 (Brinkley et al). Alternatively, reference may be made to the fluorochromes described in U.S. Pat. Nos. 5,227,487, 5,274,113, 5,405,975, 5,433,896, 5,442,045, 5,451,663, 5,453,517, 5,459,276, 5,516,864, 5,648,270 and 5,723,218.

In the case of an enzyme immunoassay, an enzyme is conjugated to the second antibody, generally by means of glutaraldehyde or periodates. As will be readily recognised, however, a wide variety of different conjugation techniques exist which are readily available to the skilled artisan. The substrates to be used with the specific enzymes are generally chosen for the production of, upon hydrolysis by the corresponding enzyme, a detectable colour change. Examples of suitable enzymes include those described supra. It is also possible to employ fluorogenic substrates, which yield a fluorescent product rather than the chromogenic substrates noted above. In all cases, the enzyme-labelled antibody is added to the first antibody-antigen complex. It is then allowed to bind, and excess reagent is washed away. A solution containing the appropriate substrate is then added to the complex of antibody-antigen-antibody. The substrate will react with the enzyme linked to the second antibody, giving a qualitative visual signal, which may be further quantitated, usually spectrophotometrically, to give an indication of the amount of antigen which was present in the sample.

Alternately, fluorescent compounds, such as fluorescein, rhodamine and the lanthanide, europium (EU), may be chemically coupled to antibodies without altering their binding capacity. When activated by illumination with light of a particular wavelength, the fluorochrome-labelled antibody adsorbs the light energy, inducing a state to excitability in the molecule, followed by emission of the light at a characteristic colour visually detectable with a light microscope. The fluorescent-labelled antibody is allowed to bind to the first antibody-antigen complex. After washing off the unbound reagent, the remaining tertiary complex is then exposed to light of an appropriate wavelength. The fluorescence observed indicates the presence of the antigen of interest. Immunofluorometric assays (IFMA) are well established in the art. However, other reporter molecules, such as radioisotope, chemiluminescent or bioluminescent molecules may also be employed.

It will be well understood that other means of testing IMPDH polypeptide levels are available, including, for instance, those involving testing for an altered level of kinase binding activity to an IMPDH polypeptide, or Western blot analysis of IMPDH polypeptide levels in tissues, cells or fluids using anti-IMPDH antigen-binding molecules, or assaying the amount of antigen-binding molecule or other IMPDH binding partner which is not bound to a sample, and subtracting from the total amount of antigen-binding molecule or binding partner added.

6. Therapeutic and Prophylactic Uses

In accordance with the present invention, it is proposed that agents that antagonise IMPDH activity are useful as actives for the treatment or prophylaxis of excess adipogenesis, including obesity, obesity-related conditions, lipomas and lipomatosis. It is also proposed that agents that agonise IMPDH activity are useful for enhancing adipogenesis for example in cachexia and cachexia-related conditions. Such drugs can be administered to a patient either by themselves, or in pharmaceutical compositions where they are mixed with a suitable pharmaceutically acceptable carrier.

The adipogenesis-modulating agents of the present invention may be conjugated with biological targeting agents which enable their activity to be restricted to particular cell types. Such biological-targeting agents include substances which are immuno-interactive with cell-specific surface antigens. For example, an agent which modulates the activity of an IMPDH polypeptide may be conjugated with an agent which is immuno-interactive with a preadipocyte-specific protein or a protein whose expression is substantially enhanced during adipogenesis, such as, for example, adipose differentiation related protein (ADRP). The presence of this immuno-interactive conjugate confers preadipocyte-specificity or preference to the effects of the IMPDH-modulating agent.

Depending on the specific conditions being treated, the drugs may be formulated and administered systemically or locally. Techniques for formulation and administration may be found in "Remington's Pharmaceutical Sciences," Mack Publishing Co., Easton, Pa., latest edition. Suitable routes may, for example, include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections. For injection, the drugs of the invention may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art. Intra-muscular and subcutaneous injection is appropriate, for example, for administration of immunogenic compositions, vaccines and DNA vaccines.

The drugs can be formulated readily using pharmaceutically acceptable carriers well known in the art into dosages suitable for oral administration. Such carriers enable the compounds of the invention to be formulated in dosage forms such as tablets, pills, capsules, liquids, gels, syrups, slurries, suspensions and the like, for oral ingestion by a patient to be treated. These carriers may be selected from sugars, starches, cellulose and its derivatives, malt, gelatine, talc, calcium sulphate, vegetable oils, synthetic oils, polyols, alginic acid, phosphate buffered solutions, emulsifiers, isotonic saline, and pyrogen-free water.

Pharmaceutical compositions suitable for use in the present invention include compositions wherein the active ingredients are contained in an effective amount to achieve its intended purpose. The dose of drug administered to a patient should be sufficient to effect a beneficial response in the patient over time such as an enhancement or reduction in adipogenesis. The quantity of the drug(s) to be administered may depend on the subject to be treated inclusive of the age, sex, weight and general health condition thereof. In this regard, precise amounts of the drug(s) for administration will depend on the judgement of the practitioner. In determining the effective amount of the drug to be administered in the modulation of adipogenesis, the physician may evaluate tissue levels of Impdh expression products, and degree of adiposity. In any event, those of skill in the art may readily determine suitable dosages of the drugs of the invention.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilisers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatine, gum tragacanth, methyl cellulose, hydroxypropylmethyl-cellulose, sodium carboxymethylcellulose, or polyvinylpyrrolidone (PVP). If desired, disintegrating agents may be added, such as the cross-linked polyvinyl pyrrolidone, agar, or alginic acid or a salt thereof such as sodium alginate. Such compositions may be prepared by any of the methods of pharmacy but all methods include the step of bringing into association one or more drugs as described above with the carrier which constitutes one or more necessary ingredients. In general, the pharmaceutical compositions of the present invention may be manufactured in a manner that is itself known, e.g., by means of conventional mixing, dissolving, granulating, dragee-making, levigating, emulsifying, encapsulating, entrapping or lyophilising processes.

Dragee cores are provided with suitable coatings. For this purpose, concentrated sugar solutions may be used, which may optionally contain gum arabic, talc, polyvinyl pyrrolidone, carbopol gel, polyethylene glycol, or titanium dioxide, lacquer solutions, and suitable organic solvents or solvent mixtures. Dyestuffs or pigments may be added to the tablets or dragee coatings for identification or to characterise different combinations of active compound doses.

Pharmaceutical which can be used orally include push-fit capsules made of gelatine, as well as soft, sealed capsules made of gelatine and a plasticiser, such as glycerol or sorbitol.

The push-fit capsules can contain the active ingredients in admixture with filler such as lactose, binders such as starches, or lubricants such as talc or magnesium stearate and, optionally, stabilisers. In soft capsules, the active compounds may be dissolved or suspended in suitable liquids, such as fatty oils, liquid paraffin, or liquid polyethylene glycols. In addition, stabilisers may be added.

Dosage forms of the drugs of the invention may also include injecting or implanting controlled releasing devices designed specifically for this purpose or other forms of implants modified to act additionally in this fashion. Controlled release of an agent of the invention may be effected by coating the same, for example, with hydrophobic polymers including acrylic resins, waxes, higher aliphatic alcohols, polylactic and polyglycolic acids and certain cellulose derivatives such as hydroxypropylmethyl cellulose. In addition, controlled release may be effected by using other polymer matrices, liposomes or microspheres.

The drugs of the invention may be provided as salts with pharmaceutically compatible counterions. Pharmaceutically compatible salts may be formed with many acids, including but not limited to hydrochloric, sulphuric, acetic, lactic, tartaric, malic, succinic, etc. Salts tend to be more soluble in aqueous or other protonic solvents that are the corresponding free base forms.

For any compound used in the method of the invention, the therapeutically effective dose can be estimated initially from cell culture assays. For example, a dose can be formulated in animal models to achieve a circulating concentration range that includes the IC50 as determined in cell culture (e.g., the concentration of a test agent, which achieves a half-maximal inhibition or enhancement in activity of an IMPDH polypeptide). Such information can be used to more accurately determine useful doses in humans.

Toxicity and therapeutic efficacy of such drugs can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. The data obtained from these cell culture assays and animal studies can be used in formulating a range of dosage for use in human. The dosage of such compounds lies preferably within a range of circulating concentrations that include the ED50 with little or no toxicity. The dosage may vary within this range depending upon the dosage form employed and the route of administration utilised. The exact formulation, route of administration and dosage can be chosen by the individual physician in view of the patient's condition. (See for example Fingl et al., 1975, in "The Pharmacological Basis of Therapeutics", Ch. 1 p 1).

Dosage amount and interval may be adjusted individually to provide plasma levels of the active agent which are sufficient to maintain IMPDH-inhibitory or enhancement effects. Usual patient dosages for systemic administration range from 1-2000 mg/day, commonly from 1-250 mg/day, and typically from 10-150 mg/day. Stated in terms of patient body weight, usual dosages range from 0.02-25 mg/kg/day, commonly from 0.02-3 mg/kg/day, typically from 0.2-1.5 mg/kg/day. Stated in terms of patient body surface areas, usual dosages range from 0.5-1200 mg/m$^2$/day, commonly from 0.5-150 mg/m$^2$/day, typically from 5-100 mg/m$^2$/day.

Alternately, one may administer the compound in a local rather than systemic manner, for example, via injection of the compound directly into a tissue, which is preferably subcutaneous or omental tissue, often in a depot or sustained release formulation.

Furthermore, one may administer the drug in a targeted drug delivery system, for example, in a liposome coated with tissue-specific antibody. The liposomes will be targeted to and taken up selectively by the tissue.

In cases of local administration or selective uptake, the effective local concentration of the agent may not be related to plasma concentration.

The present invention also contemplates a method of gene therapy of a mammal. Such a method utilises a gene therapy construct which includes an isolated polynucleotide comprising a nucleotide sequence encoding an IMPDH polypeptide, or a biologically active fragment thereof, wherein the polynucleotide is ligated into a gene therapy vector which provides one or more regulatory sequences that direct expression of the polynucleotide in the mammal. Typically, gene therapy vectors are derived from viral DNA sequences such as adenovirus, adeno-associated viruses, herpes-simplex viruses and retroviruses. Suitable gene therapy vectors currently available to the skilled person may be found, for example, in Robbins et al. (1998, *Proc. Natl. Acad. Sci. USA* 95:10182-10187). If "anti-sense" therapy is contemplated (e.g., Impdh), then one or more selected portions of an Impdh polynucleotide may be oriented 3'→5' in the gene therapy vector.

Administration of the gene therapy construct to the mammal, suitably a human, may include delivery via direct oral intake, systemic injection, or delivery to selected tissue(s) or cells, or indirectly via delivery to cells isolated from the mammal or a compatible donor. An example of the latter approach would be stem-cell therapy, wherein isolated stem cells having potential for growth and differentiation are transfected with the vector comprising an Impdh polynucleotide. The stem-cells are cultured for a period and then transferred to the mammal being treated.

Delivery of the gene therapy construct to cells or tissues of the mammal or the compatible donor may be facilitated by microprojectile bombardment, liposome mediated transfection e.g., lipofectin or lipofectamine), electroporation, calcium phosphate or DEAE-dextran-mediated transfection, for example. A discussion of suitable delivery methods may be found in Chapter 9 of Ausubel et al., (1994-1998, supra).

For example, a polynucleotide encoding IMPDH-1 may be introduced into a cell to enhance the ability of that cell to promote adipogenesis, conversely, Impdh-1 antisense sequences such as 3'→5' oligonucleotides may be introduced to decrease or impair differentiation of the cell to an adipocyte or lipid accumulation in an adipocyte.

In an alternate embodiment, a polynucleotide encoding a modulatory agent of the invention may be used as a therapeutic or prophylactic composition in the form of a "naked DNA" composition as is known in the art. For example, an expression vector comprising the polynucleotide operably linked to a regulatory polynucleotide (e.g. a promoter, transcriptional terminator, enhancer etc) may be introduced into an animal, preferably a mammal, where it causes production of a modulatory agent in vivo, preferably in preadipocyte tissue.

The step of introducing the expression vector into a target cell or tissue will differ depending on the intended use and species, and can involve one or more of non-viral and viral vectors, cationic liposomes, retroviruses, and adenoviruses such as, for example, described in Mulligan, R. C., (1993). Such methods can include, for example:

(A) Local application of the expression vector by injection (Wolff et al., 1990), surgical implantation, instillation or any other means. This method can also be used in combination with local application by injection, surgical implantation, instillation or any other means, of cells responsive to the protein encoded by the expression vector so as to increase the effectiveness of that treatment. This method can also be used in combination with local application by injection, surgical implantation, instillation or any other means, of another factor or factors required for the activity of the protein.

(B) General systemic delivery by injection of DNA, (Calabretta et al., 1993), or RNA, alone or in combination with liposomes (Zhu et al., 1993), viral capsids or nanoparticles (Bertling et al., 1991) or any other mediator of delivery. Improved targeting might be achieved by linking the polynucleotide/expression vector to a targeting molecule (the so-called "magic bullet" approach employing, for example, an antigen-binding molecule), or by local application by injection, surgical implantation or any other means, of another factor or factors required for the activity of the protein encoded by the expression vector, or of cells responsive to the protein. For example, in the case of a liposome containing antisense Impdh polynucleotides, the liposome may be targeted to adipocytes by the incorporation of immuno-interactive agents into the liposome coat which are specific for adipocyte-surface antigens.

(C) Injection or implantation or delivery by any means, of cells that have been modified ex vivo by transfection (for example, in the presence of calcium phosphate: Chen et al., 1987, or of cationic lipids and polyamines: Rose et al., 1991), infection, injection, electroporation (Shigekawa et al., 1988) or any other way so as to increase the expression of the polynucleotide in those cells. The modification can be mediated by plasmid, bacteriophage, cosmid, viral (such as adenoviral or retroviral; Mulligan, 1993; Miller, 1992; Salmons et al., 1993) or other vectors, or other agents of modification such as liposomes (Zhu et al., 1993), viral capsids or nanoparticles (Bertling et al., 1991), or any other mediator of modification. The use of cells as a delivery vehicle for genes or gene products has been described by Barr et al., 1991 and by Dhawan et al., 1991. Treated cells can be delivered in combination with any nutrient, growth factor, matrix or other agent that will promote their survival in the treated subject.

In order that the invention may be readily understood and put into practical effect, particular preferred embodiments will now be described by way of the following non-limiting examples.

EXAMPLES

Example 1

Insulin Promotes Phosphorylation of IMPDH

Figure 1:
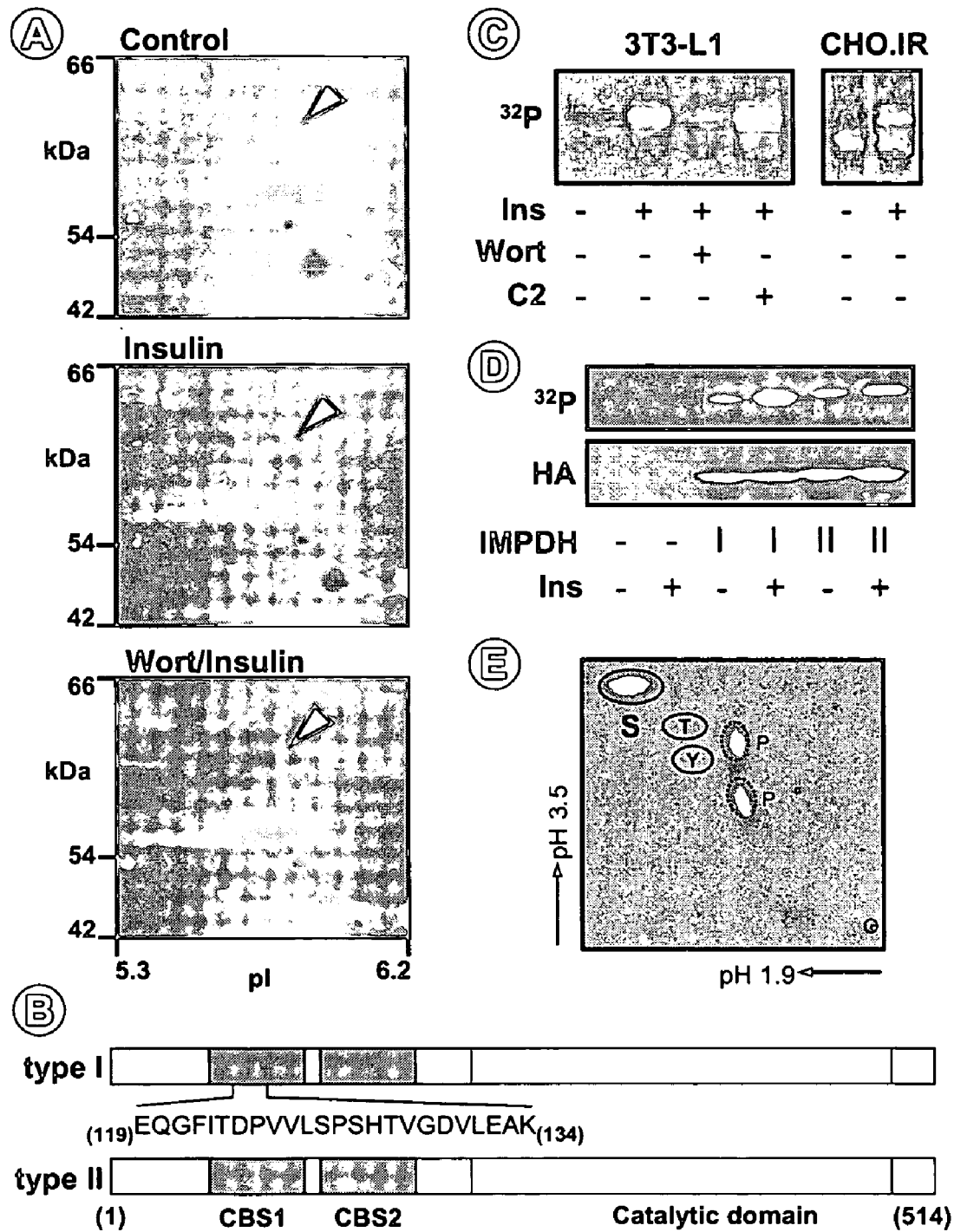
FIG. 1 consists of photographic and graphical representations showing the identification of IMPDH as an insulin-regulated phosphoprotein. Panel (A): 3T3-L1 adipocytes were labelled with $^{32}P$ and incubated in the absence or presence of insulin (1 μM—15 min), or wortmannin (100 nM—25 min) followed by insulin as indicated. Cells were homogenised and fractionated by differential centrifugation to isolate the HSP fraction, as described in materials and methods, which was analysed by 2-DE and autoradiography. Panel (B): Schematic of IMPDH type I and type II. LC-MS/MS analysis of a single phosphoprotein spot (arrow in A) identified a single tryptic peptide from the IMPDH type I enzyme, which is shown. (Mouse IMPDH type I and II-SwissProt accession no. P50096 and P24547). CBS—Cystathionine β-synthase domain. Panel (C): 3T3-L1 adipocytes or CHO.IR cells were labelled with $^{32}P$ and pretreated with wortmannin (100 nM—25 min) or C2-ceramide (C2, 100 μM—2 h), then treated with insulin (1 μM—15 min) as indicated. IMPDH was immunoprecipitated from cell lysates and immunoprecipitates analysed by SDS-PAGE and autoradiography ($^{32}P$). Panel (D): CHO.IR cells were transfected with empty vector (−) or vector encoding HA-IMPDH type I or type II, labelled with $^{32}P$ and incubated in the absence or presence of insulin (100 μM—15 min) as indicated. Recombinant HA-IMPDH was immunoprecipitated using anti-HA antibody and analysed by SDS-PAGE and autoradiography ($^{32}$P) or immunoblotting using anti-HA antibody. Panel (E): $^{32}$P labelled HA-IMPDH type I, immunoprecipitated from insulin treated cells, was subjected to partial acid hydrolysis after transfer to PVDF membrane. Phospho amino acids were identified by 2-DE and autoradiography. The position of cold marker phospho amino acids; S—phospho Ser, T—phospho Thr and Y—phospho Tyr are shown. P—partial hydrolysis products. O—origin. All images are representative of at least three independent experiments.

The phosphoprotein spot indicated in FIG. 1A, previously termed H38 (2), exhibited insulin-stimulated phosphorylation and this was inhibited by pretreatment of cells with the PI 3-kinase inhibitor wortmannin. To identify this protein, a large-scale isolation was performed and the spot was excised and subjected to in-gel tryptic digestion followed by liquid chromatography/tandem mass spectrometry. One of the proteins identified was inosine-5' monophosphate dehydrogenase (IMPDH) type I (FIG. 1B). Immunoprecipitation studies were performed to confirm that IMPDH is a bona-fide insulin regulated phosphoprotein. Insulin stimulation increased incorporation of $^{32}P$ into IMPDH immunoprecipitated from 3T3-L1 adipocytes or Chinese hamster ovary cells overexpressing the insulin receptor (CHO.IR) and this effect was dependent on PI 3-kinase activity (FIG. 1C).

While sequencing data revealed the presence of the type I isoform in the insulin-stimulated phosphorylated spot, in view of the high degree of sequence identity between the two isoforms it remained a possibility that insulin may stimulate phosphorylation of both isoforms. To address this, the inventor examined insulin's ability to promote phosphorylation of transiently expressed hemagluttinin-(HA) tagged forms of either type I or type II IMPDH in CHO.IR cells. Insulin stimulated phosphorylation of both IMPDH type I and type II (FIG. 1D). While phospho-specific antibodies (including a range of commercially available phosphotyrosine, phosphoserine and phosphothreonine antibodies) failed to recognise IMPDH, phospho amino acid analysis of $^{32}P$ labelled IMPDH indicated that both isoforms were phosphorylated on Ser following insulin treatment (FIG. 1E & data not shown). Although the stoichiometry of phosphorylation of IMPDH directly was not assessed, various approaches indicate that only a small proportion of IMPDH (less than 5%) undergoes insulin-stimulated phosphorylation. For example, in parallel experiments insulin-stimulated phosphorylation of HA-IMPDH was approximately 100 fold less than that of HA-Akt, which undergoes almost stoichiometric phosphorylation on two sites, suggesting that approximately 2% of the total IMPDH pool was phosphorylated under these conditions (data not shown).

To further define the pathways involved in insulin-stimulated IMPDH phosphorylation, the inventor examined the effects of several kinase inhibitors. C2-ceramide, which inhibits Akt (21), was without effect on insulin-stimulated IMPDH phosphorylation (FIG. 1C), although it reduced insulin-stimulated Akt phosphorylation by 70% (data not shown). This is intriguing because it has recently been shown, using yeast two hybrid and in vitro and transient overexpression systems, that Akt is able to interact with IMPDH type II and promote its phosphorylation (22). However, both IMPDH isoforms lack good consensus Akt phosphorylation sites (RxRxxS/T) (23). The lack of effect of C2-ceramide to modulate IMPDH phosphorylation is also consistent with the inventor's unpublished studies demonstrating that mutation of the best fitting, albeit weak, Akt consensus site, ($Ser^{496}$ to Ala in human IMPDH type II-KFEKRTSS) did not inhibit IMPDH phosphorylation. Putative roles for other Ser/Thr kinases known to act downstream of PI 3-kinase, including the atypical PKCs and mTOR and p70S6 kinase, were eliminated by studies with the inhibitors Gö6983 (1 μM) and rapamycin (22 nM) respectively (data not shown). The inventor did not formally test for the involvement of MAPK as PDGF stimulated MAPK activation but not IMPDH phosphorylation in differentiated 3T3-L1 adipocytes (2). With the exception of an unknown insulin-regulated kinase the remaining candidates include PI 3-kinase and PDK1. Alternatively, insulin may promote increased IMPDH phosphorylation through inhibition of a serine phosphatase, which is currently being investigated by the inventor.

Example 2

Insulin and Oleate Promote Translocation of IMPDH to Lipid Bodies

Figure 2:
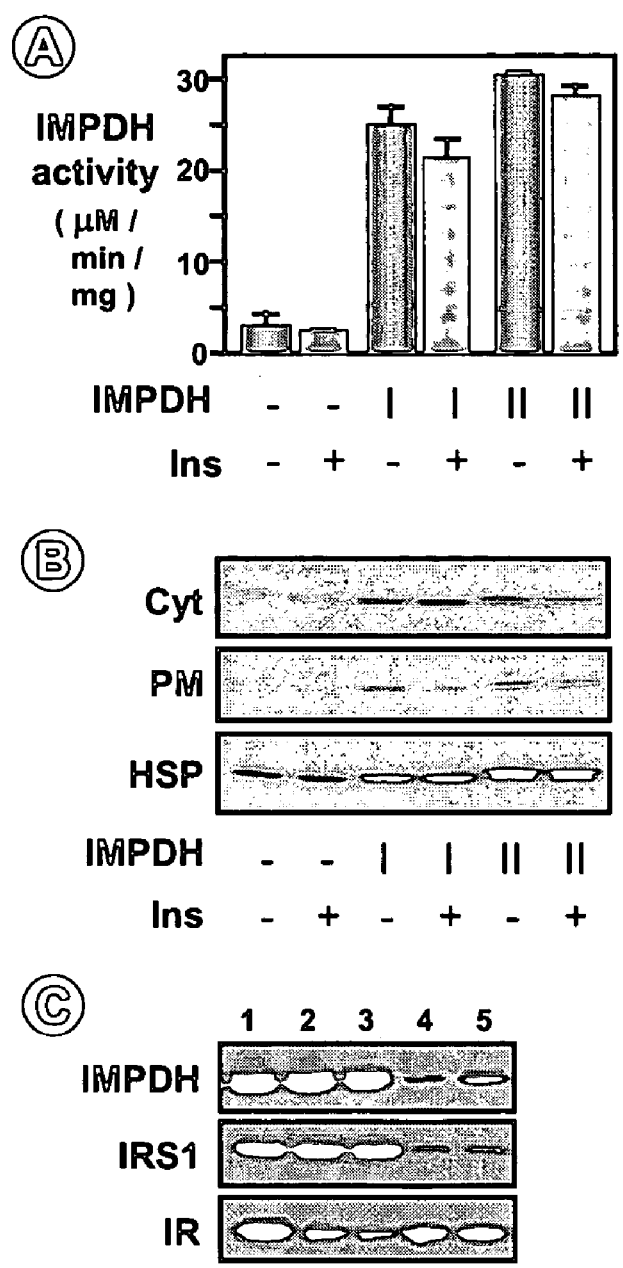
FIG. 2 consists of graphical and photographic representations showing the lack of effect of insulin on IMPDH activity. Panels (A & B): CHO.IR cells were transfected with empty vector (−) or vector encoding HA-IMPDH type I or type II and incubated in the absence or presence of insulin (100 μM—15 min) as indicated. Panel (A): Cells were harvested and IMPDH activity determined at room temperature by measuring the production of NADH at 340 nM as described in the materials and methods section relating to Example 1. Data are representative of four separate experiments. Error bars represent standard deviation (sd). Panel (B): Cells were fractionated by differential centrifugation to produce a fraction enriched in plasma membrane (PM), a high speed pellet (HSP) and supernatant (Cyt). Equivalent protein (5 μg) from each fraction was analysed by immunoblotting using anti-IMPDH antibody. Panel (C): CHO.IR cells were homogenised and centrifuged to isolate a particulate fraction (containing PM and HSP) and supernatant. The pellet was resuspended and incubated on ice for 60 min in buffer containing: 1—No addition; 2—1% Triton-X-100; 3—60 mM β-octylglucoside; 4—0.1 M Na$_2$CO$_3$-pH 11; 5—1 M NaCl, and then re-pelleted by centrifugation. The association of IMPDH, IRS-1 and Insulin Receptor (IR) proteins in the pellet were determined by immunoblotting.

Next, the inventor investigated the effects of insulin on IMPDH function. First a series of experiments was conducted to examine whether insulin altered the enzymatic activity of IMPDH. IMPDH activity was measured in cleared cell lysates incubated in the presence of IMP and NAD, and NADH production was determined. Insulin was without significant effect on endogenous IMPDH activity in 3T3-L1 adipocytes (data not shown) or CHO.IR cells (FIG. 2A). Overexpression of HA-IMPDH (type I or type II) resulted in a >5 fold increase in IMPDH activity compared to control cells, indicating that the recombinant HA-tagged enzymes were functional (FIG. 2A). Despite this a significant effect on IMPDH activity following insulin treatment was not observed.

Another possibility is that insulin may modify the subcellular distribution of the enzyme, creating local changes in its activity at specific loci. By differential centrifugation IMPDH was found to be enriched in a high speed pellet (HSP) fraction that was shown previously to be enriched in small vesicular elements as well as large protein polypeptide complexes (24) (FIG. 2B). Insulin did not modify the distribution of IMPDH by these criteria. The presence of IMPDH in the HSP fraction does not appear to denote its association with membranes because its association with a particulate fraction was unaffected by treatment with non-ionic detergents whereas it was released in the presence of high salt or carbonate (pH 11) (FIG. 2C). Thus, like IRS-1 (24), the sedimentation properties of IMPDH are consistent with its presence in large protein complexes.

Figure 3:
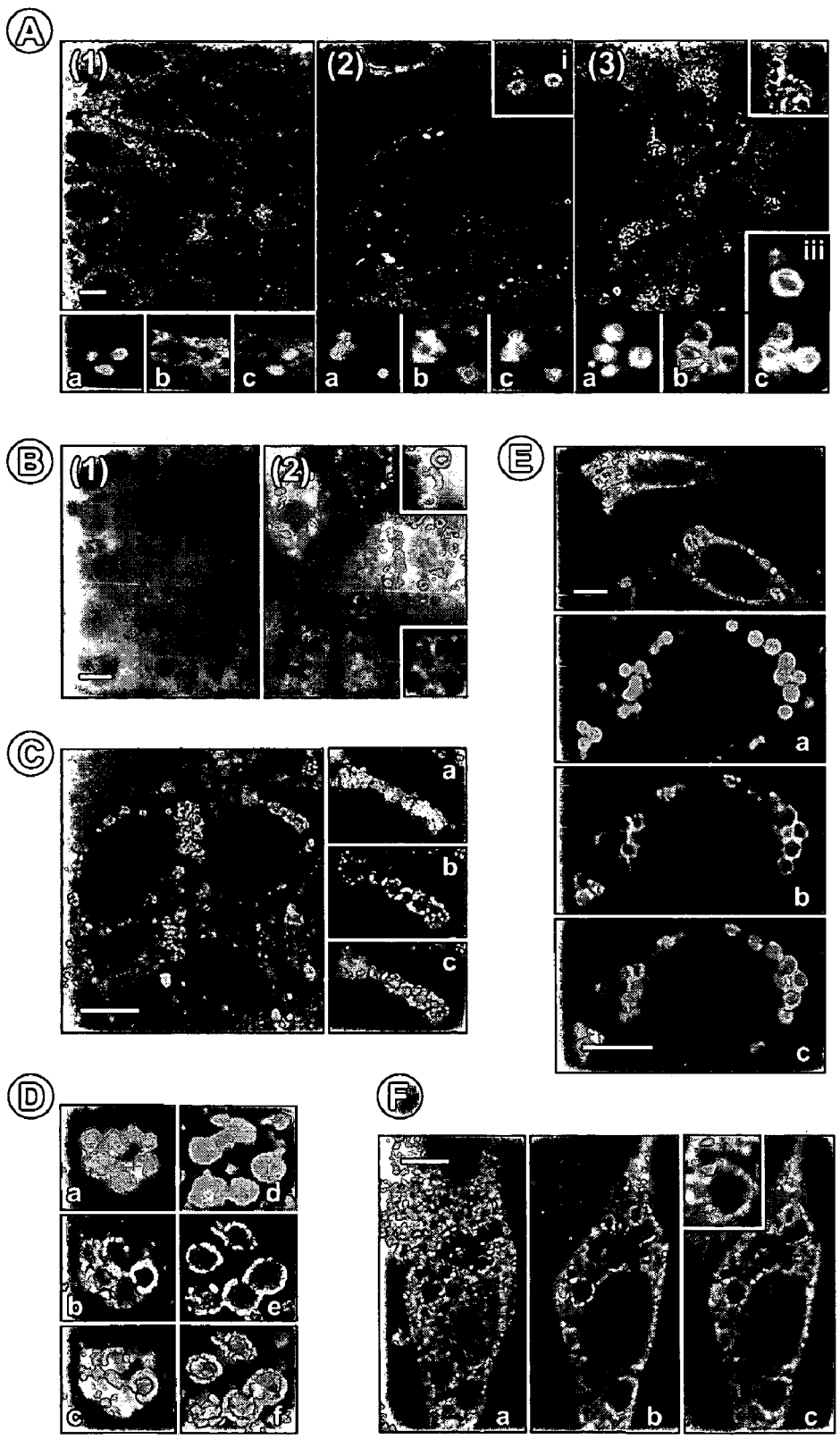
FIG. 3 is a photographic representation showing that insulin and oleate promote translocation of IMPDH to lipid bodies. Panel (A): CHO.IR cells were untreated (1) or treated with insulin for 15 min (2) or oleate for 48 h (3). Cells were fixed, labelled with anti-IMPDH antibodies, and analysed by confocal microscopy. Insets in upper panels (i and ii) show magnified images of IMPDH in spherical structures, following insulin or oleate treatment. Lower panels show staining of lipid bodies (Nile red-a), IMPDH (b) and corresponding merged images (c). The inset (iii) shows two lipid bodies, with prominent IMPDH co-localisation apparent only on the lower lipid body. Panel (B): 3T3-L1 adipocytes (day 7) were untreated (1) or treated with insulin for 15 min (2). Cells were then fixed, immunostained with anti-IMPDH antibodies, and analysed by confocal microscopy. Insets show magnified images of IMPDH in spherical structures, following insulin treatment. Panel (C): Images show IMPDH associated with lipid bodies in cells lacking intermediate filaments (Vim$^{−/−}$) following oleate treatment for 24 h. Additional panels show single and merged images as in A. Panel (D): Images show association of IMPDH (a—Nile red, b—IMPDH and c—merged) and adipophilin (d—Nile red, e—adipophilin and f—merged) with lipid bodies in primary rat hepatocytes. Panel (E): CHO.IR cells were transfected with HA-IMPDH type II and treated with oleate for 24 h. Cells were fixed and immunostained with anti-HA antibodies (green) and Nile red (red). The panels below show staining of lipid bodies (Nile red-a), HA-IMPDH (b) and corresponding merged images (c). Panel (F): CHO.IR cells were transfected with HA-IMPDH type I and treated with oleate. Images show localisation of PDI (a) and HA-IMPDH (b) and a merged image (c) with inset showing a magnified view. Scale bars represent 5 μm throughout. Images are representative of at least two independent experiments.

Indirect immunofluorescence microscopy was then employed to determine the localisation of the protein in intact cells in the hope that this might increase the resolution of any changes in IMPDH distribution with insulin. In CHO.IR cells, IMPDH showed a punctate cytosolic staining pattern (FIG. 3A—panel 1). Upon insulin treatment labelling of ring like structures of 0.5 to 2 μm diameter was observed, scattered throughout the cytoplasm (FIG. 3A—panel 2). Insulin promoted a similar redistribution of IMPDH in 3T3-L1 adipocytes (FIG. 3B). This staining resembled the characteristic spherical staining pattern common to a group of proteins that associate with lipid bodies (11-14, 25-27). Treatment of CHO.IR cells with oleic acid for 24-48 h increased the size and number of lipid bodies, as determined by Nile red which stains the neutral lipid core of the lipid bodies (FIG. 3A—Lower panels, a & data not shown), and was also sufficient to promote translocation of IMPDH to these organelles (FIG. 3A—panel 3). However, recruitment of IMPDH to all lipid bodies was not observed (FIG. 3A—inset panel iii), which raises the possibility that IMPDH is only recruited to a subset of these structures. The inventor has observed redistribution of IMPDH to lipid bodies in all cell-types examined to date. In addition to CHO.IR cells and 3T3-L1 adipocytes, these include 3T3-L1 fibroblasts (data not shown) as well as fibroblasts derived from vimentin knockout mice (FIG. 3C). As these cells lack intermediate filaments (28), which form a cage like structure around lipid bodies, this observation suggests that intermediate filaments are not essential for the association of IMPDH with lipid bodies. Translocation of IMPDH to lipid bodies in HepG2 cells (data not shown) and primary rat hepatocytes (FIG. 3D) was also observed. Labelling of IMPDH associated with lipid bodies typically resembled that observed for adipophilin, a marker for lipid bodies (FIG. 3D).

Both IMPDH isoforms were found to redistribute to lipid bodies upon insulin or oleate treatment, in transfected cells expressing either HA-IMPDH type I or type II (FIG. 3E & data not shown). Whilst a greater proportion of lipid bodies staining positive for IMPDH was typically observed in cells overexpressing HA-IMPDH type I or type II, there was no obvious difference in the number or size of lipid bodies compared with those in control cells.

Biogenesis of lipid bodies occurs at specialised sites on the endoplasmic reticulum (ER) (10). To determine whether IMPDH is localised to lipid bodies at the ER, the inventor performed double labelling confocal microscopy of HA-IMPDH type I expressing cells treated with oleate (FIG. 3F). In this study, IMPDH and Protein disulphide Isomerase (PDI), a marker for the ER, were found to be localised on the same lipid bodies although very little, if any, co-localisation was apparent (FIG. 3F). The absence of any obvious overlap between PDI and IMPDH indicates that IMPDH is not an ER associated protein.

Example 3

Translocation of IMPDH to Lipid Bodies is Dependent on PI 3-Kinase

Figure 4:
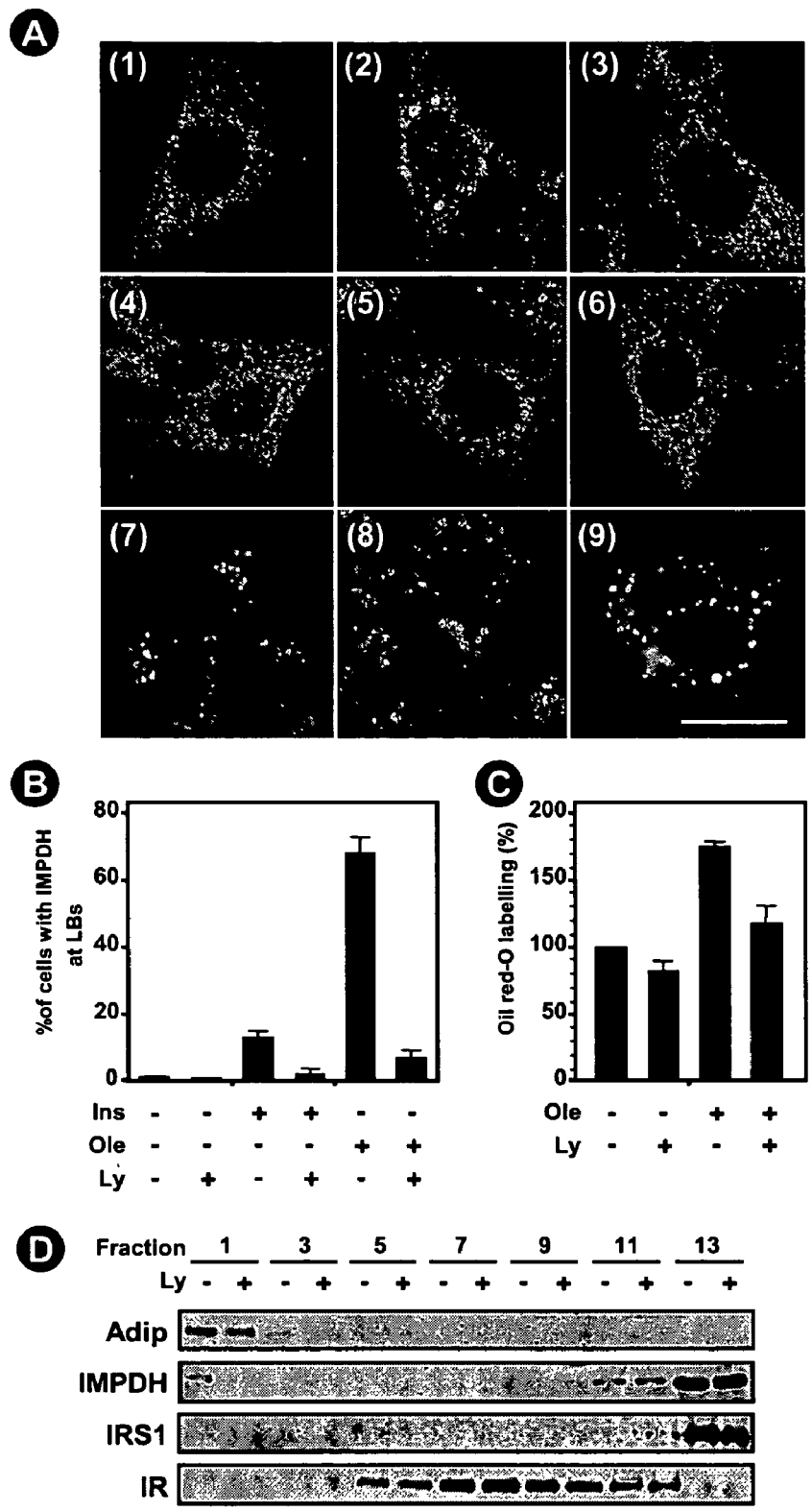
FIG. 4 consists of photographic and graphical representations showing that PI 3-kinase is required for IMPDH translocation and association with lipid bodies. Panel (A): CHO.IR cells were treated as follows: Control—1 & 7; Insulin (15 min)—2; Ly+Insulin (15 min)—3; Ly—4; Oleate (5 h)—5 & 8; Ly+Oleate (5 h)—6 & 9. Confocal images show the distribution of IMPDH (panels 1-6) or adipophilin (panels 7-9). Scale bar represents 10 μm. Panel (B): Quantitation of images from Panel A. The percentage of cells showing IMPDH association with lipid bodies was determined for at least 100 cells in each condition (Cells were counted in a blinded manner). Data are from two independent experiments. Error bars represent sd. Panel (C): CHO.IR cells were treated with Oleate and/or Ly for 5 h as indicated. Cells were fixed and stained with the lipid dye Oil red-O prior to lipid extraction and quantitation of lipid accumulation by measurement of Oil red-O labelling at $A_{492nm}$. Data are from four independent experiments. Error bars represent standard error of the mean (sem) (p=0.005−Ole vs Ly/Ole-using students t-test). Panel (D): CHO.IR cells were treated with oleate in the absence (−) or presence (+) of Ly for 24 h. The post nuclear supernatant was subjected to flotation analysis by centrifugation. Fractions (162 μL) were collected from the top (fraction 1) to the bottom (fraction 14) of the gradient. distribution of adipophilin (Adip), IMPDH, IRS-1 and the insulin receptor (IR) was determined by immunoblotting of equal volumes from fractions as indicated. Results are representative of three separate experiments.

Next, the inventor investigated a putative role for PI 3-kinase in insulin- or oleate-stimulated translocation of IMPDH to lipid bodies. Pre-treatment of CHO.IR cells with LY294002 (which is a more stable PI 3-kinase inhibitor than wortmannin) blocked insulin- or oleate-stimulated translocation of IMPDH suggesting a common PI 3-kinase-dependent mechanism (FIGS. 4A & B). Localisation of adipophilin to lipid bodies was apparent in all cells, irrespective of treatment (FIG. 4A). Inhibition of PI 3-kinase reduced oleate-induced lipid accumulation by approximately 50%, as determined by quantification of Oil red-O staining (FIG. 4C).

To assess the apparent association of IMPDH with lipid bodies biochemically, the flotation of IMPDH was examined in sucrose. Post-nuclear supernatants of CHO.IR cell homogenates were loaded at the bottom of a sucrose gradient and centrifuged for 16 h prior to removal and analysis of gradient fractions. In the absence of oleate treatment the inventor was unable to detect any proteins, including adipophilin, in the fractions from the top of the gradient (corresponding to lipid body containing fractions-data not shown). After induction of lipid bodies by treatment with oleate for 24 h, which also promotes increased expression of adipophilin (29), expression of adipophilin was detected and this was restricted to the buoyant fraction at the top of the gradient (FIG. 4D). Consistent with the immunofluorescence data, a small but reproducible translocation of IMPDH to the lipid body containing fraction was observed (FIG. 4D). The presence of IMPDH in this fraction is not likely due to contamination as other non-lipid body associated proteins such as the insulin receptor or IRS-1 were excluded from the top of the gradient (FIG. 4D). Inhibition of PI 3-kinase did not prevent the appearance of adipophilin in the buoyant fraction; although adipophilin levels were consistently reduced in cells treated simultaneously with LY294002 and oleate (FIG. 4D). In contrast, oleate-induced redistribution of IMPDH to fraction 1 was blocked by inhibition of PI 3-kinase (FIG. 4D). The absolute amount of IMPDH recovered in the buoyant fraction was quite small however this may be due to dissociation from lipid bodies during the isolation procedure. Consistent with this, IMPDH was not identified in two recent proteomic analyses of lipid body associated proteins isolated from CHO cells or human carcinoma A431 cells (30, 31).

Example 4

Oleate Induced Translocation of IMPDH is Independent of Phosphorylation

Figure 5:
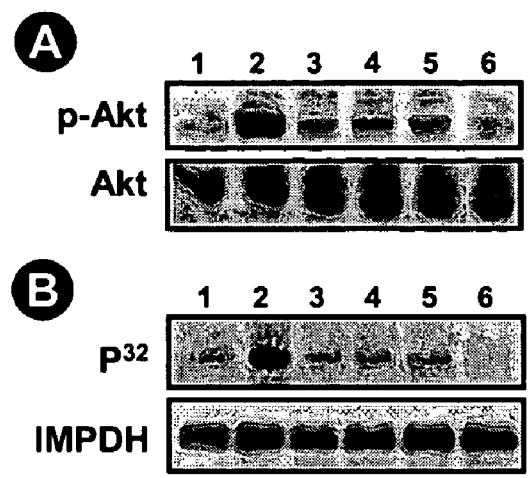
FIG. 5 is a photographic representation showing that oleate does not stimulate phosphorylation of IMPDH. Panel (A): CHO.IR cells were treated as follows: Control—1; Insulin, 15 min—2; Oleate, 5 min—3; 15 min—4; 60 min—5; 20 h—6, then harvested and subjected to immunoblotting with anti-phospho Akt (Ser$^{473}$) or Akt as indicated. Panel (B): CHO.IR cells were labelled with $^{32}$P for 16 h and treated as follows: Control—1; Insulin, 15 min—2; Oleate, 15 min—3; 60 min—4; 16 h—5; Ly+Oleate 16 h—6. IMPDH was immunoprecipitated from cell lysates and immunoprecipitates analysed by SDS-PAGE and autoradiography ($^{32}$P) and immunoblotting (IMPDH).

In view of the PI 3-kinase dependence of oleate-induced translocation of IMPDH to lipid bodies, the inventor examined the ability of oleate to stimulate PI 3-kinase activity, using Akt phosphorylation as an indirect readout of PI 3-kinase activity. Akt phosphorylation was increased after 15 min incubation with oleate and this effect was inhibited by the PI 3-kinase inhibitor LY294002 (FIG. 5A & data not shown). This effect of oleic acid was transient, with Akt phosphorylation returning to basal levels after 20 h of treatment. A similar effect was observed in 3T3-L1 adipocytes (data not shown). These data are consistent with the rapid, two-fold activation of PI 3-kinase observed in response to oleate treatment of MDA-MB-231 cells (32). In contrast to Akt the inventor could find no evidence of phosphorylation of IMPDH following oleic acid treatment (FIG. 5B). Oleate failed to promote detectable IMPDH phosphorylation at early time points (15 min), when oleate-induced Akt phosphorylation was maximal, or after more chronic exposure (16 h). Taken together these observations suggest that IMPDH phosphorylation may not be essential for translocation of IMPDH to lipid bodies, at least in response to stimulation with certain agonists.

Discussion of Examples 1-4

In the current study, IMPDH was identified as a novel target of the insulin signal transduction cascade and a lipid body associated protein. Insulin promotes phosphorylation and translocation of IMPDH to lipid bodies. Treatment of cells with the fatty acid oleate also promotes translocation of IMPDH to lipid bodies and inhibition of oleate-induced IMPDH translocation correlates with reduced lipid accumulation. These observations are consistent with a role for IMPDH enzyme in lipid body metabolism.

IMPDH catalyses a key step in the synthesis of guanine nucleotides, at a branch point in the pathway for purine nucleotide biosynthesis. IMPDH is a key regulator of the production and balance of GTP and ATP and is subject to feedback inhibition by GMP. In contrast to current understanding of its biochemistry (7), there is a paucity of knowledge regarding the cell biological properties of IMPDH.

Using both morphological and biochemical approaches, the inventor was able to show that insulin or oleic acid promoted a redistribution of IMPDH to lipid bodies. Insulin- or oleate-induced translocation was blocked by inhibition of PI 3-kinase, as was insulin-stimulated IMPDH phosphorylation. However, the inventor could find no evidence of oleic acid-induced phosphorylation of IMPDH. This observation raises the possibility that phosphorylation and translocation of IMPDH may not be coupled events and contrasts with the recent description of oleic acid-induced phosphorylation of the phosphoinositide-transfer protein (PI-TP) Nir2 (17). Oleate-stimulated phosphorylation of Nir2 was found to be both necessary and sufficient to promote translocation of Nir2 to lipid bodies, although a putative role for PI 3-kinase was not examined in these studies (17). Given the lack of a detectable effect of oleate on IMPDH phosphorylation the inventor considers that phosphorylation of IMPDH in response to insulin may constitute another level of regulation.

Insulin promotes an increase in intracellular lipids by regulation of multiple events (1). Treatment of cells with oleic acid also increases synthesis and storage of TAGs in lipid bodies. Thus, the translocation of IMPDH to lipid bodies occurs during periods of increased synthesis of TAGs and lipid bodies, both of which are synthesised at the ER by processes which are poorly understood (10). The current model suggests neutral lipids accumulate within specific microdomains of the ER membrane forcing the monolayers apart until the lipid body eventually buds off into the cytoplasm, surrounded by an ER derived phospholipid monolayer (20). A constitutive cycle of lipid body formation and turnover, also occurring at the ER, may occur at low levels in most cells and this cycle may be upregulated in response to extracellular factors (10). Such a cycle may explain the appearance of lipid bodies as both independent structures and continuations of the ER (33). By confocal microscopy it was observed that IMPDH may be recruited to only a subset of lipid bodies. IMPDH was also found to be present on the same lipid bodies as PDI, although there was no evidence for localisation of IMPDH to the ER. Taken together these observations suggest that IMPDH may be recruited to lipid bodies that are involved in dynamic reorganisation at the ER. One possibility is that IMPDH is involved in the biogenesis of nascent lipid bodies at the ER or an alternative explanation is that IMPDH is recruited to those lipid bodies that are undergoing turnover at the ER. In support of the former, inhibition of translocation of IMPDH to lipid bodies correlated with decreased lipid accumulation. Either way, recruitment of IMPDH to these sites would be expected to produce a localised increase in the concentration of XMP (GTP) and NADH (redox potential).

Recently, it was reported that the fatty acid composition of the phospholipid monolayer of lipid bodies differs from that of the ER bilayer, leading to the suggestion that the monolayer of lipid bodies represents a highly differentiated membrane and that targeting of phospholipids and esters to discrete areas of the ER may involve lipid body associated proteins (33). Hence Nir2 may be required for the efficient biogenesis or turnover of the phospholipid monolayer during periods of increased lipid body synthesis or dynamics (17). Whilst it has been reported that overexpression of adipophilin was sufficient to increase lipid body formation (34) overexpression of IMPDH, like Nir2 (17) or caveolin (35), did not appear to affect lipid body size or lipid body number suggesting that these proteins may play a more subtle role in lipid body dynamics.

Current understanding of the roles that lipid bodies play in cells is still far from comprehensive. In addition to facilitating storage of intracellular lipid, lipid bodies are thought to serve important roles in various aspects of lipid trafficking including transport of lipid intermediates and lipid membrane components as well as specialised roles in certain cell types (10, 36). For example, lipid bodies appear to play an important role in the process of lipid trafficking in the retina (37) and this is thought to be critical for viability of the photoreceptors, especially the rods (38). Mutations in IMPDH type I, which are not predicted to interfere with IMPDH activity (8, 9, 39), cause the RP10 form of the degenerative retinal disorder adRP (8, 9), a condition characterised by degeneration of the rods (40). One possibility is that IMPDH, like Nir2 (41), may be required for efficient membrane turnover in rods, through its association with lipid bodies, and that mutant forms of IMPDH may be defective in this process.

A role for lipid bodies in common metabolic disorders has been suggested, with increased numbers of lipid bodies or "ectopic fat" found in skeletal muscle or liver from insulin resistant patients with obesity and type 2 diabetes (42, 43). In the present study, the inventor has identified IMPDH as a novel lipid body associated protein. IMPDH translocates to lipid bodies in response to insulin or oleate in a PI 3-kinase dependent manner and inhibition of this process correlates with reduced lipid accumulation. Based on these observations, the inventor proposes that alterations in lipid body dynamics, possibly biogenesis, may be facilitated at least in part by the actions of IMPDH.

Example 5

PDGF Stimulates Phosphorylation of IMPDH

Figure 6:
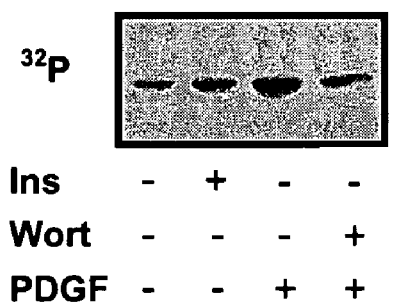
FIG. 6 is a photographic representation showing that PDGF stimulates phosphorylation of IMPDH. 3T3-L1 fibroblasts were labelled with $^{32}$P and pretreated with wortmannin (100 nM—25 min) then treated with insulin (1 μM—15 min) or PDGF (50 ng/mL—15 min) as indicated. IMPDH was immunoprecipitated from cell lysates and immunoprecipitates analysed by SDS-PAGE and autoradiography ($^{32}$P).

Platelet Derived Growth Factor (PDGF) stimulated IMPDH phosphorylation in 3T3-L1 fibroblasts and this was also dependent upon PI 3-kinase activation (FIG. 6). This indicates that the PI 3-kinase dependent phosphorylation of IMPDH is not specific to insulin, but may represent a common effect of agonists that are able to promote robust activation of PI 3-kinase. PDGF has recently been shown to promote increased synthesis of membrane lipids, and this also occurs through a PI 3-kinase dependent pathway (51).

Example 6

IMPDH Protein Levels are Transiently Increased During Adipogenesis

Figure 7:
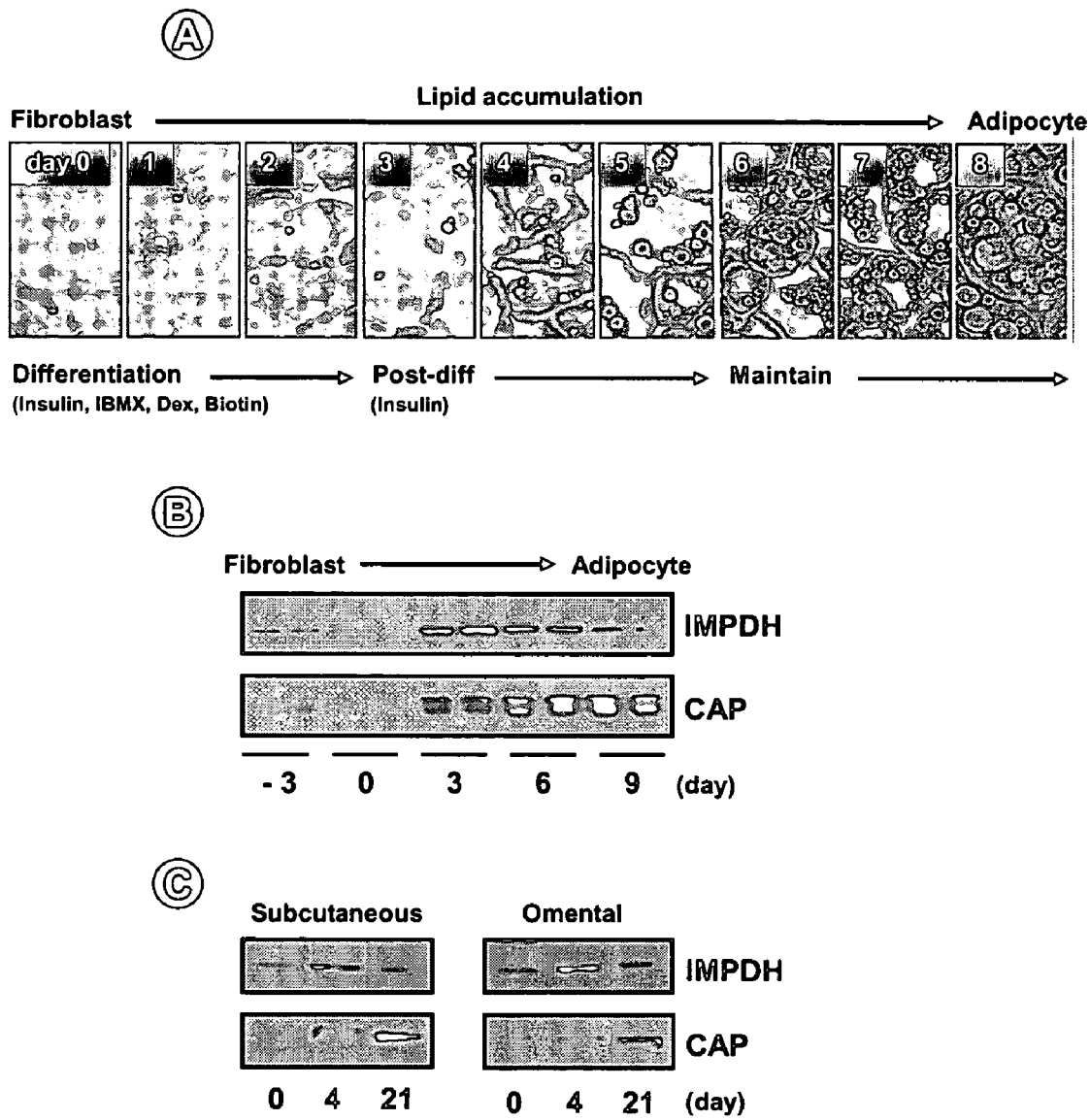
FIG. 7 is a photographic representation showing expression of IMPDH during adipogenesis. (A) 3T3-L1 preadipocytes were induced to differentiate (day 0) into mature adipocytes and images were captured on the days indicated. The differentiation protocol is indicated below, showing the periods of differentiation (days 0-3), post-differentiation (3-6) and maintenance (6-9). (B) 3T3-L1 cells and (C) primary human preadipocytes were harvested on the days indicated and analysed by immunoblotting for IMPDH or CAP (a marker of differentiation). In 3T3-L1 cells IMPDH expression peaks between days 3 to 6. A similar trend is observed upon differentiation of primary human preadipocytes, with IMPDH showing a transient, 5- to 10-fold, increase in expression during differentiation. Data are representative of at least 4 independent experiments.

IMPDH protein expression was examined during differentiation of the murine 3T3-L1 cell line, which is arguably the best characterised model of adipogenesis. IMPDH expression was increased markedly and transiently during differentiation of the 3T3-L1 cells (FIG. 7B). The period of maximal IMPDH expression correlated with the period of maximal lipid body formation (days 3-6) (FIGS. 7A & B). A recently described in vitro model of primary human preadipocyte adipogenesis was also employed, which is dependent on continued culture in the presence of FGF-1 for efficient differentiation (52). In cells differentiated in the presence of FGF-1 we observed a transient increase in IMPDH expression comparable to that seen in the 3T3-L1 cell line (FIG. 7D). In the absence of FGF-1 treatment, cells failed to differentiate with high efficiency (typically attaining only 20% differentiation by morphological analysis) and changes in IMPDH expression were modest (data not shown). Thus, increase in IMPDH expression appears to correlate with the efficient in vitro differentiation of the murine 3T3-L1 cell line and primary human preadipocytes.

Example 7

IMPDH Activity is Required for Adipogenesis

Figure 8:
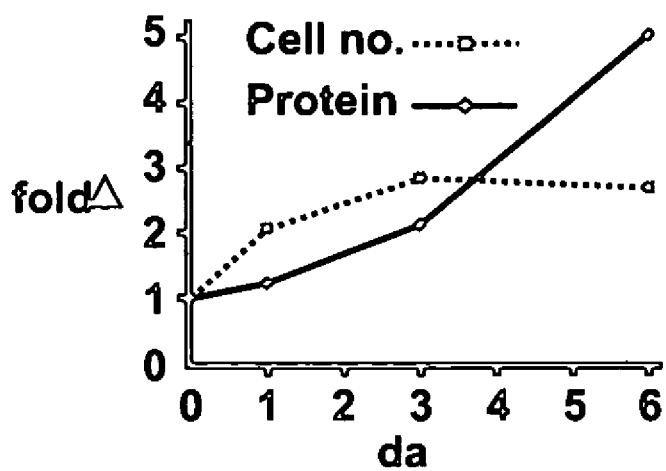
FIG. 8 is a graphical representation showing clonal expansion and protein accumulation during adipogenesis of 3T3-
Figure 8:
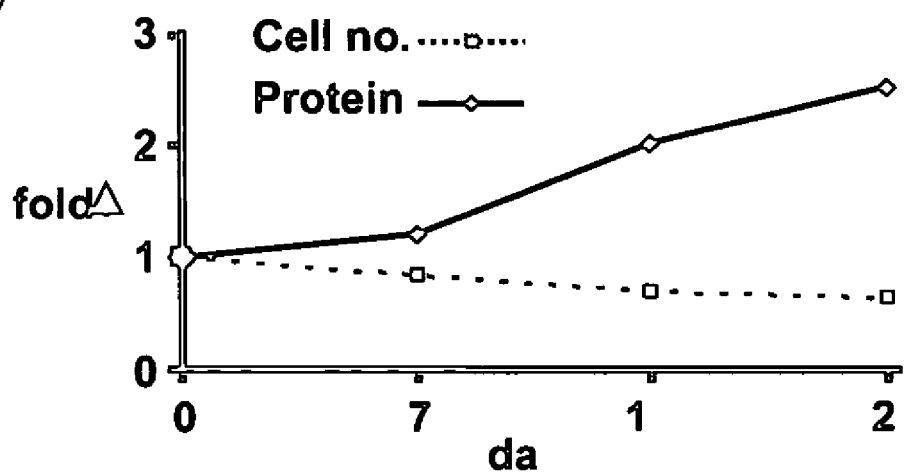

During adipogenesis of 3T3-L1 cells or primary human preadipocytes neutral lipids accumulate over 100-fold (via de novo lipid synthesis in our in vitro system of human preadipocyte differentiation) and proteins increase 3- to 5-fold (FIG. 8A). 3T3-L1 cells also go through one to two rounds of cell division during differentiation (FIG. 8A), a process termed mitotic clonal expansion. In contrast, primary human preadipocytes do not proliferate during adipogenesis in vitro (FIG. 8B) (53).

Having shown that IMPDH expression increases transiently during adipogenesis the inventor examined the requirement for IMPDH activity during differentiation. Inhibition of IMPDH, using the specific inhibitor mycophenolic acid (MPA—1 µM), for the first 6 days of differentiation inhibited lipid accumulation (determined morphologically—FIG. 9A) and differentiation (determined by measuring G3PDH activity and protein levels—FIG. 9B) in a dose dependent fashion ($IC_{50} \approx 0.1$-$0.2$ µM).

In order to determine the mechanism by which inhibition of IMPDH blocks adipogenesis the inventor characterised various markers of adipogenesis during differentiation of the 3T3-L1 cells treated with MPA for various periods. MPA treatment for the first 3 days of differentiation blocked clonal expansion (FIG. 10A). MPA appeared to act by promoting cell arrest, as removal of MPA after the first 3 days of differentiation resulted in clonal expansion and an increase in cell number similar to that seen in differentiated cells was observed. Various lines of evidence suggest the cells are "primed" during this early differentiation period in the presence of MPA. First, induction of expression of the adipogenic transcription factors CEBPβ and PPARγ, but not CEBPα, was apparent (FIG. 10B). Second, exposure of cells to insulin from day 3-6, recapitulating the post-differentiation period, failed to elicit an increase in cell number and clonal expansion (data not shown) unless cells had been primed by prior treatment with the differentiation cocktail in the presence of MPA. Morphological and biochemical analysis indicated that treatment of cells with MPA for the first 3 days of differentiation (0-3) or the second 3 days of differentiation (3-6) reduced lipid accumulation and G3PDH activity but treatment with MPA for 6 days (0-6) was required to block differentiation completely (FIG. 10C).

Example 8

Guanosine Supplementation Reverses the Inhibitory Effects of MPA

In order to confirm the specificity of the effects of MPA on adipogenesis the inventor supplemented cells with guanosine, which serves as a substrate for the salvage pathway of guanine nucleotide biosynthesis, circumventing the requirement for the IMPDH dependent de novo pathway. Treatment of 3T3-L1 cells with 60 µM guanosine restored lipid accumulation (FIG. 11A) and differentiation, as determined by G3PDH activity—FIG. 11B. Surprisingly, treatment with 300 µM guanosine alone inhibited lipid accumulation and adipogenesis, although this was still able to reverse the effects of MPA treatment to some extent (FIGS. 11A & B). Co-treatment with 60 µM guanosine also reversed the inhibition of proliferation by MPA (FIG. 11C). MPA treatment of cells promoted an increase in IMPDH expression and this was prevented by co-treatment with guanosine (FIG. 11D) providing further evidence that MPA inhibits adipogenesis through inhibition of IMPDH.

Example 9

IMPDH is Required for Adipogenesis of Primary Human Adipocytes

Similar experiments were performed as those described above in primary human adipocytes. Treatment of primary human cells with MPA reduced lipid accumulation and expression of G3PDH activity (FIGS. 12A & B). Unlike 3T3-L1 cells, treatment with 60 µM guanosine also inhibited differentiation (FIG. 12B). This latter observation suggests that primary human preadipocytes may be more sensitive to perturbation of intracellular guanine levels than the 3T3-L1 cells. It is also noteworthy that as adipogenesis of primary human preadipocytes does not involve cell proliferation these inhibitory effects are independent of clonal expansion.

Materials and Methods

Reagents and Antibodies

Reagents were from Sigma unless specified otherwise. Tissue culture media and Lipofectamine were from Invitrogen Life Technologies Inc. (Victoria, Australia). Foetal calf serum was from Trace Biosciences (Clayton, Australia). Insulin and C2-ceramide were from Calbiochem (La Jolla, Calif.). $^{32}P_i$ was from ICN (NSW, Australia). Monoclonal IMPDH antibody, raised against purified Chinese hamster IMPDH protein, has been described previously (45). Monoclonal and polyclonal anti-influenza hemagluttinin (HA) antibodies were from Babco (Richmond, Calif.) and Sigma. Polyclonal IR and IRS-1 antibodies were from Santa Cruz Biotechnology (Santa Cruz, Calif.). Polyclonal phospho Akt (Ser$^{473}$) and pan Akt antibodies were from Upstate Biotechnology (Lake Placid, N.Y.) and Cell Signaling Technology (Beverly, Mass.). Monoclonal PDI and adipophilin antibodies were from Affinity Bioreagents (Golden, Colo.) and Progen (Heidelberg, Germany). Monoclonal tubulin antibody was from Sigma. Polyclonal CEBPα and CEBPβ antibodies were from Santa Cruz (CA, USA). Polyclonal PPARγ antibody was from Cell Signaling Technology (Beverly, Mass.). Peroxidase-coupled secondary-antibodies were from Amersham Pharmacia Biotech (Little Chalfont, UK). Alexa 488- and 594-conjugated secondary-antibodies were from Molecular Probes (Eugene, Oreg.). Protein concentration was determined using the Pierce BCA protein assay (Rockford, Ill.). Protein G-agarose was from Pierce. Sequence encoding a HA-epitope tag was inserted at the 5' end of the human IMPDH type I or type II cDNA by PCR. Following sequence confirmation, HA-IMPDH type I or type II cDNAs were inserted into pcDNA 3.1+, downstream of the CMV promoter.

Cell Culture, Transfection and Treatment

3T3-L1 cells, CHO.IR cells (46) and fibroblast cells derived from vimentin null (Vim$^{-/-}$) mice were cultured as described (28, 47). Human preadipocytes were cultured and differentiated as described (47). Transfections were performed using Lipofectamine. Cells were serum starved for at least 2 h before treatment with insulin (1 μM, 15 min) or pre-treatment with wortmannin (100 nM, 25 min), LY294002 (50 μM, 10 min) or C2-ceramide (100 μM, 2 h) followed by insulin or oleate. To induce lipid body accumulation cells were cultured in regular growth medium supplemented with 200 μM oleate complexed to fatty acid free bovine serum albumin (BSA) in a 6:1 molar ratio. Mycophenolic acid (MPA) was dissolved in methanol to give a stock solution of 30 mM. This was further diluted in methanol, prior to direct addition to the culture media such that the final concentration of methanol was always 0.1%. Guanosine was dissolved in DMSO to give a stock solution of 100 mM. This was further diluted in DMSO, prior to direct addition to the culture media such that the final concentration of DMSO was always 0.33%. Media was refreshed, with addition of fresh MPA, guanosine, or vehicle, every 3 days as appropriate.

Subcellular Fractionation

Subcellular fractionation was performed as previously described (24, 47). In brief, cells were rinsed twice in ice-cold HES buffer (20 mM HEPES, pH 7.4, 1 mM EDTA, 250 mM sucrose) and homogenised in the same buffer supplemented with phosphatase and protease inhibitors. Subcellular fractions were isolated by differential centrifugation. After a clearing spin of 2,000×g for 10 min, lysates were centrifuged at 18,000×g for 20 min to pellet the crude PM fraction. This pellet was resuspended in HES buffer with inhibitors and centrifuged again at 2,000×g for 10 min to remove contaminating material. The supernatant from this spin was centrifuged again at 18,000×g for 20 min to pellet the PM fraction. The supernatant from the first 18,000×g spin was centrifuged at 170,000×g for 75 min to generate the High speed pellet (HSP) and the supernatant (Cytosol).

Radiolabelling Studies

Radiolabelling and subcellular fractionation of cells followed by 2-DE and liquid chromatography/tandem mass spectrometry were essentially performed as described (2, 48). For immunoprecipitation studies, following appropriate treatment, cells were harvested in lysis buffer (50 mM HEPES (pH 7.4), 150 mM NaCl, 1% Triton-X-100, 1 mM $Na_3VO_4$, 30 mM NaF, 10 mM $Na_4P_2O_7$, 10 mM EDTA, 1 μg/mL aprotinin, 1 μg/ml leupeptin, 2 mM PMSF) and clarified by centrifugation (2,000×g for 10 min). Supernatants were incubated with 2-5 μg of anti-IMPDH or anti-HA antibody and protein G-agarose for 2-4 h at 4° C. Immunecomplexes were washed in lysis buffer and resuspended in Laemmli sample buffer containing 100 mM DTT. Samples were subjected to SDS-PAGE and analysed by immunoblotting and autoradiography. Phospho amino acid analysis was performed using standard techniques.

Measurement of IMPDH Activity

The IMPDH activity assay was based on that described (49). Cells were harvested on ice in assay buffer (100 mM Tris (pH 8), 100 mM KCl, 3 mM EDTA, 1 mM DTT, 30 mM NaF, 10 mM $Na_4P_2O_7$, 1 μg/mL aprotinin, 1 μg/mL leupeptin, 1 mM PMSF), homogenised by 15 passes through a 22 G needle and clarified by centrifugation (2,000×g for 10 min). Samples (200 μL) were transferred to a 96-well plate (Corning Costar) and NAD and IMP added to a final concentration of 0.25 mM. Samples, in duplicate, were incubated at room temperature and the production of NADH was monitored by measuring the increase in $A_{340nm}$ ($\epsilon$=6.22×10$^3$ M$^{-1}$ cm$^{-1}$). Background for each sample was determined by performing an identical reaction in the presence of the IMPDH inhibitor mycophenolic acid or in the absence of IMP. Protein concentration was determined for each sample and activity was converted to μM/min/mg.

Fluorescence Microscopy and Cell Counting

Fluorescence microscopy was performed as described (50) except cells were fixed in 4% paraformaldehyde in PBS for 1 h before permeabilising in 0.1% saponin for 5 min. For lipid body staining cells were mounted on moviol containing Nile red (1:1,000 from a saturated stock solution in acetone). Cells were viewed using either a Leica DMR SP laser scanning confocal microscope or Bio-Rad Radiance 2000 confocal microscope. Scoring of cells exhibiting localisation of IMPDH at lipid bodies was performed in a blinded fashion, with at least 100 cells counted for each condition.

Oil Red-O Staining

The neutral lipid Oil red-O stain was used to determine lipid accumulation. Following incubation in the presence of 200 μM oleic acid-/+ LY294002 for 5-7 h, cells (in 24 well plates) were washed twice in PBS and fixed in 4% paraformaldehyde for 1 h. After rinsing in 60% isopropanol, cells were incubated in Oil red-O working solution for 15 min (stock Oil red-O solution was made by dissolving 0.74 g Oil red-O in 200 mL isopropanol, filtering and storing at 4° C.; working stock was made by adding 3 parts stock to 2 parts water and filtering just prior to use). Cells were rinsed three times in water and lipids were extracted by incubation in 100% isopropanol for 15 min. Quantification of lipids was determined by measuring Oil red-O staining at $A_{492nm}$. Protein concentration was determined in parallel and values were normalised to protein. Values are presented as percentage of control, set at 100% for each experiment.

Sucrose Gradient Flotation Analysis

Sucrose gradient analysis was based on the method described by Pol et al. (16). Following incubation in the presence of 200 μM oleic acid–/+ LY294002 for 24 h, cells (in 10 cm dishes) were scraped into 150 μL of homogenisation buffer (50 mM HEPES-KOH (pH 7.4), 50 mM KCl, 10 mM EGTA, 1.92 mM $MgCl_2$, 10 mM NaF, 1 mM $Na_4P_2O_7$, 2 mM $Na_3VO_4$, 1 μg/mL aprotinin, 1 μg/mL leupeptin, 1 mM PMSF), homogenised by gentle sonication (2×5 sec) followed by 15 passes through a 22 G needle. After clarification by centrifugation at 2,000 g for 10 min the supernatant was made up to a final volume of 400 μL and 40% sucrose and loaded on top of a 200 μL cushion of 50% sucrose at the bottom of a S55-S tube. This was overlayed sequentially with 35-5% sucrose (5% increments, 7×230 μL steps) and centrifuged for 16 h at 50,000 rpm using a Sorvall S55-S rotor. Fractions (162 μL) were collected from the top of the gradient and analysed by immunoblotting equal volumes of each fraction.

Western Blotting

For western blotting, following appropriate treatment, cells were harvested in lysis buffer (50 mM HEPES (pH 7.4), 150 mM NaCl, 1% Triton-X-100, 1 mM $Na_3VO_4$, 30 mM NaF, 10 mM $Na_4P_2O_7$, 10 mM EDTA, 1 μg/ml aprotinin, 1 μg/ml leupeptin, 2 mM PMSF) and clarified by centrifugation (2,000×g for 10 min). Protein concentration was determined using the BCA assay. Equal protein was subjected to SDS-PAGE and immunoblotting and visualized by autoradiography (using enhanced chemiluminescence) or fluorescent analysis using the L1-Cor Odyssey system.

Measurement of Glycerol 3-Phosphate Dehydrogenase (G3PDH) Activity

Cells were washed in ice cold PBS (pH 7.4) and harvested in 1 ml of ice-cold 50 mM Tris (pH 7.5) containing 1 mM EDTA and 500 μM DTT. Cells were disrupted by sonication and centrifuged at 12000 g for 15 min at 4° C. Before assay, 5 μl of 100 mM DTT was added. The supernatant was then assayed for G3PDH activity in a final concentration of 100 mM triethanolamine-HCl (pH 7.5), 2.5 mM EDTA, 0.24 mM NADH, 50 μM DTT and 0.4 mM dihydroxyacetone phosphate (DAP). The reaction was initiated by addition of DAP and the rate of change in $A_{340}$ was measured using a FLU-Ostar Optimem spectrophotometer (BMG labtech, Victoria Australia). Each of three culture wells was assayed in duplicate with a reagent blank containing distilled water instead of substrate (DAP). An aliquot of the supernatant was assayed to determine protein concentration.

Measurement of Cell Number Using Syto60

Essentially Syto60 staining was used to determine cell number following the manufacturers protocol. In brief, cells (in a 24 well plate) were fixed in 4% formaldehyde (made up in PBS) for 20 min and washed 3 times 10 min with 0.1% Triton X-100/PBS with gentle shaking to permeabilise. Permeabilised cells were incubated with 200 μl of blocking buffer (1:1 LI-COR Odyssey Blocking Buffer:PBS) per well for 1 h with moderate shaking. Blocked cells were then incubated in blocking buffer containing Syto60 (1/10,000 dilution) and DAPI (4' 6-diamidino-2-phenylindole, 1/500 dilution) for 45 min (in the dark) with gentle shaking. Cells were washed 3 times 10 min in PBS containing 0.1% Tween-20 with gentle shaking. Finally, wells were aspirated and Syto60 staining was detected and quantitated using the LI-COR Odyssey Infrared Imaging System. DAPI was detected by fluorescence microscopy and was used to validate the Syto60 data in preliminary experiments.

The disclosure of every patent, patent application, and publication cited herein is hereby incorporated herein by reference in its entirety.

The citation of any reference herein should not be construed as an admission that such reference is available as "Prior Art" to the instant application.

Throughout the specification the aim has been to describe the preferred embodiments of the invention without limiting the invention to any one embodiment or specific collection of features. Those of skill in the art will therefore appreciate that, in light of the instant disclosure, various modifications and changes can be made in the particular embodiments exemplified without departing from the scope of the present invention. All such modifications and changes are intended to be included within the scope of the appended claims.

BIBLIOGRAPHY

1. Saltiel A R. Kahn C R. Insulin signalling and the regulation of glucose and lipid metabolism. Nature 2001; 414:799-806.
2. Hill M M, Connolly L M, Simpson R J, James D E. Differential Protein Phosphorylation in 3T3-L1 Adipocytes in Response to Insulin Versus Platelet-derived Growth Factor. No evidence for a phosphatidylinositide 3-kinase-independent pathway in insulin signaling. J Biol Chem 2000; 275:24313-24320.
3. Collart F R, Huberman E. Cloning and sequence analysis of the human and Chinese hamster inosine-5'-monophosphate dehydrogenase cDNAs. J Biol Chem 1988; 263: 15769-72.
4. Natsumeda Y, Obno S, Kawasaki H, Konno Y, Weber O, Suzuki K. Two distinct cDNAs for human IMP dehydrogenase. J Biol Chem 1990; 265:5292-5295.
5. Carr S F, Papp E, Wu J C, Natsumeda Y. Characterization of human type I and type II IMP dehydrogenases. J Biol Chem 1993; 268:27286-27290.
6. Jackson R C, Weber G, Morris H P. IMP dehydrogenase, an enzyme linked with proliferation and malignancy. Nature 1975; 256:331-333.
7. Sintchak M D, Nimmesgem E. The structure of inosine 5'-monophosphate dehydrogenase and the design of novel inhibitors. Immunopharmacology 2000; 47:163-184.
8. Bowne S J, Sullivan L S, Blanton S H, Cepko C L, Blackshaw S, Birch D G, Hughbanks-Wheaton D, Heckenlively J R. Daiger S P. Mutations in the inosine monophosphate dehydrogenase 1 gene (IMPDH1) cause the RP10 form of autosomal dominant retinitis pigmentosa. Hum Mol Genet 2002; 11:559-568.
9. Kennan A, Aherne A, Palfi A, Humphries M, McKee A, Stitt A, Simpson D A, Demtroder K, Omtoft T, Ayuso C, Kenna P F, Farrar G J, Humphries P. Identification of an IMPDH1 mutation in autosomal dominant retinitis pigmentosa (RP10) revealed following comparative microarray analysis of transcripts derived from retinas of wild-type and Rho(−/−) mice. Hum Mol Genet 2002; 11:547-557.
10. Murphy D J. The biogenesis and functions of lipid bodies in animals, plants and microorganisms. Prog Lipid Res 2001; 40:325-438.
11. Jiang H P, Serrero G. Isolation and characterization of a full-length cDNA coding for an adipose differentiation-related protein. Proc Natl Acad Sci USA 1992; 89:7856-7860.

12. Eisinger D P, Serrero G. Structure of the gene encoding mouse adipose differentiation-related protein (ADRP). Genomics 1993; 16:638-644.
13. Egan J, Greenberg A, Chang M, Londos C. Control of endogenous phosphorylation of the major cAMP-dependent protein kinase substrate in adipocytes by insulin and beta-adrenergic stimulation. J Biol Chem 1990; 265: 18769-18775.
14. Greenberg A, Egan J, Wek S, Garty N, Blanchette-Mackie E, Londos C. Perilipin, a major hormonally regulated adipocyte-specific phosphoprotein associated with the periphery of lipid storage droplets. J Biol Chem 1991; 266:11341-11346.
15. Londos C, Brasaemle D L, Schultz C J, Segrest J P, Kimmel A R. Perilipins, ADRP, and other proteins that associate with intracellular neutral lipid droplets in animal cells. Semin Cell Dev Biol 1999; 10:51-58.
16. Pol A, Martin S, Fernandez M A, Ferguson C, Carozzi A, Luetterforst R, Caries E, Parton R G. Dynamic and Regulated Association of Caveolin with Lipid Bodies: Modulation of Lipid Body Motility and Function by a Dominant Negative Mutant. Mel Biol Cell 2004; 15:99-110.
17. Litvak V, Shaul Y, Shulewitz M, Amarilio R, Carmon S, Lev S. Targeting of Nir2 to Lipid Droplets Is Regulated by a Specific Threonine Residue within Its PI-Transfer Domain. Curr Biol 2002; 12:1513-1518.
18. Wolins N E, Skinner J R. Schoenfish M J, Tzekov A, Bensch K G, Bickel P E. Adipocyte protein S3-12 coats nascent lipid droplets. J Bid Chem 2003; 278:37713-37721.
19. Liu P, Ying Y, Thao Y, Mundy D I, Zhu M, Anderson R G W. CHO K2 cell lipid droplets appear to be metabolic organelles involved in membrane traffic. J Biol Chem 2004; 279:3787-3792.
20. Brown D A. Lipid droplets: Proteins floating on a pool of fat. Curr Biol 2001; 11:R446-R449.
21. Summers S A, Garza L A, Zhou H, Bimbaum M J. Regulation of insulin-stimulated glucose transporter GLUT4 translocation and Akt kinase activity by ceramide. Mol Cell Biol 1998; 18:5457-5464.
22. Ingley E, Hemmings B A. PKB/Akt interacts with inosine-5' monophosphate dehydrogenase through its pleckstrin homology domain. FEBS Letters 2000; 478(3): 253-259.
23. Yaffe M B, Leparc G G, Lai J, Obata T, Volinia S, Cantley L C. A motif-based profile scanning approach for genome-wide prediction of signaling pathways. Nat Biotechnoi 2001; 19:348-353.
24. Clark S F, Martin S. Carozzi A J, Hill M M, James D E. Intracellular localization of phosphatidylinositide 3-kinase and insulin receptor substrate-1 in adipocytes: Potential involvement of a membrane skeleton. J Cell Biol 1998; 140:1211-1225.
25. Ostermeyer A G, Paci J M, Zeng Y, Lublin D M, Munro S, Brown D A. Accumulation of caveolin in the endoplasmic reticulum redirects the protein to lipid storage droplets. J Cell Biol 2001; 152:1071-1078.
26. Fujimoto T, Kogo H, Ishiguro K, Tauchi K, Nomura R. Caveolin-2 Is Targeted to Lipid Droplets, a New "Membrane Domain" in the Cell. J Cell Biol 2001; 152:1079-1086.
27. Pol A, Luetterforst R, Lindsay M, Heino S, Ikonen E, Parton R G. A caveolin dominant negative mutant associates with lipid bodies and induces intracellular cholesterol imbalance. J Cell Biol 2001; 152:1057-1070.
28. Holwell T A, Schweitzer S C, Evans R M. Tetracycline regulated expression of vimentin in fibroblasts derived from vimentin null mice. J Cell Sci 1997; 110:1947-1956.
29. Brasaemle D L, Barber T, Wolins N E, Serrero G, Blanchette-Mackie E J, Londos C. Adipose differentiation-related protein is an ubiquitously expressed lipid storage droplet-associated protein. J Lipid Res 1997; 38:2249-2263.
30. Liu P, Ying Y, Zhao Y, Mundy D I, Thu M, Anderson R G W. CHO K2 cell lipid droplets appear to be metabolic organelles involved in membrane traffic. J Bid Chem 2004; 279:3787-3792.
31. Umlauf E, Csaszar E, Moertelmaier M, Schuetz G, Parton R G, Prohaska R. Association of stomatin with lipid bodies. J Biol Chem 2004; 279:23699-23709
32. Hardy S, Langeiier Y, Prentki M. Oleate activates phosphatidylinositol 3-kinase and promotes proliferation and reduces apoptosis of MDA-MB-231 breast cancer cells, whereas palmitate has opposite effects. Cancer Res 2000; 60:6353-6358.
33. Tauchi-Sato K, Ozeki S, Houjou T, Taguchi R, Fujimoto T. The Surface of Lipid Droplets Is a Phospholipid Monolayer with a Unique Fatty Acid Composition. J Biol Chem 2002; 277:44507-44512.
34. Imamura M, Inoguchi T, Ikuyama S, Taniguchi S, Kobayashi K, Nakashima N, Nawata H. Adipose differentiation-related protein (ADRP) stimulates lipid accumulation and lipid droplet formation in murine fibroblasts. Am J Physiol Endocrinol Metab 2002; 283:E775-E783.
35. Ostermeyer A G, Ramcharan L T, Zeng Y, Lublin D M, Brown D A. Role of the hydrophobic domain in targeting caveolin-1 to lipid droplets. J Cell Bid 2004; 164:69-78.
36. Murphy D J, Vance J. Mechanisms of lipid-body formation. Trends Biochem Sci 1999; 24:109-115.
37. Imanishi Y, Batten M L, Piston D W, Baehr W, Palczewski K. Noninvasive two-photon imaging reveals retinyl ester storage structures in the eye. J. Cell Biol. 2004; 164:373-383.
38. Stone J, Maslim J, Valter-Kocsi K, Mervin K, Bowers F, Chu Y, Barnett N, Provis J, Lewis G, Fisher S K, Bisti S. Gargini C, Cervetto L, Menn S, Peer J. Mechanisms of photoreceptor death and survival in mammalian retina. Prog Retin Eye Res 1999; 18:689-735.
39. Hyle J W, Shaw R I, Reines D. Functional Distinctions between IMP Dehydrogenase Genes in Providing Mycophenolate Resistance and Guanine Prototrophy to Yeast. J Biol Chem 2003; 278:28470-28478.
40. Phelan J K, Bok D. A brief review of retinitis pigmentosa and the identified retinitis pigtnentosa genes. Mel Vis 2000; 6:116-124.
41. Tian D, Lev S. Cellular and developmental distribution of human homologues of the *Drosophilia* rdgB protein in the rat retina. Invest Ophthalmol Vis Sci 2002; 43:1946-1953.
42. Hwang J H, Pan J W, Heydari S, Hetherington H P, Stein D T. Regional differences in intramyocellular lipids in humans observed by in vivo 1H-MR spectroscopic imaging. J Appl Physiol 2001; 90:1267-1274.
43. Hakmnaki J M, Kauppinen R A. 1H NMR visible lipids in the life and death of cells. Trends in Biochemical Sciences 2000; 25:357-362.

44. Yu C, Chen Y, Zong H, Wang Y, Bergeron R, Kim J K, et al. Mechanism by which fatty acids inhibit insulin activation of IRS-1 associated phosphatidylinositol 3-kinase activity in muscle. J Biol Chem 2002; 277:50230-50236.
45. Glesne D A, Collart F R, Huberman E. Regulation of IMP dehydrogenase gene expression by its end products, guanine nucleotides. Mel Cell Biol 1991; 11:5417-5425.
46. White M F. The insulin receptor tyrosine kinase. In: Peptide Hormone Action: A Practical Approach. Siddle K, Hutton J C, editors. New York: Oxford University Press; 1990. p. 223-250.
47. Whitehead J P, Molero J C, Clark S, Martin S, Meneilly G, James D E. The role of Ca2+ in insulin-stimulated glucose transport in 3T3-L1 cells. J Biol Chem 2001; 276:27816-27824.
48. Miele C, Riboulet A, Maitan M A, Oriente F, Romano C, Formisano P, Giudicelli J, Beguinot F, Van Obberghen E. Human Glycated Albumin Affects Glucose Metabolism in L6 Skeletal Muscle Cells by Impairing Insulin-induced Insulin Receptor Substrate (IRS) Signaling through a Protein Kinase C{alpha}-mediated Mechanism. J Biol Chem 2003; 278:47376-47387.
49. Proffitt R T, Pathak V K, Villacorte D G, Presant C A. Sensitive radiochemical assay for inosine 5'-monophosphate dehydrogenase and determination of activity in murine tumor and tissue extracts. Cancer Res 1983; 43:1620-1623.
50. Molero J C, Whitehead J P, Meerloo T, James D E. Nocodazole inhibits insulin-stimulated glucose transport in 3T3-L1 adipocytes via a microtubule-independent mechanism. J Biol Chem 2001; 276:43829-35.
51. Demoulin, J.-B., Ericsson, J., Kallin, A., Rorsman, C., Ronnstrand, L., and Heldin, C.-H. (2004). Platelet-derived growth factor stimulates membrane lipid synthesis through activation of phosphatidylinositol 3-kinase and sterol regulatory element-binding proteins. J. Biol. Chem., M405924200.
52. Hutley, L. I., Shurety, W., Newell, F. M., McGeary, R., Pelton, N., Grant, J., Herrington, A., Cameron, D. P., Whitehead, J. P., and Prins, J. (2004). Fibroblast growth factor 1: a key regulator of human adipogenesis. Diabetes 53, 3097-3106
53. Entenmann, G., and Hauner, H. (1996). Relationship between replication and differentiation in cultured human adipocyte precursor cells. Am J Physiol 270, C1011-1016.

What is claimed is:

1. A method for treating obesity in humans wherein the obesity is not related to excess food intake, comprising administering to a patient in need of such treatment an adipogenesis-inhibiting effective amount of an inosine-5' monophosphate dehydrogenase (IMPDH) antagonist, wherein the IMPDH antagonist is a compound selected from the group consisting of mycophenolic acid and derivatives thereof, and optionally a pharmaceutically acceptable carrier and/or diluent, wherein the IMPDH antagonist antagonizes the function of an IMPDH for decreasing the differentiation potential and/or proliferation of a human preadipocyte.

2. The method of claim 1, wherein the IMPDH antagonist antagonizes the function of an IMPDH for decreasing the accumulation of lipids in an adipocyte.

3. A method according to claim 1, wherein the compound is represented by formula (I):

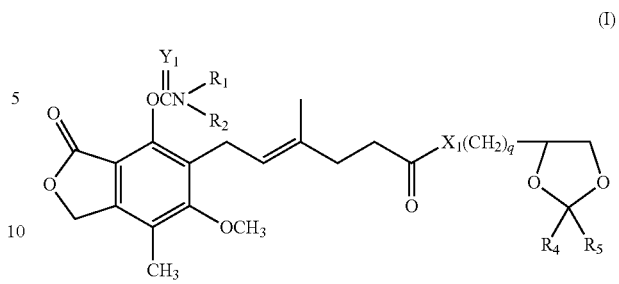

and pharmaceutically acceptable salts thereof,
wherein:
$R_1$ is H or lower alkyl having 1 to 6 carbon atoms;
$R_2$ is H, lower alkyl having 1 to 6 carbon atoms or -phenyl-4-$CO_2R_3$, in which
$R_3$ is H, lower alkyl having 1 to 6 carbon atoms or a pharmaceutically acceptable cation;
$R_4$ and $R_5$ are each independently H or lower alkyl having 1 to 6 carbon atoms;
$X_1$ and $Y_1$ are each independently O or S; and
q is an integer of 1-6.

4. A method according to claim 1, wherein the compound is represented by formula (II):

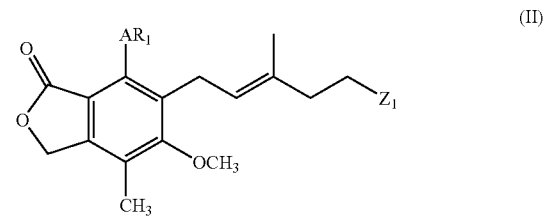

and pharmaceutically acceptable salts thereof,
wherein:
$R_1$ is selected from the group consisting of:

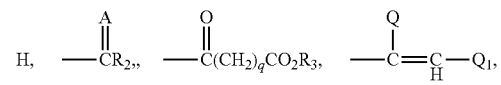

in which:
A is oxygen or sulfur;
q is an integer from 0-6;
$R_2$ is alkyl, haloalkyl or —$NR_4R_5$, where:
$R_4$ and $R_5$ are independently H, alkyl, haloalkyl, cycloalkyl, phenyl optionally monosubstituted with halogen, hydroxy, carboxy, chlorocarbonyl, sulfonylamino, nitro, cyano, phenyl, alkyl, acyl, alkoxycarbonyl, acylamino, dialkylamino or dialkylaminoethoxycarbonyl, phenyl optionally disubstituted with hydroxy, carboxy, nitro or alkyl, or benzyl optionally substituted with dialkylamino;
$R_3$ is H, alkyl or a pharmaceutically acceptable cation;
Q and $Q_i$ are independently H or —$CO_2R_3$; and
$Z_1$ is selected from the group consisting of: IH-tetrazolyl, —$CH_2OH$, —CHO, —CN, —$C(O)A_2R_6$ and —$C(O)NR_7R_8$, in which:
$A_2$ is oxygen or sulfur;
$R_6$ is H, alkyl, alkenyl, cycloalkyl, optionally substituted phenyl, optionally substituted benzyl or a pharmaceutically acceptable cation; and $R_7$ and $R_8$ are independently H, alkyl or cycloalkyl, or $R_7$ and $R_8$ taken together are —$(CH_2)_2$—O—$(CH_2)_2$—, —$(CH_2)_4$— or —$(CH_2)_5$—.

5. A method according to claim 1, wherein the compound is represented by formula (III):

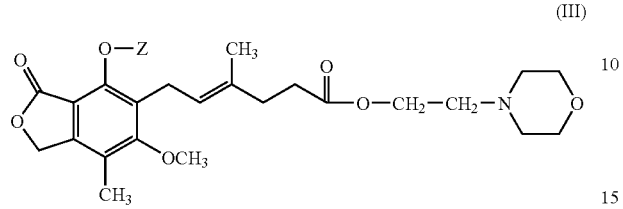
(III)

wherein:

Z is hydrogen or —C(O)R, where R is lower alkyl or aryl, and the pharmaceutically acceptable salts thereof.

6. A method according to claim 1, wherein the compound is represented by formula (IV):

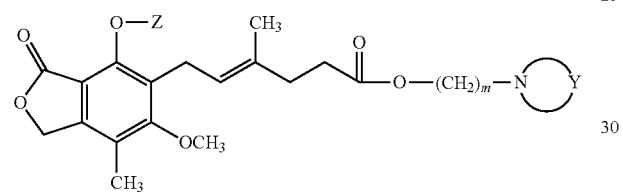
(IV)

wherein:

m is an integer from two to four;

Z is selected from Formulae (a), (b), (c), or (d), as follows:

(a)

in which:

$R^2$ is hydrogen, alkyl having seven or more carbon atoms including cycloalkyl such as adamantyl, or —$NR^2R^3$, where $R^2$ is hydrogen or lower alkyl, and $R^3$ is hydrogen, lower alkyl,-phenyl-4-$CO_2R^2$ or a pharmaceutically acceptable cation;

(b)

in which:

$R^4$ is hydrogen, alkyl, aryl or —$NR^2R^3$;

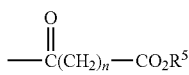
(c)

in which:

n is an integer from zero to six, and;

$R^5$ is hydrogen, lower alkyl, or a pharmaceutically acceptable cation;

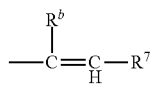
(d)

in which:

$R^6$ and $R^7$ are independently hydrogen or —$CO_2R^5$; and

Y is lower alkylene of four to six carbon atoms, or lower alkylene of three to five carbon atoms and one member that is —O—, —S— or

where $R^8$ is hydrogen or alkyl of one to five carbon atoms.

7. A method according to claim 1, wherein the compound is represented by formula (V):

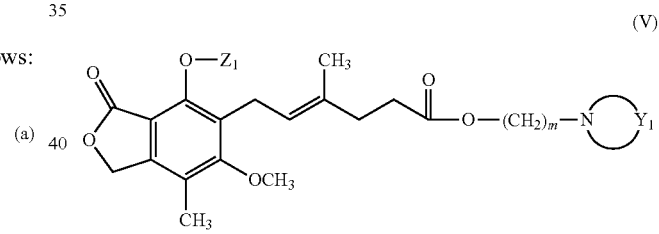
(V)

wherein:

m is an integer from two to four;

$Z^1$ is hydrogen or —C(O)$R^9$, where $R^9$ is lower alkyl or aryl; and $Y^1$ is lower alkylene of four to six carbon atoms, or lower alkylene of three to five carbon atoms and one member that is —O—, —S—, or

where $R^8$ is hydrogen or alkyl of one to five carbon atoms; and the pharmaceutically acceptable salts thereof;

except that when m is two, $Y^1$ does not include —$(CH_2)_2$—O—$(CH_2)_2$.

8. A method according to claim 1, wherein the compound is represented by formula (VI):

(VI)

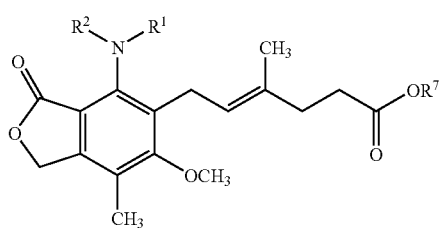

wherein:
$R^1$ is hydrogen or lower alkyl;
$R^2$ is hydrogen, lower alkyl, —C(O)$R_3$, —C(O)N$R^4R^5$, —CO$_2$R6, or —SO$_2R^3$
where:
$R^3$ is hydrogen, lower alkyl, halo lower alkyl or optionally substituted phenyl;
$R^4$ is hydrogen, lower alkyl or optionally substituted phenyl;
$R^5$ is hydrogen, lower alkyl or optionally substituted phenyl;
$R^6$ is lower alkyl or optionally substituted phenyl; and
$R^7$ is hydrogen, lower alkyl, optionally substituted phenyl, or —(CH$_2$)$_m$—N═Y, wherein:
m is an integer from two to four; and
Y is lower alkylene of four to six carbon atoms or lower alkylene of three to five carbon atoms and one member that is —O—, —S—, or —N($R^8$)— where $R^8$ is hydrogen or lower alkyl,
and the pharmaceutically acceptable salts thereof.

9. A method according to claim 1, wherein the compound is represented by formula (VII):

(VII)

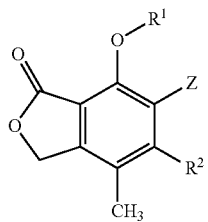

wherein:
$R^1$ is H or C(O)$R^{10}$, where $R^{10}$ is lower alkyl, aryl or NH-aryl;
$R^2$ is lower alkyl, cycloalkyl, vinyl, fluorovinyl, difluorovinyl, trifluorovinyl, alkenyl, —C≡C—$R^{11}$, allenyl, CHO or CH$_2$O$R^{12}$, where
$R^{11}$ is H or lower alkyl, and
$R^{12}$ is H or 4-methoxybenzyl; and
Z is a side chain selected from Formulae ZA, ZB, ZC, ZD, ZE, ZF, ZG and ZH:

(VII-A)

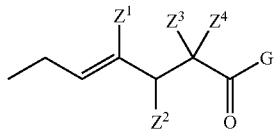

wherein:
$Z^1$ is H, lower alkyl, halo or CF$_3$;

$Z^2$ is H, lower alkyl, lower alkoxy, aryl, or CH$_2$—$Z^{11}$, where
$Z^{11}$ is halo, CN, aryl or heteroaryl;
$Z^3$ is H, lower alkyl, lower alkenyl, lower alkoxy, phenyl, or S(O)$_m$-lower alkyl, where m is 0, 1 or 2;
$Z^4$ is H, lower alkyl, or phenyl;
or $Z^3$ and $Z^4$ taken together with the carbon to which they are attached form cycloalkyl of three to five carbon atoms; and
G is OH, lower alkoxy, lower thioalkyl, N$G^1G^2$, O—(CH$_2$)$_n$—N$G^1G^2$, or O—(CH$_2$)$_n$—N═$G^3$,
where
n is an integer from 1 to 6,
$G^1$ is H or lower alkyl,
$G^2$ is H or lower alkyl, and
═$G^3$ is lower alkylene of four to six carbon atoms, or lower alkylene of three to five carbon atoms plus one member that is —O—, —S—, or —N(G4)- where $G^4$ is H or lower alkyl; or (VII-B)

![structure VII-B]

wherein:
$Z^5$ is H or lower alkyl;
$Z^8$ is H, lower alkyl or forms a double bond with $D^2$;
$D^1$ and $D^2$ together with their adjacent carbon atoms form an optionally substituted, saturated or unsaturated carbocyclic or heterocyclic ring of 3 to 7 atoms; and
G is as defined above; or (VII-C)

![structure VII-C]

wherein:
$Z^8$ is H or lower alkyl; and
$Z^5$ and G are as defined above; or (VII-D)

![structure VII-D]

wherein:
$D^3$ is —CH$_2$— or —CH$_2$—CH$_2$—; and
G is as defined above; or

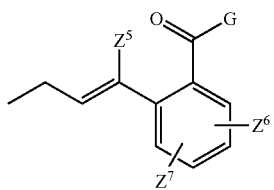

(VII-E)

wherein:
$Z^6$ is H, lower alkyl, COOH, $NH_2$, azido or halo;
$Z^7$ is H, lower alkyl or halo; and
$Z^5$ and G are as defined above;

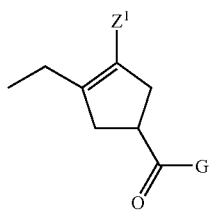

(VII-F)

wherein:
$Z^1$ and G are as defined above; or

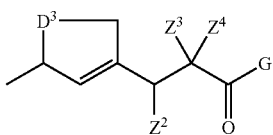

(VII-G)

wherein:
$D^3$, $Z^2$, $Z^3$, $Z^4$ and G are as defined above; or

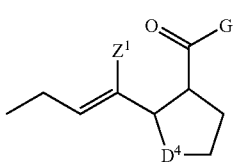

(VII-H)

wherein:
$D^4$ is $-CH_2-$, $-CH_2-CH_2-$, $-CH_2-CH_2-CH_2-$, $-O-$, or $-O-CH_2-$; and
$Z^1$ and G are as defined above;
and the pharmaceutically acceptable salts thereof.

10. The method of claim 1, wherein the IMPDH antagonist reduces the expression of the gene or the level or functional activity of an expression product of that gene by at least 10% relative to the expression, level or functional activity in the absence of the antagonist.

\* \* \* \* \*

UNITED STATES PATENT AND TRADEMARK OFFICE
CERTIFICATE OF CORRECTION

PATENT NO.       : 7,915,255 B2
APPLICATION NO.  : 11/205279
DATED            : March 29, 2011
INVENTOR(S)      : Jonathan Paul Whitehead It is certified that error appears in the above-identified patent and that said Letters Patent is hereby corrected as shown below:

At Item 56, Column 2, Page 2, Line 45, Under Other Publications, change "precurors" to --precursors--.

At Item 56, Column 2, Page 2, Line 56, Under Other Publications, change "84:3881-387." to --84:381-387.--.

At Column 6, Line 31, change "comprising" to --comprise--.

At Column 9, Line 26, after "shown)" insert --.--.

At Column 14, Line 54, change "pyrrazolyl," to --pyrazolyl,--.

At Column 24, Line 30, change " 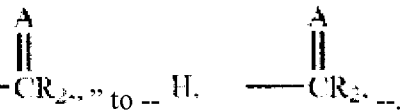 " to -- 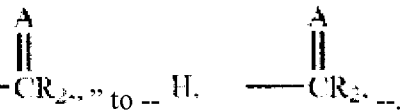 --.

At Column 25, Line 64, change "$O_2R^5$; and" to -- —$CO_2R^5$; and--.

At Column 52, Line 5, change "$(C^1-C^5)$" to --$(C_1-C_5)$--.

At Column 57, Lines 17-24 (Approx.), after " 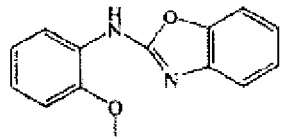 " insert --,--.

At Column 69, Line 54, after "oxazolamine" insert --.--.

At Column 73, Line 49, change "$(C_{04}$ alkyl)" to --$(C_0-C_4$ alkyl)--.

At Column 75, Line 4, after "$S(O)_2$" insert --;--.

At Column 75, Line 45 (Approx.), after "$R^3$" insert --;--.

At Column 75, Line 46 (Approx.), change "H, $R^3$," to --H, $R^2$, $R^3$,--.

At Column 78, Line 19 (Approx.), change "—$CF_3$; $C_1-C_6$)" to -- —$CF_3$; —$(C_1-C_6)$--.

At Column 78, Line 19 (Approx.), change "$C_2-C_6$)" to -- —$(C_2-C_6)$--.

Signed and Sealed this
Eighteenth Day of September, 2012

David J. Kappos
*Director of the United States Patent and Trademark Office*

At Column 78, Line 20 (Approx.), change "$C_1$-$C_6$)" to -- —($C_1$-$C_6$)--.

At Column 78, Line 23 (Approx.), change "$C_1$-$C_6$)" to -- —($C_1$-$C_6$)--.

At Column 78, Line 24 (Approx.), change "$R_7$" to --$R_7$;--.

At Column 78, Lines 47-48, change "—C(O)[($C_1$-$C_6$)" to -- —C(O)—[($C_1$-$C_6$)--.

At Column 78, Line 48, change "—C(O)[($C_2$-$C_6$)" to -- —C(O)—[($C_2$-$C_6$)--.

At Column 78, Line 49, change "—C(O)[($C_1$-$C_6$)" to -- —C(O)—[($C_1$-$C_6$)--.

At Columns 103-104, Line 3, change " 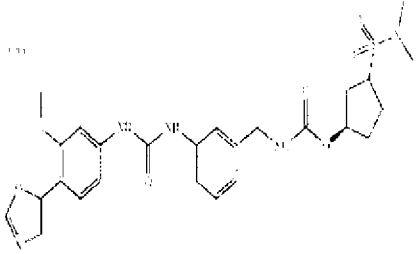 " to -- 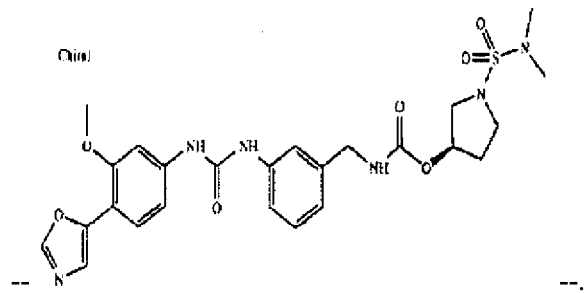 --.

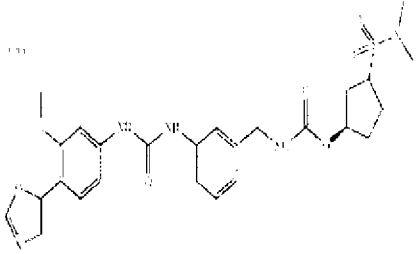

At Column 144, Line 56, change "$C_3$-C," to --$C_3$-$C_6$--.

At Column 146, Lines 59-60, change "($C_0$|-$C_4$" to --($C_0$-$C_4$--.

At Column 151, Line 17, change "amino and" to --amino; and--.

At Column 172, Line 63, change "tiazoflirin," to --tiazofurin,--.

At Column 172, Line 64, change "fro example" to --for example--.

At Column 175, Line 34, after "supra" insert --.--.

At Column 181, Line 25, change "450456)." to --450-456).--.

At Column 181, Line 55, change "495497)," to --495-497),--.

At Column 181, Line 64, change "dabs)," to --dAbs),--.

At Column 188, Line 40, change "e.g.," to --(e.g.,--.

At Column 190, Line 7, change "hemagluttinin-(HA)" to --hemagglutinin-(HA)--.

At Column 196, Line 67, change "hemagluttinin (HA)" to --hemagglutinin (HA)--.

At Column 199, Line 30, change "L1-Cor" to --Li-Cor--.

At Column 200, Line 35 (Approx.), change "Obno" to --Ohno--.

At Column 200, Line 35 (Approx.), change "O," to --G,--.

At Column 200, Line 55, change "Omtoft" to --Orntoft--.

At Column 201, Line 20, change "Caries" to --Carlos--.

CERTIFICATE OF CORRECTION (continued)
U.S. Pat. No. 7,915,255 B2

At Column 201, Line 23, change "Mel Biol" to --Mol Biol--.

At Column 201, Line 30 (Approx.), change "J Bid" to --J Biol--.

At Column 201, Line 32 (Approx.), change "Thao" to --Zhao--.

At Column 201, Line 39 (Approx.), change "H, Bimbaum" to --H, Birnbaum--.

At Column 201, Line 49, change "Biotechnoi" to --Biotechnol--.

At Column 202, Line 10, change "Thu" to --Zhu--.

At Column 202, Line 12, change "J Bid" to --J Biol--.

At Column 202, Line 17, after "23709" insert --.--.

At Column 202, Line 18, change "Langeiier" to --Langelier--.

At Column 202, Line 36, change "Bid" to --Biol--.

At Column 202, Line 46, change "Menn" to --Merin--.

At Column 202, Line 50 (Approx.), change "R I," to --R J,--.

At Column 202, Line 55, change "pigtnentosa genes. Mel" to --pigmentosa genes. Mol--.

At Column 202, Line 65 (Approx.), change "Hakmnaki" to --Hakumaki--.

At Column 203, Line 8 (Approx.), change "Mel" to --Mol--.

At Column 203, Line 40 (Approx.), change "L. I.," to --L. J.,--.

At Column 203, Line 45, after "3106" insert --.--.

At Column 204, Lines 42-45 (Approx.), In Claim 4, change "$H$ —$\overset{\overset{A}{\|}}{C}R_2$" to --$H$ —$\overset{\overset{A}{\|}}{C}R_2$--.

At Column 204, Line 60, In Claim 4, change "$Q_i$" to --$Q_1$--.

At Column 204, Line 61, In Claim 4, change "IH" to --1H--.

At Column 206, Line 9, In Claim 6, change "Rb" to --$R^6$--.

At Column 207, Line 15, In Claim 8, change "-CO2R6" to --$CO_2R^6$--.

At Column 207, Lines 55-56, In Claim 9, change "ZA, ZB, ZC, ZD, ZE, ZF, ZG and ZH" to --VII-A, VII-B, VII-C, VII-D, VII-E, VII-F, VII-G and, VII-H--.

At Column 208, Line 22, In Claim 9, change "-N(G4)-" to -- -N($G^4$)- --.